(12) United States Patent
Babul

(10) Patent No.: US 11,607,407 B2
(45) Date of Patent: Mar. 21, 2023

(54) DERMAL PHARMACEUTICAL COMPOSITIONS OF 1-METHYL-2',6'-PIPECOLOXYLIDIDE AND METHOD OF USE

(75) Inventor: Najib Babul, Blue Bell, PA (US)

(73) Assignee: Relmada Therapeutics, Inc., Coral Gables, FL (US)

( * ) Notice: Subject to any disclaimer, the term of this patent is extended or adjusted under 35 U.S.C. 154(b) by 1879 days.

(21) Appl. No.: 13/641,240

(22) PCT Filed: Apr. 13, 2011

(86) PCT No.: PCT/US2011/032381
§ 371 (c)(1),
(2), (4) Date: Feb. 26, 2014

(87) PCT Pub. No.: WO2011/130455
PCT Pub. Date: Oct. 20, 2011

(65) Prior Publication Data
US 2017/0333410 A1 Nov. 23, 2017

Related U.S. Application Data

(60) Provisional application No. 61/323,780, filed on Apr. 13, 2010.

(51) Int. Cl.
*A61K 9/06* (2006.01)
*A61K 31/445* (2006.01)
(Continued)

(52) U.S. Cl.
CPC .......... *A61K 31/445* (2013.01); *A61K 9/0014* (2013.01); *A61K 9/06* (2013.01); *A61K 9/107* (2013.01); *A61K 9/14* (2013.01); *A61K 9/703* (2013.01); *A61K 31/44* (2013.01); *A61K 47/06* (2013.01); *A61K 47/08* (2013.01); *A61K 47/10* (2013.01); *A61K 47/12* (2013.01); *A61K 47/14* (2013.01); *A61K 47/18* (2013.01);
(Continued)

(58) Field of Classification Search
CPC ...... A61K 31/445; A61K 47/26; A61K 47/32; A61K 47/20; A61K 9/14
See application file for complete search history.

(56) References Cited

U.S. PATENT DOCUMENTS

| 3,598,122 A | 8/1971 | Zaffaroni |
| 3,598,123 A | 8/1971 | Zaffaroni |

(Continued)

FOREIGN PATENT DOCUMENTS

| CN | 1358495 A | 7/2002 |
| DE | 102004056838 A1 | 3/2006 |

(Continued)

OTHER PUBLICATIONS

Porto et al., Med Oral Patol Oral Cir Bucal., 2007;12:E60-4.*
(Continued)

*Primary Examiner* — San Ming R Hui
(74) *Attorney, Agent, or Firm* — Wood Herron & Evans LLP

(57) ABSTRACT

The present invention is directed to therapeutic pharmaceutical compositions of 1-Methyl-2', 6'-pipecoloxylidide or it pharmaceutically acceptable salts for application to the skin and the use thereof.

8 Claims, 7 Drawing Sheets

(51) Int. Cl.

| | | |
|---|---|---|
| *A61K 9/00* | (2006.01) | |
| *A61K 47/10* | (2017.01) | |
| *A61K 47/12* | (2006.01) | |
| *A61K 47/26* | (2006.01) | |
| *A61K 47/32* | (2006.01) | |
| *A61K 47/20* | (2006.01) | |
| *A61K 47/44* | (2017.01) | |
| *A61K 9/14* | (2006.01) | |
| *A61K 47/18* | (2017.01) | |
| *A61K 47/38* | (2006.01) | |
| *A61K 31/44* | (2006.01) | |
| *A61K 9/107* | (2006.01) | |
| *A61K 47/14* | (2017.01) | |
| *A61K 9/70* | (2006.01) | |
| *A61K 47/06* | (2006.01) | |
| *A61K 47/08* | (2006.01) | |
| *A61K 47/22* | (2006.01) | |

(52) U.S. Cl.
CPC ............. *A61K 47/20* (2013.01); *A61K 47/22* (2013.01); *A61K 47/26* (2013.01); *A61K 47/32* (2013.01); *A61K 47/38* (2013.01); *A61K 47/44* (2013.01)

(56) References Cited

U.S. PATENT DOCUMENTS

| | | |
|---|---|---|
| 3,742,951 A | 7/1973 | Zaffaroni |
| 3,814,097 A | 6/1974 | Ganderton et al. |
| 3,921,636 A | 11/1975 | Zaffaroni |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,199,564 A | 4/1980 | Silver et al. |
| 4,201,211 A | 5/1980 | Chandrasekaran et al. |
| 4,230,105 A | 10/1980 | Harwood |
| 4,292,299 A | 9/1981 | Suzuki et al. |
| 4,292,303 A | 9/1981 | Keith et al. |
| 4,374,126 A | 2/1983 | Cardarelli et al. |
| 4,393,076 A | 7/1983 | Noda et al. |
| 4,466,953 A | 8/1984 | Keith et al. |
| 4,470,962 A | 9/1984 | Keith et al. |
| 4,542,012 A | 9/1985 | Dell |
| 4,584,192 A | 4/1986 | Dell et al. |
| 4,588,580 A | 5/1986 | Gale et al. |
| 4,626,539 A | 12/1986 | Aungst et al. |
| 4,645,502 A | 2/1987 | Gale et al. |
| 4,806,341 A | 2/1989 | Chien et al. |
| 4,814,173 A | 3/1989 | Song et al. |
| 4,906,463 A | 3/1990 | Cleary et al. |
| 4,911,707 A | 3/1990 | Heiber et al. |
| 4,911,916 A | 3/1990 | Cleary |
| 4,915,950 A | 4/1990 | Miranda et al. |
| 4,917,676 A | 4/1990 | Heiber et al. |
| 4,927,408 A | 5/1990 | Haak et al. |
| 4,938,759 A | 7/1990 | Enscore et al. |
| 4,941,880 A | 7/1990 | Burns |
| 4,950,475 A | 8/1990 | Vishnupad et al. |
| 4,956,171 A | 9/1990 | Chang |
| 4,978,527 A | 12/1990 | Brink et al. |
| 4,990,501 A | 2/1991 | Imrie et al. |
| 5,006,342 A | 4/1991 | Cleary et al. |
| 5,017,369 A | 5/1991 | Marhevka |
| 5,023,085 A | 6/1991 | Francoeur et al. |
| 5,026,556 A | 6/1991 | Drust et al. |
| 5,069,909 A | 12/1991 | Sharma et al. |
| 5,080,646 A | 1/1992 | Theeuwes et al. |
| 5,135,480 A | 8/1992 | Bannon et al. |
| 5,147,296 A | 9/1992 | Theeuwes et al. |
| 5,149,538 A | 9/1992 | Granger et al. |
| 5,169,382 A | 12/1992 | Theeuwes et al. |
| 5,173,291 A | 12/1992 | Brink et al. |
| 5,186,939 A | 2/1993 | Cleary et al. |
| 5,203,768 A | 4/1993 | Haak et al. |
| 5,225,199 A | 7/1993 | Hidaka et al. |
| 5,232,438 A | 8/1993 | Theeuwes et al. |
| 5,236,714 A | 8/1993 | Lee et al. |
| 5,240,711 A | 8/1993 | Hille et al. |
| 5,310,559 A | 5/1994 | Shah et al. |
| 5,323,769 A | 6/1994 | Bommannan et al. |
| 5,374,645 A | 12/1994 | Kurihara-Bergstrom et al. |
| 5,411,738 A | 5/1995 | Hind |
| 5,446,070 A | 8/1995 | Mantelle |
| 5,462,744 A | 10/1995 | Gupte et al. |
| 5,464,387 A | 11/1995 | Haak et al. |
| 5,474,783 A | 12/1995 | Miranda et al. |
| 5,503,844 A | 4/1996 | Kwiatek et al. |
| 5,508,024 A | 4/1996 | Tranner |
| 5,525,358 A | 6/1996 | Popp |
| 5,556,635 A | 9/1996 | Istin et al. |
| 5,589,195 A | 12/1996 | Potter |
| 5,601,839 A | 2/1997 | Quan et al. |
| 5,629,014 A | 5/1997 | Kwiatek et al. |
| 5,635,204 A | 6/1997 | Gevirtz et al. |
| 5,656,286 A | 8/1997 | Miranda et al. |
| 5,662,926 A | 9/1997 | Wick et al. |
| 5,667,773 A | 9/1997 | Farrar et al. |
| 5,679,373 A | 10/1997 | Wick et al. |
| 5,686,112 A | 11/1997 | Liedtke |
| 5,697,896 A | 12/1997 | McNichols et al. |
| 5,705,186 A | 1/1998 | Hille et al. |
| 5,711,943 A | 1/1998 | Grossman |
| 5,762,952 A | 6/1998 | Barnhart et al. |
| 5,776,479 A | 7/1998 | Pallos et al. |
| 5,807,957 A | 9/1998 | Samour et al. |
| 5,827,529 A | 10/1998 | Ono et al. |
| 5,834,010 A | 11/1998 | Quan et al. |
| 5,843,979 A | 12/1998 | Wille et al. |
| 5,869,600 A | 2/1999 | Causton et al. |
| 5,888,494 A | 3/1999 | Farrar et al. |
| 5,906,814 A | 5/1999 | Epstein |
| 5,906,822 A | 5/1999 | Samour et al. |
| 5,908,846 A | 6/1999 | Bundgaard et al. |
| 5,911,980 A | 6/1999 | Samour et al. |
| 5,948,433 A | 9/1999 | Burton et al. |
| 5,948,882 A | 9/1999 | Causton et al. |
| 5,958,379 A | 9/1999 | Regenold et al. |
| 5,958,446 A | 9/1999 | Miranda et al. |
| 5,968,528 A | 10/1999 | Deckner et al. |
| 5,985,317 A | 11/1999 | Venkateshwaran et al. |
| 5,989,570 A | 11/1999 | Lion et al. |
| 5,993,849 A | 11/1999 | Assmus et al. |
| 6,004,969 A | 12/1999 | Hu |
| 6,010,715 A | 1/2000 | Wick et al. |
| 6,024,976 A | 2/2000 | Miranda et al. |
| 6,063,399 A | 5/2000 | Assmus et al. |
| 6,110,488 A | 8/2000 | Hoffmann |
| 6,113,921 A | 9/2000 | Friedman et al. |
| 6,126,920 A | 10/2000 | Jones et al. |
| 6,139,866 A | 10/2000 | Chono et al. |
| 6,171,294 B1 | 1/2001 | Southam et al. |
| 6,181,963 B1 | 1/2001 | Chin et al. |
| 6,203,817 B1 | 3/2001 | Cormier et al. |
| 6,216,033 B1 | 4/2001 | Southam et al. |
| 6,219,576 B1 | 4/2001 | Gupta et al. |
| 6,228,354 B1 | 5/2001 | Jeng |
| 6,238,654 B1 | 5/2001 | Tournilhac et al. |
| 6,238,679 B1 | 5/2001 | de la Poterie |
| 6,254,877 B1 | 7/2001 | De La Poterie et al. |
| 6,296,858 B1 | 10/2001 | Agostini et al. |
| 6,306,411 B1 | 10/2001 | Jager Lezer |
| 6,365,178 B1 | 4/2002 | Venkateshwaran et al. |
| 6,379,696 B1 | 4/2002 | Asmussen et al. |
| 6,425,892 B2 | 7/2002 | Southam et al. |
| 6,432,423 B1 | 8/2002 | Maignan et al. |
| 6,458,339 B1 | 10/2002 | Cox |
| 6,461,644 B1* | 10/2002 | Jackson ............ A61M 16/0443 424/499 |

(56) References Cited

U.S. PATENT DOCUMENTS

| | | | |
|---|---|---|---|
| 6,488,959 B2 | 12/2002 | Stanley et al. | |
| 6,500,407 B1 | 12/2002 | Cox | |
| 6,582,680 B2 | 6/2003 | Cox | |
| 6,682,757 B1 | 1/2004 | Wright | |
| 6,716,419 B2 | 4/2004 | Zoltowski et al. | |
| 6,730,288 B1 | 5/2004 | Abram | |
| 6,756,052 B1 | 6/2004 | Koch et al. | |
| 6,759,032 B2 | 7/2004 | Murphy et al. | |
| 6,791,003 B1 | 9/2004 | Choi et al. | |
| 6,797,262 B2 | 9/2004 | O'Halloran et al. | |
| 6,818,226 B2 | 11/2004 | Reed et al. | |
| 6,835,184 B1 | 12/2004 | Sage et al. | |
| 6,838,078 B2 | 1/2005 | Wang et al. | |
| 6,868,286 B1 | 3/2005 | Hille et al. | |
| 6,881,208 B1 | 4/2005 | Phipps et al. | |
| 6,893,655 B2 | 5/2005 | Flanigan et al. | |
| 6,916,486 B2 | 7/2005 | Klose et al. | |
| 6,916,487 B2 | 7/2005 | Klose et al. | |
| 6,923,983 B2 | 8/2005 | Morgan et al. | |
| 6,929,801 B2 | 8/2005 | Klose et al. | |
| 6,955,819 B2 | 10/2005 | Zhang et al. | |
| 6,962,691 B1 | 11/2005 | Lulla et al. | |
| 6,978,945 B2 | 12/2005 | Wong et al. | |
| 6,998,138 B2 | 2/2006 | Chew et al. | |
| 7,005,557 B2 | 2/2006 | Klofta et al. | |
| 7,018,370 B2 | 3/2006 | Southam et al. | |
| 7,029,659 B2 | 4/2006 | Abram | |
| 7,054,682 B2 | 5/2006 | Young et al. | |
| 7,083,781 B2 | 8/2006 | Fotinos et al. | |
| 7,094,422 B2 | 8/2006 | Chew et al. | |
| 2002/0006435 A1* | 1/2002 | Samuels | A61K 31/245 424/449 |
| 2002/0022009 A1 | 2/2002 | De La Poterie et al. | |
| 2002/0034535 A1 | 3/2002 | Kleiner et al. | |
| 2002/0132008 A1 | 9/2002 | Mumper et al. | |
| 2002/0142042 A1 | 10/2002 | Mumper et al. | |
| 2003/0007944 A1 | 1/2003 | O'Halloran et al. | |
| 2003/0026815 A1 | 2/2003 | Scott et al. | |
| 2003/0026816 A1 | 2/2003 | Zoltowski et al. | |
| 2003/0026829 A1 | 2/2003 | Venkatraman et al. | |
| 2003/0077307 A1 | 4/2003 | Klofta et al. | |
| 2003/0082221 A1 | 5/2003 | O'Halloran et al. | |
| 2003/0086954 A1 | 5/2003 | O'Halloran et al. | |
| 2003/0118655 A1 | 6/2003 | Kundel | |
| 2003/0194387 A1 | 10/2003 | Murphy et al. | |
| 2003/0194415 A1 | 10/2003 | Wang et al. | |
| 2003/0224053 A1 | 12/2003 | Fotinos et al. | |
| 2004/0013716 A1 | 1/2004 | Gale et al. | |
| 2004/0022755 A1 | 2/2004 | Kamath | |
| 2004/0071760 A1 | 4/2004 | Dvoretzky et al. | |
| 2004/0161402 A1 | 8/2004 | Brooks et al. | |
| 2004/0213832 A1 | 10/2004 | Venkatraman et al. | |
| 2005/0025794 A1 | 2/2005 | Wang et al. | |
| 2005/0095279 A1 | 5/2005 | Gale et al. | |
| 2005/0152957 A1* | 7/2005 | Cleary | A61K 31/165 424/448 |
| 2005/0186152 A1 | 8/2005 | Bonda et al. | |
| 2005/0186153 A1 | 8/2005 | Bonda et al. | |
| 2005/0186154 A1 | 8/2005 | Bonda et al. | |
| 2005/0191249 A1 | 9/2005 | Bonda et al. | |
| 2005/0208117 A1 | 9/2005 | Venkatraman et al. | |
| 2006/0064068 A1 | 3/2006 | Klofta et al. | |
| 2006/0165626 A1 | 7/2006 | Ricard et al. | |
| 2006/0193789 A1 | 8/2006 | Tamarkin et al. | |
| 2007/0025943 A1 | 2/2007 | Patel | |
| 2008/0286299 A1 | 11/2008 | Battaglia | |
| 2009/0053290 A1* | 2/2009 | Sand | A61K 8/553 424/449 |
| 2010/0041704 A1 | 2/2010 | Aberg et al. | |

FOREIGN PATENT DOCUMENTS

| | | |
|---|---|---|
| EP | 0488137 A2 | 6/1992 |
| EP | 1125578 A1 | 8/2001 |
| WO | 9619975 A1 | 7/1996 |
| WO | 2003035000 A2 | 5/2003 |
| WO | 2005105009 A1 | 11/2005 |

OTHER PUBLICATIONS

Buffer List, chapter 75, Handbook of Biochemistry and Molecular Biology (4th Edition), Taylor & Francis, 2010 (Year: 2010).*
Eappen, S et al., "Pharmacology of Local Anesthetics," Seminars in Anesthesia, 1998.
Written Opinion in International Patent Application No. PCT/US2011/032381, dated Aug. 16, 2011, 10 pgs.
International Search Report in International Patent Application No. PCT/US2011/032381, dated Aug. 16, 2011, 2 pgs.
Kanai, Y. et al., Graded, Irreversible Changes in Crayfish Giant Axon as Manifestations of Lidocaine Neurotoxicity In Vitro, Anesth Analg 1998;86:569-73.
McNulty, J.P. et al, "Update on managing neuropathic pain," Intl J Pharm Cmpd, 2009.
Radwan, A. M. et al., The Neurotoxicity of Local Anesthetics on Growing Neurons: A Comparative Study of Lidocaine, Bupivacaine, Mepivacaine, and Ropivacaine, Anesth Analg 2002; 94:319-24.
Strichartz, GR, Sanchez V, Arthur GR, Chafetz R, Martin D. Fundamental properties of local anesthetics. II. Measured octanol:buffer partition coefficients and pKa values of clinically used drugs. Anesth Analg 1990;71:158-70.
Babul, N. et al., Efficacy and Safety of Extended-Release, Once-Daily Tramadol in Chronic Pain: A Randomized 12-Week Clinical Trial in Osteoarthritis of the Knee, Journal of Pain and Symptom Management 2004;28(1):59-71.
Caldwell, J. R. et al., Efficacy and Safety of a Once-Daily Morphine Formulation in Chronic, Moderate-to-Severe Osteoarthritis Pain: Results from a Randomized, Placebo-Controlled, Double-Blind Trial and an Open-Label Exension Trial, Journal of Pain and Symptom Management 2002;23:278-91.
Hodgson, P. S. et al., The Neurotoxicity of Drugs Given Intrathecally (Spinal), Anesth. Analg. 1999;88:797-809.
Kanai, Y. et al., Lidocaine Disrupts Axonal Membrane of Rat Sciatic Nerve In Vitro, Anesth Analg 2000;91:944-48.
Matsumoto, A. K. et al., Oxymorphone Extended-Release Tablets Relieve Moderate to Severe Pain and Improve Physical Function in Osteoarthritis: Results of a Randomized, Double-Blind, Placebo- and Active-Controlled Phase III Trial, Pain Medicine 2005;6:357-66.
Peloso, P. M. et al., Double Blind Randomized Placebo Control Trial of Controlled Release Codeine in the Treatment of Osteoarthritis of the Hip or Knee, Journal of Rheumatology 2000;27:764-71.
Australian Examination Report No. 1 in Australian Patent Application No. 2016259348, dated Nov. 3, 2017, 5 pgs.
Chinese Office Action in Chinese Patent Application No. 201710323695.0 (English language translation), dated Jan. 16, 2020, 13 pgs.
Indian Office Action in Indian Patent Application No. 9424/CHENP/2012, dated Jan. 25, 2018, 6 pgs.

* cited by examiner

DERMAL PHARMACEUTICAL COMPOSITIONS OF 1-METHYL-2',6'-PIPECOLOXYLIDIDE AND METHOD OF USE

This application is entitled to priority to the applicant's U.S. provisional patent application No. 61/323,780, filed Apr. 13, 2010 which is herein incorporated in its entirety for all purposes.

FIELD OF THE INVENTION

The present invention is directed to therapeutic pharmaceutical compositions of 1-methyl-2',6'-pipecoloxylidide or it pharmaceutically acceptable salts for application to the skin and the use thereof.

BACKGROUND OF THE INVENTION

The present invention relates to the application of 1-methyl-2',6'-pipecoloxylidide (mepivacaine) to the skin for the treatment of mepivacaine responsive medical conditions such as pain and neuropathy.

Mepivacaine

Mepivacaine was synthesized in the mid 1950's in Sweden and introduced into clinical medicine in 1957 as an injectable local anesthetic. Presently injectable mepivacaine is indicated "for the production of local or regional analgesia and anesthesia by local infiltration, peripheral nerve block techniques, and central neural techniques including epidural and caudal blocks." To the applicant's knowledge, there are no working prototypes or therapeutic trials of mepivacaine in the prior art for application to the skin to treat pain.

In order to provide analgesia following application to the skin, a local anesthetic must be able to reach the epidermis and dermis where the cutaneous nerve endings are located, and once there it must be capable of blocking the generation and/or propagation of aberrant or ectopic impulses in sensory nerve fibers. The former property depends on the pharmacokinetic behavior of the local anesthetic, i.e., how efficiently it can penetrate the stratum corneum (the outermost layer of the skin), and how long it dwells in the deeper skin layers before diffusing into underlying tissue. The latter property depends on the pharmacologic activity of the local anesthetic, i.e., its ability to bind to and inhibit specific ion channels essential for the generation and/or propagation of the aberrant or ectopic impulses in sensory nerve fibers.

Although lidocaine has demonstrated some efficacy when applied to the skin of patients with certain pain states, these results are not generalizable to other local anesthetics. For example, an important predictor of skin penetration and penetration into the receptor site for local anesthetics is its octanol:water partition coefficient. In one report, the octanol: water partition coefficient of lidocaine was 3.6 fold greater than for mepivacaine (Ferrante F M, Pharmacology of local anesthetics, p. 1330-1362, In: Longnecker D E, Tinker J H, Morgan, Jr., GE (eds), Principles and practice of anesthesiology, 1998 (2nd ed), Mosby-Year Book, Inc. St. Louis, Mo.). In another study, the octanol:water partition coefficient of lidocaine was 2.6 fold greater than for mepivacaine. Similarly, the ratio of relative concentrations of protonated and neutral drug, respectively, between octanol and water was 2.8 fold greater for Lidocaine, compared with mepivacaine (Strichartz G R, Sanchez V, Arthur G R, Chafetz R, Martin D. Fundamental properties of local anesthetics. II. Measured octanol:buffer partition coefficients and pKa values of clinically used drugs. Anesth Analg 1990; 71:158-70.). All of the foregoing observations support the superior skin and subsequent nerve tissue penetration of lidocaine and the purported lack of efficacy for mepivacaine when applied to the skin. Goodman & Gilman's The Pharmacological Basis of Therapeutics, a textbook of pharmacology used by physicians from all therapeutic and surgical specialties, clinical pharmacologists, clinical research professionals and pharmacists states that "Mepivacaine is not effective as a topical anesthetic".

Neuropathic Pain

Pain is most often classified by time course, etiology or mechanism as acute pain, inflammatory pain, visceral pain, breakthrough pain, nociceptive pain, neuropathic pain, chronic pain, or cancer-related pain.

The International Association for the Study of Pain (IASP) defines neuropathic pain as "pain initiated or caused by a primary lesion or dysfunction of the nervous system". Neuropathic pain may be classified as peripheral neuropathic pain and central neuropathic pain (central pain). Many terms may be used by patients with neuropathies to describe their painful neuropathic sensations. Clinical trials of putative analgesics will frequently assess: (i) steady pain (patient descriptors often include "burning", "aching", "stinging", "throbbing", "itching", "numbing", "pins & needles", "pulling"; (ii) brief pain (patient descriptors often include "sharp", "jabbing", "shooting", "electric"; and (iii) evoked pain (assessed by the clinician or self-reported using "mechanical" and "thermal stimulus). (Watson and Babul, Neurology, 1998).

Pharmacological investigations have been conducted in a wide variety of painful neuropathies, particularly peripheral neuropathies. Among the peripheral neuropathies most widely investigated for pharmacologic response are painful diabetic neuropathy, postherpetic neuralgia, trigeminal neuralgia and painful HIV-associated distal symmetrical neuropathy.

It is estimated that approximately 20 million individuals in the United States have diabetes and about one-fifth of them suffer from painful diabetic neuropathy, which is a distal, symmetrical, axonal-sensory neuropathy usually involving the feet and legs initially and later the hands. A limited number of treatment options are available for the treatment of painful diabetic neuropathy and only two drugs (pregabalin and duloxetine) have been approved by the Food and Drug Administration (FDA) for the treatment of this condition. Even for effective and/or approved drugs, pain relief is often suboptimal and few patients obtain a complete response. Importantly, these pharmacologic agents can have troublesome side effects, an important issue given the co-morbid pathology in many patients with diabetes.

To the applicant's knowledge, there are no data from placebo controlled randomized clinical trials (which are considered the gold standard in evidence based medicine) demonstrating the efficacy of any local anesthetic application to the skin for the treatment of painful diabetic neuropathy.

HIV infection and HIV medications are both associated with the development of neuropathy which usually manifests as distal, symmetrical, predominantly sensory, polyneuropathy [Bailey et al, 1988; Corblath and MacArthur, 1988; Fuller et al, 1993]. Causative factors include nerve infiltration by HIV and the toxicity of antiretrovirals such as didanosine (ddI) or zalcitabine (ddC) [Fuller et al, 1991; Grafe and Wiley, 1989; Griffin et al, 1994; Paice et al, 2000; Penfold and Clark, 1992; Rizzuto et al, 1995; Simpson and Olney, 1992]. Progressive and painful HIV-associated neuropathy significantly impairs patients' quality of life, and it impairs function, by rendering walking difficult. Painful HIV-associated neuropathy is also a toxicity of antiretroviral therapy and as such it limits patients' ability to remain on antiviral regimens containing these life saving compounds. It has been documented that painful HIV-associated neuropathy can lead to patient refusal to take anti-retroviral therapy, with potentially life threatening consequences.

To date no drugs have been approved in the U.S. for painful HIV-associated neuropathy. Several therapies have been evaluated for the treatment of painful HIV-associated neuropathy. With the exception of recombinant nerve growth factor [McArthur et al, 2000], lamotrigine [Simpson et al, 2000; Simpson et al, 2003] and high dose topical capsaicin [Simpson et al, 2006], most treatments, including mexiletine, peptide T, acupuncture and amitriptyline have demonstrated no significant benefit for this debilitating condition [Kemper et al, 1998; Kieburtz et al, 1998; Schlay et al, 1998; Simpson et al, 1996].

To the applicant's knowledge, there are no data from placebo controlled randomized clinical trials demonstrating the efficacy of any topically applied local anesthetic for the treatment of painful HIV-associated neuropathy. Indeed, in the only placebo controlled randomized clinical trial of topical lidocaine, there were no significant efficacy differences from placebo [Estanislao et al, J Acquir Immune Defic Syndr. 2004 Dec. 15; 37:1584-6.].

Herpes zoster, also known Varicella-Zoster or shingles is a viral infection whose pathology is characterized by acute inflammation. In a minority of patients with the painful but self-limiting condition of herpes zoster (also known as Varicella-Zoster or shingles), the pain persists after the healing of the acute lesions and a chronic pain state develops (Watson et al., 1991; Watson, 1989; Watson et al., 1988). This pain is referred to as postherpetic neuralgia (PHN). The pain of PHN is unrelenting and is characterized by burning, aching or itching with superimposed lancinating pains.

Four drugs are approved in the United States for the management of postherpetic neuralgia: (i) topical lidocaine patch (Lidoderm™); (ii) oral gabapentin (Neurontin™); (iii) oral pregabalin (Lyrica™) and high dose topical capsaicin patch (Qutenza™). A number of drugs, including the opioid OxyContin™ (Watson and Babul, 1998), tricyclic antidepressants (Max, 1995; Sindrup, 1999) and tramadol (Boureau et al., 2003) have demonstrated efficacy in postherpetic neuralgia and are used "off-label".

The efficacy of topical lidocaine has been evaluated studies in postherpetic neuralgia. In addition to modest efficacy, such studies have suffered from severe design shortcomings, including very short duration of treatment and evaluation, and patient population enrichment (Rowbotham et al. Pain, 1996; Galer et al., Pain, 1999; Galer et al., Clin J Pain, 2002). The efficacy of topical lidocaine was evaluated by Meier et al (Pain, 2003) in 58 patients with painful peripheral neuropathies (approximately 55% of the patients had postherpetic neuralgia), using a randomized, placebo-controlled, two-way, cross-over study. On average, 4.4 patients had to be treated for one patient to obtain ≥50% relief from ongoing pain and 8.4 patients had to be treated for one patient to obtain ≥50% relief from allodynia.

The UK National Institute of Health and Clinical Excellence (NICE) clinical guideline on neuropathic pain (March 2010) states that there is a "lack of evidence for the efficacy of topical lidocaine for treating neuropathic pain" and that topical lidocaine should be considered as "third line" treatment for neuropathic pain (http://guidance.nice.org.uk/CG9).

There is a need for new local anesthetic pharmaceutical compositions for application to the skin and methods for the treatment of postherpetic neuralgia that have high efficacy.

There is a need for new local anesthetic pharmaceutical compositions for application to the skin and methods for the treatment of other peripheral neuropathies and peripheral neuropathic pain.

There is a need for new local anesthetic pharmaceutical compositions for application to the skin and methods for the treatment of other neuropathic pain that is of non-peripheral origin.

To the applicant's knowledge, with the possible exception of application by skin infiltration, there are no: (i) recommendations on mepivacaine application to the skin' for the management of neuropathy or neuropathic pain; (ii) no public data on mepivacaine application to the skin for the management of neuropathy or neuropathic pain; (iii) no working examples of topical mepivacaine for application to the skin for the treatment of neuropathy or neuropathic pain (iv) no approved mepivacaine product for application to the skin for the management of neuropathy or neuropathic pain; and (v) no mepivacaine products for application to the skin for the treatment of neuropathy or neuropathic pain in development, regulatory review or on the market any major market.

One challenge in the treatment of peripheral sources of neuropathy, mechanical and thermal allodynia, hyperalgesia and ongoing pain in patients with peripheral neuropathic pain and chronic pain relates to attaining adequate and sustained concentrations of drug at the peripheral sites of pain initiation, pain propagation and pain maintenance. This is particularly problematic with application of drugs through the skin. Another challenge in attaining adequate and sustained concentrations of drug at the peripheral sites of pain initiation, pain propagation and pain maintenance is that such high concentrations have the potential of producing systemic toxicity (e.g., cardiac and CNS toxicity).

Contrary to the established view about the purported in efficacy of topical mepivacaine, the applicant is of the view that topical mepivacaine of the present invention is also beneficial, because unlike lidocaine and many other anesthetics, mepivacaine has intrinsic vasoconstrictor effects, thereby reducing the rate at which drug is cleared (away) from peripheral sites of pain. This allows mepivacaine to provide adequate and sustained concentrations of drug at the peripheral sites pain initiation, pain propagation and pain maintenance with a reduced risk of systemic toxicity (e.g., cardiac and CNS toxicity).

Present topical treatments of peripheral neuropathic pain rely entirely on a local or peripheral effect, targeting peripheral "irritable" nociceptors. There is no reference in the literature to application to the skin of local anesthetics to target non-peripheral (e.g., deep tissue, viscera, spinal cord, brain) sources of pain. Indeed, application of drugs to the skin for the treatment of neuropathic pain have been positioned as advantageous to the extent they restrict their therapeutic effects to skin and peripheral sources of pain (Endo Pharmaceuticals Citizen's Petition to the U.S. FDA, Dec. 18, 2006, Petition No. 2006P-0522).

There is a need therefore for new local anesthetic pharmaceutical compositions for application to the skin and methods for the treatment of peripheral neuropathy and peripheral neuropathic pain that target both peripheral and central mechanisms of the pain.

There is a need therefore for new local anesthetic pharmaceutical compositions for application to the skin and methods for the treatment of non-peripheral neuropathy (e.g., central pain) that target non-peripheral sources of pain (e.g., in the spinal cord and brain).

The inefficacy and suboptimal efficacy of topically applied lidocaine in many patients with peripheral neuropathy and peripheral neuropathic pain provides a pharmacologic basis for improving the overall efficacy of local anesthetics for the treatment of peripheral neuropathy by modulating spinal and supraspinal (central) mechanisms of neuropathic pain. Such central mechanisms are particularly important in patients with peripheral neuropathy and peripheral neuropathic pain who have significant loss of nerve fiber in the periphery and in patients with no mechanical and tactile allodynia.

Certain aspects of the invention relate to topical and transdermal mepivacaine pharmaceutical compositions and methods for the treatment of painful neuropathies that target both mepivacaine responsive aberrant peripheral and central mechanisms of the neuropathic pain, with robust efficacy.

Other aspects of the invention relate to topical and transdermal mepivacaine pharmaceutical compositions and methods for the treatment of painful neuropathies that target both mepivacaine responsive aberrant peripheral and central mechanisms of the neuropathic pain, without significant untoward toxicity.

Previous treatments for peripheral neuropathic pain involving application of the dosage form to the skin have all been premised on a local effect in the skin. The applicant asserts that such local targeting may in part be why topical lidocaine patch has had suboptimal efficacy. Dosage forms for application to the skin need to target both peripheral nociceptor sensitization, as well as other heretofore dismissed mechanisms of neuropathic pain, including: (i) enhanced membrane excitability of primary afferents; (ii) enhanced synaptic transmission; (iii) central disinhibition (iv) descending facilitatory activity (descending facilitation); and (v) central reorganization. Consequently, and without being bound by theory, in some embodiments, the applicant's pharmaceutical compositions and methods target peripheral, systemic and central mechanisms of pain initiation, propagation, maintenance and integration which are responsive to "local" anesthetics.

Chronic Pain

Non-neuropathic chronic pain (or chronic non-neuropathic pain, commonly referred to as "chronic pain" in comparison with chronic neuropathic pain, commonly referred to as "neuropathic pain") is an even greater health problem that afflicts a significant number of patients, resulting in personal suffering, reduced productivity and substantial health care costs. Chronic pain includes back pain, rheumatoid arthritis, osteoarthritis, inflammatory pain, non-inflammatory pain, myofascial pain, fibromyalgia, cancer pain, visceral pain, somatic pain, pelvic pain, musculoskeletal pain and idiopathic pain.

There are differences between neuropathic and non-neuropathic pain. Neuropathic pain is defined as pain following injury to nerves or as a consequence of nerve dysfunction. In contrast, chronic pain can be caused by a variety infectious, genetic, physiologic, pathologic, mechanical and inflammatory factors and it involves many anatomic locations and tissue types. In many cases of chronic pain, the etiology of the chronic pain is unclear. The distinction between neuropathic and non-neuropathic pain reflects partially distinct mechanisms and patterns of treatment response.

Chronic non-neuropathic pain states are also associated with spinal and supraspinal changes which can initiate, maintain, propagate and integrate pain. For example, chronic back pain patients show less neocortical gray matter volume than control subjects. The magnitude of decrease is equivalent to the gray matter volume lost in 10-20 years of normal aging.

Osteoarthritis (OA) is a degenerative disease involving the synovial joints and is characterized by focal loss of cartilage, hypertrophic reaction at the margin of joints and sclerosis in the subchondral bone affecting an estimated 40 million people in the United States. It has been viewed as a pain limited to nociception from the affected joint and pharmacologic interventions have been targeted to maximizing local therapeutic concentrations in the affected joints while minimizing systemic concentrations in order to provide efficacy with reduced toxicity. However, this approach fails to exploit the non-local or central manifestations of the pain symptoms of OA.

There is a need therefore for new local anesthetic pharmaceutical compositions for application to the skin and methods for the treatment of chronic pain, including back pain, osteoarthritis and fibromylagia.

There is a need therefore for new local anesthetic pharmaceutical compositions for application to the skin and methods for the treatment of back pain and osteoarthritis that target both peripheral and central mechanisms of the pain.

There is a need for mepivacaine pharmaceutical compositions for application to the skin and methods for the treatment of chronic pain that target both mepivacaine responsive aberrant peripheral and central mechanisms of the neuropathic pain, without significant untoward toxicity.

In the case of chronic pain, the applicant asserts that in some embodiments, peripheral effects of local anesthetics play no role or a negligible role in modulating nociception and at the most account for only one of targets of the pain process. Other important mechanisms include: enhanced synaptic transmission, central disinhibition, descending facilitatory activity (descending facilitation); and central reorganization. Consequently, and without being bound by theory, the applicant's pharmaceutical compositions and methods target systemic and central mechanisms of pain initiation, propagation, maintenance and integration are important for efficient pain relief in some embodiments.

To the applicant's knowledge, with the possible exception of application by skin infiltration, there are no: (i) recommendations on mepivacaine application to the skin for the management of chronic pain; (ii) no public data on mepivacaine application to the skin for the management of chronic pain; (ii) no public data on mepivacaine application to the skin for the management of chronic pain; (iii) no third-party working prototypes or approved mepivacaine products for application to the skin for the management of chronic pain; and (iv) no mepivacaine products for application to the skin for the treatment of chronic pain in development, regulatory review or on the market any major market.

There is a need for new topical and transdermal therapies for the treatment of pain that provide robust efficacy, improved safety and tolerability, and that work through new and different mechanism from existing therapies.

There is a need for additional topical and transdermal therapies for pain that work through a spinal and supraspinal mechanism.

Neuropathy, neuropathic pain and chronic pain can sometimes require weeks months, years and even decades of therapy. Consequently, the safety of long-term therapy is of paramount importance. Since local anesthetics are sometimes applied to sites where peripheral nerves may be growing or regenerating after injury (e.g., after exposure to chemical injury, mechanical injury, or neurodegenerative disease), their effects on growing neurons are of clinical importance. Similarly, the effects of drugs including local anesthetics on growing or regenerating nerves after injury (e.g., after exposure to chemical injury, mechanical injury, or neurodegenerative disease) are of clinical importance, particularly in postsurgical and post-traumatic pain where nerve fibers are regenerating and creating new sprouts. Radwan et al., (Anesth Analg 2002; 94:319-24) have evaluated the effects of the local anesthetics lidocaine, bupivacaine, mepivacaine, and ropivacaine to produce morphological changes in growing neurons and demonstrated that the $IC_{50}$ in the growth cone collapse assay was highest for mepivacaine and lowest for lidocaine, demonstrating that lidocaine had a greater potential neurotoxic effect on the developing or regenerating primary cultured neurons. These data confirmed previous histopathologic, electrophysiologic, behavioral, and neuronal cell models, where lidocaine had a greater potential for neurotoxicity than bupivacaine (Baiton et al, Anesthesiology 1994; 81:657-67; Kanai et al., Anesth Analg 1998; 86:569-73; Lambert et al., Anesthesiology 1994; 80:1082-93). Additionally, in a previous histopathological study, Kanai et al. (Anesth Analg 2000; 91:944-48) demonstrated that 80 mM (2.17%) lidocaine induced neuronal damage in rat sciatic nerve.

There is a need for new local anesthetic pharmaceutical compositions for application to the skin and methods for the treatment of pain that have an optimal safety profile.

There is a need for local anesthetic pharmaceutical compositions for application to the skin and methods for the treatment of acute pain, neuropathy, neuropathic pain and chronic pain that have reduced potential for neurotoxicity than lidocaine.

The present invention relates to mepivacaine pharmaceutical compositions for application to the skin and methods for the treatment of pain. The invention also relates to topical and transdermal application to the skin which provide therapeutically effective mepivacaine concentrations to target both the aberrant central and/or peripheral mechanisms of pain. The invention further relates to topical and transdermal application to the skin to provides therapeutically effective mepivacaine concentrations to target both the aberrant central and/or peripheral mechanisms of pain.

In view of the foregoing presentation, it is immediately apparent that a serious need exists for an improvement in the delivery of topical mepivacaine for its therapeutic effect. The need exists to provide a novel therapeutic composition comprising topical mepivacaine, the need exists to provide a novel dosage form comprising topical mepivacaine, and the need exists to provide a novel method of administering mepivacaine to a patient in need of mepivacaine or local anesthetic therapy. The invention provides a topical, relatively easy mode and manner of mepivacaine administration.

DESCRIPTION OF THE INVENTION

Applicant has now surprisingly discovered that topical application of mepivacaine to the skin can provide robust penetration across the skin barrier.

Applicant has now also surprisingly demonstrated that topical application of mepivacaine to the skin can provide robust antinociceptive effects in neuropathic and non-neuropathic pain states.

The present invention is directed at pharmaceutical compositions of mepivacaine for application to the skin (from time to time referred to as "topical", "topical application", "transdermal", "transdermal application", each having the same meaning as "application to the skin" for any local and/or systemic effects) for therapeutic effect and methods for use thereof.

Initial trials conducted by the applicant demonstrated surprising analgesia with topical mepivacaine in validated models of peripheral neuropathic pain. However, the analgesic effect was shortlived and highly variable. Applicant has surprisingly discovered that when the dosage form of mepivacaine can be advantageously made to provide robust, longlived and consistent analgesia upon application to the skin.

In some embodiments, the invention contemplates topical mepivacaine administration to the skin at a higher flux rate than after topical administration of lidocaine to achieve comparable or superior efficacy.

In some embodiments, the invention contemplates topical mepivacaine administration to the skin with a shorter lag time than after topical administration lidocaine to achieve comparable or superior efficacy.

In some embodiments, the invention contemplates topical mepivacaine administration to the skin with greater skin retention than after topical administration lidocaine to achieve comparable or superior efficacy.

In some embodiments, the invention contemplates topical administration to the skin which provides therapeutically effective mepivacaine concentrations at the peripheral site of pain (the site of application).

In some embodiments, the invention contemplates topical administration to the skin which provides therapeutically effective mepivacaine concentrations at the peripheral site of nerve dysfunction.

In some embodiments, the invention contemplates topical administration to the skin which provides therapeutically effective mepivacaine concentrations at the systemic sites of pain and pain regulation.

In some embodiments, the invention contemplates topical administration to the skin which provides therapeutically effective mepivacaine concentrations at the systemic sites of nerve dysfunction.

In some embodiments, the invention contemplates topical administration to the skin which provides therapeutically effective mepivacaine concentrations at both the peripheral and systemic sites of pain and pain regulation.

In some embodiments, the invention contemplates topical administration to the skin which provides therapeutically effective mepivacaine concentrations at the peripheral and systemic sites of nerve dysfunction.

In some embodiments, the invention contemplates topical administration to the skin which provides therapeutically effective mepivacaine concentrations to target the aberrant peripheral mechanisms of pain.

In some embodiments, the invention contemplates topical administration to the skin which provides therapeutically effective mepivacaine concentrations to target both the aberrant peripheral and central mechanisms of pain.

In some embodiments, the invention contemplates topical administration to the skin which provides therapeutically effective mepivacaine concentrations to target both the aberrant peripheral and central mechanisms of pain, without significant local or systemic toxicity.

In some embodiments, the present invention is directed at methods to substantially improve the efficiency and quality of pain management.

It is an object of certain embodiments of the present invention to provide topical mepivacaine formulations for application to the skin which provide pain relief for up to about 1, 2, 4, 6, 8, 12, 16, 18 or 24 hours.

It is an object of certain embodiments of the present invention to provide topical mepivacaine formulations for application to the skin which provide pain relief for up to about 36, 48, or 72 hours.

It is an object of certain embodiments of the present invention to provide topical mepivacaine formulations for application to the skin which provide pain relief for up to about 1, 2, 3, or 4 weeks.

It is an object of certain embodiments of the invention to provide a topical mepivacaine formulation which provides a sustained duration of therapeutic effect. In some embodiments of the invention, a single topical administration provides pain relief for up to about 1, 2, 4, 6, 8, 12, 18, or 24 hours. In other embodiments, a single topical administration provides pain relief for up to about 2, 3, 4, 7, 14, 21, 28 days, or 30 days.

It is an object of certain embodiments of the invention to provide a topical mepivacaine formulation which provides an early onset and sustained duration of therapeutic effect.

It is an object of certain embodiments of the invention to provide a topical mepivacaine formulation suitable for application about every 4, 6, 8, 12, 18, 24, 48, or 72 hours.

It is an object of certain embodiments of the invention to provide a topical mepivacaine formulation suitable for application about every 1, 2, 3, or 4 weeks.

It is an object of certain embodiments of the present invention to provide topical mepivacaine formulations for application to the skin for a duration of up to about 4, 6, 8, 12, 18, 24, 48, or 72 hours.

It is an object of certain embodiments of the present invention to provide topical mepivacaine formulations for application to the skin for duration of up to about 1, 2, 3, or 4 weeks.

It is an object of certain embodiments of the present invention to provide topical mepivacaine formulations as a patch.

It is an object of certain embodiments of the present invention to provide topical mepivacaine formulations as a topical patch.

It is an object of certain embodiments of the present invention to provide topical mepivacaine formulations as transdermal patch.

It is an object of certain embodiments of the present invention to provide topical mepivacaine formulations as a patch which provides therapeutic effects through topical and transdermal delivery.

It is an object of certain embodiments of the present invention to provide topical mepivacaine formulations as a patch with local and systemic effects.

It is an object of certain embodiments of the present invention to provide mepivacaine formulations for application to the skin in the form of a patch, wherein the mepivacaine is dispersed within a matrix.

It is an object of certain embodiments of the present invention to provide mepivacaine formulations for application to the skin in the form of a patch wherein the mepivacaine is dispersed within an adhesive.

It is an object of certain embodiments of the present invention to provide mepivacaine formulations for application to the skin in the form of a patch, wherein the mepivacaine is contained within a reservoir.

It is an object of certain embodiments of the invention to provide a method and formulations of mepivacaine for application to the skin for the treatment of pain, said application at the site of the pain.

It is an object of certain embodiments of the invention to provide a method and formulations of mepivacaine for application to the skin for the treatment of pain, said application proximal to the site of the pain.

It is an object of certain embodiments of the invention to provide a method and formulations of mepivacaine for application to the skin for the treatment of pain, said application distal to the site of the pain.

It is an object of certain embodiments of the present invention to provide a topical mepivacaine formulation with therapeutic effects at the site of peripheral nervous system dysfunction or injury.

It is an object of certain embodiments of the present invention to provide topical mepivacaine formulations with therapeutic effects at the site of central nervous system dysfunction or injury.

It is an object of certain embodiments of the present invention to provide topical mepivacaine formulations with therapeutic effects directed at the sites of pain summation, pain amplification, pain integration and descending pain facilitation.

It is an object of certain embodiments of the present invention to provide topical mepivacaine formulations with peripheral and systemic effects.

It is an object of certain embodiments of the present invention to provide topical or transdermal mepivacaine formulations with therapeutic effects in the peripheral nervous system.

It is an object of certain embodiments of the present invention to provide topical or transdermal mepivacaine formulations with therapeutic effects in the central nervous system.

It is an object of certain embodiments of the present invention to provide topical or transdermal mepivacaine formulations as a patch with therapeutic effects in both the peripheral and central nervous system.

It is an object of certain embodiments of the present invention to provide topical or transdermal mepivacaine formulations as a topical patch with therapeutic effects at the site of peripheral nervous system dysfunction or injury.

It is an object of certain embodiments of the present invention to provide topical or transdermal mepivacaine formulations as transdermal patch with therapeutic effects at the site of central nervous system dysfunction or injury.

In some embodiments, the dosage of the invention provides therapeutic effects that persist despite the low or undectable mepivacaine concentrations It is an object of certain embodiments of the invention to provide a method and formulations of mepivacaine for application to the skin for the treatment of acute pain, neuropathy, neuropathic pain and chronic pain.

It is an object of certain embodiments of the invention to provide a method and formulations of mepivacaine for application to the skin for the treatment of pain by targeting the central nervous system mechanism of pain and symptom initiation, propagation, summation, maintenance and integration.

It is an object of certain embodiments of the invention to provide a method and formulations of mepivacaine for application to the skin for the treatment of pain by targeting the peripheral and central nervous system mechanisms of neuropathy.

It is an object of certain embodiments of the invention to provide a method and formulations of mepivacaine for application to the skin to provide relief from pain by targeting what the applicant characterizes as peripheral and central "nocistatic" controls.

It is an object of certain embodiments of the invention to provide a method and formulations of mepivacaine for application to the skin to provide relief from pain by readjusting the "setpoint" for pain perception.

It is an object of certain embodiments of the invention to provide a method and formulations of mepivacaine for application to the skin for the treatment of pain, said formulations and methods not having: (i) a propensity of substantial drug accumulation, (ii) a propensity of cardiac toxicity, (iii) a propensity of CNS toxicity, or (iv) a propensity of clinically significant cardiac dysrhythmias.

Some or all of the above objects and others are achieved by embodiments of the present invention, which is directed in part to a dosage form of mepivacaine for application to the skin for local effects.

Some or all of the above objects and others are achieved by embodiments of the present invention, which is directed in part to a dosage form of mepivacaine for application to the skin for systemic effects.

Some or all of the above objects and others are achieved by embodiments of the present invention, which is directed in part to a dosage form of mepivacaine for application to the skin for local and systemic effects.

In some preferred embodiments, the invention comprises a pharmaceutical composition for application to the skin comprising a therapeutically effective amount of mepivacaine or a pharmaceutically acceptable salt of mepivacaine in racemic or enantiomeric form or a mixture thereof for the treatment of neuropathy, acute pain, peripheral neuropathic pain, central neuropathic pain, chronic pain, idiopathic pain, regardless of the mechanisms, anatomic location and etiology.

It is an object of certain embodiments of the invention to provide a method and formulations of mepivacaine for application to the skin for the treatment of pain, said formulations and methods not having a propensity for: (i) substantial peak to trough fluctuation, (ii) peripheral toxicity, or (iii) systemic toxicity.

It is an object of certain embodiments of the present invention to provide mepivacaine formulations for application to the skin in the form of a patch, wherein the mepivacaine is contained within a reservoir, said reservoir having a membrane layer on the side of the patch proximal to the skin.

It is an object of certain embodiments of the present invention to provide mepivacaine formulations for application to the skin in the form of a patch, wherein the mepivacaine is contained within a reservoir, said reservoir having a membrane layer on the side of the patch proximal to the skin, said membrane layer being substantially permeable to mepivacaine.

It is an object of certain embodiments of the present invention to provide mepivacaine formulations for application to the skin in the form of a patch, wherein the mepivacaine is contained within a reservoir, said reservoir having a membrane layer on the side of the patch proximal to the skin, said membrane layer being substantially permeable to mepivacaine, said membrane layer providing for a controlled release of mepivacaine.

It is an object of certain embodiments of the present invention to provide mepivacaine formulations for application to the skin in the form of a plaster.

It is an object of certain embodiments of the present invention to provide mepivacaine formulations for application to the skin in the form a gel or emulgel.

It is an object of certain embodiments of the present invention to provide mepivacaine formulations for application to the skin in the form a cream.

It is an object of certain embodiments of the present invention to provide mepivacaine formulations for application to the skin in the form an ointment.

It is an object of certain embodiments of the present invention to provide mepivacaine formulations for application to the skin in liposomes.

It is an object of certain embodiments of the present invention to provide mepivacaine formulations for application to the skin in the form a solution.

It is an object of certain embodiments of the present invention to provide mepivacaine formulations for application to the skin in the form of foam.

It is an object of certain embodiments of the present invention to provide mepivacaine formulations for application to the skin in the form a suspension.

It is an object of certain embodiments of the present invention to provide mepivacaine formulations for application to the skin in the form a lotion.

It is an object of certain embodiments of the present invention to provide mepivacaine formulations for application to the skin in the form a hydrogel matrix.

It is an object of certain embodiments of the present invention to provide mepivacaine formulations for application to the skin for aerosolized delivery.

It is an object of certain embodiments of the present invention to provide mepivacaine formulations for application to the skin, wherein said mepivacaine is in a sprayable pharmaceutical formulation.

It is an object of certain embodiments of the present invention to provide mepivacaine formulations for application to the skin, wherein said mepivacaine is in a sprayable pharmaceutical formulation capable of forming a thin barrier film on topical administration.

It is an object of certain embodiments of the present invention to provide mepivacaine formulations for application to the skin, wherein said mepivacaine is in a sprayable pharmaceutical formulation capable of forming a thin barrier film on topical administration.

It is an object of certain embodiments of the present invention to provide mepivacaine formulations for application to the skin, wherein said mepivacaine is in a sprayable pharmaceutical formulation capable of forming a thin film on topical administration, said film being substantially water washable, partially water washable, or resistant to removal with water.

Some or all of the above objects and others are achieved by embodiments of the present invention, which is directed in part to a dosage form of mepivacaine for application to the skin.

The invention is also directed to kits of the dosage forms disclosed herein.

In additional aspects, the dosage form of the invention comprises mepivacaine in reservoir comprising one or more polymeric matrix and optionally one or more permeation enhancers for the mepivacaine.

In some preferred embodiments of the invention, the semisolid (e.g., gel, cream, lotion, ointment, etc) and patch (e.g., drug-in-adhesive) dosage forms of mepivacaine for application to the skin drug have a pH of about 5 to about 9, or about 5.5 to about 8.5, or about 5.8 to about 8.5, or about 6 to about 8.5, or about 6.2 to about 8.5.

In some more preferred embodiments of the invention, the semisolid (e.g., gel, cream, lotion, ointment, etc) and patch (e.g., drug-in-adhesive) dosage forms of mepivacaine for application to the skin drug have a pH of about 6.3 to about 8.3, or about 6.5 to about 8.2, or about 6.5 to about 8.0.

In some especially preferred embodiments of the invention, the semisolid (e.g., gel, cream, lotion, ointment, etc) and patch (e.g., drug-in-adhesive) dosage forms of mepivacaine for application to the skin drug have a pH of about 6.6 to about 8 or about 6.7 to about 7.8, or about 6.8 to about 7.5, or about 6.8 to about 7.2, or about 7 to about 7.5.

In some preferred embodiments, the delivery of the mepivacaine from the topical dosage form can be assisted by application of an occlusive or non-occlusive material which is applied over the patch or gel dosage form, said occlusive material with or without an adhesive.

In some preferred embodiments, the mepivacaine dosage form is a patch. The patch may be of any shape, for example round, square or rectangular.

In some preferred embodiments, the delivery of the mepivacaine from a patch dosage form can be assisted by application of an adhesive material (bandage, patch, etc) over the patch dosage form.

In some preferred embodiments, the delivery of the mepivacaine from a patch dosage form can be assisted by inclusion in a portion of the patch dosage form of layer which has greater or substantially greater skin adhesion than the remainder of the patch. In some preferred embodiments, the portion of the patch dosage form with greater or substantially greater skin adhesion is along a portion or all of the border or perimeter of the patch. In some preferred embodiments, the portion of the patch dosage form with greater or substantially greater skin adhesion is devoid of or substantially devoid of mepivacaine. In some other preferred embodiments, the portion of the patch dosage form with greater or substantially greater skin adhesion contains some, a substantial amount or about the same amount of mepivacaine as the rest of the skin exposed area, but has greater skin adhesion that the remained of the patch.

In some preferred embodiments, the inclusion in the dosage form of portion with greater or substantially greater skin adhesion provides for: (i) improved retention of the patch at rest; (ii) improved retention of the patch with physical activity; (iii) improved retention of the patch with exercise and sweating; (iv) improved retention of the patch upon brief or sustained exposure to water; and/or (v) improved retention of the patch during sleep. In some preferred embodiments, the skin retention failure rate (i.e., failure to fully or substantially retain the dosage form on the skin) is at least 10%, 20%, 30%, 40%, 50%, 70%, 100%, 120%, 150%, 180%, 200%, 230%, 250%, 280%, 300%, 350% or 400% less than with Lidoderm™ patch. In some preferred embodiments, the skin retention failure rate (i.e., failure to fully or substantially retain the dosage form on the skin) is at least 10%, 20%, 30%, 40%, 50%, 70%, 100%, 120%, 150%, 180%, 200%, 230%, 250%, 280%, 300%, 350% or 400% less than with the same patch devoid of a portion with greater or substantially greater skin adhesion.

In some preferred embodiments, the inclusion in the dosage form of portion with greater or substantially greater skin adhesion provides for: (i) improved skin hydration; (ii) improved skin permeability; (iii) improved systemic blood levels (AUC); (iv) improved skin tissue levels; (v) more rapid onset of effect; (vi) a shorter time to Cmax; (vii) a higher Cmax; and/or (viii) improved efficacy. In some preferred embodiments, said improvement is at least 10%, 20%, 30%, 40%, 50%, 70%, 100%, 120%, 150%, 180%, 200%, 230%, 250%, 280%, or 300% greater than with Lidoderm™ patch. In some preferred embodiments, said improvement is at least 10%, 20%, 30%, 40%, 50%, 70%, 100%, 120%, 150%, 180%, 200%, 230%, 250%, 280%, or 300% greater than with the same patch devoid of a portion with greater or substantially greater skin adhesion.

In some preferred embodiments, the surface area of the patch dosage form with greater or substantially greater skin adhesion than the remainder of the patch is less than about 1%, or less than about 2%, or less than about 3%, or less than about 4%, or less than about 5%, or less than about 6%, or less than about 7%, or less than about 8%, or less than about 9%, or less than about 10%, or less than about 12%, or less than about 15%, or less than about 17%, or less than about 20%, or less than about 25%, or less than about 35% of the total surface area of the patch in contact with the skin.

In another aspect, the dosage form of the invention comprises mepivacaine in reservoir comprising an aqueous gel, a permeation enhancer for the mepivacaine, and a gelling agent.

In another embodiment, the dosage form of the invention comprises mepivacaine in reservoir or matrix and further comprises a mepivacaine release rate controlling means; said mepivacaine release rate controlling means releasing the mepivacaine upon securing the dosage form to a human patient for a period of up to about 6 hours. In other embodiments, the dosage form is secured for a period of up to about 8, 12, 18 or 24 hours or up to about 1, 2, 3, 7, 14, 21 or 30 days.

In some preferred embodiments, the dosage from provides a topical pharmaceutical composition comprising a therapeutically effective amount of mepivacaine; said dosage form providing a therapeutic effect longer than would be expected based on the prevailing plasma concentrations. In some preferred embodiments of the invention, the dosage form provides persistent therapeutic effects despite short lived, low or negligible prevailing plasma concentrations.

In some preferred embodiments of the invention, the dosage form provides sustained therapeutic effects of up to about 0.1, 0.2, 0.3, 0.5, 1, 2, or about 3, or about 7, or about 14 or about 21 or about 30 days despite being administered as a single application to the skin.

In some preferred embodiments of the invention, the dosage form provides sustained therapeutic effects that are about up to 800 times the terminal elimination half-life of the mepivacaine, administered as the base or a pharmaceutically acceptable salt in racemic or enantiomeric form, or a mixture thereof. In other embodiments the dosage form for application to the skin provides therapeutic effects that are up to about 2, or about 4, or about 6, or about 8, or about 10, or about 12, or about 15, or about 18, or about 20, or about 24, or about 30, or about 40, or about 50, or about 80, or about 100, or about 120, or about 160, or about 200, or about 300, or about 400, or about 600, or about 700 or up to about 800 times the terminal elimination half-life of the mepivacaine.

In some preferred embodiments of the invention, the dosage form provides sustained therapeutic effects up to about 1.5, 2, 3, 4, 5, 6, 8, 10, 12, 15, 20, 25, 30, 40, or 60 times longer than the duration of application to the skin. In some preferred embodiments of the invention, the dosage form provides sustained therapeutic effects up 2, 3, 4, 7, 14, 21, or 30 days after a single application to the skin lasting up to 24 hours. In some preferred embodiments, the topical dosage from provides a pharmaceutical composition comprising a therapeutically effective amount of mepivacaine or a pharmaceutically acceptable salt of mepivacaine in racemic or enantiomeric form, or a mixture thereof.

In some preferred embodiments, the topical dosage from provides a pharmaceutical composition comprising a therapeutically effective amount of mepivacaine; said dosage form providing therapeutic effects for up to about 720 hours after a single application to the skin. In other preferred embodiments, the dosage from provides. In other preferred embodiments, the dosage form provides up to about 504 hours, or up to about 336 hour, or up to about 168 hours, or up to about 140 hours, or up to about 120 hours, or up to about 96 hours, or up to about 72 hours, or up to about 48 hours, or up to about 24 hours, or up to about 18 hours, or up to about 12 hours, or up to about 8 hours, or up to about 6 hours, or up to about 4 hours of therapeutic effect after a single application to the skin.

In some preferred embodiments, the topical dosage from provides a pharmaceutical composition comprising a therapeutically effective amount of mepivacaine; said dosage form providing long lasting therapeutic effects for up to about 720 hours after a single short-term application to the skin; said short-term application lasting for not more than about 80% of the duration of therapeutic effect. In other preferred embodiments, said short-term application lasts for not more than about 75%, or about 60% or about 50%, or about 40%, or about 30%, or about 25%, or about 20%, or about 15%, or about 10%, or about 7.5%, or about 5%, or about 2.5%, or about 1% of the duration of therapeutic effect.

In some preferred embodiments, the topical dosage from provides a pharmaceutical composition comprising a therapeutically effective amount of mepivacaine; said dosage form suitable for up to about 168 hours of administration to a human patient. In other preferred embodiments, the dosage form is suitable for up to about 144 hours, or up to about 120 hours, or up to about 96 hours, or up to about 72 hours, or up to about 48 hours, or up to about 24 hours, or up to about 18 hours, or up to about 12 hours, or up to about 8 hours, or up to about 6 hours, or up to about 4 hours of application to the skin.

In some preferred embodiments, the topical dosage from provides a pharmaceutical composition comprising a therapeutically effective amount of mepivacaine; said dosage form providing a mean flux which is at least 10%, 20%, 30%, 40%, 50%, 70%, 100%, 120%, 150%, 180%, 200%, 230%, 250%, 280%, 300%, 350%, 400%, 450%, 500%, 600%, 700%, 800%, 900% or 1000% greater than the mean flux from Lidoderm™ patch.

In some preferred embodiments, the topical dosage from provides a pharmaceutical composition comprising a therapeutically effective amount of mepivacaine; said dosage form providing a mean absorption lag time to which is at least 10%, 20%, 30%, 40%, 50%, 70%, 100%, 120%, 150%, 180%, 200%, 230%, 250%, 280%, 300%, 350%, 400%, 450%, or 500% shorter than the mean lag time from Lidoderm™ patch.

In some preferred embodiments, the topical dosage from provides a pharmaceutical composition comprising a therapeutically effective amount of mepivacaine; said dosage form providing a skin retention which is at least 10%, 20%, 30%, 40%, 50%, 70%, 100%, 120%, 150%, 180%, 200%, 230%, 250%, 280%, 300%, 350%, 400%, 450%, or 500% greater than the skin retention from Lidoderm™ patch.

In some preferred embodiments, the topical dosage from provides a pharmaceutical composition comprising a therapeutically effective amount of mepivacaine in a patch; said dosage form providing the percent of drug released from the patch which is at least 10%, 20%, 30%, 40%, 50%, 70%, 100%, 120%, 150%, 180%, 200%, 230%, 250%, 280%, 300%, 350%, 400%, 450%, or 500% greater than amount released from the Lidoderm™ patch.

In some preferred embodiments, the topical dosage from provides a pharmaceutical composition comprising a therapeutically effective amount of mepivacaine in a patch; said dosage form providing a percent loading of drug per $cm^2$ of patch which is at least 10%, 20%, 30%, 40%, 50%, 70%, 100%, 120%, 150%, 180%, 200%, 230%, 250%, 280%, 300%, 350%, 400%, 450%, 500%, 600%, 700%, 800%, 900% or 1000% less than the percent loading per $cm^2$ of Lidoderm™ patch; said dosage form providing therapeutic efficacy comparable to the Lidoderm™ patch.

In some preferred embodiments, the topical dosage from provides a pharmaceutical composition comprising a therapeutically effective amount of mepivacaine in a patch; said dosage form providing a coefficient of variation for the amount released from the patch (measured as the amount in the patch to application minus the amount remaining in the patch at the end of the dosing interval, expressed as a percentage) which is at least 10%, 20%, 30%, 40%, 50%, 70%, 100%, 120%, 150%, 180%, 200%, 230%, 250%, 280%, 300%, 350%, 400%, 450%, or 500% less than for the Lidoderm™ patch.

In some preferred embodiments, the topical dosage from provides a pharmaceutical composition comprising a therapeutically effective amount of mepivacaine; said dosage form providing a mean mepivacaine flux of not less than about 0.09 $mg/cm^2/hr$, or not less than about 0.08 $mg/cm^2/hr$, or not less than about 0.07 $mg/cm^2/hr$, or not less than about 0.06 $mg/cm^2/hr$, or not less than about 0.05 $mg/cm^2/hr$, or not' less than about 0.04 $mg/cm^2/hr$, or not less than about 0.03 $mg/cm^2/hr$, or not less than about 0.02 $mg/cm^2/hr$, or not less than about 0.01 $mg/cm^2/hr$, or not less than about 0.009 $mg/cm^2/hr$, or not less than about 0.008 $mg/cm^2/hr$, or not less than about 0.007 $mg/cm^2/hr$, or not less than about 0.006 $mg/cm^2/hr$, or not less than about 0.005 $mg/cm^2/hr$, or not less than about 0.004 $mg/cm^2/hr$, or not less than about 0.003 $mg/cm^2/hr$, or not less than about 0.002 $mg/cm^2/hr$.

In some more preferred embodiments, the topical dosage from provides a pharmaceutical composition comprising a therapeutically effective amount of mepivacaine; said dosage form providing a mean mepivacaine flux of not less than about 5 $mg/cm^2/hr$, or not less than about 4 $mg/cm^2/hr$, or not less than about 3.5 $mg/cm^2/hr$, or not less than about 3 $mg/cm^2/hr$, or not less than about 2.75 $mg/cm^2/hr$, or not less than about 2.5 $mg/cm^2/hr$, or not less than about 2.25 $mg/cm^2/hr$, or not less than about 2 $mg/cm^2/hr$, or not less than about 1.75 $mg/cm^2/hr$, or not less than about 1.5 $mg/cm^2/hr$, or not less than about 1.4 $mg/cm^2/hr$, or not less than about 1.3 $mg/cm^2/hr$, or not less than about 1.2 $mg/cm^2/hr$, or not less than about 1.1 $mg/cm^2/hr$, or not less than about 1 $mg/cm^2/hr$, or not less than about 0.9 $mg/cm^2/hr$, or not less than about 0.8 $mg/cm^2/hr$, or not less than about 0.7 $mg/cm^2/hr$, or not less than about 0.6 $mg/cm^2/hr$, or not less than about 0.55 $mg/cm^2/hr$, or not less than about 0.5 $mg/cm^2/hr$, or not less than about 0.45 $mg/cm^2/hr$, or not less than about 0.4 $mg/cm^2/hr$, or not less than about 0.35 $mg/cm^2/hr$, or not less than about 0.3 $mg/cm^2/hr$, or not less than about 0.25 $mg/cm^2/hr$, or not less than about 0.2 $mg/cm^2/hr$, or not less than about 0.18 $mg/cm^2/hr$, or not less than about 0.17 $mg/cm^2/hr$, or not less than about 0.15 $mg/cm^2/hr$, or not less than about 0.14 $mg/cm^2/hr$, or not less than about 0.13 $mg/cm^2/hr$, or not less than about 0.12 $mg/cm^2/hr$, or not less than about 0.11 $mg/cm^2/hr$, or not less than about 0.1 $mg/cm^2/hr$.

In some preferred embodiments, the topical dosage from provides a pharmaceutical composition comprising a therapeutically effective amount of mepivacaine; said dosage form providing a mean absorption or permeation lag time of less than about 1.7 hr, or less than about 1.6 hr, or less than about 1.5 hr.

In some more preferred embodiments, the topical dosage from provides a pharmaceutical composition comprising a therapeutically effective amount of mepivacaine; said dosage form providing a mean absorption or permeation lag time of less than about 1.4 hr, or less than about 1.4 hr, or less than about 1.2 hr, or less than about 1.1 hr, or less than about 1 hr, or less than about 0.9 hr, or less than about 0.8 hr, or less than about 0.7 hr, or less than about 0.6 hr, or less than about 0.5 hr, or less than about 0.4 hr, or less than about 0.35 hr, or less than about 0.3 hr, or less than about 0.25 hr, or less than about 0.2 hr.

In some preferred embodiments, the topical dosage from provides a pharmaceutical composition comprising a therapeutically effective amount of mepivacaine in a patch; said dosage form providing a mean mepivacaine release from the patch (measured as the amount in the patch prior to application minus the amount remaining in the patch at the end of the dosing interval divided by the amount in the patch prior to application, expressed as a percentage) greater than about 4%, or greater than about 5%, or greater than about 6%, or greater than about 7%, or greater than about 8%.

In some preferred embodiments, the topical dosage from provides a pharmaceutical composition comprising a therapeutically effective amount of mepivacaine in a patch; said dosage form providing a mean mepivacaine release from the patch (measured as the amount of mepivacaine in the patch prior to application minus the amount of mepivacaine remaining in the patch 12 hours after first application to the skin, expressed as a percentage) greater than about 4%, or greater than about 5%, or greater than about 6%, or greater than about 7%, or greater than about 8%.

In some more preferred embodiments, the topical dosage from provides a pharmaceutical composition comprising a therapeutically effective amount of mepivacaine in a patch; said dosage form providing a mean mepivacaine release from the patch (measured as the amount of mepivacaine in the patch prior to application minus the amount of mepivacaine remaining in the patch at the end of the dosing interval divided by the amount in the patch prior to application, expressed as a percentage) greater than about 9%, or greater than about 10%, or greater than about 12%, or greater than about 14%, or greater than about 15%, or greater than about 16%, or greater than about 18%, or greater than about 20%, or greater than about 22%, or greater than about 25%, or greater than about 30%, or greater than about 35%, or greater than about 40%, or greater than about 45%, or greater than about 50%, or greater than about 55%, or greater than about 60%, or greater than about 65%, or greater than about 70%, or greater than about 75%.

In some more preferred embodiments, the topical dosage from provides a pharmaceutical composition comprising a therapeutically effective amount of mepivacaine in a patch; said dosage form providing a mean mepivacaine release from the patch (measured as the amount of mepivacaine in the patch prior to application minus the amount of mepivacaine remaining in the patch 12 hours after first application to the skin, expressed as a percentage) greater than about 9%, or greater than about 10%, or greater than about 12%, or greater than about 14%, or greater than about 15%, or greater than about 16%, or greater than about 18%, or greater than about 20%, or greater than about 22%, or greater than about 25%, or greater than about 30%, or greater than about 35%, or greater than about 40%, or greater than about 45%, or greater than about 50%, or greater than about 55%, or greater than about 60%, or greater than about 65%, or greater than about 70%, or greater than about 75%.

In some preferred embodiments, the topical dosage from provides a pharmaceutical composition comprising a therapeutically effective amount of mepivacaine in a patch; said dosage form providing a coefficient of variation for the amount released from the patch (measured as the amount in the patch to application minus the amount remaining in the patch at the end of the dosing interval, expressed as a percentage) which is less than about 170%, or less than about 150%, or less than about 130%, or less than about 120%, or less than about 110%, or less than about 100%, or less than about 90%, or less than about 85%; said amount released measured 6 hours after single application to human skin in vivo.

In some more preferred embodiments, the topical dosage from provides a pharmaceutical composition comprising a therapeutically effective amount of mepivacaine in a patch; said dosage form providing a coefficient of variation for the amount released from the patch (measured as the amount in the patch to application minus the amount remaining in the patch at the end of the dosing interval, expressed as a percentage) which is less than about 80%, or less than about 75%, or less than about 70%, or less than about 65%, or less than about 60%, or less than about 55%, or less than about 50%, or less than about 85%; said amount released measured 6 hours after single application to human skin in vivo.

In some preferred embodiments, the topical dosage from provides a pharmaceutical composition comprising a therapeutically effective amount of mepivacaine in a patch; said dosage form providing a coefficient of variation for the amount released from the patch (measured as the amount in the patch to application minus the amount remaining in the patch at the end of the dosing interval, expressed as a percentage) which is less than about 230%, or less than about 200%, or less than about 180%, or less than about 160%, or less than about 130%, or less than about 110%, or less than about 100%; said amount released measured 12 hours after single application to human skin in vivo.

In some more preferred embodiments, the topical dosage from provides a pharmaceutical composition comprising a therapeutically effective amount of mepivacaine in a patch; said dosage form providing a coefficient of variation for the amount released from the patch (measured as the amount in the patch to application minus the amount remaining in the patch at the end of the dosing interval, expressed as a percentage) which is less than about 95%, or less than about 90%, or less than about 85%, or less than about 80%, or less than about 75%, or less than about 70%, or less than about 65%, or less than about 60%; said amount released measured 12 hours after single application to human skin in vivo.

In some preferred embodiments, the topical dosage from provides a pharmaceutical composition comprising a therapeutically effective amount of mepivacaine in a patch; said dosage form providing a coefficient of variation for the amount released from the patch (measured as the amount in the patch to application minus the amount remaining in the patch at the end of the dosing interval, expressed as a percentage) which is less than about 75%, or less than about 70%, or less than about 65%, or less than about 60%; said amount released measured 24 hours after single application to human skin in vivo.

In some more preferred embodiments, the topical dosage from provides a pharmaceutical composition comprising a therapeutically effective amount of mepivacaine in a patch;

said dosage form providing a coefficient of variation for the amount released from the patch (measured as the amount in the patch to application minus the amount remaining in the patch at the end of the dosing interval, expressed as a percentage) which is less than about 58%, or less than about 55%, or less than about 53%, or less than about 51%, or less than about 50%, or less than about 48%, or less than about 45%, or less than about 42%, or less than about 40%, or less than about 38%, or less than about 36%, or less than about 35%, or less than about 30%; said amount released measured 24 hours after single application to human skin in vivo.

In some preferred embodiments, the topical dosage from provides a pharmaceutical composition comprising a therapeutically effective amount of mepivacaine in a patch; said dosage form providing a percent loading per cm² of patch (expressed as amount of mepivacaine base) of less than about 4.7 mg, or less than about 4.5 mg, or less than about 4.4 mg, or less than about 4.3 mg, or less than about 4.2 mg, or less than about 4.1 mg.

In some more preferred embodiments, the topical dosage from provides a pharmaceutical composition comprising a therapeutically effective amount of mepivacaine in a patch; said dosage form providing a percent loading per cm² of patch (expressed as amount of mepivacaine base) is less than about 4 mg, or less than about 3.9 mg, or less than about 3.8 mg, or less than about 3.7 mg, or less than about 3.6 mg, or less than about 3.5 mg, or less than about 3.4 mg, or less than about 3.3 mg, or less than about 3.2 mg, or less than about 3.1 mg, or less than about 3 mg, or less than about 2.8 mg, or less than about 2.5 mg, or less than about 2.2 mg, or less than about 2 mg, or less than about 2.5 mg, or less than about 2.2 mg, or less than about 2 mg.

In some preferred embodiments, the topical dosage from provides a pharmaceutical composition comprising a therapeutically effective amount of mepivacaine; said dosage from providing a $C_{max}$ of mepivacaine from about 5 ng/mL to about 6000 ng/mL. In other preferred embodiments, the dosage from provides a $C_{max}$ about 15 ng/mL to about 6000 ng/mL, or about 25 ng/mL to about 6000 ng/mL, or about 50 ng/mL to about 6000 ng/mL, or about 100 ng/mL to about 6000 ng/mL, or about 250 ng/mL to about 6000 ng/mL, or about 500 ng/mL to about 6000 ng/mL, or about 1000 ng/mL to about 6000 ng/mL, or about 1500 ng/mL to about 6000 ng/mL, or about 2000 ng/mL to about 6000 ng/mL, or about 3000 ng/mL to about 6000 ng/mL, or about 4000 ng/mL to about 6000 ng/mL, or about 5 ng/mL to about 5000 ng/mL, or about 5 ng/mL to about 4000 ng/mL, or about 5 ng/mL to about 3500 ng/mL, or about 5 ng/mL to about 3000 ng/mL, or about 5 ng/mL to about 3000 ng/mL, or about 5 ng/mL to about 2000 ng/mL, or about 5 ng/mL to about 1500 ng/mL, or about 5 ng/mL to about 1000 ng/mL, or about 5 ng/mL to about 750 ng/mL, or about 5 ng/mL to about 500 ng/mL, or about 5 ng/mL to about 400 ng/mL, or about 5 ng/mL to about 300 ng/mL, or about 50 ng/mL to about 2000 ng/mL, or about 50 ng/mL to about 1500 ng/mL, or about 50 ng/mL to about 1000 ng/mL, or about 100 ng/mL to about 1000 ng/mL, or about 100 ng/mL to about 800 ng/mL.

In some preferred embodiments, the topical dosage from provides a pharmaceutical composition comprising a therapeutically effective amount of mepivacaine; a controlled release material to render said dosage form suitable for up to one week of administration to a human patient; said dosage from providing a $C_{max}$ of mepivacaine from about 5 ng/mL to about 6000 ng/mL. In other preferred embodiments, the dosage from provides a $C_{max}$ about 15 ng/mL to about 6000 ng/mL, or about 15 ng/mL to about 6000 ng/mL, or about 25 ng/mL to about 6000 ng/mL, or about 50 ng/mL to about 6000 ng/mL, or about 100 ng/mL to about 6000 ng/mL, or about 250 ng/mL to about 6000 ng/mL, or about 500 ng/mL to about 6000 ng/mL, or about 1000 ng/mL to about 6000 ng/mL, or about 1500 ng/mL to about 6000 ng/mL, or about 2000 ng/mL to about 6000 ng/mL, or about 3000 ng/mL to about 6000 ng/mL, or about 4000 ng/mL to about 6000 ng/mL, or about 5 ng/mL to about 5000 ng/mL, or about 5 ng/mL to about 4000 ng/mL, or about 5 ng/mL to about 3500 ng/mL, or about 5 ng/mL to about 3000 ng/mL, or about 5 ng/mL to about 3000 ng/mL, or about 5 ng/mL to about 2000 ng/mL, or about 5 ng/mL to about 1500 ng/mL, or about 5 ng/mL to about 1000 ng/mL, or about 5 ng/mL to about 750 ng/mL, or about 5 ng/mL to about 500 ng/mL, or about 5 ng/mL to about 400 ng/mL, or about 5 ng/mL to about 300 ng/mL, or about 50 ng/mL to about 2000 ng/mL, or about 50 ng/mL to about 1500 ng/mL, or about 50 ng/mL to about 1000 ng/mL, or about 100 ng/mL to about 1000 ng/mL, or about 100 ng/mL to about 800 ng/mL.

In some preferred embodiments, the topical dosage from provides a pharmaceutical composition comprising a therapeutically effective amount of mepivacaine; said dosage from providing a $C_{max}$ of mepivacaine from about 5 ng/mL to about 6000 ng/mL; said $C_{max}$ occurring from a mean of about 1 to about 168 hours. In other preferred embodiments, the dosage from provides a $C_{max}$ of mepivacaine occurring from a mean of about 1 to about 160 hours, or about 1 to about 144 hours, or about 1 to about 120 hours, or about 1 to about 96 hours, or about 1 to about 72 hours, or about 1 to about 48 hours, or about 1 to about 20 hours, or about 1 to about 18 hours, or about 1 to about 16 hours, or about 1 to about 12 hours, or about 1 to about 10 hours, or about 1 to about 8 hours, or about 1 to about 6 hours, or about 1 to about 4 hours.

In some preferred embodiments, the topical dosage from provides a pharmaceutical composition comprising a therapeutically effective amount of mepivacaine; a controlled release material to render said dosage form suitable for up to one week of administration to a human patient; said dosage from providing a $C_{max}$ of mepivacaine from about 5 ng/mL to about 6000 ng/mL; said $C_{max}$ occurring from a mean of about 6 to about 168 hours. In other preferred embodiments, the dosage from provides a $C_{max}$ of mepivacaine occurring from a mean of about 1 to about 160 hours, or about 1 to about 144 hours, or about 1 to about 120 hours, or about 1 to about 96 hours, or about 1 to about 72 hours, or about 1 to about 48 hours, or about 1 to about 20 hours, or about 1 to about 18 hours, or about 1 to about 16 hours, or about 1 to about 12 hours, or about 1 to about 10 hours, or about 1 to about 8 hours, or about 1 to about 6 hours, or about 1 to about 4 hours.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage from providing a $C_{max}$ of mepivacaine of up to 6000 ng/mL; said $C_{max}$ occurring from a mean of about 1 to about 168 hours.

In some preferred embodiments, the dosage form provides a pharmaceutical composition for application to the skin for the treatment of pain comprising a therapeutically effective amount of mepivacaine; said dosage from providing a $C_{min}$ of mepivacaine from about 1 ng/mL to about 3000 ng/mL. In other preferred embodiments, the dosage from provides a $C_{min}$ of less than about 2500 ng/mL, or less than about 2000 ng/mL, or less than about 1500 ng/mL, or of less than about 1250 ng/mL, or of less than about 1000 ng/mL, or of less than about 750 ng/mL, or less than about 500 ng/mL, or less than about 400 ng/mL, or of less than about 300 ng/mL, or of less than about 200 ng/mL, or of less than about 100 ng/mL, or less than about 75 ng/mL, or less than about 50 ng/mL, or of less than about 25 ng/mL, or of less than about 15 ng/mL, or of less than about 5 ng/mL.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage from providing a $C_{min}$ of mepivacaine from about 1 ng/mL to about 3000 ng/mL. In other preferred embodiments, the dosage from provides a $C_{min}$ of less than about 2500 ng/mL, or less than about 2000 ng/mL, or less than about 1500 ng/mL, or of less than about 1250 ng/mL, or of less than about 1000 ng/mL, or of less than about 750 ng/mL, or less than about 500 ng/mL, or less than about 400 ng/mL, or of less than about 300 ng/mL, or of less than about 200 ng/mL, or of less than about 100 ng/mL, or less than about 75 ng/mL, or less than about 50 ng/mL, or of less than about 25 ng/mL, or of less than about 15 ng/mL, or of less than about 5 ng/mL.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage from providing a $C_{min}$ of mepivacaine from about 1 ng/mL to about 3000 ng/mL; said $C_{min}$, measured from a mean of about 2 to about 168 hours. In other preferred embodiments, the dosage from provides a $C_{min}$ of less than about 2500 ng/mL, or less than about 2000 ng/mL, or less than about 1500 ng/mL, or of less than about 1250 ng/mL, or of less than about 1000 ng/mL, or of less than about 750 ng/mL, or less than about 500 ng/mL, or less than about 400 ng/mL, or of less than about 300 ng/mL, or of less than about 200 ng/mL, or of less than about 100 ng/mL, or less than about 75 ng/mL, or less than about 50 ng/mL, or of less than about 25 ng/mL, or of less than about 15 ng/mL, or of less than about 5 ng/mL.

In some preferred embodiments, the dosage form provides a pharmaceutical composition for application to the skin for the treatment of pain comprising a therapeutically effective amount of mepivacaine; said dosage from providing a of mepivacaine of up to 3000 ng/mL; said $C_{min}$ measured from a mean of about 2 to about 168 hours. In other preferred embodiments, the dosage from provides a $C_{min}$ of mepivacaine occurring from a mean of about 2 to about 160 hours, or about 1 to about 144 hours, or about 1 to about 120 hours, or about 1 to about 96 hours, or about 1 to about 72 hours, or about 1 to about 48 hours, or about 1 to about 20 hours, or about 1 to about 18 hours, or about 1 to about 16 hours, or about 1 to about 12 hours, or about 1 to about 10 hours, or about 1 to about 8 hours, or about 1 to about 6 hours, or about 1 to about 4 hours.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage from providing a $C_{min}$ of mepivacaine of up to 3000 ng/mL; said $C_{min}$ measured from a mean of about 2 to about 168 hours. In other preferred embodiments, the dosage from provides a $C_{min}$ of mepivacaine occurring from a mean of about 2 to about 160 hours, or about 1 to about 144 hours, or about 1 to about 120 hours, or about 1 to about 96 hours, or about 1 to about 72 hours, or about 1 to about 48 hours, or about 1 to about 20 hours, or about 1 to about 18 hours, or about 1 to about 16 hours, or about 1 to about 12 hours, or about 1 to about 10 hours, or about 1 to about 8 hours, or about 1 to about 6 hours, or about 1 to about 4 hours.

In some preferred embodiments, the dosage form provides a pharmaceutical composition for application to the skin for the treatment of pain comprising a therapeutically effective amount of mepivacaine; said dosage form providing a systemic exposure as assessed by the mean area under the plasma concentration time curve ($AUC_{0-24}$) of about 50 ng·hr/mL to about 80000 ng·hr/mL. In other preferred embodiments, the dosage from provides an $AUC_{0-24}$ of about 50 ng·hr/mL to about 70,000 ng·hr/mL, or about 50 ng·hr/mL to about 60,000 ng·hr/mL, or about 50 ng·hr/mL to about 50,000 ng·hr/mL, or about 50 ng·hr/mL to about 40,000 ng·hr/mL, or about 50 ng·hr/mL to about 30,000 ng·hr/mL, or about 50 ng·hr/mL to about 20,000 ng·hr/mL, or about 50 ng·hr/mL to about 15,000 ng·hr/mL, or about 50 ng·hr/mL to about 10,000 ng·hr/mL, or about 50 ng·hr/mL to about 7,500 ng·hr/mL, or about 50 ng·hr/mL to about 5,000 ng·hr/mL, or about 50 ng·hr/mL to about 4,000 ng·hr/mL, 50 ng·hr/mL to about 3,000 ng·hr/mL, 50 ng·hr/mL to about 2,500 ng·hr/mL, or about 50 ng·hr/mL to about 2,000 ng·hr/mL, or about 50 ng·hr/mL to about 1,500 ng·hr/mL, or about 50 ng·hr/mL to about 1,000 ng·hr/mL, or about 50 ng·hr/mL to about 750 ng·hr/mL, 50 ng·hr/mL to about 500 ng·hr/mL, 50 ng·hr/mL to about 350 ng·hr/mL, or about 1000 ng·hr/mL to about 50,000 ng·hr/mL, or about 1000 ng·hr/mL to about 40,000 ng·hr/mL, or about 2,500 ng·hr/mL to about 30,000 ng·hr/mL, or about 5,000 ng·hr/mL to about 20,000 ng·hr/mL, 7,500 ng·hr/mL to about 15,000 ng·hr/mL, 10,000 ng·hr/mL to about 15,000 ng·hr/mL.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage form providing a systemic exposure as assessed by the mean area under the plasma concentration time curve ($AUC_{0-24}$) of about 50 ng·hr/mL to about 80000 ng·hr/mL. In other preferred embodiments, the dosage from provides an $AUC_{0-24}$ of about 50 ng·hr/mL to about 70,000 ng·hr/mL, or about 50 ng·hr/mL to about 60,000 ng·hr/mL, or about 50 ng·hr/mL to about 50,000 ng·hr/mL, or about 50 ng·hr/mL to about 40,000 ng·hr/mL, or about 50 ng·hr/mL to about 30,000 ng·hr/mL, or about 50 ng·hr/mL to about 20,000 ng·hr/mL, or about 50 ng·hr/mL to about 15,000 ng·hr/mL, or about 50 ng·hr/mL to about 10,000 ng·hr/mL, or about 50 ng·hr/mL to about 7,500 ng·hr/mL, or about 50 ng·hr/mL to about 5,000 ng·hr/mL, or about 50 ng·hr/mL to about 4,000 ng·hr/mL, 50 ng·hr/mL to about 3,000 ng·hr/mL, 50 ng·hr/mL to about 2,500 ng·hr/mL, or about 50 ng·hr/mL to about 2,000 ng·hr/mL, or about 50 ng·hr/mL to about 1,500 ng·hr/mL, or about 50 ng·hr/mL to about 1,000 ng·hr/mL, or about 50 ng·hr/mL to about 750 ng·hr/mL, 50 ng·hr/mL to about 500 ng·hr/mL, 50 ng·hr/mL to about 350 ng·hr/mL, or about 1000 ng·hr/mL to about 50,000 ng·hr/mL, or about 1000 ng·hr/mL to about 40,000 ng·hr/mL, or about 2,500 ng·hr/mL to about 30,000 ng·hr/mL, or about 5,000 ng·hr/mL to about 20,000 ng·hr/mL, 7,500 ng·hr/mL to about 15,000 ng·hr/mL, 10,000 ng·hr/mL to about 15,000 ng·hr/mL.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage form providing a systemic exposure as assessed by the mean area under the plasma concentration time curve ($AUC_{0-24}$) of up to 8000 ng·hr/mL.

In some preferred embodiments, the dosage form provides a pharmaceutical composition for application to the skin for the treatment of pain comprising a therapeutically effective amount of mepivacaine; said dosage form providing at least 80% of the steady state therapeutic concentration of mepivacaine after administration of ≤three doses at their intended dosing frequency. In other preferred embodiments, the dosage from provides at least about 85%, or at least about 82.5% or at least about 87.5%, or at least about 90%, or at least about 92.5% of the steady state therapeutic concentration after administration of ≤three doses at their intended dosing frequency.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage form providing at least 80% of the steady state therapeutic concentration of mepivacaine after administration of ≤three doses at their intended dosing frequency. In other preferred embodiments, the dosage from provides at least about 85%, or at least about 82.5% or at least about 87.5%, or at least about 90%, or at least about 92.5% of the steady state therapeutic concentration after administration of ≤three doses at their intended dosing frequency.

In some preferred embodiments, the dosage form provides a pharmaceutical composition for application to the skin for the treatment of pain comprising a therapeutically effective amount of mepivacaine; said dosage form after administration to a human patient providing a $C_{min}/C_{max}$ ratio of 0.1 to about 1.0; and said dosage form providing a therapeutic effect for up to about one week. In other preferred embodiments, the dosage from provides a therapeutic effect for up to about 4 hours, or up to about 6 hours, or up to about 8 hours, or up to about 12 hours, or up to about 18 hours, or up to about 24 hours, or up to about 36 hours, or up to about 48 hours, or up to about 72 hours. In other preferred embodiments, the dosage from provides a $C_{min}/C_{max}$ ratio of about 0.1 to about 0.9, or about 0.1 to about 0.8, or about 0.1 to about 0.7, or about 0.1 to about 0.6, or about 0.1 to about 0.5, or about 0.1 to about 0.4, or about 0.1 to about 0.3, or about 0.2 to about 1.0, or about 0.25 to about 1.0, or about 0.4 to about 1.0, or about 0.5 to about 1.0, or about 0.65 to about 1.0, or about 0.75 to about 1.0, or about 0.2 to about 0.9, or about 0.3 to about 0.8, or about 0.4 to about 0.8, or about 0.4 to about 0.7, or about 0.4 to about 0.6.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage form after administration to a human patient providing a $C_{min}/C_{max}$ ratio of 0.1 to about 1.0; and said dosage form providing a therapeutic effect for up to about one week. In other preferred embodiments, the dosage from provides a therapeutic effect for up to about 4 hours, or up to about 6 hours, or up to about 8 hours, or up to about 12 hours, or up to about 18 hours, or up to about 24 hours, or up to about 36 hours, or up to about 48 hours, or up to about 72 hours. In other preferred embodiments, the dosage from provides a $C_{min}/C_{max}$ ratio of about 0.1 to about 0.9, or about 0.1 to about 0.8, or about 0.1 to about 0.7, or about 0.1 to about 0.6, or about 0.1 to about 0.5, or about 0.1 to about 0.4, or about 0.1 to about 0.3, or about 0.2 to about 1.0, or about 0.25 to about 1.0, or about 0.4 to about 1.0, or about 0.5 to about 1.0, or about 0.65 to about 1.0, or about 0.75 to about 1.0, or about 0.2 to about 0.9, or about 0.3 to about 0.8, or about 0.4 to about 0.8, or about 0.4 to about 0.7, or about 0.4 to about 0.6.

In some preferred embodiments, the dosage form provides a pharmaceutical composition for application to the skin for the treatment of pain comprising a therapeutically effective amount of mepivacaine; said dosage form after administration to a human patient providing a percent fluctuation of less than 400%; and said dosage form providing a therapeutic effect for up to about one week. In other preferred embodiments, the dosage from provides a percent fluctuation of less than 350%, or less than 300%, or less than 250%, or less than 200%, or less than 150%, or less than 100%, or less than 75%, or less than 50%, or less than 25%.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage form after administration to a human patient providing a percent fluctuation of less than 400%; and said dosage form providing a therapeutic effect for up to about one week. In other preferred embodiments, the dosage from provides a percent fluctuation of less than 350%, or less than 300%, or less than 250%, or less than 200%, or less than 150%, or less than 100%, or less than 75%, or less than 50%, or less than 25%.

In some preferred embodiments, the dosage form provides a pharmaceutical composition for application to the skin for the treatment of pain comprising a therapeutically effective amount of mepivacaine; said dosage form after administration to a human patient providing a $W_{50}$ on of about 1 to about 6 hours for each 6 hour time period of intended dosing frequency or intended duration of action; and said dosage form providing a therapeutic effect for up to about one week. In other preferred embodiments, the dosage from provides a $W_{50}$ for each 6 hour time period of intended dosing frequency or intended duration of action of about 1 to about 5 hours, or about 1 to about 4 hours, or about 1 to about 3 hours, or about 1 to about 2 hours, or 2 to about 6 hours, or about 3 to about 6 hours, or about 4 to about 6 hours, or about 2 to about 4 hours.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage form after administration to a human patient providing a $W_{50}$ on of about 1 to about 6 hours for each 6 hour time period of intended dosing frequency or intended duration of action; and said dosage form providing a therapeutic effect for up to about one week. In other preferred embodiments, the dosage from provides a $W_{50}$ for each 6 hour time period of intended dosing frequency or intended duration of action of about 1 to about 5 hours, or about 1 to about 4 hours, or about 1 to about 3 hours, or about 1 to about 2 hours, or 2 to about 6 hours, or about 3 to about 6 hours, or about 4 to about 6 hours, or about 2 to about 4 hours.

In some preferred embodiments, the dosage form provides a pharmaceutical composition for application to the skin for the treatment of pain comprising a therapeutically effective amount of mepivacaine; said dosage form after administration to a human patient providing a HVD on of about 1.5 to about 6 hours for each 6 hour time period of intended dosing frequency or intended duration of action; and said dosage form providing a therapeutic effect for up to about one week. In other preferred embodiments, the dosage from provides a HVD for each 6 hour time period of intended dosing frequency or intended duration of action of about 1.5 to about 5 hours, or about 1.5 to about 4 hours, or about 1.5 to about 3 hours, or about 1.5 to about 2 hours, or 2 to about 6 hours, or about 3 to about 6 hours, or about 4 to about 6 hours, or about 2 to about 4 hours.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage form after administration to a human patient providing a HVD on of about 1.5 to about 6 hours for each 6 hour time period of intended dosing frequency or intended duration of action; and said dosage form providing a therapeutic effect for up to about one week. In other preferred embodiments, the dosage from provides a HVD for each 6 hour time period of intended dosing frequency or intended duration of action of about 1.5 to about 5 hours, or about 1.5 to about 4 hours, or about 1.5 to about 3 hours, or about 1.5 to about 2 hours, or 2 to about 6 hours, or about 3 to about 6 hours, or about 4 to about 6 hours, or about 2 to about 4 hours.

In some preferred embodiments, the dosage form provides a pharmaceutical composition for application to the skin for the treatment of pain comprising a therapeutically effective amount of mepivacaine or a pharmaceutically acceptable salt of mepivacaine or a mixture thereof; said dosage form providing pulse dosing aided by electroporation, iontophoresis, localized electroporation, photo-mechanical energy, magnetophoresis, thermoporation, thermal energy and/or mechanical energy; said dosage form after administration to a human patient providing a $W_{50}$ of mepivacaine of about 0.01× to 4×, where "x" is the intended dosing frequency or intended duration of action. In other preferred embodiments, the said dosage from provides a $W_{50}$ of mepivacaine of about 0.05× to 4×, or about 0.05× to 2×, or about 0.05× to 1×, or about 0.1× to 4×, or about 0.1× to 3×, or about 0.1× to 2×, or about 0.1× to 1×, or about 0.1× to 0.7×, or about 0.1× to 0.5×, or about 0.05× to 1×, where "x" is the intended dosing frequency or intended duration of action.

In some preferred embodiments, the dosage form provides a pharmaceutical composition for application to the skin for the treatment of pain comprising a therapeutically effective amount of mepivacaine or a pharmaceutically acceptable salt of mepivacaine or a mixture thereof; said dosage form providing pulse dosing aided by electroporation, iontophoresis, localized electroporation, photo-mechanical energy, magnetophoresis, thermoporation, thermal energy and/or mechanical energy; said dosage form after administration to a human patient providing a HVD of mepivacaine of about 0.01× to 4×, where "x" is the intended dosing frequency or intended duration of action. In other preferred embodiments, the said dosage from provides a HVD of mepivacaine of about 0.05× to 4×, or about 0.05× to 2×, or about 0.05× to 1×, or about 0.1× to 4×, or about 0.1× to 3×, or about 0.1× to 2×, or about 0.1× to 1×, or about 0.1× to 0.7×, or about 0.1× to 0.5×, or about 0.05× to 1×, where "x" is the intended dosing frequency or intended duration of action.

In some preferred embodiments, where the dosage form of the invention provides a mepivacaine pharmaceutical composition for application to the skin for the treatment of pain intended with a dosing frequency or intended duration of action of less than 6 hours, the HVD and $W_{50}$ of mepivacaine is about 0.01× to 1×, where "x" is the intended dosing frequency or intended duration of action. In other embodiments of the foregoing, the HVD and $W_{50}$ of mepivacaine is about 0.05× to 1×, or about 0.1× to 1×, or about 0.25× to 1×, or about 0.3× to 1×, where "x" is the intended dosing frequency or intended duration of action.

In some preferred embodiments, the dosage form provides a pharmaceutical composition for application to the skin for the treatment of pain comprising a therapeutically effective amount of mepivacaine; said dosage form after administration to a human patient providing an AI of not more than about 3.0; and said dosage form providing a therapeutic effect for up to about one week. In other preferred embodiments, the dosage from provides an AI of not more than about 2.5, or not more than about 2, or not more than about 1.75, or not more than about 1.5, or not more than about 1.25, or not more than about 1, or not more than about 0.75, or not more than about 0.5, or not more than about 0.25.

In some preferred embodiments, the dosage form provides a pharmaceutical composition for application to the skin for the treatment of pain comprising a therapeutically effective amount of mepivacaine; a controlled release material to render said dosage form suitable for up to one week of administration to a human patient; said dosage form after administration to a human patient providing an AI of not more than about 3.0; and said dosage form providing a therapeutic effect for up to about one week. In other preferred embodiments, the dosage from provides an AI of not more than about 2.5, or not more than about 2, or not more than about 1.75, or not more than about 1.5, or not more than about 1.25, or not more than about 1, or not more than about 0.75, or not more than about 0.5, or not more than about 0.25.

In some preferred embodiments, the topical dosage from provides a pharmaceutical composition comprising a therapeutically effective amount of mepivacaine; said dosage form providing permeability which is at least 10%, 20%, 30%, 40%, 50%, 70%, 100%, 120%, 150%, 180%, 200%, 230%, 250%, 280%, 300%, 350%, 400%, 450%, or 500% greater than the permeability from Lidoderm™ patch.

In some preferred embodiments, the dosage form provides a pharmaceutical composition for application to the skin for the treatment of pain comprising a therapeutically effective amount of mepivacaine; said therapeutically effective amount in a reservoir comprising: (i) mepivacaine or a pharmaceutically acceptable salt of mepivacaine in racemic or enantiomeric form, or a mixture thereof; (ii) a membrane layer, said membrane being substantially permeable to mepivacaine; wherein the dosage form releases the mepivacaine from the dosage form to render said dosage form suitable for up to one week of administration to a human patient; and said dosage form providing a therapeutic effect for up to about one week.

In some preferred embodiments, the dosage form provides a pharmaceutical composition for application to the skin for the treatment of pain comprising a therapeutically effective amount of mepivacaine; said therapeutically effective amount incorporated into a matrix; wherein the dosage form releases the mepivacaine from the dosage form to render said dosage form suitable for up to one week of administration to a human patient; and said dosage form providing a therapeutic effect for up to about one week.

In some preferred embodiments, the dosage form provides a pharmaceutical composition for application to the skin for the treatment of pain comprising a therapeutically effective amount of mepivacaine; said therapeutically effective amount incorporated into an adhesive; wherein the dosage form releases the mepivacaine from the dosage form to render said dosage form suitable for up to one week of administration to a human patient; and said dosage form providing a therapeutic effect for up to about one week.

In some preferred embodiments, the dosage form is intended for application to the skin at the site of pain. In other preferred embodiments, the dosage form is intended for application to the skin proximal to the site of pain. In yet other preferred embodiments, the dosage form is intended for application to the skin distal to the site of pain.

In some preferred embodiments, the dosage form comprises a topical patch. In other preferred embodiments, the dosage form comprises a transdermal patch. In other preferred embodiments, the dosage form comprises a plaster. In other preferred embodiments, the dosage form comprises a gel. In other preferred embodiments, the dosage form comprises drug in liposomes. In other preferred embodiments, the dosage form comprises a liquid or semisolid selected from a group consisting of solution, suspension, lotion, cream, ointment or foam. In other preferred embodiments, the dosage form is delivered in aerosol form. In other preferred embodiments, the dosage form is delivered is in a sprayable aerosol or non-aerosol pharmaceutical formulation. In other preferred embodiments, the sprayable dosage form is capable of forming a thin barrier film on topical administration. In other preferred embodiments, the barrier film of the sprayable dosage form is substantially water washable. In other preferred embodiments, the sprayable dosage form is capable of forming a thin barrier film on topical administration. In other preferred embodiments, the barrier film of the sprayable dosage form is substantially partially or substantially resistant to removal with water.

In some preferred embodiments, the dosage form is intended for the treatment of acute pain. In some preferred embodiments, the dosage form is intended for the treatment of acute exacerbations of chronic pain. In some preferred embodiments, the dosage form is intended for the treatment of acute postsurgical pain. In some preferred embodiments, the dosage form is intended for the treatment of acute traumatic pain. In some preferred embodiments, the dosage form is intended for the treatment of acute procedure related pain. In some preferred embodiments, the dosage form is intended for the treatment of neuropathy. In other preferred embodiments, the dosage form is intended for the treatment of neuropathic pain. In other preferred embodiments, the dosage form is intended for the treatment of central neuropathic pain. In other preferred embodiments, the dosage form is intended for the treatment of peripheral neuropathy. In other preferred embodiments, the dosage form is intended for the treatment of painful peripheral neuropathy. In other preferred embodiments, the dosage form is intended for the treatment of painful peripheral polyneuropathy. In other preferred embodiments, the dosage form is intended for the treatment of painful peripheral mononeuropathy. In other preferred embodiments, the dosage form is intended for the treatment of chronic pain. In other preferred embodiments, the dosage form is intended for the treatment of back pain, myofascial pain. In other preferred embodiments, the dosage form is intended for the treatment of fibromylagia. In other preferred embodiments, the dosage form is intended for the treatment of chronic idiopathic pain. In other preferred embodiments, the dosage form is intended for the treatment of musculoskeletal pain. In other preferred embodiments, the dosage form is intended for the treatment of radicular pain. In other preferred embodiments, the dosage form is intended for the treatment of complex regional pain syndrome Type I and Type II. In other preferred embodiments, the dosage form is intended for the treatment of cancer pain. In other preferred embodiments, the dosage form is intended for the treatment of breakthrough pain. In other preferred embodiments, the dosage form is intended for the treatment of somatic, visceral or inflammatory pain. In other preferred embodiments, the dosage form is intended for the treatment of pain through spinal and supraspinal mechanisms. In other preferred embodiments, the dosage form is intended for the treatment of pain through peripheral mechanisms.

In some preferred embodiments of the invention, the pharmaceutical dosage form contains a therapeutically effective amount of S(+)-mepivacaine as the base or a pharmaceutically acceptable salt thereof.

In some preferred embodiments of the invention, the pharmaceutical dosage form contains a therapeutically effective amount of and R(−)-mepivacaine as the base or a pharmaceutically acceptable salt thereof.

In some preferred embodiments of the invention, the pharmaceutical dosage form contains a therapeutically effective amount of S(+)-mepivacaine and R(−)-mepivacaine in a ratio of 1:10 to 10:1 as the base or a pharmaceutically acceptable salt thereof.

Also disclosed are methods of providing relief in a human patient suffering from pain comprising application to the skin of a therapeutically effective amount of mepivacaine or a pharmaceutically acceptable salt of mepivacaine in racemic or enantiomeric form, or a mixture thereof.

Also disclosed are kits for use in treating or preventing the pain with the application of mepivacaine or pharmaceutically acceptable salts thereof or mixtures thereof to the skin in a subject in need of such treatment, comprising: (i) a dosage form of the invention; (ii) a container for the dosage form; and optionally, any of (iii) to (ix): (iii) a container for individual units of the dosage form (e.g., individual patches); (iv) educational instructions in any media about various medical conditions, their etiology, pathophysiology, consequences and treatment, including information on the proper use and disposal of the medication; (v) containers or bags for the safe disposal of any used or remaining unused dosage form, preferably child proof and flushable; (vi) tamper evident and child proof packaging for the kit and its contents; (vii) gloves; (viii) adhesive or non-adhesive dressing or fasteners to cover the site of application; (ix) a cleansing swab, solution or gel for use before or after the application.

In some preferred embodiments, the in vivo pharmacokinetic parameters of the specifications and claims are derived or determined from first administration. In other preferred embodiments, the in vivo pharmacokinetic parameters are derived or determined from steady state administration.

In some preferred embodiments, the in vivo pharmacokinetic parameters of the specifications and claims are derived or determined in subjects having a Body Mass Index (BMI) between 18 and 26 kg/m$^2$, inclusive (BMI=[weight in kg/height in m$^2$]×10,000). In some preferred embodiments, the in vivo pharmacokinetic parameters of the specifications and claims are derived or determined in subjects having a Body Mass Index (BMI)≥38 kg/m².

In some preferred embodiments, the in vivo pharmacokinetic parameters of the specifications and claims are derived or determined from an individual subject. In other preferred embodiments, the in vivo pharmacokinetic parameters are derived or determined from a population of subjects.

In some preferred embodiments, the dosage form of the invention is intended for the treatment of painful peripheral neuropathy through peripheral, spinal and supraspinal mechanisms.

The amount of mepivacaine in the dosage form will vary depending on variety of physiologic, pharmacologic, pharmacodynamic, pharmacokinetic, pharmaceutical and physicochemical factors, including: (i) the choice of mepivacaine as the racemate, enantiomer, base, pharmaceutically acceptable salt or mixtures thereof; (ii) the nature of the dosage form (e.g, immediate release or extended release); (iii) the anatomical location of the pain relieving target (e.g., peripheral nervous system, central nervous system, joint, muscle, fascia); (iv) the intensity and intractability of the pain; (v) the contribution of systemic mechanism to the initiation, propagation, summation and maintenance of the pain; (vi) the absorption, metabolism, distribution and excretion of topical or transdermally administered mepivacaine; (vii) the presence of comorbid pathology; (viii) the patients risk of developing cardiac arrhythmias; (ix) the tolerability of the dose, including the patient's propensity for mepivacaine associated cardiovascular and CNS side effects; and (x) the efficiency of the dosage form.

In some preferred embodiments, the topical dosage from provides a pharmaceutical composition comprising a therapeutically effective amount of mepivacaine or a pharmaceutically acceptable salt of mepivacaine or a mixture thereof; said dosage form providing an in-vitro release of between 0% to about 95% by weight of the mepivacaine from the dosage form at 30 minutes when measured by the USP Apparatus 5 (paddle over disk method) at 50 rpm in 500 mL of acetic acid/sodium acetate buffer (pH 4.0) at 32° C. In other preferred embodiments, said release is 0% to about 10%, or 0% to about 20%, or 0% to about 30%, or 0% to about 40%, or 0% to about 50%, or 0% to about 60%, or 0% to about 70%, or 0% to about 80%, or 0% to about 85%, or 0% to about 90%.

In some preferred embodiments, the topical dosage from provides a pharmaceutical composition comprising a therapeutically effective amount of mepivacaine or a pharmaceutically acceptable salt of mepivacaine or a mixture thereof; said dosage form providing an in-vitro release of between 10% to about 95% by weight of the mepivacaine from the dosage form at 30 minutes when measured by the USP Apparatus 5 (paddle over disk method) at 50 rpm in 500 mL of acetic acid/sodium acetate buffer (pH 4.0) at 32° C. In other preferred embodiments, said release is about 10% to about 20%, or about 10% to about 30%, or about 10% to about 40%, or about 10% to about 50%, or about 10% to about 60%, or about 10% to about 70%, or about 10% to about 80%, or about 10% to about 85%, or about 10% to about 90%.

In some preferred embodiments, the topical dosage from provides a pharmaceutical composition comprising a therapeutically effective amount of mepivacaine or a pharmaceutically acceptable salt of mepivacaine or a mixture thereof; said dosage form providing an in-vitro release of between 0% to about 99% by weight of the mepivacaine from the dosage form at 60 minutes when measured by the USP Apparatus 5 (paddle over disk method) at 50 rpm in 500 mL of acetic acid/sodium acetate buffer (pH 4.0) at 32° C. In other preferred embodiments, said release is 0% to about 10%, or 0% to about 20%, or 0% to about 30%, or 0% to about 40%, or 0% to about 50%, or 0% to about 60%, or 0% to about 70%, or 0% to about 80%, or 0% to about 85%, or 0% to about 90%, or 0% to about 95%.

In some preferred embodiments, the topical dosage from provides a pharmaceutical composition comprising a therapeutically effective amount of mepivacaine or a pharmaceutically acceptable salt of mepivacaine or a mixture thereof; said dosage form providing an in-vitro release of between 10% to about 99% by weight of the mepivacaine from the dosage form at 60 minutes when measured by the USP Apparatus 5 (paddle over disk method) at 50 rpm in 500 mL of acetic acid/sodium acetate buffer (pH 4.0) at 32° C. In other preferred embodiments, said release is about 10% to about 20%, or about 10% to about 30%, or about 10% to about 40%, or about 10% to about 50%, or about 10% to about 60%, or about 10% to about 70%, or about 10% to about 80%, or about 10% to about 85%, or about 10% to about 90%, or 0% to about 95%.

In some preferred embodiments, the topical dosage from provides a pharmaceutical composition comprising a therapeutically effective amount of mepivacaine or a pharmaceutically acceptable salt of mepivacaine or a mixture thereof; said dosage form providing an in-vitro release by weight of the mepivacaine from the dosage form when measured by the USP Apparatus 5 (paddle over disk method) at 50 rpm in 500 mL of acetic acid/sodium acetate buffer (pH 4.0) at 32° C. from 0% to about 40% at 10 minutes, about 1% to about 60% at 20 minutes, from about 2% to about 80% at 30 minutes, from about 5% to about 95% at 60 minutes, over 30% at 120 minutes and over 40% at 180 minutes. In other preferred embodiments, said release is (1) from 0% to about 30% at 10 minutes, about 1% to about 50% at 20 minutes, from about 2% to about 60% at 30 minutes, from about 5% to about 80% at 60 minutes, over 20% at 120 minutes and over 30% at 180 minutes; or (2) from 0% to about 50% at 10 minutes, about 2% to about 50% at 20 minutes, from about 5% to about 50% at 30 minutes, from about 10% to about 80% at 60 minutes, over 20% at 120 minutes and over 30% at 180 minutes; or (3) from 0% to about 60% at 10 minutes, about 5% to about 60% at 20 minutes, from about 10% to about 90% at 30 minutes, from about 10% to about 100% at 60 minutes, over 50% at 120 minutes and over 60% at 180 minutes; or (4) from 0% to about 70% at 10 minutes, about 3% to about 80% at 20 minutes, from about 5% to about 90% at 30 minutes, from about 5% to about 95% at 60 minutes, from about 10% to about 100% at 120 minutes and from about 20% to about 100% at 180 minutes; or (5) from 5% to about 70% at 10 minutes, about 5% to about 80% at 20 minutes, from about 10% to about 90% at 30 minutes, from about 10% to about 95% at 60 minutes, from about 20% to about 100% at 120 minutes and from about 30% to about 100% at 180 minutes; or (6) from 0% to about 60% at 10 minutes, about 5% to about 80% at 20 minutes, from about 10% to about 90% at 30 minutes, from about 20% to about 100% at 60 minutes, from about 30% to about 100% at 120 minutes and from about 40% to about 100% at 180 minutes; or (7) from 0% to about 70% at 10 minutes, about 3% to about 80% at 20 minutes, from about 5% to about 90% at 30 minutes, from about 5% to about 95% at 60 minutes, from about 10% to about 100% at 120 minutes and from about 20% to about 100% at 180 minutes; or (8) from 0% to about 30% at 10 minutes, about 2% to about, 50% at 20 minutes, from about 5% to about 70% at 30 minutes, from about 10% to about 100% at 60 minutes, from about 15% to about 100% at 120 minutes and from about 30% to about 100% at 180 minutes; or (9) greater than about 5% at 30 minutes, greater than about 10% at 60 minutes, greater than about 15% at 120 minutes and greater than about 20% at 180 minutes; or (10) greater than about 10% at 30 minutes, greater than about 20% at 60 minutes, greater than about 30% at 120 minutes and greater than about 40% at 180 minutes; or (11) greater, than about 15% at 30 minutes, greater than about 30% at 60 minutes, greater than about 50% at 120 minutes and greater than about 70% at 180 minutes; or (12) greater than about 5% at 30 minutes, greater than about 10% at 60 minutes, greater than about 20% at 120 minutes and greater than about 30% at 180 minutes; or (13) greater than about 10% at 30 minutes, greater than about 20% at 60 minutes, greater than about 30% at 120 minutes and greater than about 40% at 180 minutes; or (14) greater than about 20% at 30 minutes, greater than about 30% at 60 minutes, greater than about 40% at 120 minutes and greater than about 50% at 180 minutes; (15) greater than about 30% at 30 minutes, greater than about 40% at 60 minutes, greater than about 50% at 120 minutes and greater than about 60% at 180 minutes.

In some preferred embodiments, the topical dosage from provides a pharmaceutical composition comprising a therapeutically effective amount of mepivacaine or a pharmaceutically acceptable salt of mepivacaine or a mixture thereof; said dosage form providing an in-vitro release of between 0% to about 50% by weight of the mepivacaine from the dosage form at one hour when measured by the USP Apparatus 5 (paddle over disk method) at 50 rpm in 900 mL of distilled water at 37° C.

In some preferred embodiments, the topical dosage from provides a pharmaceutical composition comprising a therapeutically effective amount of mepivacaine or a pharmaceutically acceptable salt of mepivacaine or a mixture thereof; said dosage form providing an in-vitro release by weight of the mepivacaine from the dosage form when measured by the USP Apparatus 5 (paddle over disk method) at 50 rpm in 500 mL of acetic acid/sodium acetate buffer (pH 4.0) at 32° C. between 0% to about 90% at 0.5 hours, and greater than about 60% at 1 hour; or between 0% to about 90% at 1 hour, and greater than about 40% at 2 hours; or between 0% to about 90% at 1 hour, and greater than about 70% at 2 hours; or between 0% to about 50% at 1 hour, and greater than about 30% at 2 hours; or between 0% to about 100% at 0.5 hours, and greater than about 60% at 1 hour; or between 0% to about 100% at 1 hour, and greater than about 40% at 2 hours; or between 0% to about 100% at 1 hour, and greater than about 60% at 1 hour; or 0% to about 40% at 10 minutes, about 1% to about 60% at 20 minutes, from about 2% to about 80% at 30 minutes, from about 5% to about 95% at 60 minutes, over 30% at 120 minutes and over 40% at 180 minutes; or between 0% to about 100% at 1 hour, between about 10% and about 100% at 2 hours, between about 20% and about 100% at 3 hours, between about 30% and about 100% at 4 hours and greater than about 60% at 6 hours; or between 10% to about 80% at 1 hour, between about 20% and about 100% at 2 hours, between about 30% and about 100% at 3 hours, between about 50% and about 100% at 4 hours and greater than about 70% at 6 hours; or between 10% to about 80% at 1 hour, between about 20% and about 100% at 2 hours, between about 30% and about 100% at 3 hours, between about 50% and about 100% at 4 hours and greater than about 70% at 6 hours; or between 1% to about 90% at 0.5 hours, and greater than about 40% at 1 hour; or between 1% to about 90% at 0.25 hours, and greater than about 60% at 0.5 hour; between about 1% to about 90% at 0.17 hours, between about 5% to about 90% at 0.25 hours, between 10% to about 100% at 0.5 hours and greater than about 60% at 1 hour; or greater than about 5% at 0.5 hours, greater than about 10% at 0.75 hours, and greater than about 40% at 1 hour; or greater than about 5% at 0.5 hours, greater than about 10% at 0.75 hours, and greater than about 40% at 1 hour.

In some preferred embodiments, the in-vitro release utilizes, instead of a media of acetic acid/sodium acetate buffer (pH 4.0) at 32° C., (1) 40% ethanol in distilled water at 37° C.; or (2) an aqueous buffer at a pH of between 1.6 and 7.2 at 37° C.; or (3) a dissolution media volume of 600 mL to 900 mL.

The dosage form of the invention may be applied to the skin for a period of up to about 30 days, preferably for up to about a week (e.g., up to about 1, 2, 3, 4, 7 or 10 days).

In some preferred embodiments of the dosage form intended for administration or application to the skin for a period of x hours, at least 0.001% but not more than 60% of the total amount of the mepivacaine in the dosage form is delivered transdermally during approximately the first 0.35× hours; at least 0.002% but not more than 70% of the total amount of the mepivacaine is delivered transdermally during approximately the first 0.7× hours; and at least 1%, but not more than 85%, of the total amount of the mepivacaine is delivered transdermally during the total period of application (i.e., over x hours).

In some preferred embodiments of the dosage form intended to provide a duration of effect of x hours on administration or application to the skin, at least 0.001% but not more than 60% of the total amount of the mepivacaine in the dosage form is delivered transdermally during approximately the first 0.35× hours; at least 0.002% but not more than 70% of the total amount of the mepivacaine is delivered transdermally during approximately the first 0.7× hours; and at least 1%, but not more than 85%, of the total amount of the mepivacaine is delivered transdermally during the total duration of therapeutic effect (i.e., over x hours).

In some preferred embodiments of the dosage form intended for application to the skin for a period of about 12 hours, at least 0.25% but not more than 30% of the total amount of the mepivacaine in the dosage form is delivered into the skin during the first 8 hours of use; at least 0.5% but not more than 85% of the total amount of the mepivacaine is delivered into the skin during the first 12 hours of use.

In some preferred embodiments of the dosage form intended for application to the skin for a period of about 24 hours, at least 0.5% but not more than 50% of the total amount of the mepivacaine in the dosage form is delivered into the skin during the first 8 hours of use; at least 1% but not more than 65% of the total amount of the mepivacaine is delivered into the skin during the first 12 hours of use; and at least 2%, but not more than 85%, of the total amount of the mepivacaine is delivered into the skin during the 24 hour administration period.

In some preferred embodiments of the dosage form intended for application to the skin for a period of about 48 to about 168 hours, at least 0.1% but not more than 60% of the total amount of the mepivacaine in the dosage form is delivered into the skin during the first 24 hours of use; at least 0.5% but not more than 70% of the total amount of the mepivacaine is delivered into the skin during the first 48 hours of use.

In some preferred embodiments of the dosage form intended for about 12 or about 24 hour administration, at least 1% but not more than 50% of the total amount of the mepivacaine in the dosage form is delivered transdermally during approximately the first 8 hours of use; at least 2% but not more than 65% of the total amount of the mepivacaine is delivered transdermally during approximately the first 12 hours of use; and at least 5%, but not more than 85%, of the total amount of the mepivacaine is delivered transdermally during the 24 hour administration period.

In some preferred embodiments of the dosage form intended for about every two-day administration, at least 1% but not more than 60% of the total amount of the mepivacaine in the dosage form is delivered transdermally during approximately the first 24 hours of use; at least 4% but not more than 85% of the total amount of the mepivacaine is delivered transdermally during the 48 hour administration period.

In some preferred embodiments of the dosage form intended for about twice-a-week administration (every 3 to 4 days), at least 2% but not more than 60% of the total amount of the mepivacaine in the dosage form is delivered transdermally during approximately the first 24 hours of use; at least 4% but not more than 70% of the total amount of the mepivacaine in the dosage form is delivered transdermally during approximately the second 24 hours of use and at least 5% but not more than 90% of the total amount of the mepivacaine is delivered transdermally over 3-days of administration.

In some preferred embodiments of the dosage form intended for about once-a-week administration, at least 2% but not more than 60% of the total amount of the mepivacaine in the dosage form is delivered transdermally during approximately the first 24 hours of use; at least 5% but not more than 90% of the total amount of the mepivacaine is delivered transdermally over 7-days of administration.

The invention is also directed to methods directed at the use of the dosage form for the treatment of mepivacaine responsive medical conditions.

The invention is also directed to methods directed at the use of the dosage form for the treatment of pain.

The invention is also directed to a process for the preparation and manufacture of the dosage form.

The invention is also directed to methods of preparing the dosage forms disclosed herein.

Aspects of Application of Mepivacaine to the Skin

The medical condition of pain is a complex physiological process that involves a number of sensory and neural mechanisms. Pain can be defined as an unpleasant sensory or emotional experience associated with actual or potential tissue damage, or described in terms of such damage.

Pain is most often classified by time course or mechanism as acute pain, inflammatory pain, visceral pain, breakthrough pain, nociceptive pain, neuropathic pain, chronic pain, or cancer-related pain. Acute pain is a normal, predictable physiological response to an adverse chemical, thermal, or mechanical stimulus. Acute pain is normally self-limiting. When the condition producing the pain resolves, the pain goes away. Chronic pain is usually defined as pain persisting longer than the expected time of tissue healing, usually more than 30, 60 90, 120 or 180 days. Chronic pain generally includes such syndromes as low back pain, myofascial pain, osteoarthritis, cancer pain, neuropathic pain, fibromyalgia, and inflammatory pain states such as rheumatoid arthritis.

Acute Pain States

Acute pain is usually a consequence of an identifiable insult, such as surgery or other trauma, or a consequence of a disease, e.g., kidney stones, mechanical low back pain, etc.

According to public health statistics, several hundred million people worldwide undergo inpatient or outpatient surgery each year. In addition, several hundred million visits are made annually to the emergency room. Of these emergency room visits, it is estimated by survey data that more than 20% require analgesic treatment. Recent studies have shown that more than 60% of patients who undergo surgery experience moderate to severe pain despite analgesic treatment.

Currently, medical practitioners may choose from several well-accepted classes of pharmaceutical agents in their attempts to alleviate pain. Acute pain is managed with a variety of drugs, frequently in combination, including opioid analgesics, e.g., morphine, hydromorphone, hydrocodone, oxycodone, tramadol, and codeine; acetaminophen; non-steroidal anti-inflammatory drugs (NSAIDs) e.g., ketoprofen, ibuprofen, naproxen, tiaprofenic acid, aceclofenac, diclofenac, piroxicam, loxaprofen, fenoprofen, flurbiprofen, tenoxicam, lornoxicam, acetylsalicylic acid, flufenamic acid, mefenamic acid, niflumic acid, tolfenamic acid, diflunisal, etodolac, fenbufen, isoxicam, pirprofen, sulindac, tolmetin, and piketoprofen; cyclo-oxygenase isoform 2 (COX-2) selective NSAIDs, e.g., celecoxib, valdecoxib, piketoprofen, etoricoxib, rofecoxib, and lumiracoxib; tramadol; and acetaminophen.

Treatment of acute pain is usually with the oral route of administration. However, parenteral drug formulations have become a very important component in the arsenal of available drug delivery options, particularly for drugs having analgesic, anti-inflammatory or antipyretic effects. Parenteral routes of administration, including subcutaneous, intramuscular, intrathecal, epidural and intravenous injection, offer numerous benefits over oral delivery in particular situations, for a wide variety of drugs. For example, parenteral administration of a drug typically results in attainment of a therapeutically effective blood concentration of the drug in a shorter time than is achievable by oral administration. This is especially true of intravenous injection, whereby the drug is placed directly into the bloodstream. Parenteral administration can also result in more predictable blood serum concentrations of a drug, because drug loss in the gastrointestinal tract due to absorption, distribution, metabolism, binding to food and other causes are eliminated. Parenteral administration is generally the preferred method of drug delivery in emergency situations, and is also useful in treating subjects who are uncooperative, unconscious, or otherwise unable or unwilling to accept oral medication.

Parenteral drugs are particularly useful for treating a condition such as pain and inflammation when: 1) the condition is of severe intensity; 2) there is a need for rapid onset of effect; 3) there is a need for rapid or frequent dose titration to keep condition under control; 4) the patient is unable to receive oral medication e.g., due to nausea, vomiting, confusion, obtundation, loss of consciousness and bowel obstruction.

A major drawback to the use of parenteral agents is that in a majority of patients with acute pain, including acute postsurgical pain, venous access is lacking or available for only a limited period of time. Additionally, parenteral administration, particularly intravenous administration requires skilled nursing care and aseptic conditions.

Of the many challenges that occur when pharmacologically treating any disease or pathological condition, including pain and inflammation, alleviating the symptoms without causing counterproductive side effects is often the greatest. This challenge presents itself when medical practitioners use medicinal agents to treat pain and inflammation. Although the aforementioned pharmacological classes are frequently effective for the treatment of certain types of pain and/or inflammation, use of these analgesic agents produces a number of significant undesirable side effects.

Opioids are well-known for their potential for physical dependence and addiction. Other side effects of opioids, particularly in the acute setting and more particularly in non-opioid tolerant or opioid naïve patients, include nausea, vomiting, pruritus, constipation, sedation, and potentially fatal respiratory depression. When a subject is tolerant to opioids, increased doses are required to achieve a satisfactory analgesic effect. For this reason, alternative therapies for the management of acute pain are widely sought, so as to minimize the amount of opioid, patients will require for pain management. Compounds which serve as replacements for opioids or reduce the required opioid dose (opioid sparing) have utility in the treatment of pain.

The NSAIDs as a class are highly effective as analgesics. Traditional NSAIDs inhibit both enzymes. NSAIDs may also inhibit other lipogenic enzymes, such as 5-lipooxygenase. Although NSAIDs are not addictive, they are not without significant toxic effects, such as gastrointestinal injury, hepatotoxicity and decrease clotting ability.

Presently, multimodal treatment of acute pain is recommended by both expert consensus and evidence based medicine guidelines in order to provide improved efficacy and reduced side effects.

There are no recommendations on the mepivacaine application to the skin for the management of any pain state, including acute pain.

There is no information on the mepivacaine application to the skin for the management of any pain state, including acute pain.

The use of local anesthetics in the acute setting is largely limited to parenteral administration for (i) local infiltration analgesia and anesthesia prior to surgical incisions; (ii) local oromucosal analgesia and anesthesia prior to endotracheal intubation, endoscopy, ENT procedures and other painful, invasive procedures; (iii) epidural and intrathecal analgesia; and rarely (iv) intravenous administration.

The prior art describes selective local anesthetics for local application to the sites of postsurgical incision (e.g., closed wound) and other pathology using various drug delivery systems. Such pharmaceutical compositions, devices and methods of administration have several disadvantages, including: (i) they are only useful for locally accessible pharmacologic targets (e.g., closed surgical incision in acute postsurgical pain, accessible joints, etc); (ii) they have no utility for the large number of acute pain states where there are no superficial or skin-proximal sites of nociception; (iii) they fail to target the significant the significant deep sources of pain in tissue (e.g., organs, muscle, viscera and bone) from surgical manipulation and trauma (that are distal and often non-contiguous to the closed incision) and from non-surgical trauma; (iv) they fail to account for spinal and supraspinal sources of pain generation, pain propagation, pain summation and pain maintenance.

The applicant asserts that acute pain involves more than nociception from peripheral sites of trauma and pathology. Instead, acute pain involves in addition to nociception, inflammation and ectopia from peripheral sites of trauma and pathology, the active involvement of systemic and central sites of pain initiation, maintenance, propagation and summation. The applicant asserts that soon after surgical trauma, nonsurgical trauma and other acute pathologic events, there are profound changes in both the peripheral and central nervous system and in other tissues, and that spinal and supraspinal involvement is significant in pain summation, pain amplification, pain integration, pain maintenance and descending pain facilitation.

Therefore, without being bound by theory, the applicant asserts that application of mepivacaine to the skin needs to target a number of sources of pain initiation, pain summation, pain amplification, pain integration, pain maintenance and descending pain facilitation.

The present invention involves application to the skin of mepivacaine pharmaceutical compositions and methods of use that, in some embodiments provide systemic therapeutic concentrations and effects from the dosage form for the treatment of acute pain.

There are no recommendations on the use of mepivacaine for the treatment of acute pain by the topical or transdermal route.

There is a need for new pharmaceutical compositions and methods for the treatment of acute pain.

There is a need for new pharmaceutical compositions and methods for the treatment of acute pain that have high efficacy.

There is a need for new pharmaceutical compositions and methods for the treatment of acute pain that have good tolerability.

Although the oral route is preferred for the treatment of most maladies, it is not appropriate under all circumstances. For example, following general anesthesia, particularly prolonged general anesthesia, and following regional anesthesia with the use of intravenous sedation and opioids, patients are often sedated, unable to tolerate oral intake and have reduced gastrointestinal function.

The advantages and disadvantages of the parenteral route have been described above. The application of medicaments to the skin for systemic effects has the potential to provide several advantages, including consistent delivery, reduced peak to tough fluctuations and improved patient convenience and compliance. In addition, this route of administration reduces the need for awakening at night to take pain medications, is non-invasive, avoids drug-food interactions and can provide several days of therapy to weeks of therapy from a single application.

There is a need for local anesthetic pharmaceutical compositions and methods for the treatment of acute pain There is also a need for local anesthetic pharmaceutical compositions for application to the skin and methods for the treatment of acute pain.

There is also a need for local anesthetic pharmaceutical compositions for application to the skin and methods for the treatment of acute pain that can be used in combination with other drugs, preferably drugs with different mechanisms of action and drugs with additive or synergistic effects.

There is a need for local anesthetic pharmaceutical compositions for application to the skin and methods for the treatment of the acute pain with improved efficacy, but without increased local or systemic toxicity.

There is a need for new therapies for the treatment of acute pain that work through new and different mechanism from existing therapies.

There is a need for additional therapies for acute pain that work through a spinal and supraspinal mechanism.

Chronic Neuropathy, Neuropathic Pain and Non-Neuropathic Pain

Injury to nerves and various diseases can precipitate a variety of metabolic and functional responses that are responsible for chronic neuropathic pain. Among the pathophysiological changes are electrical hyperexcitability and abnormal impulse generation which develop in injured sensory neurons. Ectopia involves spontaneous firing in some neurons, and abnormal responsiveness to mechanical, thermal and chemical stimuli in others. The mechanism underlying ectopic hyperexcitability is the remodeling of voltage-sensitive $Na^+$ and $K^+$ channels and receptors in the cell membrane.

Pathophysiological phenomena associated with hyperexcitable primary afferent neurons produce a number of sensory abnormalities, including ongoing dysesthesic pain, pain on weight bearing, hypersensitivity to stimuli, paroxysmal pain and hyperalgesia.

The recent development of animal models of neuropathic pain have dramatically improved our understanding of the underlying pathophysiology and treatment of neuropathic pain. These models offer a number of behavioral measures by which the effects of putative analgesics can be characterized. Importantly, these animal models shown positive responses for drugs that are clinically useful in treating various painful neuropathies.

The International Association for the Study of Pain (IASP) defines neuropathic pain as "pain initiated or caused by a primary lesion or dysfunction of the nervous system".

Neuropathic pain can be classified in various ways. One broad categorization is that of peripheral neuropathic pain and central neuropathic pain (central pain). Among the peripheral neuropathic pains, it is common to categorize the pain based on the anatomical distribution pattern of the affected nerves.

Painful peripheral neuropathies may be categorized in various ways. One categorization is into: (i) symmetrical polyneuropathies, i.e., disease affecting many nerves simultaneously, typically in a glove and stocking distribution and (ii) asymmetrical neuropathies with a mono- or multiplex distribution affecting the brachial or lumbosacral plexuses. Common painful peripheral neuropathies include (i) traumatic mononeuropathies, such as stump pain, nerve transection, causalgia, entrapment neuropathies, mastectomy, and post-thoracotomy; (ii) other mononeuropathies and multiple mononeuropathies, such as borreliosis, vasculitis, diabetic mononeuropathy, herpes zoster, postherpetic neuralgia, malignant plexus invasion, radiation plexopathy and trigeminal neuralgia; (iii) polyneuropathies, including metabolic (e.g., diabetic) or nutritional neuropathy (e.g., alcoholic, Beriberi, pellagra), drug induced neuropathy (e.g., antiretrovirals, cancer chemotherapy, isoniazid), hereditary neuropathy amyloid neuropathy, Fabry's disease), malignant (e.g., paraneoplastic syndromes, myeloma), infective (e.g., Guillain-Barré syndrome, HIV).

Since a wide variety of clinical conditions can cause painful peripheral neuropathy pain, both symptom-based and mechanism based approaches to treatment has been suggested. A major challenge is that the same mechanism can often produce a variety of symptoms of neuropathic pain and drugs that appear to be mechanistically specific will frequently treat more than one symptom of neuropathic pain. For example, opioid analgesics have been demonstrated efficacy in relieving ongoing or steady pain, allodynia and paroxysmal pain (Watson and Babul, Neurology, 1998). Similar observations have been reported with antidepressants, gabapentin and pregabalin (http://www.fda.gov/ohrms/dockets/ac/02/slides/38640PH1_01_Babul.ppt). The symptoms may be further categorized as "unprovoked" (stimulus-independent) and present when "provoked" (stimulus-induced). Provocation can include the application of a variety of mechanical or thermal stimuli.

Many terms may be used by patients with neuropathies to describe their painful neuropathic sensations. Clinical trials of putative analgesics will frequently assess: (i) steady pain (patient descriptors often include "burning", "aching", "stinging", "throbbing", "itching", "numbing", "pins & needles", "pulling"; (ii) brief pain (patient descriptors often include "sharp", "jabbing", "shooting", "electric"; and (iii) evoked pain (assessed by the clinician or self-reported using "mechanical" and "thermal stimulus"). (Watson and Babul, Neurology, 1998).

The diagnosis of peripheral neuropathy is often made by history and symptom presentation, although clinical neurophysiologic testing and nerve biopsies can provide useful information.

Pharmacological investigations have been conducted in a wide variety of painful neuropathies, particularly peripheral neuropathies. Among the peripheral neuropathies most widely investigated for pharmacologic response are painful diabetic neuropathy, postherpetic neuralgia, trigeminal neuralgia and painful HIV-associated distal symmetrical neuropathy.

It is estimated that approximately 20 million individuals in the United States have diabetes and about one-fifth of them suffer from painful diabetic neuropathy, which is a distal, symmetrical, axonal-sensory neuropathy usually involving the feet and legs initially and later the hands. Numbness and paresthesia are common presenting complaints. The paresthesia often involves a burning sensation. Patients often also have ongoing and paroxysmal pain. Nerve biopsies indicate a predominant axonal degeneration primarily involving small myelinated and unmyelinated fibers.

A limited number of treatment options are available for the treatment of painful diabetic neuropathy and only, two (pregabalin and duloxetine) have been approved by the Food and Drug Administration (FDA). The mean number needed to treat or NNT (defined as the number of patients who need to be treated for one patient to have $\geq 50\%$ pain relief) for most classes of drugs that have demonstrated efficacy in painful diabetic neuropathy has generally ranged from about 3 to 5, meaning that approximately 3 to 5 patients have to be treated for one patient to have $\geq 50\%$ pain relief. Additionally, few patients who respond obtain a complete response and the use of polypharmacy is quite common. Importantly, these pharmacologic agents can have troublesome side effects, an important issue given the co-morbid pathology in many patients with diabetes To the applicant's knowledge, there are no data from placebo controlled randomized clinical trials demonstrating the efficacy of any topically applied local anesthetic, including lidocaine and mepivacaine for the treatment of painful diabetic neuropathy.

There is a need for new pharmaceutical compositions and methods for the treatment of painful diabetic neuropathy.

There is a need for new topical pharmaceutical compositions and methods for the treatment of painful diabetic neuropathy.

There is a need for topical local anesthetic pharmaceutical compositions and methods for the treatment of painful diabetic neuropathy.

There is a need for new local anesthetic pharmaceutical compositions for application to the skin and methods for the treatment of painful diabetic neuropathy that have high efficacy.

There is a need for new local anesthetic pharmaceutical compositions for application to the skin and methods for the treatment of painful diabetic neuropathy that have good tolerability.

There is also a need for new local anesthetic pharmaceutical compositions for application to the skin and methods for the treatment of painful diabetic neuropathy that can be used in combination with other drugs, preferably drugs with different mechanisms of action and drugs with additive or synergistic effects.

HIV infection and HIV medications are both associated with the development of neuropathy which usually manifests as distal, symmetrical, predominantly sensory, polyneuropathy (DSPN) [Bailey et al, 1988; Corblath and MacArthur, 1988; Fuller et al, 1993]. The chief clinical complaints of persons with HIV-associated neuropathy are burning sensations in the soles of the feet, as well as paresthesias of the dorsum and soles of the feet. Typically, complaints of sensory problems are symmetrical, following a stocking distribution [Penfold and Clark, 1992]. Other findings include depressed or absent reflexes at the ankle, elevated thresholds to vibration, pinprick, and cold in the feet, and mild foot weakness. Hand sensation and strength are usually affected later in the disease. The clinical and electrophysiological features are consistent with a distal axonal degeneration of primary sensory neurons and this has been confirmed by morphological studies [Paice et al, 2000].

Causative factors include nerve infiltration by HIV and the toxicity of antiretrovirals such as didanosine (ddI) or zalcitabine (ddC) [Fuller et al, 1991; Grafe and Wiley, 1989; Griffin et al, 1994; Paice et al, 2000; Penfold and Clark, 1992; Rizzuto et al, 1995; Simpson and Olney, 1992].

While signs and symptoms of DSPN (paresthesia, depressed ankle reflexes, elevated thresholds to vibration and pinprick and foot weakness) can be bothersome, most are non-painful. A minority of patients have painful HIV-associated neuropathy. The mechanisms of painful symptoms associated with this polyneuropathy are also poorly understood. As a group, patients with a painful polyneuropathy present with decreased mechanical pain thresholds and increased responses to suprathreshold mechanical stimuli, suggestive of static mechanical allodynia (i.e. reduction in the mechanical pain threshold) and hyperalgesia (i.e. increased pain induced by suprathreshold mechanical stimuli). [Bouhasirra et al, 1999; Paice et al, 2000].

The epidemiology of HIV and AIDS has changed significantly since the introduction of highly active antiretroviral therapy (HAART), which has had a significant impact on suppressing HIV viral load, prolonging lifespan and improving the prognosis of the disease. In the developed world, where there is access to HAART, HIV infection is now considered by many to be a "chronic disease" rather than an acute fatal illness. Consequently, many patients with painful HIV-associated neuropathy have a chronic painful syndrome that can persist from several years to several decades.

Progressive and painful HIV-associated neuropathy significantly impairs patients' quality of life, and it impairs function, by rendering walking difficult. Painful HIV-associated neuropathy is also a toxicity of antiretroviral therapy and as such it limits patients' ability to remain on antiviral regimens containing these life saving compounds. The painful, disabling nature of painful HIV-associated neuropathy and the absence of an effective treatment has led to its characterization as "one of the most devastating and unresponsive complications of HIV disease" [Kemper et al, 1998]. Rosenfeld et al [1996] have demonstrated that pain has a substantial adverse impact on the psychological well-being and quality of life in ambulatory patients with AIDS.

It has been documented that painful HIV-associated neuropathy can lead to patient refusal to take anti-retroviral therapy, with potentially life threatening consequences. Previous studies have demonstrated that a compliance rate of <95% can lead to an increase in viral load. The recent premature discontinuation of enrollment in the SMART (Strategies for Management of Anti-Retroviral Therapy) study funded by MAID further underscores the need to minimize the complications of HAART. The study was designed to compare two approaches to anti-HIV drug therapy: continual anti-HIV drug therapy vs. "episodic" therapy guided by laboratory markers. It was conducted in part due to the difficulty with adherence to HAART (http://www.nlm.nih.gov/databases/alerts/aids_smart.html). The study was halted after just 15 months of the expected 3.5 year follow-up. Patients receiving episodic HAART had approximately 1.7 times the risk of disease progression than people receiving continuous therapy. This further underscores the view that non-compliance from complications of HAART, such as painful HIV-associated neuropathy can lead to serious health consequences.

To date no drug has been approved for painful HIV-associated neuropathy. Several therapies have been evaluated for the treatment of painful HIV-associated neuropathy. With the exception of recombinant nerve growth factor [McArthur et al, 2000] and Lamictal® (lamotrigine) [Simpson et al, 2000; Simpson et al, 2003], most treatments, including mexiletine, peptide T, acupuncture and amitriptyline have demonstrated no significant benefit for this debilitating condition [Kemper et al, 1998; Kieburtz et al, 1998; Schlay et al, 1998; Simpson et al, 1996].

Unfortunately, lamotrigine is not approved by the FDA for this indication and can produce both serious and bothersome side effects, including serious rashes requiring hospitalization and discontinuation of treatment, Stevens-Johnson syndrome, toxic epidermal necrolysis, rash-related death, permanently disabling or disfiguring consequences from rashes, fatal or life threatening hypersensitivity reactions, multiorgan failure, hepatic abnormalities, disseminated intravascular coagulation and blood dyscrasias, including neutropenia, leukopenia, anemia, thrombocytopenia, pancytopenia, and, rarely, aplastic anemia and pure red cell aplasia (Lamictal™ United States Prescribing Information, 2006).

In addition to its potential for serious and life threatening toxicity, lamotrigine demonstrates only modest efficacy in painful HIV-associated neuropathy and few patients obtain a complete response. Therefore, the use of polypharmacy is quite common.

To the applicant's knowledge, there are no data from placebo controlled randomized clinical trials demonstrating the efficacy of any topically applied local anesthetic, including lidocaine and mepivacaine for the treatment of painful HIV-associated neuropathy. Indeed, in the only placebo controlled randomized clinical trial of topical lidocaine, there were no significant efficacy differences from placebo [Estanislao et al, J Acquir Immune Defic Syndr. 2004 Dec. 15; 37:1584-6.].

There is a need for new pharmaceutical compositions and methods for the treatment of painful HIV-associated neuropathy.

There is a need for new topical pharmaceutical compositions and methods for the treatment of painful HIV-associated neuropathy.

There is a need for new local anesthetic pharmaceutical compositions for application to the skin and methods for the treatment of painful HIV-associated neuropathy.

There is a need for new local anesthetic pharmaceutical compositions for application to the skin and methods for the treatment of painful HIV-associated neuropathy that have high efficacy.

There is a need for new local anesthetic pharmaceutical compositions for application to the skin and methods for the treatment of painful HIV-associated neuropathy that have good tolerability.

There is a need for new local anesthetic pharmaceutical compositions for application to the skin and methods for the treatment of painful HIV-associated neuropathy that can be used in combination with other drugs, preferably drugs with different mechanisms of action and drugs with additive or synergistic effects.

Herpes zoster, also known Varicella-Zoster or shingles is a viral infection whose pathology is characterized by acute inflammation. The clinical syndrome associated with acute herpes zoster is readily identified by a rash and vesicular eruption, with subsequent crusting. Pain or itching frequently precede the appearance of the rash by several days. Although it is painful, acute herpes zoster is transient.

In a small minority of patients with the painful but self-limiting condition of herpes zoster (also known as Varicella-Zoster or shingles), the pain persists after the healing of the acute lesions and a chronic pain state develops (Watson et al., 1991; Watson, 1989; Watson et al., 1988). This pain is referred to ad postherpetic neuralgia (PHN). The pain of PHN is unrelenting and is characterized by burning, aching or itching with superimposed lancinating pains.

Hyperesthesia, dysesthesia and allodynia frequently accompany the neuralgia. The most common anatomic sites for herpes zoster and postherpetic neuralgia are the midthoracic dermatomes and the ophthalmic division of the trigeminal nerve, but they may occur in any dermatome. Most patients have ongoing pain (often described variously as burning, aching or tearing) as well as superimposed paroxysmal pains (often described as stabbing, shooting or shock-like). In addition to pain, patients frequently report unpleasant skin sensitivity. Otherwise non-noxious thermal (e.g., gentle cool breeze) and mechanical (e.g., wearing a shirt) will often exacerbate the pain in patients (allodynia) and this allodynia is often the most unbearable part of postherpetic neuralgia. In a most patients with postherpetic neuralgia, the pain resolves spontaneously in the first year, although some patients may have prolonged pain (Watson, 1989).

Three drugs are approved in the United States for the management of postherpetic neuralgia: (i) topical lidocaine patch (Lidoderm™); (ii) oral gabapentin (Neurontin™) and (iii) oral pregabalin (Lyrica™). A number of drugs, including the opioid OxyContin® (Watson and Babul, 1998), tricyclic antidepressants (Max, 1995; Sindrup, 1999) and tramadol (Boureau et al., 2003) have demonstrated efficacy in postherpetic neuralgia and are used "off-label".

The efficacy of topical lidocaine has been rather modest. Rowbotham et al (Pain, 1996) demonstrated that lidocaine patch was superior to placebo in a 35 patient study, although a majority of patients reported only modest pain relief and the study involved two 12-hour applications, unlike the 3 month parallel group studies that are now required by the FDA and other major regulatory agencies. The efficacy of the lidocaine patch was also evaluated over 2 weeks in a placebo controlled study involving 32 patients (Galer et al., Pain, 1999). Lidocaine patch was superior to placebo, but the study involved an enrichment design, i.e., only patients who had previously been successfully treated with the lidocaine were included. In another prospective, randomized, double-blind, vehicle controlled study, lidocaine patch was superior to placebo over three weeks of treatment, although the difference between drug treatment and placebo was rather modest (Galer et al, Clin J Pain, 2002). In another study, Meier et al (Pain, 2003) assessed the efficacy of lidocaine patch in 58 patients with painful peripheral neuropathies (approximately 55% of the patients had postherpetic neuralgia), using a randomized, placebo-controlled, two-way, cross-over study. This study reported numbers needed to treat (NNT). The NNT for ongoing pain was 4.4 (95% CI 2.5-17.5). This means that on average, 4.4 patients need to be treated for one patient to obtain ≥50% relief from ongoing pain. The NNT for a 50% reduction of allodynia was 8.4 (95% CI 3.5-∞). This means that on average, approximately 8 patients need to be treated for one patient to obtain ≥50% relief from allodynia. In the study by Meier, the effect size for reduction of ongoing pain was 0.4. Meir et al. note that "a general interpretation of the ES suggests that an ES of 0.2 is small, an ES of 0.5 is medium, and an effect size of 0.8 is high (Cohen, J. Statistical power analysis for behavioral sciences. Hillsdale: Erlbaum; 1988). Other pharmacologic agents used in PHN patients, such as gabapentin (Rowbotham et al., JAMA, 1998) and oxycodone (Watson and Babul, Neurology, 1998) showed higher effect size's up to 0.75." There are no studies of topical mepivacaine in PHN.

There is a need for new pharmaceutical compositions and methods for the treatment of postherpetic neuralgia.

There is a need for new topical pharmaceutical compositions and methods for the treatment of postherpetic neuralgia.

There is a need for new local anesthetic pharmaceutical compositions for application to the skin and methods for the treatment of postherpetic neuralgia.

There is a need for new local anesthetic pharmaceutical compositions for application to the skin and methods for the treatment of postherpetic neuralgia that have high efficacy.

There is a need for new local anesthetic pharmaceutical compositions for application to the skin and methods for the treatment of postherpetic neuralgia that have improved efficacy over lidocaine patch (Lidoderm™).

There is a need for new local anesthetic pharmaceutical compositions for application to the skin and methods for the treatment of postherpetic neuralgia that have good tolerability.

There is a need for new local anesthetic pharmaceutical compositions for application to the skin and methods for the treatment of postherpetic neuralgia that have improved efficacy over lidocaine patch (Lidoderm™) without an increase in local toxicity.

There is also a need for new local anesthetic pharmaceutical compositions for application to the skin and methods for the treatment of postherpetic neuralgia that have improved efficacy over lidocaine patch (Lidoderm™) without an increase in systemic toxicity.

There is also a need for new local anesthetic pharmaceutical compositions for application to the skin and methods for the treatment of postherpetic neuralgia that can be used in combination with other drugs, preferably drugs with different mechanisms of action and drugs with additive or synergistic effects.

There is a need for new local anesthetic pharmaceutical compositions and methods for the treatment of postherpetic neuralgia that have improved efficacy over lidocaine patch (Lidoderm™).

There is a need for local anesthetic pharmaceutical compositions for application to the skin and methods for the treatment of neuropathy, neuropathic pain and chronic pain that have improved tolerability over lidocaine.

There is a need for local anesthetic pharmaceutical compositions for application to the skin and methods for the treatment of postherpetic neuralgia that have good tolerability.

There is a need for local anesthetic pharmaceutical compositions for application to the skin and methods for the treatment of neuropathy, neuropathic pain and chronic pain that have reduced potential for neurotoxicity than lidocaine.

One challenge in the treatment of peripheral sources of neuropathy, mechanical and thermal allodynia, hyperalgesia and ongoing pain in patients with peripheral neuropathic pain and chronic pain relates to attaining adequate and sustained concentrations of drug at the peripheral sites pain initiation, pain propagation and pain maintenance. This is particularly problematic with application of drugs through the skin. Another challenge in attaining adequate and sustained concentrations of drug at the peripheral sites of pain initiation, pain propagation and pain maintenance is that such high concentrations have the potential of producing systemic toxicity (e.g., cardiac and CNS toxicity). The selection of mepivacaine for the present invention is also beneficial in this regard because unlike lidocaine and many other anesthetics, mepivacaine has intrinsic vasoconstrictor effects, thereby reducing the rate at which drug is cleared (away) from peripheral sites of pain. This allows mepivacaine to provide adequate and sustained concentrations of drug at the peripheral sites pain initiation, pain propagation and pain maintenance with a reduced risk of systemic toxicity (e.g., cardiac and CNS toxicity).

As noted before, topical lidocaine patch provides only modest pain relief in patients with postherpetic neuralgia, with an NNT of 4.4 patients for one patient to obtain ≥50% relief from ongoing pain and an NNT of 8.4 patients for one patient to obtain ≥50% relief from allodynia. This is in contrast to NNT's for other systemically administered drugs. Collins et al. analyzed data from randomized trials to calculate NNT values for antiepileptics and antidepressants used to treat neuropathic pain in patients with PHN [J Pain Symptom Manage, 2000; Backonja and Serra, Pain Medicine, 2004]. They report that the NNT to obtain a ≥50% pain relief in one patient is 3.2 for antiepileptics and 2.1 for antidepressants. Sindrup and Jensen reported NNT values of 2.3 for TCA's, 2.5 for oxycodone, and 5.3 for topical capsaicin in postherpetic neuralgia (Pain, 1999; Backonja and Serra, Pain Medicine, 2004).

There is a need for new local anesthetic pharmaceutical compositions for application to the skin and methods for the treatment of postherpetic neuralgia and other neuropathic pain states.

There is a need for new local anesthetic pharmaceutical compositions for application to the skin and methods for the treatment of postherpetic neuralgia and other neuropathic pain states with high efficacy.

There is a need for new local anesthetic pharmaceutical compositions for application to the skin and methods for the treatment of postherpetic neuralgia and other neuropathic pain states with improved efficacy, but without increased local or systemic toxicity.

Postherpetic neuralgia and other painful peripheral neuropathies are not merely conditions characterized by ectopic impulses from irritable or otherwise injured neurons and nociceptors. For example, in the case of postherpetic neuralgia, in the months following the acute herpes zoster lesions, fibrosis has been documented in the dorsal root ganglion, peripheral nerve and nerve root. In post-mortem studies, findings of dorsal horn atrophy and cell, axon and myelin loss with fibrosis in the sensory ganglion have been shown only in patients with persistent pain (Watson et al., 1991; Watson, 1989; Watson et al., 1988). In one patient who had had postherpetic neuralgia for 22 months prior to death, there were marked inflammatory changes with lymphocytic infiltration bilaterally in the dorsal root ganglia of four adjacent segments. Recently, Petersen and Rowbotham (Pain 2007; 1-2:214-28) have demonstrated that surgical removal of painful thoracic skin comprising the entire area of pain and allodynia in a patient with PHN provided benefit in the form of reduced pain, elimination of allodynia, and reduced medication consumption during the first post-operative year. Unfortunately, pain steadily increased over time and now exceeds pre-surgery levels despite increased medication use. These finding provide further support to a complex interplay between peripheral and central mechanisms even in "peripheral" neuropathy and "peripheral" neuropathic pain The data indicate that in postherpetic neuralgia, changes in both the central and peripheral nervous system contribute to the initiation, maintenance and propagation of pain.

There is a need therefore for new local anesthetic pharmaceutical compositions for application to the skin and methods for the treatment of postherpetic neuralgia that target both peripheral and central mechanisms of the pain.

Similarly, in painful diabetic neuropathy, there are changes in the dorsal root ganglion, including abnormal expression of sodium channels, which indicate that in addition to irritable nociceptors in the peripheral nerve terminals, the spinal cord may provide a target for the treatment of painful diabetic neuropathy.

There is a need therefore for new local anesthetic pharmaceutical compositions for application to the skin and methods for the treatment of painful diabetic neuropathy that target both peripheral and central mechanisms of the pain.

In painful HIV-associated neuropathy, it has been demonstrated that the two major presumed causes of neuropathic pain, namely secreted viral envelope glycoproteins (gp 120) and anti-retroviral therapy result in dorsal root ganglion neuronal death, axonal degeneration and mitochondrial membrane depolarization.

There is a need therefore for new local anesthetic pharmaceutical compositions for application to the skin and methods for the treatment of painful HIV-associated neuropathy that target both peripheral and central mechanisms of the pain.

The inefficacy and suboptimal efficacy of topically applied lidocaine in many patients with peripheral neuropathy and peripheral neuropathic pain provides a pharmacologic basis for improving the overall efficacy of local anesthetics for the treatment of peripheral neuropathy by modulating spinal and supraspinal (central) mechanisms of peripheral neuropathic pain, in addition to peripheral mechanisms. Such central mechanisms may be particularly important in patients with peripheral neuropathy and peripheral neuropathic pain who have significant loss of nerve fiber in the periphery and in patients with no mechanical and tactile allodynia.

There is therefore also a need for new local anesthetic pharmaceutical compositions for application to the skin and methods for the treatment of various peripheral neuropathies that target both peripheral and central mechanisms of the pain.

As noted above, there are central nervous system (CNS) consequences to peripheral nervous system (PNS) injury. For example, peripheral nerve transection or partial ligation results in changes in expression of a large number of molecules in the in the sensory dorsal root ganglia. These molecules include enzymes, G-protein-coupled receptors, neuropeptides and ion channels. There is evidence that nerve injury-induced phenotypic changes in the dorsal horn may be responsible for neuropathic pain. In contrast to neuropathic pain, most of the changes observed in DRG's after nerve injury are not observed after inflammatory pain.

Many changes occur in dorsal root ganglion and the spinal cord in response to peripheral nerve injury. Some of the changes may play a role in the generation and maintenance of neuropathic pain. In the spinal cord, the terminals of sensory afferents undergo plasticity, including reduced inhibitory control in the spinal cord, expanded receptive fields, ongoing activity and after-discharges. The overall excitatory drive in the dorsal horn may also be increased via an NMDA mechanism.

There is therefore a need for new local anesthetic pharmaceutical compositions for application to the skin and methods for the treatment of various peripheral neuropathies that target both local anesthetic responsive aberrant peripheral and central mechanisms of the neuropathic pain.

In a book on neuropathic pain, Galer (an investigator and author of three out of the four randomized clinical trials on Lidoderm™) and the former VP, Scientific Affairs at Endo Pharmaceutical Inc. (the company that currently owns intellectual property rights and markets the Lidoderm™ patch) notes about the mechanism of action of Lidoderm® patch: "Lidocaine is a local anesthetic agent whose main mechanism of action in neuropathic pain is believed to be sodium channel blockade in damaged or dysfunctional peripheral nerves. By binding to the sodium channel of nerves of the skin, there is a reduction in ectopic impulse generation and thus less pain . . . . . In clinically studies, it has been shown that the lidocaine patch does not produce clinically relevant serum levels" (Galer and Dworkin, A Clinical Guide to Neuropathic Pain, Healthcare Information, a Division of McGraw-Hill, 2000). Another textbook chapter by the same author, under a section titled "Mechanism of Action", notes the following about Lidoderm® patch "Lidocaine applied topically is thought to provide relief by reducing ectopic discharges in the superficial somatic nerves. In addition, the topical patch may protect the allodynic postherpetic neuralgia skin from direct mechanical stimulation" (p. 124. Galer B S and Argoff C E. Zoster and Postherpetic Neuralgia: In Evaluation and Treatment of Chronic Pain, Aronoff G M (Ed), Third Edition, Williams & Wilkins, B).

The President and Chief Executive Officer of Endo Pharmaceutical Inc., the company that owns intellectual property rights and markets the Lidoderm™ patch made the following statement from prepared text with regard to Lidoderm™ patch: "It should be noted that unlike transdermal systemic patches, Lidoderm is a topical product that works locally only at the site of application, rather than through systemic absorption of the active ingredient" and "We believe that systemic blood levels have no therapeutic relevance or any demonstrated correlation to Lidoderm's effect on the pain associated with postherpetic neuralgia. I would also like to point out that Lidoderm produces its therapeutic effect of local analgesia without introducing complete sensory nerve block." (Transcript of Endo Pharmaceutical Press Conference and Webcast, Oct. 17, 2006, entitled "Lidoderm Conference Call")

The Executive Vice President, Research & Development and Chief Scientific Officer of Endo Pharmaceutical Inc., the company that owns intellectual property rights and markets the Lidoderm patch notes: "well, you know there are blood levels measurable, blood levels of lidocaine measurable after application of Lidoderm® but those blood levels are we believe irrelevant to the therapeutic efficacy of the product and only have relevance for assessing the safety of the product. Lidoderm is clearly described in the package insert to be applied to the site of pain, which only reinforces the fact that this a product that works locally, its mechanism of effect on the pain locally, and any blood levels that are generated are, again, have no systemic therapeutic relevance" and "We have no evidence that these blood levels are in any way correlated to efficacy and their only relevance is to assess the safety of the product" (Transcript of Endo Pharmaceutical Press Conference and Webcast, Oct. 17, 2006, entitled "Lidoderm Conference Call"). These concepts are reiterated in Endo Pharmaceuticals Citizen's Petition to the FDA (http://www.fda.gov/ohrms/dockets/dockets/06p0522/06p-0522-amd0001-02-vol2.pdf, Dec. 18, 2006, Petition No. 2006P-0522, Accessed Jan. 8, 2008).

The present invention relates to topical and transdermal mepivacaine pharmaceutical compositions and methods for the treatment of painful neuropathies.

The present inventions relates to topical and transdermal mepivacaine pharmaceutical compositions and methods for the treatment of painful neuropathies that target both mepivacaine responsive aberrant peripheral and central mechanisms of the neuropathic pain, without significant untoward toxicity.

In the case of peripheral neuropathic pain, the applicant believes that peripheral nociceptor sensitization is only one of many mechanisms of neuropathic pain. Other important mechanisms include: (i) enhanced membrane excitability of primary afferents; (ii) enhanced synaptic transmission; (iii) central disinhibition (iv) descending facilitatory activity (descending facilitation); and (v) central reorganization. Consequently, and without being bound by theory, the applicant's pharmaceutical compositions and methods target peripheral, systemic and central mechanisms of pain initiation, propagation, maintenance and integration which are responsive to "local" anesthetics.

Like neuropathic pain, non-neuropathic chronic pain or chronic non-neuropathic pain ("chronic pain") is a major health problem that afflicts a significant number of patients, resulting in personal suffering, reduced productivity and substantial health care costs. There are important differences between neuropathic and non-neuropathic pain. Neuropathic pain is defined as pain following injury to nerves or as a consequence of nerve dysfunction. In contrast, chronic pain can be caused by a variety infectious, genetic, physiologic, pathologic, mechanical and inflammatory factors and it involves many anatomic locations and tissue types. In many cases of chronic pain, the etiology of the chronic pain is unclear.

The distinction between neuropathic and non-neuropathic pain reflects partially distinct mechanisms and patterns of treatment response. Dworkin et al (Journal of Pain, In Press, 2006. DOI: 10.1016/j.jpain.2006.06.005) recently tested whether patients with neuropathic and non-neuropathic pain have different profiles of symptoms and signs. Pain intensity, unpleasantness, quality, and spatial characteristics were examined in patients with peripheral neuropathic pain conditions (painful diabetic peripheral neuropathy, painful idiopathic sensory polyneuropathy, or postherpetic neuralgia) and compared with those in patients with chronic non-neuropathic pain (osteoarthritis pain or low back pain). Patients with osteoarthritis pain and low back pain did not differ from each other in their profile of pain quality and spatial characteristics. Patients with peripheral neuropathic pain reported significantly more intense hot, cold, sensitive, itchy, and surface pain and significantly less intense dull and deep pain than patients with non-neuropathic chronic pain. The overall pattern of pain quality and spatial characteristics differed significantly between patients with neuropathic and non-neuropathic pain. This study demonstrated that specific pain symptoms differ between patients with peripheral neuropathic pain and those with non-neuropathic chronic pain. Specifically, patients with neuropathic pain reported significantly more intense hot, cold, sensitive, itchy, and surface pain and significantly less intense dull and deep pain than patients with non-neuropathic chronic pain.

Chronic pain includes back pain, rheumatoid arthritis, osteoarthritis, inflammatory pain, non-inflammatory pain, myofascial pain, fibromyalgia, cancer pain, visceral pain, somatic pain, pelvic pain, musculoskeletal pain and idiopathic pain.

Musculoskeletal conditions such as low back pain, myofascial pain and joint pain are the leading causes of disability in individuals of working age. A congressionally mandated Committee on Pain, Disability and Chronic Illness Behavior of the Institute of Medicine noted that total disability expenditures among working adults in the United States more than doubled between 1970 and 1982 from $60.2 billion to $121.5 billion in real 1982 dollars, and social security disability insurance benefits increased by 778% between 1960 and 1985, far outstripping the 135% increase in the working population insured for disability. According to the American College of Rheumatology, OA affects more than 21 million Americans; it accounts for more than 7 million physician visits and 36 million lost work days annually and in 1995, the total cost of arthritis was estimated to be in excess of 82 billion dollars. Recently, the Center for Disease Control (CDC) issued revised estimates of the number of adults with arthritis and chronic joint symptoms at 70 million, a substantial increase over the previous estimates. There is, therefore, a need for optimized pharmacologic and nonpharmacologic treatment strategies for the management of chronic nonmalignant pain.

Chronic non-neuropathic pain states are also associated with spinal and supraspinal changes which can initiate, maintain, propagate and integrate pain. For example inflammation causes the induction of cyclooxygenase-2 (COX-2), leading to the release of prostanoids, which sensitize peripheral nociceptor terminals and produce localized pain hypersensitivity. Peripheral inflammation also generates pain hypersensitivity in neighboring uninjured tissue (secondary hyperalgesia) due to increased neuronal excitability in the spinal cord (central sensitization). There is widespread induction of COX-2 expression in spinal cord neurons and in other regions of the CNS, which elevates prostanoid levels in the cerebrospinal fluid. Prostanoids contribute to the development of peripheral sensitization through protein kinase A-mediated phosphorylation of sodium channels in nociceptor terminals, increasing excitability and reducing the pain threshold. [Samad et al., Nature 2001:410:771-75].

Low back pain is also an important is associated with high healthcare utilization, time away from work and disability. The subgroup of patients with chronic low back pain, which comprises approximately 5 to 10% of patients with low back pain is responsible for a majority of the health care utilization in this population. Low back pain is usually defined as pain, muscle stiffness localized below the costal margin and above the inferior gluteal folds, with or without leg pain (sciatica). Low back pain is typically classified as being 'specific' or 'non-specific'. Approximately 90% of patients have non-specific low back pain, which is defined as symptoms without an identified etiology.

Treatment of chronic low back pain involves exercise, NSAIDs, COX-2 inhibitors, and opioid analgesics. A majority of patients with chronic back pain obtain little or no relief from available therapies.

Apkarian et al. [J Neurosci 2004; 24:10410-15] recently reported the results of the first study that showed brain morphometric abnormalities in chronic pain. The study compared brain morphology of 26 chronic back pain (CBP) patients to matched control subjects, using magnetic resonance imaging. Patients with CBP showed 5-11% less neocortical gray matter volume than control subjects. The magnitude of this decrease was equivalent to the gray matter volume lost in 10-20 years of normal aging. The decreased volume was related to pain duration, indicating a 1.3 cm$^3$ loss of gray matter for every year of chronic pain. The observed regional pattern of atrophy was distinct from that seen in chronic depression or anxiety and appears to be specific to chronic pain, especially because the regions showing atrophy, the thalamus and dorsolateral prefrontal cortex participate in pain perception. Gray matter density was reduced in bilateral dorsolateral prefrontal cortex and right thalamus and was strongly related to pain characteristics in a pattern distinct for neuropathic and non-neuropathic CBP. The results suggest that CBP is accompanied by brain atrophy and suggest that the pathophysiology of chronic pain includes thalamocortical processes.

There is a need for new therapies for the treatment of CBP.

There is a need for new topical and transdermal therapies for the treatment of CBP.

There is a need for new topical and transdermal therapies for the treatment of the CBP that work through new and different mechanism from existing therapies for CBP.

There is a need for additional topical and transdermal therapies for CBP that work through a spinal and supraspinal mechanism.

There is a need for local anesthetic pharmaceutical compositions for application to the skin and methods for the treatment of the CBP.

There is a need for local anesthetic pharmaceutical compositions for application to the skin and methods for the treatment of the CBP.

There is a need for local anesthetic pharmaceutical compositions for application to the skin and methods for the treatment of the CBP with improved efficacy, but without increased local or systemic toxicity.

Osteoarthritis is a degenerative disease involving the synovial joints and is characterized by focal loss of cartilage, hypertrophic reaction at the margin of joints and sclerosis in the subchondral bone. It can involve axial, spinal or peripheral joints, including those that bear weight, such as the hips and knees. Changes in cartilage are characterized by degeneration, regeneration and microfractures. An estimated 40 million people in the United States have signs and symptoms of osteoarthritis, making it an important public health issue. Pathologic changes result in symptoms, including joint pain, stiffness, swelling, decreased mobility, instability and deformity.

In a survey of symptoms in 500 patients with osteoarthritis, use-related pain was recorded in 89% of patients, compared with pain at night in 59% and pain at rest in 44%. The innervation of synovial joints and their relationship to nociception has been described by several investigators. The capsule, ligaments and their insertions are the areas of greatest innervation, although there is also substantial innervation to the periosteum close to joint margins and the blood vessels supplying the synovium and subchondral bone.

Osteoarthritis pain has largely been viewed as a pain limited to nociception from the affected joint. Bajaj et al (Pain, 2001:93:107-114) recently demonstrated manifestations of central sensitization to muscle nociceptor input in patients with osteoarthritis. Patients with osteoarthritis had significantly higher local pain duration and intensity, larger pain areas and significantly increased referred and radiating pain intensity after infusion of hypertonic saline in the legs as compared with the healthy controls. Bajaj et al propose that long term nociceptive input from the osteoarthritic joints result in central sensitization in the spinal cord.

Current management of OA is symptomatic and directed primarily towards relief of pain, optimization of joint function and minimization of disability. Nonpharmacologic management is aimed at improving range of motion, increasing muscle strength and restoring favorable mechanics. Drug treatment includes nonsteroidal anti-inflammatory drugs (NSAIDs), Cox-2 inhibitors, acetaminophen and opioids. Although NSAIDs are effective in ameliorating the symptoms of osteoarthritis, their inhibition of COX-1 is believed to be responsible for a number of common and severe adverse effects, including coagulopathies, gastrointestinal injury and renal impairment. Elderly patients, who are more likely to have symptomatic and disabling osteoarthritis, are particularly prone to NSAID-induced gastropathy and nephropathy. COX-2 inhibitors carry a variety of iatrogenic adverse effects including cardiovascular effects. Chronic acetaminophen use has been associated with both the risk of developing end-stage renal disease and hepatic impairment. Opioids have also demonstrated efficacy in the pain of OA [Peloso et al., Journal of Rheumatology 2000; 27:764-71; Caldwell et al., Journal of Pain and Symptom Management 2002; 23:278-91; Babul et al., Journal of Pain and Symptom Management 2004; 28:59-71; Matsumoto et al., Pain Medicine 2005; 6:357-66].

There is a need for new therapies for the treatment of the chronic pain of osteoarthritis.

There is a need for new topical and transdermal therapies for the treatment of the chronic pain of osteoarthritis.

There is a need for new topical and transdermal therapies for the treatment of the chronic pain of osteoarthritis that work through new and different mechanism from existing therapies for OA.

There is a need for additional topical and transdermal therapies for the chronic pain of osteoarthritis that work through a spinal and supraspinal mechanism.

There is a need for local anesthetic pharmaceutical compositions for application to the skin and methods for the treatment of the chronic pain of osteoarthritis.

There is a need for local anesthetic pharmaceutical compositions for application to the skin and methods for the treatment of the chronic pain of osteoarthritis with high efficacy.

There is a need for local anesthetic pharmaceutical compositions for application to the skin and methods for the treatment of the chronic pain of osteoarthritis with improved efficacy, but without increased local or systemic toxicity.

Fibromyalgia is a chronic pain syndrome of unknown etiology characterized by diffuse pain and tender points, which must be present for more than 3 months. A majority of fibromylagia patients are female. Patients complain of pain, insomnia, fatigue, and psychological distress. Additionally, patients may have co-morbid pathology with pain similar to fibromylagia, including polymyalgia rheumatica, rheumatoid arthritis, and inflammatory myopathies. Most fibromylagia patients report the insidious onset of pain and fatigue. However, almost 50% of patients describe the onset of chronic pain after a traumatic event. In 1990 the American College of Rheumatology produced new diagnostic criteria for Fibromyalgia. The criteria require the presence of widespread chronic pain (>3 months) and tender points (11 out of 18).

There is significant evidence for the presence of widespread hyperalgesia in fibromylagia patients. Fibromylagia patients show increased sensitivity to mechanical, thermal, and electrical stimuli. This would suggest that abnormal central pain mechanisms may be important to the pain experience of fibromylagia patients. Patients with fibromyalgia show psychophysical evidence of mechanical, thermal, and electrical hyperalgesia. Peripheral and central abnormalities of nociception have been described in fibromyalgia. Important nociceptor systems in the skin and muscles seem to undergo profound changes in patients with fibromyalgia through unknown mechanisms. They include sensitization of vanilloid receptor, acid-sensing ion channel receptors, and purino-receptors. Tissue mediators of inflammation and nerve growth factors can excite these receptors and cause extensive changes in pain sensitivity, but patients with fibromyalgia lack consistent evidence for inflammatory soft tissue abnormalities. Evidence suggests that fibromyalgia pain is maintained by tonic impulse input from deep tissues, such as muscle and joints, in combination with central sensitization mechanisms. This nociceptive input may originate in peripheral tissues resulting in hyperalgesia/allodynia and/or central sensitization. Evidence for abnormal sensitization mechanisms in fibromyalgia includes enhanced temporal summation of delayed pain in response to repeated heat taps and repeated muscle taps, as well as prolonged and enhanced painful after-sensations in fibromyalgia patients. Abnormal temporal summation of second pain (wind-up) and central sensitization have been described in patients with fibromyalgia. Wind-up and central sensitization, which rely on central pain mechanisms, occur after prolonged C-nociceptor input. Other abnormal central pain mechanisms recently detected in patients with fibromyalgia include diffuse noxious inhibitory controls. These pain inhibitory mechanisms rely on spinal cord and supraspinal systems involving pain facilitatory and pain inhibitory pathways.

A wide variety of pharmacologic agents have been evaluated for the treatment of fibromyalgia, including cyclobenzaprine, tricyclic antidepressants, NSAIDs, SSRI's, SNRI's and gabapentinoids. Most available treatments have demonstrated poor efficacy in the treatment of fibromylagia and none has been approved by the FDA. There is a need for new therapies for the treatment of fibromyalgia.

There is a need for new topical and transdermal therapies for the treatment of fibromyalgia.

There is a need for new topical and transdermal therapies for the treatment of fibromyalgia that work through new and different mechanism from existing therapies.

There is a need for additional topical and transdermal therapies for fibromyalgia that work through a spinal and supraspinal mechanism.

There is a need for local anesthetic pharmaceutical compositions for application to the skin and methods for the treatment of fibromyalgia.

T There is a need for local anesthetic pharmaceutical compositions for application to the skin and methods for the treatment of fibromyalgia with high efficacy.

There is a need for local anesthetic pharmaceutical compositions for application to the skin and methods for the treatment of fibromyalgia with improved efficacy, but without increased local or systemic toxicity.

There is a need for new topical and transdermal therapies for the treatment of chronic pain that work through new and different mechanism from existing therapies.

There is a need for additional topical and transdermal therapies for chronic pain that work through a spinal and supraspinal mechanism.

There is a need for local anesthetic pharmaceutical compositions for application to the skin and methods for the treatment of chronic pain.

There is a need for local anesthetic pharmaceutical compositions for application to the skin and methods for the treatment of chronic pain with robust efficacy.

There is a need for local anesthetic pharmaceutical compositions for application to the skin and methods for the treatment of chronic pain with improved efficacy, but without increased local or systemic toxicity.

Mepivacaine was synthesized in the mid 1950's in Sweden and introduced into clinical medicine in 1957 as an injectable local anesthetic. Presently mepivacaine is indicated "for the production of local or regional analgesia and anesthesia by local infiltration, peripheral nerve block techniques, and central neural techniques including epidural and caudal blocks."

To the applicant's knowledge, there are no described formulations or therapeutic trials of mepivacaine in the prior art to treat neuropathic pain. To the applicant's knowledge, there are no described topical and transdermal formulations or therapeutic trials of mepivacaine in the prior art to treat neuropathic pain.

To the applicant's knowledge, there are no described formulations or therapeutic trials of mepivacaine in the prior art to treat chronic pain. To the applicant's knowledge, there are no described topical and transdermal formulations or therapeutic trials of mepivacaine in the prior art to treat chronic pain.

To the applicant's knowledge, mepivacaine has not been administered by the topical or transdermal route for the treatment of any acute or chronic pain.

The present invention relates to topical and transdermal mepivacaine pharmaceutical compositions and methods for the treatment of acute pain, neuropathy, neuropathic pain and chronic pain. In some embodiments, the invention contemplates topical and transdermal application to the skin which provides therapeutically effective mepivacaine concentrations to target both the aberrant peripheral and central mechanisms of neuropathy, neuropathic pain and chronic pain. In some embodiments, the invention further contemplates topical and transdermal application to the skin which provides therapeutically effective mepivacaine concentrations to target both the aberrant peripheral and central mechanisms of neuropathy, neuropathic pain and, without significant toxicity.

To the applicant's knowledge, with the exception of application by skin infiltration for the treatment of acute postsurgical pain, there are no: (i) recommendations on mepivacaine application to the skin for the management of pain, including acute pain, neuropathy, neuropathic pain and chronic pain; (ii) no public data or prior art on mepivacaine application to the skin for the management of pain, including acute pain, neuropathy, neuropathic pain and chronic pain; (iii) no approved mepivacaine product for application to the skin for the management of pain, including acute pain, neuropathy, neuropathic pain and chronic pain; and (iv) no mepivacaine products for application to the skin in development, regulatory review or on the market any major market.

Definitions

The term "mepivacaine" is defined for purposes of the invention as racemic mepivacaine, R(−)-mepivacaine, S(+)-mepivacaine or mixtures thereof in various proportions, given as free base of as pharmaceutically acceptable salts, their esters, solvates, complexes, polymorphs and hydrates or mixture thereof. Preferably, the mepivacaine in the dosage form is racemic mepivacaine as the unsalified form (free base) or a pharmaceutically acceptable salt thereof or a mixture thereof.

Commercially, mepivacaine ($C_{15}H_{22}N_2O$) is available as the hydrochloride salt of racemic mepivacaine ($C_{15}H_{22}N_2O$—HCl), also known as 2-Piperidinecarboxamide, (±)-1-Methyl-2',6'-pipecoloxylidide monohydrochloride; (RS)—N-(2,6-dimethylphenyl)-1-methylpiperidine-2-carboxamide; N-Methylpipecolinoyl-2,6-xylidide; N-(2,6-dimethylphenyl)-1-methyl-, monohydrochloride; 1-Methyl-2',6'-pipecoloxylidide; N-(2,6-dimethylphenyl)-1-methylpiperidine-2-carboxamide; and 2-Piperidinecarboxamide, N-(2,6-dimethylphenyl)-1-methyl-, monohydrochloride, with a CAS number of 1722-62-9 (HCl) and a molecular weight (HCl) of 282.81.

The term "pharmaceutically acceptable salt" as used herein refers to a salt which is toxicologically safe for human and animal administration. Nonlimiting examples of salts include hydrochlorides, hydrobromides, hydroiodides, sulfates, bisulfates, nitrates, citrates, tartrates, bitartrates, phosphates, malates, maleates, napsylates, fumarates, succinates, acetates, terephlhalates, pamoates and pectinates. Any pharmaceutically acceptable salt may be incorporated in the dosage form. A particularly preferred salt is the hydrochloride salt.

As used herein, Lidoderm™ patch refers to the 5% lidocaine patch listed in FDA's Orange Book. In the absence of a commercially available Lidoderm™ patch marketed by Endo Pharmaceuticals, its affiliates or licensees in the USA, the commercially available Versatis™ 5% medicated plaster marketed in Europe by Grunenthal, its affiliates or licensees in may be substituted for testing. Both Lidoderm™ patch and Versatis™ 5% medicated plaster are manufactured by Teikoku Seiyaku Co., Ltd. In the absence of a commercially available Lidoderm™ patch and Versatis™ 5% medicated plaster, a lidocaine patch which is listed in the Orange Book as A/B generic (bioequivalent) of the Lidoderm™ patch may be used.

As used herein, the "Orange Book" as it is commonly known is the database of Approved Drug Products with Therapeutic Equivalence Evaluations maintained by or on behalf of the US Food and Drug Administration, (http://www.fda.gov/cder/ob/default.htm, accessed Feb. 15, 2008), the content of which is hereby incorporated by reference.

The term "first administration" means a single dose of the present invention at the initiation of therapy to an individual patient or a patient population.

The term "steady state" means that the amount of the drug reaching the system is approximately the same as the amount of the drug leaving the system. Thus, at "steady-state", the patient's body eliminates the drug at approximately the same rate that the drug becomes available to the patient's system through absorption into the blood stream.

All dosage forms for application to the skin are contemplated by the invention, including topical and transdermal pharmaceutical dosage forms, as these terms are used in common usage, including creams, ointments, liposomes, a liquid, semisolid, solution, sprayable aerosol, sprayable non-aerosol, powder, film, gels, lotions, liniments, plaster, topical patches, transdermal patches in sterile, nonsterile and pyrogen free forms As used herein the terms: (i) "$AUC_{0-24}$" means area under the plasma drug concentration-time curve from time zero to the last quantifiable time point up to 24 hours, calculated from timed plasma concentration data obtained during the continuous application of the dosage form to the skin over the first 24 hours of application"; (ii) "$C_{max}$" means the maximum observed drug concentration over the intended dosing interval; (iii) "half value duration" or "HVD" means the duration after dosing during which plasma concentration of drug are greater than or equal to one-half of $C_{max}$, obtained by calculating the time interval beginning when the actual or interpolated plasma concentration first equals or exceeds one-half of $C_{max}$ and ending at the first time point for which the actual or interpolated plasma concentration falls below one-half of $C_{max}$; (iv) "$W_{50}$" for purposes of the present invention means the width of the plasma concentration time curve at 50% of the height of the $C_{max}$ over the dosing interval; (v) "$C_{min}$" means the minimum plasma concentration of the drug obtained during the dosing interval or over the interval specified in a claim; (vi) "$C_{av}$" means the average plasma concentration of the drug during the dosing interval; (vii) "percent fluctuation" means the variation in plasma concentrations of the drug computed as: (a) ($C_{max}$−$C_{min}$)/$C_{min}$×100 (for an individual patient) and (mean $C_{max}$−mean $C_{min}$)/mean $C_{min}$×100 (for a population); and (b) ($C_{max}$−$C_{min}$)/$C_{av}$×100 (for an individual patient) and (mean $C_{max}$−mean $C_{min}$)/mean $C_{av}$×100 (for a population); (viii) "accumulation index" or "AI" means the ratio of the plasma concentration of the drug at the end of the intended dosing interval (e.g., 12 hours for a Q12H dosage form, and 24 hours for a Q24H dosage form) after administration, determined at steady-state to the plasma concentration of the drug at the end of the intended dosing interval determined at first administration (i.e., after the first dose); (ix) "steady state" is a state of equilibrium wherein the amount of the drug reaching the system is approximately the same as the amount of the drug leaving the system or put another way, the patient's body eliminates the drug at approximately the same rate that the drug becomes available to the patient's system through absorption into the blood stream, said "time to steady state" measured by calculating the $C_{min}$ after each sequential dosing of drug administered at the intended dosing frequency until two consecutive $C_{min}$'s are not statistically different at a 5% significance level (p=0.10)

Pharmacokinetic parameters of the invention, including $AUC_{0-24}$, $C_{max}$, time to $C_{max}$, $C_{min}$, $C_{av}$, $C_{min}/C_{max}$ ratio, HVD, $W_{50}$, ($C_{max}$−$C_{min}$)/$C_{min}$×100 and ($C_{max}$−$C_{min}$)/$C_{av}$×100 for an individual patient or a population may be computed from single dose (i.e., first administration) and/or steady state pharmacokinetic studies conducted in the fasted or fed states. The AI computation requires both single dose (i.e., first administration) and steady state pharmacokinetic assessment. The percent of steady state computation requires both single dose (i.e., first administration) and repeated (sequential) administration to steady state.

For purposes of the invention, the term "a patient" in reference to pharmacokinetic parameters means that the discussion (or claim) is directed to the pharmacokinetic parameters of an individual patient or subject.

The term "population of patients" means that the discussion (or claim) is directed to the mean pharmacokinetic parameters of at least two patients or subjects.

In certain embodiments, any one or all of the above in-vivo parameters are achieved after a first administration (often referred to as "single dose administration") of the dosage form to a human patient or a population of human patients.

In certain alternative embodiments, any one or all of the above in-vivo parameters are achieved after steady state administration of the dosage form to a human patient or a population of human patients.

The phrase "USP Apparatus 5", "paddle over disk method" or "USP Apparatus 5 (paddle over disk method)" means the USP Apparatus 5 (paddle over disk method) specified in the United States Pharmacopeia, USP-28 NF-23 (2005), published by the United States Pharmacopeial Convention, Inc, conducted using the dissolution media, temperature, volume and rotation frequency specified in the specifications or claims.

The singular forms "a," "an" and "the" include plural referents unless the context clearly dictates otherwise. Thus, for example, reference to "a polymer" includes a single polymer as well as a mixture of two or more different polymers, reference to "a permeation enhancer" includes a single permeation enhancer as well as two or more different permeation enhancer in combination, and the like.

Some of the drugs disclosed herein may contain one or more asymmetric centers and may thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

In some embodiments, the dosage form contain R(−)-mepivacaine and S(+)-mepivacaine in equal molar quantities.

As used herein, a "mepivacaine release controlling means" refers to a means to modulate the release rate of the mepivacaine, such as rate control membranes generally known in the art.

As used herein, the term "topical", "topical dosage" or "topical dosage form" and "transdermal", "transdermal" or "transdermal dosage form" includes all forms of application to skin (e.g., creams, ointments, solution, liquid and aerosol spray, powder, film, gels, emulgels, microemulsions, lotions, liniments, plaster, liposomes, topical patches, transdermal patches, each in sterile, nonsterile or pyrogen free forms) for a local and/or systemic therapeutic effect.

When referring to the invention, the phrase "transdermal dosage form", "transdermal pharmaceutical composition", "topical dosage form", topical formulation" "formulation", "dosage form", "topical system", "topical dosage" or "topical dosage form" and "transdermal system" all refer to the application of a dosage form of the present invention comprising mepivacaine to skin.

In some embodiments, application of the dosage form is to injured skin or damaged skin. In particularly preferred embodiments, application of the dosage form is to intact skin. In some embodiments, the topical dosage form is for the treatment of any medical condition responsive to treatment with mepivacaine. In particularly preferred embodiments, the topical dosage form is for the treatment of pain. In some particularly embodiments, the topical dosage form is for the treatment of chronic pain, neuropathic pain and neuropathy. In some embodiments, application of the dosage form is to skin at the site of pain or neuropathy. In other embodiments, application of the dosage form is to skin at a site which not the site where pain or neuropathy are felt, but may be proximal or distal to where pain or neuropathy are felt. In some embodiments, application of the dosage form is to healthy skin, allodynic skin, hyperalgesic skin, ulcerated skin, burned skin, diabetic ulcers, decubitus ulcers, surgical incisions, lacerated skin and the like for a local and/or systemic therapeutic effect.

All pain states are contemplated by this invention, regardless of anatomic location, etiology, mechanism, treatment responsiveness or pathophysiology. As used herein, the term "pain" includes: (i) neuropathy (which may be painful, painless, or bothersome); (ii) peripheral neuropathic pain, e.g., acute and chronic inflammatory demeyelinating polyradiculopathy, alcoholic polyneuropathy, chemotherapy-induced polyneuropathy, complex regional pain syndrome (CRPS) Type I and Type II, entrapment neuropathies (e.g., carpal tunnel syndrome), HIV sensory neuropathy, iatrogenic neuralgias (e.g., postthoracotomy pain, postmastectomy pain), idiopathic sensory neuropathy, painful diabetic neuropathy, phantom limb pain, postherpetic neuralgia, trigeminal neuralgia, radiculopathy (e.g., cervical thoracic, lumbosacral), sciatica, acute herpes zoster pain, temporomandibular joint disorder pain and postradiation plexopathy; and (iii) central neuropathic pain, e.g., compressive myelopathy from spinal stenosis, HIV myelopathy, multiple sclerosis pain, Parkinson's disease pain, postischemic myelopathy, post postradiation myelopathy, poststroke pain, posttraumatic spinal cord injury and syringomyelia; and (iv) cancer associated neuropathic pain, e.g., chemotherapy induced polyneuropathy, neuropathy, secondary to tumor infiltration or nerve compression, phantom breast pain, postmastectomy pain, postradiation plexopathy and myelopathy; (v) chronic pain, e.g., back pain, rheumatoid arthritis, osteoarthritis, inflammatory pain, non-inflammatory pain, myofascial pain, fibromyalgia, cancer pain, visceral pain, somatic pain, pelvic pain, musculoskeletal pain, post-traumatic pain, bone pain and idiopathic pain; (vi) acute pain, e.g, acute postsurgical pain (including laparoscopic, laparatomy, gynecologic, urologic, cardiothoracic, arthroscopic, gastrointestinal, neurologic, orthopedic, oncologic, maxillofacial, ophthalmic, otolaryngologic, soft tissue, plastic, cosmetic, vascular and podiatric surgery, including abdominal surgery, abdominoplasty, adenoidectomy, amputation, angioplasty, appendectomy, arthrodesis, arthroplasty, arthroscopy, bilateral cingulotomy, biopsy, brain surgery, breast biopsy, cauterization, cesarean section, cholecystectomy, circumcision, commissurotomy, cordotomy, corneal transplantation, cricothoracotomy, discectomy, diverticulectomy, episiotomy, endarterectomy, endoscopic thoracic sympathectomy, foreskin restoration, fistulotomy, frenectomy, *frontalis* lift, fundectomy, gastrectomy, grafting, heart transplantation, hemicorporectomy, hemorrhoidectomy, hepatectomy, hernia repair, hypnosurgery, hysterectomy, kidney transplantation, laminectomy, laparoscopy, laparotomy, laryngectomy, lithotripsy, lobotomy, lumpectomy, lung transplantation, mammectomy, mammoplasty, mastectomy, mastoidectomy, mentoplasty, myotomy, mryingotomy, nephrectomy, nissen fundoplication, oophorectomy, orchidectomy, parathyroidectomy, penectomy, phalloplasty, pneumotomy, pneumonectomy, prostatectomy, psychosurgery, radiosurgery, ritidoplasty, rotationplasty, sigmoidostomy, sphincterotomy, splenectomy, stapedectomy, thoracotomy, thrombectomy, thymectomy, thyroidectomy, tonsillectomy, tracheotomy, tracheostomy, tubal ligation, ulnar collateral ligament reconstruction, ureterosigmoidostomy, vaginectomy, vasectomy, vulvectomy; renal colic; incisional pain; inflammatory incisional pain; nociceptive incisional pain; acute neuropathic incisional pain following surgery), renal colic, trauma, acute back pain, burn pain, burn dressing change pain, migraine pain, tension headache pain, acute musculoskeletal pain, acute exacerbation or flare of chronic back pain, acute exacerbation or flare of osteoarthritis, acute exacerbation or flare of chronic pain, breakthrough chronic non-cancer pain, breakthrough cancer pain, acute exacerbation or flare of fibromylagia, acute exacerbation or flare of rheumatoid arthritis, acute exacerbation or flare of myofacsial pain, acute exacerbation or flare of chronic idiopathic pain, acute exacerbation or flare of neuropathic pain, procedure related pain (e.g., arthroscopy, laparoscopy, endoscopy, intubation, bone marrow biopsy, soft tissue biopsy, catheterization), and other self-limiting pain states; and (vii) other pain states.

As used herein, the term "neuropathic pain" includes: (i) peripheral neuropathic pain, e.g., acute and chronic inflammatory demeyelinating polyradiculopathy, alcoholic polyneuropathy, chemotherapy-induced polyneuropathy, complex regional pain syndrome (CRPS) Type I and Type II, entrapment neuropathies (e.g., carpal tunnel syndrome), HIV sensory neuropathy, iatrogenic neuralgias (e.g., postthoracotomy pain, postmastectomy pain), idiopathic sensory neuropathy, painful diabetic neuropathy, phantom limb pain, postherpetic neuralgia, trigeminal neuralgia, radiculopathy (e.g., cervical thoracic, lumbosacral), sciatica, acute herpes zoster pain, temporomandibular joint disorder pain and postradiation plexopathy; and (ii) central neuropathic pain, e.g., compressive myelopathy from spinal stenosis, HIV myelopathy, multiple sclerosis pain, Parkinson's disease pain, postischemic myelopathy, post postradiation myelopathy, poststroke pain, posttraumatic spinal cord injury and syringomyelia; and (iii) cancer associated neuropathic pain, e.g., chemotherapy induced polyneuropathy, neuropathy secondary to tumor infiltration or nerve compression, phantom breast pain, postmastectomy pain, postradiation plexopathy and myelopathy.

As used herein, the term "neuropathy" refers to a disease of the peripheral nervous system. The four major forms of nerve damage are polyneuropathy, autonomic neuropathy, mononeuropathy, and mononeuritis multiplex. The most common form is peripheral polyneuropathy, which mainly affects the feet and legs. Neuropathy often results in numbness, abnormal sensations called dysesthesias, hypoeststhesia, steady burning and/or "pins and needles" and/or "electric shock" sensations, hypoalgesia, sensory loss and ectopia. Neuropathy and neuropathic pain may co-exist in the same patient.

As used herein, the term "chronic pain" includes all non-neuropathic chronic pain lasting for about one month or more, including back pain, rheumatoid arthritis, osteoarthritis, inflammatory pain, non-inflammatory pain, myofascial pain, fibromyalgia, cancer pain, visceral pain, somatic pain, pelvic pain, musculoskeletal pain, post-traumatic pain, bone pain and idiopathic pain regardless of pathophysiology, intensity, duration, location, mechanisms or etiology.

The term "analgesic effectiveness" is defined for purposes of the present invention as a satisfactory prevention, reduction in or elimination of pain, along with a tolerable level of side effects, as determined by the human patient.

The term "therapeutic effectiveness" is defined for purposes of the present invention as a satisfactory prevention, reduction in or elimination of neuropathy, neuropathic pain and chronic pain, along with a tolerable level of side effects, as determined by the human patient.

"Drug", "drug substance", "substance", "therapeutic agent", "pharmacological agent", "pharmaceutical agent", "active agent" and "agent" are used interchangeably and are intended to have their broadest interpretation as to any therapeutically active substance which is delivered to a living organism to produce a desired, usually beneficial effect. In general, this includes therapeutic agents in all of the major therapeutic areas.

The term "subject" for purposes of treatment is used interchangeably with "patient", "male", "female", and includes any human who has a medical condition amenable to treatment with the dosage form of the invention.

"Pharmaceutically or therapeutically acceptable excipient or carrier" or "excipient" refers to a substance which does not interfere with the effectiveness or the biological activity of the active ingredients and which is not toxic to the subject. In some embodiments of the present invention, pharmaceutically or therapeutically acceptable excipients or carriers may play a role in imparting or optimizing the rate and extent of absorption or mepivacaine or additional drugs in the pharmaceutical composition. In some embodiments of the present invention, pharmaceutically or therapeutically acceptable excipients or carriers may play a role in stabilizing the mepivacaine or additional drugs in the pharmaceutical composition.

"Pharmaceutically or therapeutically acceptable excipient or carrier" or "excipient" may include compounds found on the FDA EAFUS database (http://vm.cfsan.fda.gov/~dms/eafus.html); FDA Food Additives Status List (http://www.cfsan.fda.gov/~dms/opa-appa.html); FDAGRAS list and database; FDA Color Additive Status List (http://www.cfsan.fda.gov/~dms/opa-appc.html); FDA Inactive Ingredients Database (http://www.accessdata.fda.gov/scripts/cder/iig/index.cfm); Rowe, Sheskey and Owen, Handbook of Pharmaceutical Excipients, APhA Publications; 5th edition (2006); Goodman & Gilman's The Pharmacological Basis of Therapeutics (Brunton, Lazo and Parker, eds, 11th ed., McGraw Hill (2005); Remington: The Science and Practice of Pharmacy, 21st ed, Lippincott Williams & Wilkins (2005); Martindale: The Complete Drug Reference, 35th Edition, Pharmaceutical Press (2007); United States Pharmacopeia-National Formulary (USP-NF), (USP 30-NF 25, 2007), the International Programme on Chemical Safety (http://www.inchem.org/), Health Canada's List of Acceptable Non-medicinal Ingredients (http://www.hc-sc.gc.ca/dhp-mps/prodnatur/legislation/docs/nmi-imn_list1_e.html); Ash, Michael (ed and compiler), Pharmaceutical Additives Electronic Handbook, Synapse Information Resources, Inc.; 3 Cdr edition (Feb. 19, 2007); Allured, M, 2009 McCutcheon's Functional Materials, McCutcheon's Publications (Apr. 1, 2009); and Allured, M. 2009 McCutcheon's Emulsifiers and Detergents, McCutcheon's Publications, Apr. 1, 2009, all hereby incorporated by reference in their entirety.

"Therapeutically effective amount" or "therapeutically-effective" refers to the amount of an active agent sufficient to induce a desired biological result. That result may be alleviation of the signs, symptoms, or causes of a disease, or any other desired alteration of a biological system.

The terms "medical condition", "malady", "disease", "disorder" and "pathological states" are used interchangeably and are intended to have their broadest interpretation to refer to any physiologic, pathologic or pathophysiologic state in a human that can be prevented, treated, managed or altered to produce a desired, usually beneficial effect.

As used herein, the phrase "suitable for up to one week of administration" means administration for any period of time up to about one week (e.g., up to 0.1, 0.5, 1, 2, 3, 4, 6, 8, 12, 16, 18, 24 and 36 hours; 2, 3, 4, 5, 6, 7, 8, 9 and 10 days).

As used herein, the phrase "providing a therapeutic effect for up to about one week" and "providing a therapeutic effect for up to about 7 days" means providing a therapeutic effect for any period of time up to about one week (e.g., up to up to 0.1, 0.5, 1, 2, 3, 4, 6, 8, 12, 16, 18, 24 and 36 hours and up to 2, 3, 4, 5, 6, 7, 8, 9 and 10 days).

The term "effective amount" means the quantity of a compound according to the invention necessary to prevent, to cure, or at least partially arrest a symptom for which the mepivacaine has been prescribed to a subject.

Active Agent

All doses of mepivacaine for application to the skin that are therapeutically effective are contemplated by the invention. In some embodiments, the dosage forms of the present invention for application to the skin preferably include a dose per application from about 0.0001 to about 100 g, or about 0.001 mg to about 50 g, or about 1 mg to about 10 g, or about 1 mg to about 5 g, or about 10 mg to about 2 g of mepivacaine base or a pharmaceutically acceptable salt thereof.

In some preferred embodiments, the invention provides comprises a mepivacaine dosage forms for application to the skin of about 0.5 to about 500 $cm^2$; preferably about 1 to about 300 $cm^2$, more preferably 2 to about 150 $cm^2$, even more preferably about 4 to about 100 $cm^2$ or about 10 to about 50 $cm^2$.

All methods and compositions of mepivacaine application to the skin are contemplated by the invention, including, without limitation: (i) reservoir patch having a membrane layer on the side of the patch proximal to the skin; (ii) matrix patch; (iii) drug in adhesive patch; (iv) iontophoretic delivery; (v) cream; (vi) ointment; (vii) liposomes; (viii) solution; (ix) foam; (x) suspension; (xi) lotion; (xii) emulsion; (xiii) hydrogel matrix; (xiv) aerosols; (xv) sprayable pharmaceutical formulations; (xvi) sprayable pharmaceutical formulations, substantially water washable; (xvii) sprayable pharmaceutical formulations, substantially resistant to removal upon casual contact with water.

It is an object of certain preferred embodiments of the present invention to provide mepivacaine formulations for application to the skin, said mepivacaine delivery across the skin caused by or substantially aided by electroporation, iontophoresis, permeation enhancers, localized electroporation, microporation, microneedles, photo-mechanical energy, magnetophoresis, thermoporation, chemical energy, thermal energy and/or mechanical energy.

In some embodiments, the mepivacaine application to the skin is followed by absorption through the skin which is aided by mechanical, thermal, electrical and/or chemical energy. In some embodiments, the mepivacaine application to the skin is followed by absorption through the skin which is aided by solvents, carriers, excipients, and/or permeation enhancers. In some embodiments, the mepivacaine application to the skin is followed by absorption through the skin which is aided by a temporary or permanent disruption of the integrity of the skin or skin surface.

In some preferred embodiments, the mepivacaine is contained in a reservoir for application to the skin (e.g., a device) and self-administered by a patient or administered on the patient's behalf by a care-giver or by medical personnel; said reservoir containing one or multiple doses of mepivacaine; said dosage form useful for the treatment of any painful condition, preferably, acute pain (e.g., acute post-surgical pain); said dosage form providing relief from pain for a duration of a few minutes to a few hours or up to a few days or a few weeks. In some embodiments, the mepivacaine is delivered by a device such as described in U.S. Pat. Nos. 5,697,896 and 6,425,892.

Mepivacaine was synthesized in the mid 1950's in Sweden and introduced into clinical medicine in 1957. Presently mepivacaine is indicated "for the production of local or regional analgesia and anesthesia by local infiltration, peripheral nerve block techniques, and central neural techniques including epidural and caudal blocks." To the applicant's knowledge, there are no described formulations of mepivacaine in the prior art for application to the skin for the treatment of pain, including acute pain, chronic pain, neuropathy and neuropathic pain.

Commercially, mepivacaine is available in racemic form as mepivacaine hydrochloride, which is 2-piperidinecarboxamide, N(2,6-dimethylphenyl)-1-methyl-, monohydrochloride and has the following structural formula:

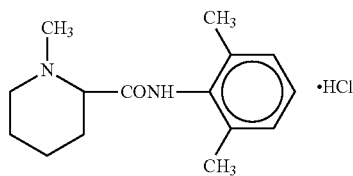

It is a white, crystalline odorless powder, soluble in water, but very resistant to both acid and alkaline hydrolysis. Mepivacaine is a local anesthetic available as sterile isotonic solutions in concentrations of 1%, 1.5%, 2% and 3% for injection via local infiltration, peripheral nerve block, and caudal and lumbar epidural blocks. Mepivacaine contains an amide linkage between the aromatic nucleus and the amino group.

An important predictor of skin penetration and penetration into the receptor site for local anesthetics is its octanol:water partition coefficient. In one report, the octanol:water partition coefficient of lidocaine was 3.6 fold greater than for mepivacaine (Ferrante F M, Pharmacology of local anesthetics, p. 1330-1362, In: Longnecker D E, Tinker J H, Morgan, Jr., GE (eds), Principles and practice of anesthesiology, 1998 (2nd ed), Mosby-Year Book, Inc. St. Louis, Mo.). In another study, the octanol:water partition coefficient of lidocaine was 2.6 fold greater than for mepivacaine. Similarly, the ratio of relative concentrations of protonated and neutral drug, respectively, between octanol and water was 2.8 fold greater for Lidocaine, compared with mepivacaine (Strichartz G R, Sanchez V, Arthur G R, Chafetz R, Martin D. Fundamental properties of local anesthetics. II. Measured octanol:buffer partition coefficients and pKa values of clinically used drugs. Anesth Analg 1990; 71:158-70.). These observations support the superior skin and subsequent nerve tissue penetration of lidocaine and the purported lack of efficacy for mepivacaine when applied to the skin. For example, Goodman & Gilman's The Pharmacological Basis of Therapeutics, a textbook of pharmacology used by physicians from all therapeutic and surgical specialties, clinical pharmacologists, clinical research professionals and pharmacists states that "Mepivacaine is not effective as a topical anesthetic".

Mepivacaine is approximately 75% bound to plasma proteins. The pharmacokinetics of mepivacaine can be significantly altered by the presence of hepatic or renal impairment, use of epinephrine, urinary pH, renal blood flow, route of drug administration and patient age. The half-life of mepivacaine is 2 to 3 hours in adults.

Due to its amide structure, mepivacaine is not biotransformed by circulating plasma esterases. Since mepivacaine is a dual-ring structure, its biotransformation pathway is different from that of lidocaine. It is rapidly metabolized, with less than 10% excreted unchanged in the urine. The liver is the primary site of biotransformation, with over 50% of the administered dose being excreted into the bile as metabolites. It is postulated that most of the metabolized mepivacaine is probably resorbed in the intestine and then excreted into the urine. The principal route of excretion is via the kidney.

Mepivacaine does not ordinarily produce irritation or tissue damage, and unlike prilocaine, does not cause methemoglobinemia.

Mepivacaine can be used for infiltration anesthesia. Mepivacaine is also used to achieve peripheral conduction block. The adverse experience database for mepivacaine has been shaped by its current indication, namely "for the production of local or regional analgesia and anesthesia by local infiltration, peripheral nerve block techniques, and central neural techniques including epidural and caudal blocks." The most commonly encountered acute adverse experiences which demand immediate countermeasures are related to the central nervous system and the cardiovascular system. These adverse experiences are generally dose related and due to high blood levels.

Over the past decade, a number of reports have implicated parenteral lidocaine as a possible cause of neurologic complications (Transient Neurologic Symptoms or TNS) after anesthesia. A recent study indicates lidocaine is associated with a higher incidence of TNS than are other local anesthetics, including bupivacaine, prilocaine, procaine, and mepivacaine, with a relative risk of 4.35 (95% confidence interval, 1.98-9.54) [Zaric et al. Anesth Analg 2005; 100: 1811-6].

Neuropathy, neuropathic pain and chronic pain can sometimes require weeks months, years and even decades of therapy. Consequently, the safety of long-term therapy is of paramount importance. Since local anesthetics are sometimes applied to sites where peripheral nerves may be growing or regenerating after injury (e.g., after exposure to chemical injury, mechanical injury, or neurodegenerative disease), their effects on growing neurons are of clinical importance. Similarly, the effects of drugs including local anesthetics on growing or regenerating nerves after injury (e.g., after exposure to chemical injury, mechanical injury, or neurodegenerative disease) are of clinical importance, particularly in postsurgical and post-traumatic pain where nerve fibers are regenerating and creating new sprouts. Recently, Radwan et al., (Anesth Analg 2002; 94:319-24) evaluated the effects of the local anesthetics lidocaine, bupivacaine, mepivacaine, and ropivacaine to produce morphological changes in growing neurons by performing in vitro cell biology experiments with isolated dorsal root ganglion neurons from chick embryos, with subsequent assessment using the growth cone collapse assay. The growth cone, a highly motile structure at the end of the growing axons and dendrites, play an important role in the development of the nervous system, including the guidance of neurite extensions and the establishment of neurite architecture. The collapse of growth cone is a validated method for examining the effects of drugs on developing neurites. The $IC_{50}$ determined by the growth cone collapse assay was highest for mepivacaine and lowest for lidocaine, demonstrating that lidocaine had a greater potential neurotoxic effect on the developing or regenerating primary cultured neurons. These data confirm previous histopathologic, electrophysiologic, behavioral, and neuronal cell models, where lidocaine had a greater potential for neurotoxicity than bupivacaine (Baiton et al, Anesthesiology 1994; 81:657-67; Kanai et al., Anesth Analg 1998; 86:569-73; Lambert et al., Anesthesiology 1994; 80:1082-93). Additionally, in a previous histopathological study, Kanai et al. (Anesth Analg 2000; 91:944-48) demonstrated that 80 mM (2.17%) lidocaine induced neuronal damage in rat sciatic nerve and 0.75% (23.1 mM) bupivacaine do not (Hodgson et al., Anesth Analg 1999; 88:797-809).

In certain preferred embodiments of the present invention, the invention allows for the use of lower doses of mepivacaine by virtue of the inclusion or co-administration of an additional drug for the treatment of pain. By using lower amounts of either or both drugs, the side effects associated with treatment in humans are reduced.

In certain preferred embodiments of the present invention, an effective amount of mepivacaine in immediate release form is included in the controlled release unit dose mepivacaine formulation to be administered. The immediate release form of the mepivacaine is preferably included in an amount which is effective to shorten the time to $C_{max}$ of the mepivacaine in the blood (e.g., plasma). One skilled in the art would recognize various means of incorporating the immediate release mepivacaine into the unit dose. By including such an effective amount of immediate release mepivacaine in the unit dose, patients may experience superior relief of pain and neuropathy symptoms.

Treatments and Additional Active Drugs

It is contemplated that the present invention may be used alone or in combination with other drugs to provide additive, complementary, or synergistic therapeutic effects or for the treatment of entirely different medical conditions.

Other pharmaceutically active ingredients from various therapeutic classes may also be used in combination with the present invention. In some embodiment, co-administered may be used to provide additive, complementary, superadditive or synergistic therapeutic effects. In some embodiment, co-administered may be used to provide a different therapeutic effects from the present invention or to treat the side effects of the present invention. They include, but are not limited to decongestants, analgesic adjuvants, antihistamines, expectorants, antitussives, diuretics, anti-inflammatory agents, antipyretics, antirheumatics, antioxidants, laxatives, proton pump inhibitors, motility modifying agents, vasodilators, inotropes, beta blockers, beta adrenergic agonists, drugs to treat asthma and COPD, antiinfectives, antihypertensives, antianginal agents, anticoagulants, lipid and cholesterol lowering drugs, anti-diabetic drugs, hormones, smooth muscle relaxants, skeletal muscle relaxants, bronchodilators, vitamins, trace minerals, amino acids, and biological peptides. They include, but are not limited to disorders, diseases and maladies, and signs and symptoms thereof referred to in Harrison's Principles of Internal Medicine, 16th Edition, 2004, Kasper D L, Braunwald W, Fauci A, Hauser S, Longo D, and Jameson J L (eds)], which is hereby incorporated in its entirety by reference The drug being used in combination therapy with the present invention can be administered by any route, including parenterally, orally, topically, transdermally, sublingually, and the like.

In some embodiments, the application of mepivacaine to the skin is intended to prevent or treat pain. An co-administered drug (in the same or different dosage form, by any route of administration) may be used to provide additive, complementary, superadditive or synergistic therapeutic analgesic effects, including other NSAIDs, COX-2 selective inhibitors, acetaminophen, tramadol, other local anesthetics, antidepressants, beta adrenergic agonists, alpha-2 agonists, selective prostanoid receptor antagonists, cannabinoid agonists, opioid receptor agonists, NMDA antagonists, gabapentin, pregabalin, gabapentinoids, neuronal nicotinic receptor agonists, calcium channel antagonists, sodium channel blockers, superoxide dismutase mimetics, p38 MAP kinase inhibitors, TRPV1 agonists, dextromethorphan, dextrorphan, ketamine, glycine receptor antagonists, antiepileptics, and any other drugs that can be shown by a person proficient in the art to prevent or treat pain.

In some preferred embodiments of the dosage form comprises, in addition to the mepivacaine, a rubefacient. Non-limiting examples of rubefacients include salicylates (e.g., oil of wintergreen, methyl salicylate), nicotinate esters, capsaicin, isopropanol, menthol, camphor, and clove oil, and their respective derivatives, and mixtures thereof.

In some preferred embodiments of the dosage form comprises, in addition to the mepivacaine, an NSAID. The NSAID may be non-selective (inhibit COX-1 and COX-2 isozymes) or COX-2 selective (preferentially inhibit the COX-2 isozymes). Non-limiting examples of NSAIDs or COX-2 selective inhibitor include ibuprofen, tiaprofenic acid, diclofenac, piroxicam, loxoprofen, fenoprofen, indoprofen, oxaprozin, tenoxicam, lornoxicam, acetylsalicylic acid, mefenamic acid, naproxen, flurbiprofen, flubufen, ketoprofen, indoprofen, carprofen, pramoprofen, muroprofen, trioxaprofen, aminoprofen, tiaprofenic acid, fluprofen, niflumic acid, tolfenamic acid, diflunisal, etodolac, fenbufen, indomethacin, isoxicam, sudoxicam, pirprofen, sulindac, tolmetin, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflunisal, flufenisal, meloxicam and nabumetone, celecoxib, valdecoxib, etoricoxib, rofecoxib, and lumiracoxib, and as well as their pharmaceutically acceptable salts, prodrugs, esters, analogs, derivatives, solvates, complexes, polymorphs, hydrates and metabolites, as racemates or an individual diastereoisomers or enantiomeric isomers thereof or mixture thereof.

BRIEF DESCRIPTION OF THE DRAWINGS

The included drawings are illustrative but not limiting of the methods and composition of the present invention. Other suitable modifications and adaptations of the variety of conditions and parameters normally encountered and obvious to those skilled in the art are within the spirit and scope of the invention.

METHODS OF CARRYING OUT THE INVENTION

Figure 1:
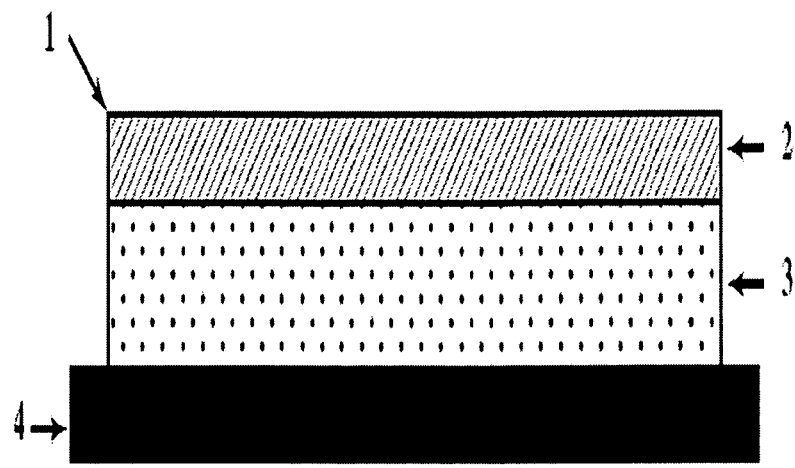
FIG. 1, depicts a preferred embodiment of the transdermal dosage form of the invention comprising a (1) patch, (2) an impermeable barrier or backing layer, (3) mepivacaine in adhesive; (4) a peelable protective layer or release liner.
Figure 2:
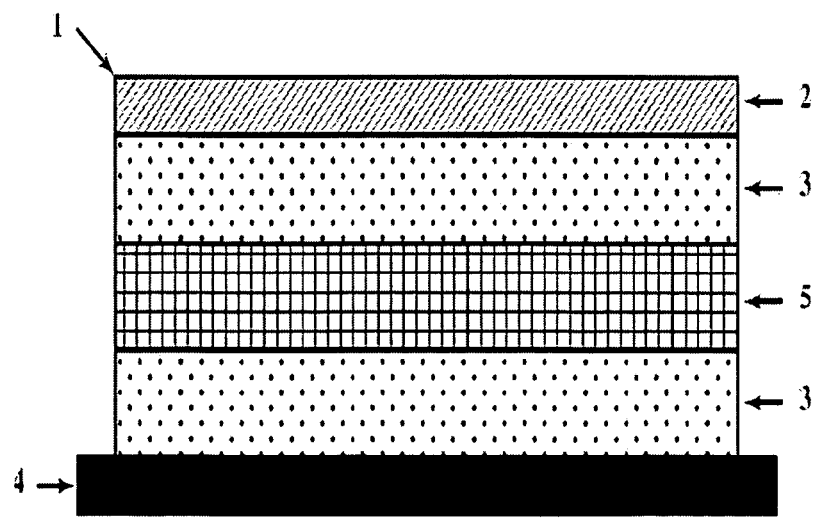
FIG. 2, depicts a preferred embodiment of the transdermal dosage form of the invention comprising a (1) patch, (2) an impermeable barrier or backing layer, (3) mepivacaine in adhesive, (4) a peelable protective layer or release liner, and (5) a rate-limiting or rate controlling membrane permeable to the mepivacaine.
Figure 3:
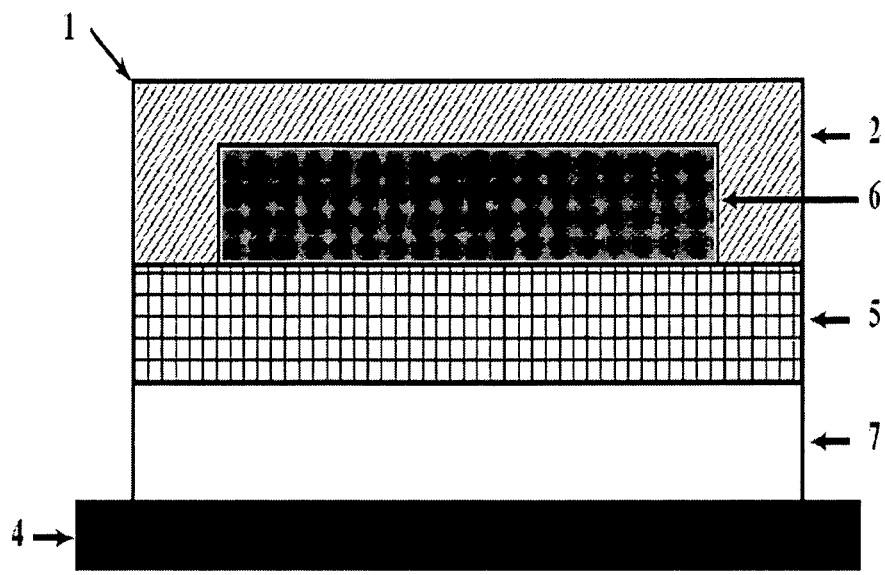
FIG. 3, depicts a preferred embodiment of the transdermal dosage form of the invention comprising a (1) patch, (2) an impermeable barrier or backing layer, (4) a peelable protective layer or release liner, (5) a rate-limiting or rate controlling membrane permeable to the mepivacaine, (6) mepivacaine in liquid form, and (7) and adhesive layer.
Figure 4:
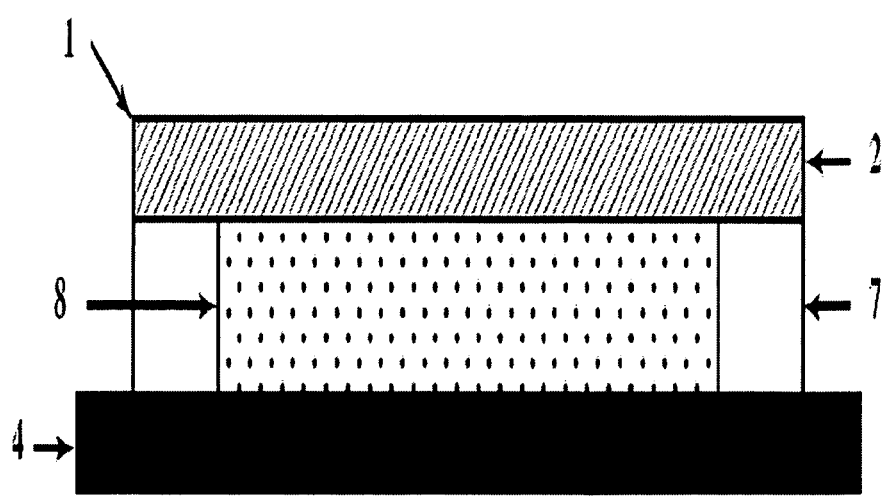
FIG. 4, depicts a preferred embodiment of the transdermal dosage form of the invention comprising a (1) patch, (2) an impermeable barrier or backing layer, (4) a peelable protective layer or release liner, (7) adhesive layer, and (8) mepivacaine in a semi-solid matrix.
Figure 5:
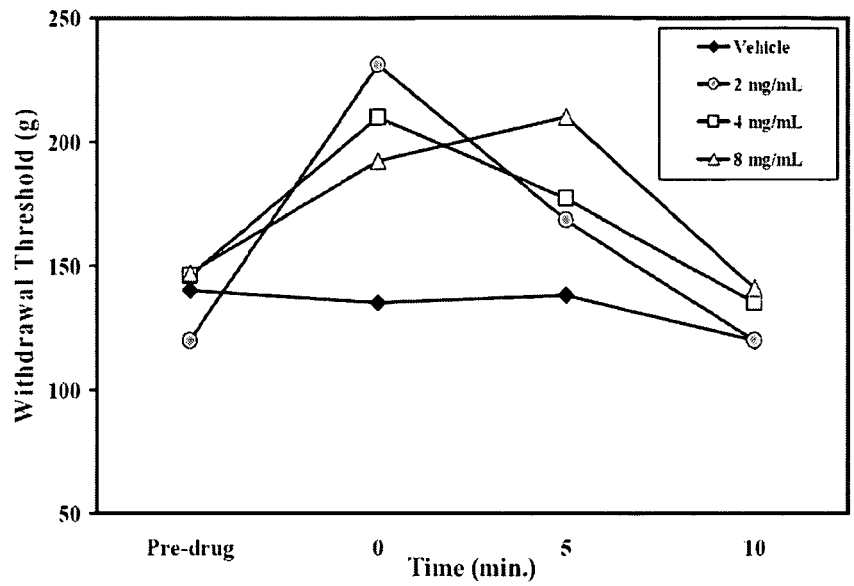
FIGS. 5 to 11 are fully described within the specifications, within Example 1 to Example 3A, inclusive.

Pharmaceutical composition and methods of the present invention contain mepivacaine base, pharmaceutically acceptable salts or mixtures thereof and they are intended for application to the skin. All pharmaceutical compositions and dosage forms for application to the skin are contemplated by the invention, including topical patch, transdermal patch, plaster, pastes, gel, liposomes, a liquid, semisolid, solution, suspension, lotion, cream, ointment, foam, sprayable aerosol, and sprayable non-aerosol. Functional pharmaceutical excipients (e.g., suitable permeation enhancers, emollients, thickening agents, solubilizers, emulsifiers and adjuvants), various processing aids, patch materials and methods for the preparation of dosage forms for application to the skin, including those in the form of topical patch, transdermal patch, plaster, pastes, gel, liposomes, a liquid, semisolid, solution, suspension, lotion, cream, ointment, foam, sprayable aerosol, sprayable non-aerosol are disclosed herein, and in the art (e.g., Williams A C. Transdermal and Topical Drug Delivery, Pharmaceutical Press, London, 2003; Remington: The Science and Practice of Pharmacy, $21^{st}$ Edition, Lippincott Williams & Wilkins, Baltimore, 2005; Walters K A. Dermatological and Transdermal Formulations, Informa Healthcare, $1^{st}$ Edition, 2002; Transdermal Drug Delivery, Hadgraft J (ed), $2^{nd}$ Edition, 2002; Transdermal and Topical Drug Delivery Systems, Hosh T K, Pfister W & Yum S I (eds), CRC, 1997; Transdermal Controlled Systemic Medications; Chien Y W (ed), Marcel Dekker, 1987; Topical Drug Delivery Formulations, Osborne D W and Amann A H (eds), Informa Healthcare, 1989; Topical Drug Bioavailability, Bioequivalence, and Penetration Shah V P and Maibach H I (eds), Springer, 1993), Jaroszeski M J. Electrochemotherapy, Electrogenetherapy, and Transdermal Drug Delivery: Electrically Mediated Delivery of Molecules to Cells. Humana Press, 1st edition 2000; Wille J J. Skin Delivery Systems: Transdermals, Dermatologicals, and Cosmetic Actives. Blackwell Publishing, 1st edition, 2006; Gurny R and Teubner A (Eds). Dermal and Transdermal Drug Delivery: New Insights and Perspectives. CRC Press, 1993], hereby incorporated by reference in their entirety and U.S. Pat. Nos. 4,466,953; 4,470,962; 4,588,580; 4,626,539; 4,645,502; 4,806,341; 4,814,173; 4,906,463; 4,911,707; 4,911,916; 4,915,950; 4,917,676; 4,927,408; 4,938,759; 4,956,171; 5,006,342; 5,026,556; 5,069,909; 5,080,646; 5,135,480; 5,147,296; 5,149,538; 5,169,382; 5,186,939; 5,203,768; 5,225,199; 5,232,438; 5,236,714; 5,240,711; 5,310,559; 5,374,645; 5,411,738; 5,462,744; 5,464,387; 5,474,783; 5,503,844; 5,556,635; 5,601,839; 5,629,014; 5,635,204; 5,656,286; 5,662,926; 5,679,373; 5,686,112; 5,705,186; 5,762,952; 5,827,529; 5,834,010; 5,843,979; 5,908,846; 5,948,433; 5,958,379; 5,958,446; 5,985,317; 5,993,849; 6,010,715; 6,024,976; 6,063,399; 6,110,488; 6,113,921; 6,139,866; 6,171,294; 6,181,963; 6,203,817; 6,216,033; 6,219,576; 6,365,178; 6,379,696; 6,425,892; 6,488,959; 6,756,052; 6,791,003; 6,835,184; 6,868,286; 6,881,208; 6,893,655; 6,916,486; 6,955,819; 7,018,370, and 7,054,682, all hereby incorporated by reference in their entirety).

Transdermal Dosage Forms

Administration is maintained for about a few minutes, about a few hours, about a few days, about a few weeks or about a month; 0.5, 1, 2, 3, and 7 day regimens being considered preferable. In preferred embodiments of the dosage form intended as 2, 3 or 7 day regimens, at least 1%, but not more than 50% of the total amount of mepivacaine in the dosage form is administered during approximately the first 24 hours of use; at least 2%, but not more than 60% of the total amount of the mepivacaine is administered during approximately the first 48 hours of use; and at least 2%, but not more than 80%, of the total amount of the mepivacaine is administered during the administration period. In preferred embodiments of the dosage form intended as 12 or 24 hour regimens, at least 1%, but not more than 50%, of the total amount of the mepivacaine in the dosage form is administered during approximately the first 6 hours of use; at least 2%, but not more than 70%, of the total amount of the mepivacaine is administered during approximately the first 8 hours of use; and at least 4%, but not more than 80%, of the total amount of the mepivacaine is administered during the administration period.

On application to the skin, the mepivacaine in the transdermal dosage form diffuses into the skin where it is absorbed into the peripheral tissue and/or the bloodstream to produce its intended therapeutic effects. The onset of effect depends on various factors, such as, potency, the solubility and diffusivity of the mepivacaine in the skin, thickness of the skin, concentration of the mepivacaine within the skin application site, and concentration of the mepivacaine in the reservoir. The concentration of the mepivacaine within the skin application sites are also significant in establishing an upper limit on the size of the transdermal dosage from.

When therapeutic effects are desired, the depleted transdermal dosage form would be removed and a fresh dosage form applied, in some embodiments generally to a new location. For example, the transdermal dosage form would be sequentially removed and replaced with a fresh dosage form at the end of the administration period to provide the required therapeutic effect. Since absorption of the mepivacaine from the fresh transdermal dosage form into the new application area usually occurs at substantially the same rate as absorption by the body of the residual mepivacaine within the previous application site of the transdermal dosage form, blood levels will remain substantially constant. Additionally, it is contemplated that doses may be increased over time and that concurrent use of other drugs for the treatment of the same malady or for a different malady may occur. In some embodiments, the dosage form of mepivacaine is consistently applied to the same skin site to produce local and/or systemic therapeutic effects.

Active-ingredient-containing transdermal drug delivery systems ("patches") are essentially divided into two major technical systems: reservoir systems and matrix systems. Both types of devices employ a backing layer that forms the protective outer surface of the finished transdermal system and which is exposed to the environment during use. A release liner or protective layer that forms the inner surface covers the polymeric adhesive which is employed for affixing the system to the skin or mucosa of a user. The release liner or protective layer is removed prior to application, exposing the adhesive, typically a pressure-sensitive adhesive.

In the "classic" reservoir-type device, the active agent is typically dissolved or dispersed in a carrier to yield a non-finite carrier form, such as, for example, a fluid or gel. In the reservoir-type device, the active agent is generally kept separate from the adhesive. The device has a pocket or "reservoir" which physically serves to hold the active agent and carrier, and which is formed in or by a backing layer. A peripheral adhesive layer is then used to affix the device to the user.

In a matrix-type device, the active agent is dissolved, dispersed or embedded in a semi-solid matrix made up of a single polymer or a blend of polymers (a carrier that typically is in a finite carrier form). The carrier form can be self-adhesive or non-adhesive. Non-adhesive matrix-type devices, that is, those which still rely on a separate adhesive means to affix the device to the user, employ a drug permeable adhesive layer (often referred to as an "in-line adhesive" since the drug must pass through this layer) applied over the drug matrix carrier layer. To better control the release rate of the releasable drug, the non-adhesive matrix-type devices often employ one or more additional drug permeable layers such as, for example, rate controlling membranes. The non-adhesive matrix-type devices often contain excipients, such as drug delivery enhancers, to help control the release rate. These devices are often referred to as multilayer or multilaminate.

In a "monolithic" or "monolayer" matrix-type device, the active agent is typically solubilized or homogenously blended in an adhesive carrier composition, typically a pressure-sensitive adhesive or bioadhesive, which functions as both the drug carrier and the means of affixing the system to the skin or mucosa. Such devices, commonly referred to as drug-in-adhesive devices, are described in the prior art.

Suitable flexible, finite delivery systems include those in which the drug is solubilized or contained directly in an adhesive matrix, typically a preferably a pressure-sensitive adhesive, that also serves as the means for attachment to the skin or mucosa of a patient. In addition to this adhesive drug layer, a drug-in-adhesive or matrix transdermal system further comprises a drug impermeable backing layer or film on one side of the adhesive layer, and a release liner on the other side. The backing layer protects the adhesive layer of the transdermal patch from the environment and prevents loss of the drug and/or release of other adhesive layer components to the environment. The release liner is removed from the transdermal patch to expose the adhesive layer prior to topical application.

Simple monolithic transdermal systems incorporate their active agents, i.e., drugs, directly into a single pressure sensitive adhesive layer. These systems have the advantage of being thin, elegant, and relatively easy to manufacture, but must compromise between optimizing the adhesive matrix for drug delivery versus its ability to adhere to the skin.

In some embodiments of the invention, application to the skin comprises a pharmaceutically acceptable carrier having uniformly dispersed within an amount of mepivacaine base, a pharmaceutically acceptable salt or mixtures thereof in a skin permeable form. The composition may be applied directly onto the skin from a container for the same, such as a bottle or tube, and subsequently covered, if desired, with a protective overlay. It is preferable, however, to quantify the dose and the area of application by placing the composition in an impermeable container of the correct size to provide a unit dose which may be held on the skin by adhesive means or other appropriate fastening means. In operation this composition would administer the mepivacaine through the skin to produce the intended therapeutic effect. In addition to the mepivacaine, the dosage form may also contain a permeation enhancer for the mepivacaine, thickeners and other additives, all as known to the art.

In another embodiment, application of mepivacaine to the skin according to this invention involves a reservoir composition. The dosage form comprises a drug reservoir composition typically in the form of a gel or polymeric carrier having uniformly dispersed within mepivacaine. The composition is preferably disposed between an impermeable backing, a mepivacaine releasing means such as release rate controlling membrane and a mepivacaine permeable adhesive, which are all known in the art. A mepivacaine impermeable release liner is applied to the adhesive layer and is removed prior to application. Suitable materials for use in manufacturing the various layers are well known in the art. In one embodiment of the invention, the mepivacaine is present in the reservoir composition in a form which is permeable through the rate controlling membrane. In practice, the dosage form of the invention would administer the mepivacaine through the skin at the rate intended for therapeutic effect.

In some embodiments, the present invention provides a dosage form for transdermal delivery of mepivacaine to a subject through intact, damaged or injured skin over an extended period of time. In particular, the dosage form of the present invention provides for the controlled release of the mepivacaine.

In some embodiments, the present invention provides a transdermal dosage with a therapeutic effect in a human patient for a period of up to 1, 2, 3, 4, 6, 8, 12 or 24 hours, or for a period of up to 1, 2, 3, 7, 14, 21, or 30 days.

On application to the skin, the mepivacaine in the reservoir of the transdermal dosage form diffuses into the skin where it is absorbed to (i) produce a local therapeutic effect and/or (ii) produce a systemic therapeutic effect. The onset of effect depends on various factors, such as, potency, solubility and diffusivity of the mepivacaine in the skin, thickness of the skin, concentration of the mepivacaine within the skin application site, concentration of the mepivacaine in the reservoir. The concentration of mepivacaine within the skin application sites are also significant in establishing an upper limit on the size of the transdermal dosage from.

When therapeutic effects are desired, the depleted transdermal dosage form would be removed and a fresh dosage form applied to the same location or to a new location. For example, the transdermal dosage form would be sequentially removed and replaced with a fresh dosage form at the end of the administration period to provide the required therapeutic effect. In some embodiments, the transdermal application will be non-sequential, e.g., about 12 hours of application followed by about 12 hours of pause where no patch is applied, followed again by a new application.

In some preferred embodiments, the invention provides for a transdermal dosage form comprises a transdermal dosage forms of about 0.5 to about 500 cm$^2$; preferably about 1 to about 300 cm$^2$, more preferably 2 to about 250 cm$^2$, even more preferably about 4 to about 150 cm$^2$ or about 10 to about 100 cm$^2$.

Parameters such as mepivacaine loading, reservoir thickness, membrane selection and surfactant modification of the rate controlling means can be varied to achieve the targeted release rate for a variety circumstances.

Any type of transdermal delivery system may be used to prepare the dosage form of the invention, including those described in U.S. Pat. Nos. 5,240,711, 4,806,341, 5,225,199, 5,069,909, 5,026,556, 4,588,580, 4,806,341, 5,225,199, 5,069,909, 5,026,556, 4,588,580, 6,004,969, 5,240,711 and 5,069,909; WO 96/19975; US Patent Application No. 20040013716, 20050208117, 20050095279, 20040213832, 20040013716, 20030026829 and 20020034535, and International Patent Application No. WO 96/19975 hereby incorporated by reference in their entirety.

Single Reservoir Based Transdermal Dosage Forms

In certain embodiments, a transdermal application to the skin according to this invention comprises a pharmaceutically acceptable carrier having uniformly dispersed within an amount of mepivacaine in a skin permeable form. The composition may be applied directly onto the skin from a container for the same, such as a bottle or tube, and subsequently covered, if desired, with a protective overlay. It is preferable, however, to quantify the dose and the area of application by placing the composition in an impermeable container of the correct size to provide a unit dose which may be held on the skin by adhesive means or other appropriate fastening means. In operation this composition would administer the mepivacaine through the skin to produce the intended therapeutic effect. In addition to the mepivacaine, the dosage form may also contain permeation enhancers, thickeners and other additives, all as known to the art. The dosage form of the invention can be in the form of an ointment, patch, cream, gel, paste, solution or lotion, for example.

In another embodiment, mepivacaine according to this invention involves a reservoir composition. The dosage form comprises a drug reservoir composition typically in the form of a gel or polymeric carrier having mepivacaine uniformly dispersed within. The composition is preferably disposed between an impermeable backing, a mepivacaine releasing means such as release rate controlling membrane and a mepivacaine permeable adhesive, which are all known in the art. A mepivacaine impermeable release liner is applied to the adhesive layer and is removed prior to application. Suitable materials for use in manufacturing the various layers are well known in the art. In this embodiment of the invention, the mepivacaine is present in the reservoir composition in a form which is permeable through the rate controlling membrane.

In some embodiments, the present invention provides a dosage form for topical or transdermal delivery of mepivacaine to a subject through intact, damaged or injured skin over an extended period of time.

In transdermal dosage forms of the invention, the release controlling means for the mepivacaine may be a monolithic or a multilaminate layer comprising a material that substantially prevents release during incidental exposure to moisture. In particular, the release controlling means comprises a breathable or occlusive material comprising fabric, porous, microporous, spun-bonded, spun laced, track etched, or impermeable material comprising polyvinyl acetate, polyvinylidene chloride, polyethylene, polypropylene, polyurethane, polyester, ethylene vinyl acetate (EVA), polyethylene terephthalate, polybutylene terephthalate, rayon (synthetic textile fibers produced by forcing a cellulose solution through fine spinnerets and solidifying the resulting filaments), wood-pulp, spun laced polyester, coated paper products, aluminum sheet, and the like, and a combination thereof. In preferred embodiments, release controlling means comprises low density polyethylene (LDPE) materials, medium density polyethylene (MDPE) materials or high density polyethylene (HDPE) materials, and the like. In preferred embodiments, the release controlling means is a single LDPE layer. In additional preferred embodiments, the release controlling means comprises a microporous layer selected from the group consisting of Solupor microporous ultra high density polyethylene (UHDPE) materials/film (Solupor™ manufactured by DSM Desotech, Denmark), microporous polypropylene (Celgard™), RoTrac Polyester Capillary Pore Membranes (OYPHEN GmbH, Germany), spun laced polyester, polypropylene or polyethylene. The microporous layer can be further modified with surfactants such as Pluracare polyethylene oxide-polypropylene oxide block copolymers (BASF, Wyandotte, Mich.) or hydrophilic polymers such as polyvinylpyrrolidone to provide additional control over the release as discussed in greater detail below.

The release controlling means has a thickness of about 0.012 mm (0.5 mil) to about 0.125 mm (5 mil); preferably 0.025 mm (1 mil) to about 0.1 mm (4 mil); more preferably 0.0375 mm (1.5 mil) to about 0.0875 mm (3.5 mil); and even more preferably 0.05 mm (2 mil) to about 0.0625 mm (2.5 mil).

The transdermal dosage form according some embodiments of the invention comprises mepivacaine in a reservoir. The reservoir may be formed from standard materials as known in the art. For example, the reservoir is formed, from a hydrophobic, a lipophilic and/or a non-polar polymeric material, such as, ethyleneoctene copolymers, ethylene-vinyl acetate copolymer (EVA), low density polyethylene (LDPE), high density polyethylene (HDPE), medium density polyethylene (MDPE), styrenic block copolymer thermoplastic elastomers, and the like.

In preferred embodiments, the reservoir is formed from a pharmaceutically acceptable pressure sensitive adhesive, preferably a polyacrylate or a styrenic block copolymer-based adhesive.

The adhesive reservoir or the adhesive coating is formed from standard pressure sensitive adhesives known in the art. Examples of pressure sensitive adhesives include, but are not limited to, polyacrylates, polysiloxanes, polyisobutylene (PIB), polyisoprene, polybutadiene, styrenic block polymers, and the like. Examples of styrenic block copolymer-based adhesives include, but are not limited to, styrene-isoprene-styrene block copolymer (SIS), styrene-butadiene-styrene copolymer (SBS), styrene-ethylenebutene-styrene copolymers (SEBS), and di-block analogs thereof.

The acrylic polymers are comprised of a copolymer or terpolymer comprising at least two or more exemplary components selected from the group comprising acrylic acids, alkyl acrylates, methacrylates, copolymerizable secondary monomers or monomers with functional groups. Examples of monomers include, but are not limited to, acrylic acid, methacrylic acid, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, and the like. Additional examples of appropriate acrylic adhesives suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, N.Y. (1989). The acrylic adhesives are commercially available (National Starch and Chemical Corporation, Bridgewater, N.J.; Solutia, Mass.). Further examples of polyacrylate-based adhesives are as follows, identified as product numbers, manufactured by National Starch (Product Bulletin, 2000): 87-4098, 87-2287, 87-4287, 87-5216, 87-2051, 87-2052, 87-2054, 87-2196, 87-9259, 87-9261, 87-2979, 87-2510, 87-2353, 87-2100, 87-2852, 87-2074, 87-2258, 87-9085, 87-9301 and 87-5298.

The acrylic polymers comprise cross-linked and non-cross-linked polymers. The polymers are cross-linked by known methods to provide the desired polymers. In preferred embodiments, the adhesive is a polyacrylate adhesive having a glass transition temperature (Tg) less than −10° C., more preferably having a Tg of about −20° C., to about −35° C. The molecular weight of the polyacrylate adhesive, expressed as weight average (MW), generally ranges from 25,000 to 10,000,000, preferably from 50,000 to about 3,000,000 and more preferably from 100,000 to 1,000,000 prior to any cross-linking reactions. Upon cross-linking the MW approaches infinity, as known to those involved in the art of polymer chemistry.

In additional embodiments, the mepivacaine reservoir may optionally contain additional components such as, additives, permeation enhancers, stabilizers, dyes, diluents, plasticizer, tackifying agent, pigments, carriers, inert fillers, antioxidants, excipients, gelling agents, anti-irritants, vasoconstrictors and other materials as are generally known to the transdermal art, provided that such materials are present below saturation concentration in the reservoir.

Examples of permeation enhancers include, but are not limited to, fatty acid esters of glycerin, such as capric, caprylic, dodecyl, oleic acids; fatty acid esters of isosorbide, sucrose, polyethylene glycol; caproyl lactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; N-octyl-2-pyrrolidone; lauraminopropionic acid; polypropylene glycol-4-laureth-2; polypropylene glycol-4-laureth-5dimethy-1 lauramide; lauramide diethanolamine (DEA). Preferred enhancers include, but are not limited to, lauryl pyroglutamate (LP), glyceryl monolaurate (GML), glyceryl monocaprylate, glyceryl monocaprate, glyceryl monooleate (GMO), and sorbitan monolaurate. Additional examples of suitable permeation enhancers are described in the prior art.

In certain preferred embodiments, the reservoir comprises diluent materials capable of reducing quick tack, increasing viscosity, and/or toughening the matrix structure, such as polymethyl methacrylate or polybutyl methacrylate (ELVACITE, manufactured by ICI Acrylics, e.g., ELVACITE 1010, ELVACITE 1020, ELVACITE 20), high molecular weight acrylates, i.e., acrylates having an average molecular weight of at least 500,000, and the like.

In certain preferred embodiments, particularly with styrenic block copolymer adhesive systems, a plasticizer or tackifying agent is incorporated in the adhesive composition to improve the adhesive characteristics. Examples of suitable tackifying agents include, but are not limited to, aliphatic hydrocarbons; aromatic hydrocarbons; hydrogenated esters; polyterpenes; hydrogenated wood resins; tackifying resins such as ESCOREZ, aliphatic hydrocarbon resins made from cationic polymerization of petrochemical feedstocks or the thermal polymerization and subsequent hydrogenation of petrochemical feedstocks, rosin ester tackifiers, and the like; mineral oil and combinations thereof.

The tackifying agent employed should be compatible with the blend of polymers. For example, the styrenic block copolymers can be formulated with rubber compatible tackifying resins, end-block compatible resins such polymethyl styrene, or plasticizers such as mineral oil.

The transdermal dosage form further comprises a peelable protective layer. The protective layer is made of a polymeric material that may be optionally metallized. Examples of the polymeric materials include, polypropylene, polystyrene, polyimide, polyethylene, polyethylene terephthalate, polybutylene terephthalate, paper, and the like, and a combination thereof. In preferred embodiments, the protective layer comprises a siliconized polyester sheet.

A preferred embodiment of the transdermal dosage form according to this invention comprises a patch, an impermeable barrier layer disposed distally, a reservoir containing mepivacaine, a rate controlling means, and an amine resistant contact adhesive layer, covered by a peelable protective layer.

Although preferred embodiments of this invention utilize an amine resistant in-line adhesive, other means for maintaining the dosage form on the skin can be employed. Such means include a peripheral ring of adhesive outside the path of mepivacaine from the dosage form to the skin, in which case the adhesive need not be amine resistant. The use of adhesive overlays or other fastening means such as buckles, belts, and elastic arm bands is also contemplated.

A wide variety of materials which can be used for fabricating the various layers of the transdermal dosage form according to this invention have been described above. This invention therefore contemplates the use of materials other than those specifically disclosed herein, including those which may hereafter become known to the art to be capable of performing the necessary functions.

The adhesive mepivacaine reservoir or the adhesive coating is formed from standard pressure sensitive adhesives known in the art. Examples of pressure sensitive adhesives include, but are not limited to, polyacrylates, polysiloxanes, polyisobutylene (PIB), polyisoprene, polybutadiene, styrenic block polymers, and the like. Examples of styrenic block copolymer-based adhesives include, but are not limited to, styrene-isoprene-styrene block copolymer (SIS), styrene-butadiene-styrene copolymer (SBS), styrene-ethylenebutene-styrene copolymers (SEBS), and di-block analogs thereof.

The acrylic polymers are comprised of a copolymer or terpolymer comprising at least two or more exemplary components selected from the group comprising acrylic acids, alkyl acrylates, methacrylates, copolymerizable secondary monomers or monomers with functional groups. Examples of monomers include, but are not limited to, acrylic acid, methacrylic acid, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, and the like. Additional examples of appropriate acrylic adhesives suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, N.Y. (1989). The acrylic adhesives are commercially available (National Starch and Chemical Corporation, Bridgewater, N.J.; Solutia, Mass.). Further examples of polyacrylate-based adhesives are as follows, identified as product numbers, manufactured by National Starch (Product Bulletin, 2000): 87-4098, 87-2287, 87-4287, 87-5216, 87-2051, 87-2052, 87-2054, 87-2196, 87-9259, 87-9261, 87-2979, 87-2510, 87-2353, 87-2100, 87-2852, 87-2074, 87-2258, 87-9085, 87-9301 and 87-5298.

The acrylic polymers comprise cross-linked and non-cross-linked polymers. The polymers are cross-linked by known methods to provide the desired polymers. In preferred embodiments, the adhesive is a polyacrylate adhesive having a glass transition temperature (Tg) less than −10° C., more preferably having a Tg of about −20° C., to about −35° C. The molecular weight of the polyacrylate adhesive, expressed as weight average (MW), generally ranges from 25,000 to 10,000,000, preferably from 50,000 to about 3,000,000 and more preferably from 100,000 to 1,000,000 prior to any cross-linking reactions. Upon cross-linking the MW approaches infinity, as known to those involved in the art of polymer chemistry.

The transdermal dosage form comprise mepivacaine reservoirs comprising a component, including mepivacaine at concentration greater than, equal to, or less than the saturation concentration. As discussed above, in preferred embodiments the mepivacaine reservoir comprises a single phase polymeric composition, free of undissolved components, containing an amount of the mepivacaine sufficient to induce and maintain the required therapeutic effect of the mepivacaine in a human for at least 4, 6, 8, 12, 16, 18 or 24 hours, or optionally, at least 2, 3, 7, 14, 21 or 30 days. The mepivacaine should be soluble in the polymer forming reservoir in a form that is as discussed below. In preferred embodiments, the mepivacaine is in the unsalified form.

In some preferred embodiments, the mepivacaine is preferably in unsalified form, wherein the material forming the reservoir has a solubility for the mepivacaine of about 0.5 wt % to about 40 wt % of the total polymer composition, preferably of about 1 wt % to about 25 wt % of the total polymer composition; more preferably about 2 wt % to about 15 wt %; even more preferably about 4 wt % to about 12 wt % of the total polymer composition. The reservoir, with or without the adhesive coating, has a thickness of about 0.0125 mm (0.5 mil) to about 0.1 mm (4 mil); preferably about 0.025 mm (1 mil) to about 0.075 mm (3 mil); more preferably 0.0375 mm (1.5 mil) to about 0.0625 (2.5 mil); and even more preferably about 0.04 mm (1.6 mil) to about 0.05 mm (2 mil).

In additional embodiments, the mepivacaine reservoir may optionally contain additional components such as, additives, permeation enhancers, stabilizers, dyes, diluents, plasticizer: tackifying agent, pigments, carriers, inert fillers, antioxidants, excipients, gelling agents, anti-irritants, vasoconstrictors and other materials as are generally known to the transdermal art, provided that such materials are present below saturation concentration in the reservoir.

In certain embodiments, the mepivacaine reservoir comprises diluent materials capable of reducing quick tack, increasing viscosity, and/or toughening the matrix structure, such as polymethyl methacrylate or polybutyl methacrylate (ELVACITE™, manufactured by ICI Acrylics, e.g., ELVACITE™ 1010, ELVACITE™ 1020, ELVACITE™ 20), high molecular weight acrylates, i.e., acrylates having an average molecular weight of at least 500,000, and the like.

In certain embodiments, particularly with styrenic block copolymer adhesive systems, a plasticizer or tackifying agent is incorporated in the adhesive composition to improve the adhesive characteristics. Examples of suitable tackifying agents include, but are not limited to, aliphatic hydrocarbons; aromatic hydrocarbons; hydrogenated esters; polyterpenes; hydrogenated wood resins; tackifying resins such as ESCOREZ™, aliphatic hydrocarbon resins made from cationic polymerization of petrochemical feedstocks or the thermal polymerization and subsequent hydrogenation of petrochemical feedstocks, rosin ester tackifiers, and the like; mineral oil and combinations thereof.

The tackifying agent employed should be compatible with the blend of polymers. For example, the styrenic block copolymers can be formulated with rubber compatible tackifying resins, end-block compatible resins such polymethyl styrene, or plasticizers such as mineral oil. Generally the polymer is about 5-50% of the total adhesive composition, the tackifier is about 30-85% of the total adhesive composition, and the mineral oil is about 2-40% of total adhesive composition.

The transdermal dosage form further comprises a mepivacaine rate controlling means disposed on the skin contacting surface of the mepivacaine reservoir, wherein at least the skin contacting surface of the mepivacaine rate controlling means is adhesive. The mepivacaine rate controlling means is made of a polymeric material such as ethylene-vinyl acetate (EVA), polyvinyl chloride (PVC), ethylene-ethyl acrylate copolymer, ethylene butylacrylate copolymer, polyisobutylene (PIB), polyethylene (PE) such as low density polyethylene (LDPE), medium density polyethylene (MDPE), high density polyethylene (HDPE), and the like, and a combination thereof; the polymeric materials may be plasticized. In preferred embodiments, the mepivacaine rate controlling means is adhered to the skin with an acrylic, silicone, or PIB adhesive material. The mepivacaine rate controlling means has a thickness of about 0.012 mm (0.5 mil) to about 0.125 mm (5 mil); preferably 0.025 mm (0.6 mil) to about 0.1 mm (4 mil); more preferably 0.0625 mm (0.8 mil) to about 0.0875 mm (3.5 mil).

The transdermal dosage form further comprises a peelable protective layer. The protective layer is made of a polymeric material that may be optionally metallized. Examples of the polymeric materials include, polypropylene, polystyrene, polyimide, polyethylene, polyethylene terephthalate, polybutylene terephthalate, paper, and the like, and a combination thereof. In preferred embodiments, the protective layer comprises a siliconized polyester sheet.

A wide variety of materials which can be used for fabricating the various layers of the transdermal dosage form according to this invention have been described above. This invention therefore contemplates the use of materials other than those specifically disclosed herein, including those which may hereafter become known to the art to be capable of performing the necessary functions.

Matrix and Drug-in-Adhesive Based Transdermal and Topical Dosage Forms

In some preferred embodiments, the invention is a silicone pressure sensitive adhesive formulation comprising a blend of mepivacaine suspended in a solvated silicone pressure sensitive adhesive. The selected solvent is one that can substantially or fully solvate or dissolve the adhesive while keeping the mepivacaine suspended in the solvated adhesive.

The formulation of the invention can be made by blending mepivacaine particles directly with one or more solvated silicone adhesives to form a suspension of mepivacaine particles in the solvated adhesive(s). Alternatively, the formulation can be made by first combining the mepivacaine particles with a silicone fluid to wet the particles and form a slurry, which slurry then can be blended with the solvated silicone adhesive(s) to also form a suspension of mepivacaine in the solvated adhesive(s).

The above formulations are useful for making monolithic devices for transdermal administration of the invention.

In some preferred embodiments, the method of making a laminate comprises the steps of: (i) selecting a solvent that can substantially or fully solvate a silicone adhesive while keeping mepivacaine particles, when blended with the solvated adhesive, suspended in the solvated adhesive; (ii) blending mepivacaine particles with one or more silicone adhesives which are solvated with the above solvent, to form a blend formulation in which mepivacaine particles are suspended in the solvated adhesives; (iii) casting the blend formulation onto a support material; and (iv) removing the solvent, to produce a laminate containing the support material and mepivacaine suspension-containing adhesive layer. In a preferred embodiment, the blend formulation formed in step (ii) is further treated prior to the casting step.

The blend formulation preferably is cast onto a backing layer or release liner. The solvent can be removed during drying by evaporation from the adhesive layer. The laminate can be further processed to produce a monolithic device containing a backing layer, mepivacaine suspension-containing adhesive layer, and release liner.

In some preferred embodiments, the monolithic patch for application of mepivacaine transdermally to the skin comprises: (i) a backing layer substantially impervious to the mepivacaine to be administered transdermally; (ii) mepivacaine-containing adhesive layer in contact with at least a portion of the backing layer, the adhesive layer being cast from a formulation comprising a blend of mepivacaine particles suspended in one or more solvated silicone adhesives; and (iii) a removable release liner in contact with the adhesive layer.

In some preferred embodiments, the monolithic patch for application of mepivacaine transdermally to the skin comprises: (i) a backing layer substantially impervious to mepivacaine to be administered transdermally; and (ii) mepivacaine-containing adhesive layer in contact with the backing layer, the adhesive layer being cast from a formulation comprising a blend of mepivacaine particles suspended in one or more solvated silicone adhesives.

In some preferred embodiments, the selected solvent is heptane.

In some preferred embodiments, the present invention provides a transdermal dosage with a therapeutic effect in a human patient for a period of up to about 4, or up to about 6, or up to about 8, or up to about 12 or about up to about 24 hours, or for a period of up to about 2, or up to about 3, or up to about 4, or up to about 7 days. In some preferred embodiments, the present invention provides a transdermal dosage with a therapeutic effect in a human patient for a period of up to up to about 10, or up to about 14, or up to about 21, or up to about 28, or up to about 30 days.

In some preferred embodiments, the present invention provides formulations in which mepivacaine particles are suspended in a solvent-based silicone adhesive. The mepivacaine suspension is produced by blending mepivacaine particles with a solvent-based silicone adhesive. The selected solvent is one that can substantially or fully solvate or dissolve the silicone adhesive. The selected solvent also must be suitable for preventing high concentrations, e.g., greater than about 1.0% w/w (dry weight), of mepivacaine particles from dissolving in the solvated adhesive.

The total amount of mepivacaine agent need not be suspended in the solvated adhesive, thus allowing for instances when a portion of the mepivacaine is dissolved in the solvated adhesive.

The solvent preferably is heptane, but also may be selected from other organic solvents, preferably closely related aliphatic solvents such hexane and octane, for example, as long as the selected solvent exhibits the above-described dissolution features.

The formulations made in accordance with the present invention are used to manufacture improved devices for delivering mepivacaine transdermally, particularly monolithic transdermal patches. The devices may be manufactured by casting the formulation onto a support material such as a backing layer or release liner to form a mepivacaine suspension-containing adhesive layer, which can be further processed to make a transdermal patch for delivering the mepivacaine.

Thus, to manufacture a device having the advantages of the present invention, in some embodiments, one must first produce a formulation comprising a blend of mepivacaine particles suspended in a solvated silicone adhesive, which formulation then is subsequently processed to make the device. Alternative methods for producing or achieving a mepivacaine suspension-containing adhesive layer according to the invention may be apparent to persons skilled in the art, and these alternative methods thus also fall within the scope of the present invention.

In a preferred embodiment, one or more silicone pressure sensitive adhesives are dissolved in heptane, while mepivacaine particles are mixed with a silicone fluid to form a slurry. The slurry of mepivacaine in silicone fluid then is blended with a portion of the heptane-solvated silicone adhesive and passed through a high shear colloid mill or other mixing device to form a suspension. This suspension then is blended with the remaining heptane-solvated silicone adhesive to form the final (and more dilute) suspension. The composition then is cast onto a release liner and passed through an oven(s) to drive off the heptane. A backing film then is laminated onto the dried adhesive matrix.

In another preferred embodiment, the device or patch is produced by casting a blend of heptane-solvated adhesive(s) and suspended (solid) mepivacaine particles. A slurry is produced by mixing mepivacaine directly with a portion of the heptane-solvated silicone adhesive(s). No silicone fluid is used. This slurry then is passed through a colloid mill or similar mixing device to form a suspension. This suspension then is blended with the remaining heptane-solvated silicone adhesive(s) to form the final (and more dilute) suspension that can be cast onto a release liner and passed through an oven to drive off the heptane. A backing film then is laminated onto the dried adhesive matrix.

The silicone pressure sensitive adhesive preferably is solvated in about 20% to about 50% heptane, and more preferably in about 30% heptane. In addition to contributing to formation of a mepivacaine suspension, other advantages of using heptane include decreased toxicity as compared to other solvents, which include, for example, toluene, xylene and other aromatics generally.

In some preferred embodiments, mepivacaine particles are suspended uniformly in the solvated silicone adhesive as small particles, preferably crystalline particles.

In some preferred embodiments, it is believed that as the mepivacaine leaves the system during the course of application, the suspended mepivacaine in the system dissolves and replenishes the delivered drug.

Suitable silicone adhesives include pressure sensitive adhesives made from silicone polymer and resin. The polymer to resin ratio can be varied to achieve different levels of tack. Examples of useful silicone adhesives which are commercially available include the standard BioPSA series (7-4400, 7-4500 and 7-4600 series) and the amine compatible (endcapped) BioPSA series (7-4100, 7-4200 and 7-4300 series) manufactured by Dow Corning. Preferred heptane-solvated silicone adhesives include BIO-PSA 7-4201, BIO-PSA 7-4301, and BIO-PSA 7-4501.

In some preferred embodiments in which silicone medical fluid is used, the preferred amount of silicone pressure sensitive adhesive used is from about 75% to about 99% w/w (dry weight), and more preferably from about 80% to about 90% w/w (dry weight).

In some preferred embodiments in which one or more different silicone adhesives may be used, optionally in the presence of silicone medical fluid, the preferred combined amount of silicone pressure sensitive adhesive is from about 75% to about 99% w/w (dry weight), more preferably from about 85% to about 95% w/w (dry weight), and most preferably about 91% w/w (dry weight).

Preferred silicone fluids include high molecular weight polydimethylsiloxane, Dimethicone NF (Dow 360 Silicone Medical Fluid, 100 cSt and other viscosities). Preferred amounts of silicone fluid are from about 0% w/w to about 25% w/w (dry weight), more preferably from about 2% w/w to about 10% w/w (dry weight), even more preferably from about 5% w/w to about 8.5% w/w (dry weight), and most preferably about 6.5% w/w (dry weight). Preferred viscosities of the silicone fluid are from about 20 cSt to about 350 cSt, and most preferably about 100 cSt.

In some preferred embodiments, alternatives to silicone fluid, such as mineral oil, also may be used and are within the scope of the invention.

The width or thickness of the adhesive layer is that width which provides at least sufficient adhesion of the device to the skin of the host. The width or thickness also may vary depending upon such factors as the amount of drug to be delivered from the composition or adhesive layer and the desired wear period. In some preferred embodiments, the thickness of the adhesive layer will usually range from about 10 to 300 μm, more preferably 70 to about 140 μm. Expressed alternatively, in some preferred embodiments, the adhesive layer will be present at about 1 to about 30 mg/cm$^2$, more preferably about 7 to about 14 mg/cm$^2$. Variations also can be determined as a matter of routine experimentation by those of ordinary skill in the art. The width also need not be uniform and may vary around the perimeter of the device, e.g., to provide a specific geometric shape or to provide a tab for removal of a protective liner.

In some preferred embodiments, the mepivacaine are administered preferably in unsalified and salified forms, respectively. The quantity of mepivacaine in the adhesive layer is preferably that quantity sufficient to provide a pharmaceutically or physiologically effective dosage rate of the active agent to a human subject. The quantity of mepivacaine also is sufficient to maintain at least a partial suspension of the mepivacaine in a solvated adhesive. This quantity can be readily determined by those of ordinary skill in the art without undue experimentation.

In some preferred embodiments, amounts are about 1% to about 10% w/w (dry weight), more preferably about 3% to about 7% w/w (dry weight), and most preferably about 4.0% w/w (dry weight) of mepivacaine. In some preferred embodiments, amounts are about 5% to about 15% w/w (dry weight), more preferably about 8% to about 12% w/w (dry weight), and most preferably about 9.1% w/w (dry weight) of mepivacaine.

In some preferred embodiments, a flux enhancer to promote the penetration of the mepivacaine through the skin is included in the adhesive layer. Suitable flux enhancers include those described in U.S. Pat. No. 4,573,966, including, monovalent, saturated and unsaturated aliphatic and cycloaliphatic alcohols having 6 to 12 carbon atoms such as cyclohexanol, lauryl alcohol and the like; aliphatic and cycloaliphatic hydrocarbons such as mineral oil; cycloaliphatic and aromatic aldehydes and ketones such as cyclohexanone; N,N-di(lower alkyl)acetamides such as N,N-diethyl acetamide, N,N-dimethyl acetamide, N-(2-hydroxyethyl)acetamide, and the like; aliphatic and cycloaliphatic esters such as isopropyl myristate and lauricidin; N,N-di(lower alkyl)sulfoxides such as decylmethyl sulfoxide; essential oils, nitrated aliphatic and cycloaliphatic hydrocarbons such as N-methyl-2-pyrrolidone and azone; salicylates, polyalkylene glycol silicates; aliphatic acids such as oleic acid and lauric acid, terpenes such as cineole, surfactants such as sodium lauryl sulfate, siloxanes such as hexamethyl siloxane; mixtures of the above materials; and the like.

The backing layer is preferably a thin film or sheet. In some instances, because of the area of skin to which the device is to be attached, the device, and therefore the backing layer, may be opaque or colored for cosmetic reasons. In one embodiment, it is a clear layer that is occlusive with respect to the active agent or drug, printed matter thereon. The backing layer normally provides support and a protective covering for the device.

The backing layer is preferably made of a material or combination of materials that is preferably impermeable, or at least substantially impermeable, to the adhesive layer and the mepivacaine contained therein.

Suitable materials for the backing layer include those known in the art for use with pressure sensitive adhesives. For example, the backing layer can comprise a polyolefin, including polyethylene; a polyester; multi-layer EVA film and polyester; polyurethane; or combinations thereof. A preferred backing material is MEDIFLEX™ 1000, a polyolefin manufactured by Mylan Technologies, Inc. Other suitable materials include, for example, cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride (e.g., SARAN™), ethylene-methacrylate copolymer (Surlyn), paper, cloth, aluminum foil and polymer-metal composites.

The material that forms the backing layer may be flexible or non-flexible. Preferably, a flexible backing layer is employed to conform to the shape of the body member to which the device is attached.

In one embodiment, the medical device contains a protective release liner attached to the device at the surface to be adhered to the skin, namely the mepivacaine-containing adhesive layer. The release liner is removed before the device is placed on the skin. The release liner is thus made of a material(s) that permits the liner to be easily stripped or peeled away from the adjacent pressure sensitive adhesive layer. The release liner may be made of the same materials suitable for use in the backing layer as discussed above. Such material is preferably made removable or releasable from the adhesive layer, for example, by conventional treatment with silicon polymers, fluoropolymers (e.g., Teflon™) or other suitable coatings on the surface thereof. The removal of the device from the release liner may also be provided by mechanical treatment of the release liner, e.g., by embossing the release liner.

Suitable release liners include those known in the art for use with pressure sensitive adhesive compositions. For example, the release liner can comprise a fluorosilicone coated polyester. A preferred release liner is MEDIRELEASE™ 2500, manufactured by Mylan Technologies, Inc., or a fluoropolymer-treated polyester, such as Scotchpak™ 1022, manufactured by 3M Pharmaceuticals. The release liner, however, can comprise various layers, including paper or paper-containing layers or laminates; various thermoplastics, such as extruded polyolefins, such as polyethylene; various polyester films; foil liners; other such layers, including fabric layers, coated or laminated to various polymers, as well as extruded polyethylene, polyethylene terephthalate, various polyamides, and the like.

In one embodiment, the release liner includes a laminate of an outer foil layer and an inner layer of plastic, such as polyethylene or the like, which is rendered releasable not only by means of a siliconized coating, but which also includes an embossed or roughened surface. Embossment is described in U.S. Pat. No. 6,010,715, which is fully incorporated herein by reference.

In one embodiment of this invention, the patch further comprises a mepivacaine-free adhesive layer in between the backing layer and the mepivacaine-free adhesive layer-containing adhesive layer. This additional adhesive layer extends beyond at least a portion of the mepivacaine-free adhesive layer-containing adhesive layer to provide a further surface area that can adhere to the skin of the wearer, thereby enhancing the adhesive qualities of the device or patch. The size and shape of the backing layer will be essentially co-extensive with the size and shape of this additional adhesive layer. This mepivacaine-free adhesive layer can comprise any conventional adhesive, such as a polyisobutylene or an acrylic acid polymer, such as alkyl acrylate or methacrylate polymers, as found in any of a variety of commercially available transdermal patches or tapes.

The compositions of this invention possess sufficient adhesive properties that once the release liner is removed and the composition is applied to the skin the composition can remain in place for a period of time sufficient to distribute the desired amount of the drug contained therein with a low incidence of de-bonding.

One skilled in the transdermal art would readily recognize the possible sizes of devices or patches in accordance with the invention. The patch sizes preferably vary depending on a wide variety of patient-related and pain-related factors (e.g., the pharmacokinetics, pharmacodynamics, efficacy, safety, tolerability, analgesic response, prior opioid exposure, pathophysiology, responsiveness of the pain to mepivacaine, etc.), physicochemical and pharmaceutical factors (e.g., physical properties of the drug and excipient, drug-excipient interaction, desired dose and dosing frequency, desired size of patch or skin application area, nature of the dosage system/device, drug formulation, etc.), preferably increasing in size as the desired delivery rate increases.

The device, once formed, may be kept sealed in an air-tight pouch prior to use. The device of the present invention is used in the same manner as those devices which are conventional in the prior art. In particular, the release liner attached to the skin-side surface of the adhesive layer of the device for contact with the skin or mucosa of the host is removed and such surface of the adhesive layer is applied to the desired area of the skin.

Film-Forming Topical and Transdermal Dosage Forms

Film-forming topical and transdermal formulations and methods for the preparation of said dosage forms are known in the art, for example in U.S. Pat. Nos. 7,029,659; 7,083,781; 7,005,557; 6,962,691; 6,838,078; 6,797,262; 6,759,032; 6,730,288; 6,716,419; 6,582,680; 6,500,407; 6,458,339; 6,432,423; 6,306,411; 6,296,858; 6,254,877; 6,238,679; 6,238,654; 6,228,354; 6,126,920; 5,989,570; 5,948,882; 5,911,980; 5,906,822; 5,906,814; 5,869,600; 5,888,494; 5,807,957; 5,776,479; 5,711,943; 5,667,773; 5,589,195; 5,525,358; 5,508,024; 5,173,291; 5,017,369; 4,990,501; 4,978,527; 4,950,475; 4,584,192; 4,542,012; 4,393,076; 4,374,126; 4,199,564 and US Patent Application Nos. 20070025943; 20060193789; 20060165626; 20060064068; 20050191249; 20050186154; 20050186153; 20050186152; 20050025794; 20040161402; 20040071760; 20040022755; 20030224053; 20030194415; 20030194387; 20030118655; 20030086954; 20030082221; 20030077307; 20020142042; 20020132008; 20030026816; 20030026815; 20030007944; 20020022009, hereby incorporated by reference in their entirety.

Film forming dosage forms can provide topical and transdermal delivery of the mepivacaine, pharmaceutically acceptable salts or mixtures thereof and have the advantage of being unobtrusive, more amenable to dose titration and easily applied to areas of the skin where patch application can be problematic (body contours, crevices, hairy skin, body extremities). For example, it is know that patients with painful diabetic neuropathy, painful HIV-neuropathy and other peripheral neuropathies that exhibit a "stocking and glove" distribution have difficulty applying topical patches, since the skin of the hands and feet does not easily lend itself to the application of a patch. Even when the application is to skin not involving the extremities, the area of application varies from patient to patient. This requires patients to cut the patch formulation to apply it to the affected area. A film-forming formulation is largely devoid of such disadvantages.

In some preferred embodiments, the film-forming formulation of the dosage form forms a film on the skin which exhibits excellent elasticity, flexibility and adhesion and is non-sticky.

In some preferred embodiments, the dosage form comprises a composition that includes a mixture of a polymer, mepivacaine, pharmaceutically acceptable salts or mixtures thereof, a solvent, and optionally pharmaceutical excipients, adjuvants and auxiliary agents capable of being preserved within a container such that on release from the container, the composition forms a peelable, water removable or water-resistant, drug-releasing film on the surface of skin so as to deliver the mepivacaine to the skin for local and/or systemic effects.

In some preferred embodiments, the dosage form includes a film-forming material wherein the film is formed upon application of the formulation to the human skin. In some preferred embodiments, the composition can be manufactured as a commercial product in an appropriate device/apparatus for application of the composition to the skin of the subject. The amount of the composition that is delivered by the device to the skin can contain an effective amount of mepivacaine in the composition. In some preferred embodiments, the composition may also include pharmaceutical excipients, adjuvants and auxiliary agents that possess multifunctional properties. The film is formed directly on the site of application after the composition is sprayed, rolled, spread or otherwise applied, and when dry the composition forms a film on the skin.

In some preferred embodiments, the film can be easily removed with water or can be peeled off. In some other preferred embodiments, the film can be may be substantially resistant to removal with water or can be peeled off; said film requiring the use of a detergent, friction, or solvent (e.g., aqueous, hydroalcoholic, or organic solvent) for easy removal.

In some preferred embodiments, the dosage form contains a polymer, for example, a polyvinyl alcohol (PVA), for example, a mixture of a first polyvinyl alcohol and a second polyvinyl alcohol of different viscosities. Other biocompatible polymers which are biologically inert polymers include cellulose, carboxymethyl cellulose, PVP/polyvinyl propylene, polyurethane, ethylene vinyl acetate, polyethylene, polypropylene, polystyrene or copolymers thereof. In some preferred embodiments, a preferred polymer is a polyvinyl alcohol, which confers sufficient viscosity to the composition so that it can form a film, which upon evaporation and concentration of the solvent can form a film that adheres to the skin.

In some preferred embodiments, the mepivacaine, pharmaceutically acceptable salts or mixtures thereof can optionally be formulated in an alcohol-based solvent system, more particularly a lower alkyl alcohol (lower alkanol), for example, methanol, n-propanol, I-propanol, more preferably ethanol, or an alcohol solution or suspension, preferably an ethanol solution or suspension.

In some preferred embodiments, one or more hydrophobic substances can be included in the formulation, for example, fumed silica, to modify the release and skin flux characteristics of the formulation system.

In some preferred embodiments, the formulation may include additives such as solvents, plasticizers, solubilizers, emollients, and preservatives known in the art to be suitable for application to the skin.

In some preferred embodiments, the formulation may be applied to the skin using a variety of available devices, including a ball-tipped container (e.g., a rollette applicator), an atomizer, an aerosol container, a pressurized container or directly from a tube or bottle.

In some preferred embodiments, the film-forming dosage form for application to the skin comprises mepivacaine as suspension in a vehicle optionally containing a polymer or combination of polymers. The compositions of the invention preferably comprise mepivacaine up to about 50% (e.g., 0.0001% to about 50%), more preferably up to about 10% (e.g., 0.0001% to about 10%) and most preferably up to about 5% (e.g., 0.0001% to about 5%) dissolved or suspended in one or more vehicles which comprise up to 99% of the composition (e.g., 0.0001% to about 99%). In some preferred embodiments, the composition may further contain one or more film former, solubilizer, permeation enhancer and plasticizer. In some preferred embodiments, the composition may contain one or more of these additives in amounts of up to about 20% film-former (e.g., 0.0001% to about 20%), up to about 20% solubilizer (e.g., 0.0001% to about 20%), up to about 20% permeation enhancer (e.g., 0.0001% to about 20%), and up to about 20% plasticizer (e.g., 0.0001% to about 20%). The composition may be sprayed or applied on the skin to form a stable, breathable film on the site, from which film the mepivacaine acts locally on the skin surface or is transdermally available. Preferably, the composition further comprises up to about 15% (w/w) of one or more water-soluble additives (e.g., 0.0001% to about 15%). The mepivacaine so deposited in the matrix of the film-former may remain solubilized or suspended. The exact formulation of the composition may vary depending on the selection of active agent or drug, the nature of the particular medicament used (for example, the solubility profile), the intended therapeutic effect, the anatomic location and the release profile desired. The compositions can be dispensed from any dispenser, preferably a dispenser which provides the composition as a spray, and may be used for systemic action or topical action. The mepivacaine from the composition may be released over a period of time or immediately.

In some preferred embodiments, the compositions of the present invention are preferably applied in a metered dose over a predetermined surface area. Preferably, the composition is dispensed from a pump dispenser or from an aerosol dispenser. In the latter case, the composition additionally may comprise from about 10% to 90% of propellant in order to provide a suitable pressure within the aerosol dispenser. Generally, propellant is not required for compositions dispensed from a pump dispenser. However, if desired, such compositions may also comprise from about 10% to 90% of a propellant which is liquid at room temperature, for example, trichloromonofluoromethane.

In some preferred embodiments, the film-formers preferably include acrylic polymers or copolymers, including methacrylic polymers and copolymers. Preferred film-formers include a non-ionic copolymer of methyl methacrylate and butyl methacrylate (Plastoid™ B), a copolymer of dimethylamine ethyl methacrylate and a neutral methacrylic acid ester (Eudragit™ E100), ammonio methacrylate copolymer type B (Eudragit RS, USP/NF), ammonio methacrylate copolymer type A (Eudragit™ RL, USP/NF), methacrylic acid copolymer type A (Eudragit™ L100, USP/NF), methacrylic acid copolymer type B (Eudragit™ S100 USP/NF), polyvinyl acetate, cellulose acetate, polyvinyl alcohol, povidone, povidone vinyl acetate, hydroxypropyl methyl cellulose, hydroxy ethyl cellulose, methyl cellulose and ethyl cellulose.

In some preferred embodiments, the breathability of the film is achieved by the absence of any occlusive backing membrane together with the generally hydrophilic properties of the film-forming polymer(s). In some preferred embodiments, these polymers can partially dissolve on exposure to moisture (from the skin or air), the dissolution resulting in the formation of a porous film. This porosity can be enhanced by including additional water-soluble additives, such as those detailed below.

In some preferred embodiments, solubilizers include a copolymer of dimethylamine ethyl methacrylate and a neutral methacrylic acid ester (Eudragit™ E100, USP/NF); surfactants, for example, sodium lauryl sulfate; polyhydric alcohols, for example, propylene glycol or polyethylene glycol; vitamin E, vitamin E TPGS (tocopheryl polyethylene glycol 1000 succinate) and labrasol; or any two or more of the above in combination. Preferably, the solubilizer is a copolymer of dimethylamine ethyl methacrylate and a neutral methacrylic acid ester (Eudragit™ E100) in combination with; a non-ionic copolymer of methyl methacrylate and butyl methacrylate (Plastoid™ B). The solubilizers serve to dissolve the mepivacaine in the chosen vehicle. Many of the solubilizers also enhance percutaneous penetration of mepivacaine and/or act as humectants.

In some preferred embodiments, preferred plasticizers include triethyl citrate, dimethyl isosorbide, acetyltributyl citrate, castor oil, propylene glycol, and polyethylene glycol, or any two or more of the above in combination.

In some preferred embodiments, the permeation enhancer is preferably a lipophilic solvent, for example, dimethyl sulfoxide, dimethyl formamide or isopropyl myristate; a surfactant, for example, Tween or sodium lauryl sulfate; menthol; oleic acid, octyl dimethyl para-amino benzoic acid (Padimate O); mixed esters of capric and caprylic acid; or a polyhydric alcohol, for example, propylene glycol or diethylene glycol monoethyl ether EP (transcutol); or any two or more of the above in combination.

In some preferred embodiments, the vehicle can be water or a non-aqueous solvent. Preferred nonaqueous vehicles include acetone, isopropyl alcohol, methylene chloride, methyl-ethyl-ketone, absolute alcohol, ethyl acetate and trichloromonofluoromethane, methylene dimethyl ether or any two or more of the above in combination.

In some preferred embodiments, the aqueous or non-aqueous vehicle may additionally comprise (weight/weight of vehicle) up to 20% of one or more humectants. In some preferred embodiments, the humectants include polyhydric alcohols and polyvinyl pyrrolidone. Preferred polyhydric alcohols are propylene glycol, butylene glycol, polyethylene glycol, glycerol and sorbitol.

In some preferred embodiments, the water-soluble additive is propylene glycol, sodium lauryl sulfate, one or more polaxomers, polyoxyl 35 castor oil, polyoxyl 40 hydrogenated castor oil, cetomacrogol, polyethylene glycol or transcutol, or any two or more of the above in combination.

In some preferred embodiments, when the composition is dispensed as an aerosol, the vehicle may partly comprises a propellant in an amount to provide from about 10% to about 90% (w/w) of the composition. The propellant can be any pharmaceutically acceptable propellant which provides a suitable pressure within an aerosol dispenser, preferably a pressure of about 20 p.s.i.g. to about 130 p.s.i.g. Preferred propellants include hydrocarbons, for example, propane, butane, isobutane, or dimethylether; hydrofluorocarbons and hydrochlorofluorocarbons, for example, dichlorodifluoromethane, trichloromonofluoromethane, dichlorofluoroethane, monochlorodifluoromethane, dichlorotetrafluoroethane, difluoroethane, tetrafluoroethane, heptafluoropropane; or compressed gases, for example, nitrogen or carbon dioxide.

In some preferred embodiments, the topical compositions are quick drying, non-occlusive formulations which cause marked enhancement of the skin permeation of the mepivacaine both in vitro and in vivo when compared with existing transdermal patches. They offer the advantages of lower skin irritation, greater ease of use, increased dosage flexibility and a simpler method of manufacture when compared to existing transdermal patches.

In some preferred embodiments, the compositions are generally prepared by mixing the ingredients, without liquefied propellant, at a temperature of from 0° C. to 100° C. and at ambient pressure. If propellant is to be added, in some preferred embodiments, the resulting mixture is then charged with the liquefied propellant into an aerosol dispenser to achieve the final, composition. Mixing is preferably carried out at a temperature of from 10° C. to 25° C. In some preferred embodiments, the mixed composition is placed in a pump dispenser, for example, a metered dose pump, which dispenses the composition typically without liquefied propellant since a pressurized atmosphere is not required. In some preferred embodiments, propellant which is liquid at room temperature may, however, be included in a pump dispenser composition as part of the aqueous vehicle. The composition so prepared is sprayed from the dispenser onto a topical site, at which site it forms a stable, plastic film or patch.

In some preferred embodiments, the container is a conventional aerosol can having a conventional metered spray aerosol valve. In some preferred embodiments, the pump dispenser is preferably a conventional can or bottle having a conventional metered spray pump. In some preferred embodiments, the aerosol dispenser has an all position valve having a shroud that permits spraying when the dispenser is held at any angle. In this way, horizontal bottom surfaces, as well as horizontal top surfaces and vertical surfaces, can be sprayed. In some preferred embodiments, the valve actuator can be any actuator which produces a spray and not foam at the nozzle. In some preferred embodiments, the valve actuator can be any actuator which produces foam at the nozzle. In some preferred embodiments, the valve actuator is a mechanical breakup actuator, which employs mechanical forces rather than expansion and evaporation of the propellant to produce a spray. In some preferred embodiments, a typical mechanical breakup actuator has a conical or cylindrical swirl chamber with an inlet channel oriented perpendicular to the axis thereof. This structure imparts a swirling motion to the aerosol mixture upon discharge. The swirling motion occurs around the axis of the swirl chamber forming a thin conical film of discharged mixture, which breaks into droplets as it leaves the swirl chamber and travels in the direction of the axis thereof. The result is a fine, soft, dispersed spray which can be easily controlled to produce a stable thin film of even thickness completely contacting the application site. In dispensing a composition of the invention, the dispenser is typically held about 2.5 to 5 cm or 2 to 20 cm from the application site and produces a film of even thickness. In some preferred embodiments, the dispensers used in the present invention are compact units which can be conveniently used for quick and easy application of a medicament over a large surface area.

In general, a polymer which can form film upon application to the skin, poly(vinyl alcohol), thermoplastic polyurethane, cellulose, carboxyvinyl polymer, poly(vinyl pyrrolidone) etc. can be used.

In some preferred embodiments, the film-forming polymers have high elasticity to reduce interfere with activities of daily living, have a low glass transition temperature to reduce deterioration of the dosage form upon drying and have a low propensity for exfoliation from the skin.

In some preferred embodiments, the film-forming formulation is a polymer comprising: (i) polyurethane; (ii) an additional polymerization polymer which includes at a main or a side chain, a carboxylic acid derivative, i.e., a carboxylic acid alkyl ester and/or carboxylic acid alkyl amide and/or carboxylic acid alkyl aminoalkyl ester group; (iii) a active agent or drug; (iv) a solvent in which the film-forming agent is dissolved; and optionally, (v) other additives.

In some preferred embodiments, the film-forming composition includes a water-soluble or water-dispersible vinyl polymer that includes amine group-containing side-chains and a copolymerized hydrophobic monomer.

In some preferred embodiments, the film-forming composition include: a water-soluble or water-dispersible vinyl polymer that includes amine group-containing side-chains and a copolymerized hydrophobic monomer; water; and a surfactant.

In some preferred embodiments, the surfactant is a non-ionic surfactant, preferably having an HLB of at least about 14 and more preferably no greater than about 19. In certain embodiments, the compositions also include a surfactant having an HLB of less than about 14 or greater than about 19. In other embodiments, the compositions also include an anionic or amphoteric surfactant, such as one selected from the group consisting of sulfates, sulfonates, phosphates, phosphonates, ammonium sulfonate, amphoterics, and mixtures thereof.

In some preferred embodiments, the compositions include a hydroxycarboxylic acid buffer, which includes, for example, an alpha-hydroxycarboxylic acid such as lactic acid, malic acid, citric acid, or a mixture thereof.

In some preferred embodiments, the vinyl polymer has a glass transition temperature of at least about 30° C. and more preferably at least about 50° C. In some preferred embodiments, the compositions further include a polymer having a higher Tg than that of the vinyl polymer having amine groups. Preferably, such a polymer is polyvinyl alcohol.

In some preferred embodiments, the dosage form is a film-forming composition that includes: a water-soluble or water-dispersible vinyl polymer including amine group-containing side-chains and a hydrophobic monomer; mepivacaine; water; and a surfactant.

In some preferred embodiments, the composition includes: a water-soluble or water-dispersible vinyl polymer prepared from monomers that include an amine group-containing monomer, about 1 wt-% to about 30 wt-% of a ($C_6$-$C_{22}$)alkyl (meth)acrylic monomer, and about 15 wt-% to about 75 wt-% of a ($C_1$-$C_4$)alkyl (meth)acrylic monomer; water; and the mepivacaine.

In some preferred embodiments, the preferred vinyl polymers are prepared from dimethylamine oxide methacrylate, isobutyl methacrylate, methyl methacrylate, and a ($C_{12-18}$) alkyl methacrylate. In certain other preferred embodiments, preferred vinyl polymers are prepared from trimethylaminioethyl acrylate chloride, butyl acrylate, methyl methacrylate, and a ($C_{12-18}$)alkyl methacrylate.

In some preferred embodiments, the film-forming composition includes: a water-soluble or water-dispersible vinyl polymer comprising amine group-containing side-chains and a copolymerized hydrophobic monomer; water; and mepivacaine.

In some preferred embodiments, the film-forming dosage forms are aqueous-based and have the following characteristics: (i) relatively short dry times; (ii) transparent film for clear viewing of the underlying skin and tissue; (iii) good adhesion to the skin when dry; (iv) little or no tack when dry; (v) capable of releasing the mepivacaine over a period of time; (vi) relatively easy removal, preferably without the need for organic solvent-based removers. In other embodiments, the film is translucent or opaque and may optionally contain excipients, dye and/or colorants to impart a preferred color to the film.

In some preferred embodiments, the film-forming dosage forms are very stable and can survive prolonged exposure to elevated temperatures for up to one day, or up to one week, or up to one month. In some preferred embodiments, the film-forming dosage forms show no visible changes in color, turbidity, and the like. In some preferred embodiments, the film-forming dosage forms are stable upon exposure to low temperatures.

In some preferred embodiments, the dried film of the composition are flexible and durable (i.e., resistant to cracking, or flaking).

In some preferred embodiments, the film-forming dosage forms possess viscosities that ensure the formulations go on easily and form a relatively thin film that can dry rapidly. In some preferred embodiments, the Brookfield viscosity of a composition is no greater than about 1000 Centipoise (cps), more preferably no greater than about 500 cps, even more preferably no greater than about 250 cps, even more preferably no greater than about 100 cps, and most preferably no greater than about 50 cps. This low viscosity ensures that the composition can be painted on the skin with little effort in a uniform thin film that will dry rapidly.

In some preferred embodiments, dry times are preferably no greater than about 5 minutes, more preferably no greater than about 3 minutes, even more preferably no greater than about 2 minutes, and most preferably no greater than about 1.5 minutes on skin measured at 23° C. at 45-55% relative humidity.

In some preferred embodiments, the film-forming dosage form is applied to the skin and allowed to dry and remain in place for up to about 4 hours, or up to about 12 hours, or up to about 24 hours, or up to about 2 days, or up to about 3 days, or up to about 4 days, or up to about 7 days, or up to about 10 days, or up to about 14 days, or up to about one month.

Film-Forming Polymers

In some preferred embodiments, one or more film-forming polymers are included in the compositions of the present invention to improve resistance to wash off, improve adhesion and/or reduce the tack of the compositions. In some preferred embodiments, film-forming polymers of the compositions are substantive and resist removal by prolonged exposure to fluids such as water, saline, sweat, yet can be easily and gently removed without the need for organic solvents.

In some preferred embodiments, the compositions incorporate film-forming polymers that have both hydrophilic and hydrophobic moieties. In some preferred embodiments, the film-forming polymers are prepared from at least two monomers (i.e., a hydrophilic monomer and a hydrophobic monomer), and or from at least three monomers.

In some preferred embodiments, the film-forming polymer is a vinyl polymer that includes amine group-containing (i.e., amine-containing) side-chains and hydrophobic character. The term vinyl polymer refers to a polymer prepared from monoethylenically unsaturated monomers. The amine groups can be quaternary amine (i.e., quaternary ammonium) groups, amine oxide groups, and/or protonated tertiary amine groups.

In some preferred embodiments, the monoethylenically unsaturated amine group-containing monomers are monoethylenically unsaturated quaternary ammonium, amine oxide, and/or protonated tertiary amine group-containing monomers. In some preferred embodiments, the side-chain amine group-containing monomers are monoethylenically unsaturated quaternary amine, amine oxide, tertiary amine, or protonated tertiary amine group-containing (meth)acrylic monomers. In some preferred embodiments, the monoethylenically unsaturated amine group-containing monomers from which the film-forming polymers are formed are quaternary ammonium and amine oxide group-containing monomers. If desired, the tertiary amine group-containing monomers can be easily converted to protonated tertiary amine groups, amine oxide groups, or quaternary ammonium groups prior to or after polymerization by the appropriate chemical reaction as described herein. In the case of quaternary ammonium group-containing polymers, it is preferred that the polymer be prepared from the quaternary ammonium group-containing monomer. In the case of protonated tertiary amine group- and amine oxide group-containing polymers, it is preferred to first make the polymer from the corresponding tertiary amine and to subsequently covert the tertiary amine groups on the polymer to the protonated tertiary amine or amine oxide group.

In some preferred embodiments, the amine group-containing monomers used to prepare the film-forming polymers are typically used in an amount of at least about 15 wt-%, preferably at least about 20 wt-%, more preferably at least about 25 wt-%, and most preferably at least about 30 wt-%, based on the total weight of polymerizable composition (preferably, based on the total weight of the polymer). The amine group-containing monomers used to prepare the film-forming polymers are typically used in an amount of no greater than about 70 wt-%, preferably no greater than 65%, more preferably no greater than about 60 wt-%, and most preferably no greater than about 55 wt-%, based on the total weight of polymerizable composition (preferably, based on the total weight of the polymer).

In some preferred embodiments, the monoethylenically unsaturated amine group-containing monomers are acrylic monomers. The acrylic monomers are understood to include (meth)acrylate (i.e., acrylate or methacrylate) and/or (meth)acrylamide (i.e., acrylamide or methacrylamide) monomers. In some preferred embodiments, the monomers include salts of trimethylaminoethylmethacrylate, trimethylaminoethylacrylate, trimethylaminopropyl acrylamide, trimethylaminopropyl methacrylamide, and protonated salts of dimethylaminoethylmethacrylate. Particularly preferred monomers are the chloride and methosulfate salts of trimethylaminoethylmethacrylate.

In some preferred embodiments, the monoethylenically unsaturated amine group-containing monomers are (meth) acrylate and/or (meth)acrylamide monomers. Preferred monomers include amine oxides of dimethylaminoethylmethacrylate, dimethylaminoethylacrylate, dimethylaminopropylacrylamide, and dimethylaminopropylmethacrylamide.

In some preferred embodiments, the amine group-containing monomers are present in a concentration sufficient to ensure water solubility or water dispersibility and substantivity of the composition. In some preferred embodiments, the amine-group containing monomer provide hydrophilic character to the polymer. However, other non-amine group-containing hydrophilic monomers may be used to prepare the film-forming polymer to assist in water solubility and/or stability. These include hydroxy-functional acrylates, polyethylene glycol-functional acrylates, vinyl-lactams such as N-vinylpyrrolidone and N-vinyl caprolactam, acrylamide, methacrylamide, hydrolyzed vinyl acetate (vinyl alcohol) and other monomers whose homopolymers result in water-soluble polymers.

In some preferred embodiments, in addition to an amine group-containing monomer, at least one hydrophobic monomer is used to prepare the film-forming polymers.

In some preferred embodiments, the vinyl polymer used in the compositions contains at least one copolymerized hydrophobic monoethylenically unsaturated alkyl (meth) acrylic monomer. As used herein, the "monoethylenically unsaturated" term in the alkyl (meth)acrylic monomer refers to the acrylic unsaturation. Preferably, "alkyl (meth)acrylic" monomers include (meth)acrylamides (e.g., octylacrylamide), (meth)acrylates, and combinations thereof. More preferably, the alkyl (meth)acrylic monomer is an alkyl (meth) acrylic acid ester (i.e., an alkyl acrylate or alkyl methacrylate), wherein the alkyl group has at least one carbon atom (on average). Preferably, the alkyl group has no greater than 50 carbon atoms, more preferably, no greater than 36 carbon atoms, and most preferably, no greater than 22 carbon atoms (on average). Alternatively stated, these alkyl (meth)acrylate monomers are (meth)acrylic acid esters of alkyl alcohols (preferably, non-tertiary alkyl alcohols), the alkyl groups of which preferably include 1 to 22 carbon atoms (on average). Of these, one preferred alkyl group includes 1 to 4 carbon atoms. Another preferred alkyl group includes 6 to 22 carbon atoms, more preferably 8 to 22 carbon atoms, and even more preferably 8 to 18 carbon atoms (on average). The alkyl group can optionally contain heteroatoms and can be linear, branched, or cyclic.

Examples of suitable alkyl (meth)acrylate monomers having shorter alkyl groups (C1-C4) useful in the present invention include, but are not limited to methyl acrylate, methyl, methacrylate, ethyl acrylate, ethyl methacrylate, and n-propyl methacrylate, n-butyl acrylate, and isobutyl acrylate, isobutyl methacrylate, t-butyl methacrylate, and the like. Particularly preferred of these are methyl methacrylate and isobutyl methacrylate.

Examples of suitable alkyl (meth)acrylate monomers having longer alkyl groups (C6-C22) useful in the present invention include, but are not limited to cyclohexyl methacrylate, decyl acrylate, 2-ethylhexyl acrylate, n-hexyl acrylate, isoamyl acrylate, isodecyl acrylate, isononyl acrylate, isooctyl acrylate, lauryl acrylate, lauryl methacrylate, stearyl acrylate, stearyl methacrylate, behenyl methacrylate, 2-methylbutyl acrylate, 4-methyl-2-pentyl acrylate, ethoxy ethoxyethyl acrylate, isobornyl acrylate, mixtures thereof, and the like. Particularly preferred of these are isobutyl methacrylate, n-butyl acrylate, 2-ethylhexyl acrylate, isooctyl acrylate, lauryl methacrylate, stearyl methacrylate, and mixtures thereof.

In some preferred embodiments, the monoethylenically unsaturated alkyl (meth)acrylic monomer(s) can be used in an amount of at least about 35 weight percent, and more preferably at least about 45 wt-%, and most preferably at least 50% wt-%, based on the total weight of the polymerizable composition (and preferably, based on the total weight of the polymer). In some preferred embodiments, the monoethylenically unsaturated alkyl (meth)acrylic monomer(s) can be used in an amount of no greater than about 85 wt-%, more preferably no greater than about 75 wt-%, and most preferably no greater than about 65 wt-%, based on the total weight of the polymerizable composition (and preferably, based on the total weight of the polymer).

In some preferred embodiments, certain combinations of the amine group-containing monomers with long chain monomers are particularly useful. The long chain alkyl monomers help to lower the glass transition temperature (Tg) of the polymer system and to improve substantivity of the polymer and composition. In general, this lower Tg helps to promote both adhesion to skin.

In some preferred embodiments, the composition has no or relatively low tack. In some preferred embodiments, the film-forming polymers is formed from at least amine group-containing monomers, long chain (meth)acrylic monomers, and short chain (meth)acrylic monomers.

In some preferred embodiments, the long chain (meth) acrylic monomer (e.g., a (C6-C22)alkyl (meth)acrylic monomer) is preferably used to prepare the polymer in an amount of at least about 1 wt-%, more preferably at least about 3-wt-%, and most preferably at least about 5 wt-%, based on the total weight of the polymerizable composition (and preferably, based on the total weight of the polymer). The long chain (meth)acrylic monomer is preferably used to prepare the polymer in an amount of no greater than about 40 wt-%, more preferably no greater than about 30 wt-%, even more preferably no greater than about 20 wt-%, and most preferably no greater than about 15 wt-%, based on the total weight of the polymerizable composition (and preferably, based on the total weight of the polymer). Most preferred polymers include about 5 wt-% to about 15 wt-% long chain (meth)acrylic monomer.

In some preferred embodiments, the short chain (meth) acrylic monomer (e.g., a (C1-C4)alkyl (meth)acrylic monomer) is preferably used to prepare the polymer in an amount of at least about 15 wt-%, more preferably at least about 25 wt-%, and most preferably at least about 30 wt-%, based on the total weight of the polymerizable composition (and preferably, based on the total weight of the polymer). The short chain acrylic monomer is preferably used to prepare the polymer in an amount of no greater than about 75 wt-%, more preferably no greater than about 65 wt-%, and most preferably no greater than about 60 wt-%, based on the total weight of the polymerizable composition (and preferably, based on the total weight of the polymer). Most preferred polymers include about 30 wt-% to about 60 wt-% short chain (meth)acrylic monomer.

In some preferred embodiments, the film-forming polymers are formed from two different short chain acrylic monomers. The first is a (C1-C2)alkyl (meth)acrylic monomer such as methyl methacrylate and the second is a (C3-C4)alkyl (meth)acrylic monomer such as n-, t-, or iso-butyl acrylate. The very short chain monomer is present to increase the glass transition temperature to reduce the tack of the composition as well as provide some hydrophobicity. The (C3-C4)alkyl (meth)acrylic monomer is present to provide hydrophobicity as well as some flexibility to the film-forming polymer to ensure it does not easily flake off in use.

In some preferred embodiments, the molecular weight of the vinyl polymers is also preferably kept low in order to maintain a low viscosity composition. In some preferred embodiments, the molecular weight of the vinyl polymers is generally no greater than about 350,000 Daltons, no greater than about 250,000 Daltons, no greater than about 150,000 Daltons, and no greater than about 100,000 Daltons.

In some preferred embodiments, one or more substantive film-forming vinyl polymers are present in the compositions of the present invention in a total amount of at least about 2 wt-%, preferably at least about 3 wt-%, and more preferably at least about 5 wt-%, based on the total weight of composition. In some preferred embodiments, one or more substantive film-forming vinyl polymers are present in the composition in a total amount of no greater than about 10 wt-%, and more preferably no greater than about 8 wt-%, based on the total weight of composition.

In some preferred embodiments, the substantive film-forming vinyl polymer is present in an amount greater than the surfactant.

Surfactants

In some preferred embodiments, the formulation includes one or more surfactants to enhance solubility and stability of the polymer in the composition and to help the compositions to wet the skin and ensure a smooth uniform coating.

In some preferred embodiments, one or more surfactants are generally added to the compositions of the present invention in an amount of at least about 0.5 wt-%, based on the total weight of the composition. In some preferred embodiments, one or more surfactants are added to the compositions in an amount no greater than about 10 wt-%, more preferably no greater than about 7 wt-%, even more preferably no greater than about 5 wt-%, and most preferably no greater than about 3 wt-%, based on the total weight of the composition.

In some preferred embodiments, the surfactant is a nonionic surfactants, including polyalkoxylated, and polyethoxylated nonionic surfactants. In some preferred embodiments, surfactants of the nonionic type: (i) polyethylene oxide extended sorbitan monoalkylates (i.e., polysorbates); (ii) polyalkoxylated alkanols; (iii) polyalkoxylated alkylphenols; (iv) polaxamers; (v) polyalkoxylated esters; and (vi) alkyl polyglucosides.

In some preferred embodiments, the surfactant is a nonionic surfactants, including amphoteric surfactants. In some preferred embodiments, the amphoteric surfactants include: (i) ammonium carboxylate amphoterics; and (ii) ammonium sulfonate amphoterics.

In some preferred embodiments, the surfactant is anionic surfactants (e.g., sulfonates, sulfates, phosphates) and amine oxides (e.g., alkyl and alkylamidoalkyldialkylamine oxides).

Vehicle

In some preferred embodiments, suitable liquid vehicles for the compositions include water, optionally in combination with acetone or an alcohol, particularly a (C1-C4) alcohol (i.e., a lower alcohol) such as ethanol, 2-propanol, and n-propanol, and mixtures thereof. The preferred vehicle is injectable-grade water, i.e., USP grade "water for injection", however, other forms of purified water may be suitable such as distilled and deionized water.

In some preferred embodiments for applications to intact skin, it may be desirable to include a lower alcohol such as ethanol, isopropanol, or n-propanol.

In some preferred embodiments, the dosage form contains one or more buffers.

In some preferred embodiments, the dosage form contains one or more other optional ingredients, including but not limited to preservatives, antioxidants, solubilzing agents, emollients, humectants, fragrances, colorants, tackifiers, plasticizers, permeation enhancers (e.g., lauryl alcohol, oleyl alcohol, lauramide DEA, lauryl pyrrolidone-5-carboxylate, ascorbyl palmitate, glycerin, propylene glycol, and tetraglycol).

In some preferred embodiments, the dosage form provides low tack or nontacky dry films, which can be readily removed with water or detergent.

In some embodiments of the invention, application to the skin comprises a pharmaceutically acceptable carrier having uniformly dispersed within an amount of mepivacaine base, a pharmaceutically acceptable salt or mixtures thereof in a skin permeable form. The composition may be applied directly onto the skin from a container for the same, such as a bottle or tube, and subsequently covered, if desired, with a protective overlay. It is preferable, however, to quantify the dose and the area of application by placing the composition in an impermeable container of the correct size to provide a unit dose which may be held on the skin by adhesive means or other appropriate fastening means. In operation this composition would administer the mepivacaine through the skin to produce the intended therapeutic effect. In addition to the mepivacaine, the dosage form may also contain a permeation enhancer for the mepivacaine, thickeners and other additives, all as known to the art.

Topical Formulations

Adhesive Gel

In some embodiments of the invention, the pharmaceutical composition is in the form of an adhesive gel. In some embodiments, the adhesive gel comprises a water-soluble high molecular weight substance, water and a water-retaining agent as essential components. In some embodiments of the invention, the water-soluble high molecular weight substance may include gelatin, starch, agar, mannan, alginic acid, polyacrylic acid, a salt of polyacrylic acid, dextrin, methylcellulose, methylcellulose sodium, carboxymethylcellulose, carboxymethylcellulose sodium, polyvinyl alcohol, polyvinyl pyrrolidone, a copolymer of methyl vinyl ether and maleic anhydride, gum arabic, tragacanth, karaya gum, locust bean gum, etc.

In some embodiments of the invention, the pharmaceutical composition is in the form of an adhesive gel. In some embodiments, the adhesive gel comprises a water-soluble high molecular weight substance, water and a water-retaining agent as essential components. In some embodiments of the invention, the water-soluble high molecular weight substance may include gelatin, starch, agar, mannan, alginic acid, polyacrylic acid, a salt of polyacrylic acid, dextrin, methylcellulose, methylcellulose sodium, carboxymethylcellulose, carboxymethylcellulose sodium, polyvinyl alcohol, polyvinyl pyrrolidone, a copolymer of methyl vinyl ether and maleic anhydride, gum arabic, tragacanth, karaya gum, locust bean gum, etc.

In some embodiments of the invention, there can also be used a metallic salt and cross-linked products (with an organic or inorganic cross-linking agent) of the above substances.

In some embodiments of the invention, one or more kinds of the water-soluble high molecular weight substance are used in the adhesive gel base. An amount of the water-soluble high molecular weight substance is in a range of 0.25 to 75% (% by weight, hereinafter the same), preferably 3 to 40%. The water content is preferably in a range of 5 to 85%, more preferably 10 to 60%. In some embodiments of the invention, the water-retaining agent prevents the evaporation of water in the adhesive gel base so that the water content in the adhesive gel base is maintained at a relatively constant level during storage and use of the preparation. In some embodiments of the invention, the water-retaining agent includes, for example, glycols or saccharides such as ethylene glycol, diethylene glycol, polyethylene glycol, glycerin, sorbitol, martitol and propylene glycol, 1,3-butylene glycol. In some embodiments of the invention, the water-retaining agent in the adhesive gel base is preferably in a range of 2 to 65%, more preferably 5 to 60%. In order to maximize the efficiency of water retention in the adhesive gel, high molecular weight substance with a large water absorption capacity may be used. Non-limiting examples include a copolymer of starch and acrylonitrile, a copolymer of starch and acrylic acid, a copolymer of starch and styrenesulfonic acid, a copolymer of starch and vinylsulfonic acid, a cross-linked product of polyvinyl alcohol, a saponification product of acrylic acid/vinyl acetate copolymer and a cross-linked product of polyethylene glycol diacrylate. The amount of water-absorbable high molecular weight substance in the adhesive gel base is preferably in a range of 0 to 30%, more preferable 0.01 to 20%. In some embodiments, conventional absorbing agents such as salicylic acid, hyaluronic acid, oleic acids N,N-diethyl-m-toluamide, n-butyl stearate, benzyl alcohol, isopropyl myristate, isopropyl palmitate, polypropylene glycol, crotamiton, diethyl sebacate, N-methylpyrrolidone, N-ethylpyrrolidone and lauryl alcohol may be included. In some embodiments, a surfactant for emulsifying the absorbing agent in the gel base may be included. Non-limiting examples are polyoxyethylene sorbitan monooleate, poly-oxyethylene sorbitan monostearate, sorbitan monooleate and sorbitan monopalmitate.

In some embodiments, a preservative, an antioxidant and other pharmaceutical excipients and auxiliary agents may be used. In some embodiments, the adhesive gel base comprising the above components preferably has a pH value of 5 to 9. The pH may be adjusted as required by adding an alkaline substance such as sodium hydroxide or an amine such as triethanolamine and diisopropanolamine, etc. or an acidic substance such as tartaric acid, citric acid, malic acid, lactic acid, acetic acid and phthalic acid.

The dosage form of the invention for application to the skin containing mepivacaine, a pharmaceutical acceptable salt (such as mepivacaine hydrochloride) or mixtures thereof can be prepared by adding the drug in an effective amount to the above-mentioned adhesive gel base to prepare a drug-retaining layer, the content of the drug being in a range of 0.25 to 40%, preferably 1 to 20%, and spreading the drug-retaining layer onto a suitable support. The drug-retaining layer is then spread onto the support. In order to protect the drug-retaining layer from the water evaporation, a liner made of a suitable material may also be affixed to the surface of said layer. The support is preferably made of a flexible material. Non-limiting example of such material includes non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like. The external preparation for application to the skin of the invention is capable of releasing the drug quantitatively, is easily manipulated, and is capable of being applied for a long period of time.

Topical Gel

The dosage form of the invention can be prepared in the form of a topical gel. In some embodiments, the topical formulation is a liquid at room temperature, but when administered topically to the skin becomes a semi-solid or gel when warmed by the body. In on such embodiment, the pharmaceutical composition comprises a clear physiological acceptable solution at room temperature or lower but which forms a semi-solid or gel when warmed to body temperature. An example of a drug delivery vehicle in accordance with this embodiment consists of an aqueous solution of, for example, a selected tetra substituted ethylene diamine block copolymer of poly(oxyethylene)-poly(oxypropylene) in which the substitution at the nitrogen is to the poly(oxypropylene) block and the polymer consists of about 40-80% as the poly(oxyethylene) unit and about 20-60% as the polypropylene unit and which has a total average molecular weight of 7,000 to 50,000 with a preferred range of 7,000-30,000. Such polymers are included in the polymers sold under the trademark "Tetronic™" polyols by BASF. Other polymers can be made according to methods known in the art (Block and Graft Copolymerization, Vol. 2 edited by R. J. Ceresa published by John Wiley and Sons, 1976) by using the appropriate initiators such as for example propylenediamine, butylenediamine, pentylenediamine and hexylenediamine. The preferred polymers are those which form gels at a concentration range of 10 to 50% of the polymer to water. A preferred example of a drug delivery vehicle in accordance with this embodiment consists of Tetronic™ 1307 which thermally gels over a concentration range of about 15 to 35% in water with gelling temperatures of about 30° C. to 10° C. at neutral pH. The gel strength at 35% is much more rigid than the 15% gel. For administration of mepivacaine to the skin in accordance with this embodiment, the pH of the system can range from 2 to 9 with the preferred pH range being 4 to 8. The pH, concentration and gelling temperatures will vary for any individual polymer falling within the class covered in this invention and these factors can be determined by those skilled in the art in possession of this concept. The pH of the drug delivery system is adjusted by adding the appropriate amount of a pharmaceutically acceptable acid or base to obtain the required pH. The acid or base can be any that are known to persons skilled in the art but are preferably hydrochloric acid or sodium hydroxide.

In general, the drug delivery vehicle of prepared in accordance with this embodiment will contain from about 0.01 to about 20% of mepivacaine or pharmaceutical, from about 10 to about 50% of the polymer and from 90 to about 45% water. In special situations, however, the amounts may be varied to increase or decrease the dosage schedule.

If desired, the drug delivery vehicle may also contain, in addition to the mepivacaine, buffering agents and preservatives, suitable water soluble preservatives which may be employed in the drug delivery vehicle which are sodium bisulfite, sodium thiosulfate, ascorbate, benzalkonium chloride, chlorobutanol, thimerosal, phenylmercuric borate, parabens, benzyl alcohol and phenylethanol. These agents may be present in amounts of from 0.01 to 5% by weight and preferably 0.01 and 2%. Suitable water soluble buffering agents are alkali or alkali earth carbonate, phosphates, bicarbonates, citrates, borates, acetates, succinates and the like, such as sodium phosphate, citrate, borate, acetate, bicarbonate and carbonate. These agents may be present in amounts sufficient to maintain a pH of the system of between 2 to 9 and preferably 4 to 8. As such the buffering agent can be as much as 5% on a weight to weight basis of the total composition.

Any pharmaceutically active material may be delivered in the drug delivery system in accordance with this embodiment the invention. Preferably the mepivacaine is water soluble. Also the mepivacaine may be insoluble and can be suspended in the polymer vehicle.

The gelling temperature of the drug delivery vehicle or pharmaceutical composition can be modulated by modifying the ionic strength. This can be done by adding a pharmaceutically acceptable salt, such as sodium chloride, potassium chloride or mixtures thereof or even suitable alkali metal salts such as sodium sulfate and the like. Typically as stated previously, the present liquid drug delivery system would contain from about 0.01 to about 10% of mepivacaine on a weight to weight basis.

The preparation of the drug delivery systems in accordance with this embodiment can be carried out as follows. Since the tetronic polymer systems of this invention dissolve better at reduced temperatures, the preferred methods of solubilization is to add the required amount of polymer to the amount of water to be used. Generally, after wetting the polymer by shaking, the mixture is capped and placed in a cold chamber or in a thermostated container at about 0° C. to 10° C. to dissolve the polymer. The mixture can be stirred or shaken to bring about a more rapid solution of the polymer. The mepivacaine and various additives such as buffers, salts and preservatives are then added and dissolved. The final desired pH adjustment can be made by adding the appropriate acids or bases such as hydrochloric acid or sodium hydroxide. Any convenient method can be used to apply the pharmaceutical composition to the skin such as a bottle from which the solution is poured on, a ball roller, a dropper-type application, an aerosolized or non-aerosolized spray, etc.

In some preferred embodiments, the topical dosage from comprises a permeation enhancers. Any amount of permeation enhancer may be used. The amount of permeation enhancer will vary depending on the concentration of mepivacaine in the dosage form, the permeability rate being sought, the onset of effect desired, the nature of the mepivacaine (e.g., base or salt), the nature of the dosage form (gel, cream, emulgel, lotion, patch), the presence of other excipients.

Examples of permeation enhancers for use in the preparation of topical dosage forms include, but are not limited to fatty acid esters of glycerin, such as capric, caprylic, dodecyl, oleic acids, fatty acid esters of isosorbide, sucrose, polyethylene glycol, caproyl lactylic acid, laureth-2, laureth-2 acetate, laureth-2 benzoate, laureth-3 carboxylic acid, laureth-4, laureth-5 carboxylic acid, oleth-2, glyceryl pyroglutamate oleate, glyceryl oleate, N-lauroyl sarcosine, N-myristoyl sarcosine, N-octyl-2-pyrrolidone, lauraminopropionic acid, polypropylene glycol-4-laureth-2, polypropylene glycol-4-laureth-5-dimethy-1 lauramide, lauramide diethanolamine, lauryl pyroglutamate, glyceryl monolaurate, glyceryl monocaprylate, glyceryl monocaprate, glyceryl monooleate, sorbitan monolaurate, alcohols (e.g., methanol, ethanol, octanol, lauryl alcohol), amides (dimethyl formamide, dimethyl acetamide), anionic surfactants (e.g., sodium dodecyl sulfate, sodium lauryl sulfate), azones (e.g., laurocapram, azacycloalkanone), cationic surfactants (e.g., cetyltrimethyl ammonium borate), fatty acids (e.g., oleic acid, undecanoic acid), nonionic surfactants (e.g., polyoxyethylene-16-acetyl ether), polyols (e.g., propylene glycol, polyethylene glycol), pyrrolidones (e.g., dodecyl pyrrolidone, methyl pyrrolidone), sulfoxides (e.g., dimethyl sulfoxide, decyl methyl sulfoxide), terpenes (e.g., menthol, thymol, limonene, terpinolene, menthone), zwitterionic surfactants (e.g., dodecyl dimethyl ammoniopropane sulfate), urea, cyclodextrins, menthone, 1-(1-adamantyl)-2-pyrrolidinone, R-3-amino-1-hydroxy-2-pyrrolidinone, and 1-(4-nitro-phenyl)-pyrrolidine-2,5-dione, surfactants (e.g., anionic surfactants, cationic surfactants, nonionic surfactants), bile salts (e.g., sodium taurocholate, sodium deoxycholate, sodium tauroglycocholate), binary systems (e.g., propylene glycol, oleic acid, 1,4-butane diol, linoleic acid).

The dosage form of the invention may also include alpha-adrenergic agonists or vaso constrictors such as epinephrine, naphazoline, phenylephrine or tetrahydrozoline to increase the retention of the mepivacaine in skin and/or to enhance the duration of action of the dosage form.

Permeation enhancers and functional excipients of the dosage form of the invention may be used in any amounts and in any combination to achieve a pharmaceutically acceptable dosage form of the invention. In some embodiments, a permeation enhancer and/or functional excipient may be comprise up to 98%, or 95%, or 90%, or 80%, or 60%, or 40%, or 20%, or 10% of the dosage form on a w/w basis. In other embodiments, a permeation enhancer and/or functional excipient may be comprise up to 9%, 8%, 7%, 6%, 4%, 2%, 1%, 0.5% or 0.1% of the dosage form on a w/w/basis.

Other examples of permeation enhancers and functional excipients for use in the preparation of topical dosage forms include, but are not limited Ethoxydiglycol oleate (Softcutol™ 0), Ethoxydiglycol (Transcutol™ CG), Butylene glycol cocoate (Cocoate BG), Glyceryl Behenate, Emulfree™ P, Brij-35™ (polyoxyethyleneglycol dodecyl ether or polyoxyethylene lauryl ether), polyoxyethylene 2-oleyl ether (Brij-92™), Polyoxyethylene 2-stearyl ether (Brij-72™), essential oils, cajeput oil, camphor, (−) Carvone, carvacrol, cetostearyl isononanoate, cineole, clove oil, cocyl caprylocaprate, d-limonene, decodecylmethyl sulfoxide, decyl oleate, dioctyl sulfosuccinate, eucalyptol, eucalyptol, eugenol, geraniol, isopropyl myristate, isopropyl palmitate, isopropyl palmitate, labrafac, labrasol, menthol, lemon grass oil, lemon oil, medium chain triglycerides, octyldodecanol, oleic acid, oleyl alcohol, oleyloleat, peppermint oil, polyoxyl 20, cetostearyl ether, propylene Glycol, terpineol, transcutol, Pluronic™ F127 and Pluronic™ F68 (i.e., poloxamers), 2-(2-Ethoxyethoxy) ethanol (diethylene glycol monoethyl ether or Transcutol™ P), oleic acid, linoleic acid, myristic acid, palmitic acid, lauric acid, stearic acid, propylene glycol mono caprylate, propylene glycol monolaurate, propylene glycol laurate, 2-pyrrolidone, N-methyl-2-pyrrolidone, polyvinyl-pyrrolidone, caprylocaproyl macrogol-8 glycerides and oleyl macrogol-6 glycerides.

Permeation enhancers and functional excipients of the dosage form of the invention may also include those referred to in Williams A C and Barry B W, Penetration Enhancers, Advanced Drug Delivery Reviews 2004; 56:603-18 and Osborne D W and Henke J J, Skin Penetration Enhancers Cited in the Technical Literature, Pharmaceutical Technology, November 2007, each hereby incorporated by reference in its entirety for all purposes.

Emulsifiers, including APIFIL™, EMULCIRE™ 61 WL 2659, GELOT™ 64, PLUROL™ STEARIQUE WL 1009, TEFOSE™ 63, TEFOSE™ 1500, PLUROL™ DIISOSTEARIQUE, SEDEFOS™ 75.

Solubilizers including CAPRYOL™ 90, CAPRYOL™ PGMC, LABRAFIL™ M 1944 CS, LABRAFIL™ M 2125 CS, LABRAFIL™ M 2130 CS, LABRASOL™, LAUROGLYCOL™ 90, LAUROGLYCOL™ FCC, PLUROL™ OLEIQUE CC 497.

Thickening agents including COMPRITOL™ 888 (glyceryl behenate), GELEOL™ (glyceryl monostearate), MONOSTEOL™ (propylene glycol).

Emollients, including propylene glycol dipelargonate, isostearyle isostearate, octyldodecyl myristate.

Surfactants and co-surfactants, including caprylocaproyl macrogolglycerides, propylene glycol monocaprylate, polyglyceryl-6 dioleate.

Other functional pharmaceutical excipients (e.g., suitable permeation enhancers, emollients, thickening agents, solubilizers, emulsifiers and adjuvants) and various processing aids for use in the preparation of topical dosage forms are described in the prior art, including FDA EAFUS database; FDA Food Additives Status List; FDA GRAS list and database; FDA Color Additive Status List; FDA Inactive Ingredients Database; Rowe, Sheskey and Owen, Handbook of Pharmaceutical Excipients, APhA Publications; 5th edition (2006); Goodman & Gilman's The Pharmacological Basis of Therapeutics (Brunton, Lazo and Parker, eds, 11th ed., McGraw Hill (2005); Remington: The Science and Practice of Pharmacy, 21st ed, Lippincott Williams & Wilkins (2005); Martindale: The Complete Drug Reference, 35th Edition, Pharmaceutical Press (2007); United States Pharmacopeia-National Formulary (USP-NF), (USP 30-NF 25, 2007), the International Programme on Chemical Safety; Health Canada's List of Acceptable Non-medicinal Ingredients; Allured, M, 2009 McCutcheon's Functional Materials, McCutcheon's Publications (Apr. 1, 2009); and Allured, M. 2009 McCutcheon's Emulsifiers and Detergents, McCutcheon's Publications, Apr. 1, 2009, all hereby incorporated by reference in their entirety.

In some more preferred embodiments, the topical dosage is a semisolid dosage form which comprises a permeation enhancers selected from the group comprising (−) Carvone, Brij 35, d-limonene, Eucalyptol, Eugenol, Geraniol, Isopropyl, Myristate, Labrasol, Menthol, Menthone, Oleic acid, DMSO and Transcutol P.

In some more preferred embodiments, the topical dosage is a semisolid dosage form which comprises (−) Carvone from about 0.01% to about 5%, more preferably from about 0.1% to about 2%, and most preferably from about 0.2% to about 1%.

In some more preferred embodiments, the topical dosage is a semisolid dosage form which comprises polyoxyethylene lauryl ether (e.g., Brij-35™) from about 0.01% to about 5%, more preferably from about 0.1% to about 2%, and most preferably from about 0.2% to about 1%.

In some more preferred embodiments, the topical dosage is a semisolid dosage form which comprises polyoxyethylene lauryl ether (e.g., Brij-35™) from about 0.01% to about 8%, more preferably from about 0.1% to about 6%, and most preferably from about 0.2% to about 4%.

In some more preferred embodiments, the topical dosage is a semisolid dosage form which comprises Eucalyptol from about 0.01% to about 8%, more preferably from about 0.1% to about 6%, and most preferably from about 0.2% to about 4%.

In some more preferred embodiments, the topical dosage is a semisolid dosage form which comprises Eugenol from about 0.01% to about 5%, more preferably from about 0.1% to about 4%, and most preferably from about 0.2% to about 1%.

In some more preferred embodiments, the topical dosage is a semisolid dosage form which comprises Geraniol from about 0.01% to about 8%, more preferably from about 0.1% to about 6%, and most preferably from about 0.2% to about 4%.

In some more preferred embodiments, the topical dosage is a semisolid dosage form which comprises Isopropyl Myristate from about 0.01% to about 8%, more preferably from about 0.1% to about 6%, and most preferably from about 0.2% to about 4%.

In some more preferred embodiments, the topical dosage is a semisolid dosage form which comprises isopropyl myristate from about 0.1% to about 10%, more preferably from about 0.1% to about 8%, and most preferably from about 0.2% to about 5%.

In some more preferred embodiments, the topical dosage is a semisolid dosage form which comprises Menthol from about 0.01% to about 5%, more preferably from about 0.1% to about 4%, and most preferably from about 0.2% to about 2%.

In some more preferred embodiments, the topical dosage is a semisolid dosage form which comprises Menthone from about 0.01% to about 5%, more preferably from about 0.1% to about 4%, and most preferably from about 0.2% to about 2%.

In some more preferred embodiments, the topical dosage is a semisolid dosage form which comprises Oleic acid from 0.01% to about 8%, more preferably from about 0.1% to about 6%, and most preferably from about 0.2% to about 4%.

In some more preferred embodiments, the topical dosage is a semisolid dosage form which comprises diethylene glycol monoethyl ether (e.g., Transcutol™ P) from about 0.1% to about 10%, more preferably from about 0.1% to about 8%, and most preferably from about 0.2% to about 5%.

In some more preferred embodiments, the topical dosage is a semisolid dosage form which comprises DMSO from about 0.1% to about 50%, more preferably from about 0.5% to about 40%, even more preferably from about 1% to about 30%, and most preferably, from about 3% to about 20%.

In some more preferred embodiments, the topical dosage is a semisolid dosage form which comprises DMSO dose per application of about 0.1 mg to about 4 mg, more preferably from about 0.2 mg to about 3 mg, even more preferably from about 0.5 mg to about 2 mg, and most preferably, from about 0.5 mg to about 1 mg.

In some more preferred embodiments, the topical dosage is a semisolid dosage form which comprises DMSO dose per day of about 0.1 mg to about 40 mg, more preferably from about 0.2 mg to about 30 mg, even more preferably from about 0.5 mg to about 15 mg, and most preferably, from about 0.5 mg to about 8 mg.

Other Formulations for Application to the Skin

In some embodiments of the invention, application to the skin comprises pharmaceutical compositions of about 1% to about 99.9% of a dermatologically acceptable carrier within which the mepivacaine of the present invention is incorporated to enable the mepivacaine, as well as other optional actives, to be delivered to the skin at an appropriate concentration.

The carrier may contain one or more dermatologically acceptable solid, semi-solid or liquid fillers, diluents, solvents, extenders and the like. The carrier may be solid, semi-solid or liquid. In some embodiments, preferred carriers are substantially semi-solid. The carrier can itself be inert or it can possess dermatological benefits of its own. Concentrations of the carrier can vary with the carrier selected and the intended concentrations of the mepivacaine and optional components.

Suitable carriers include conventional or otherwise known carriers that are dermatologically acceptable. The carrier should also be physically and chemically compatible with the essential components described herein, and should not unduly impair stability, efficacy or other use benefits associated with the compositions of the present invention. Preferred components of the compositions of this invention should be capable of being comingled in a manner such that there is no interaction which would substantially reduce the efficacy of the composition under ordinary use situations.

The type of carrier utilized in the present invention depends on the type of product form desired for the composition. The topical compositions useful in the subject invention may be made into a wide variety of product forms such as are known in the art. These include, but are not limited to, lotions, creams, gels, sticks, sprays, ointments, oils, foams, powders and pastes. These product forms may comprise several types of carriers including, but not limited to, solutions, aerosols, emulsions, gels, solids, and liposomes.

Preferred carriers contain a dermatologically acceptable, hydrophilic diluent. As used herein, "diluent" includes materials in which the particulate material can be dispersed, dissolved, or otherwise incorporated. Nonlimiting examples of hydrophilic diluents are water, organic hydrophilic diluents such as lower monovalent alcohols (e.g., $C_1$-$C_4$) and low molecular weight glycols and polyols, including propylene glycol, polyethylene glycol (e.g., MW 200-600 g/mole), polypropylene glycol (e.g., MW 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. Water is a preferred diluent. The composition preferably comprises from about 60% to about 99.99% of the hydrophilic diluent.

Solutions according to the subject invention typically include a dermatologically acceptable hydrophilic diluent. Solutions useful in the subject invention preferably contain from about 60% to about 99.99% of the hydrophilic diluent.

Aerosols according to the subject invention can be formed by adding a propellant to a solution such as described above. Exemplary propellants include chloro-fluorinated lower molecular weight hydrocarbons. Aerosols are typically applied to the skin as a spray-on product.

Preferred carriers comprise an emulsion comprising a hydrophilic phase comprising a hydrophilic component, e.g., water or other hydrophilic diluent, and a hydrophobic phase comprising a hydrophobic component, e.g., a lipid, oil or oily material. As well known to one skilled in the art, the hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions typically comprise from about 1% to about 50% of the dispersed hydrophobic phase and from about 1% to about 98% of the continuous hydrophilic phase; water-in-oil emulsions typically comprise from about 1% to about 98% of the dispersed hydrophilic phase and from about 1% to about 50% of the continuous hydrophobic phase. The emulsion may also comprise a gel network. Preferred emulsions are further described below.

In some embodiments, the compositions for application to the skin includes but is not limited to lotions and creams and may comprise a dermatologically acceptable emollient. Such compositions preferably contain from about 2% to about 50% of the emollient. Emollients tend to lubricate the skin, increase the smoothness and suppleness of the skin, prevent or relieve dryness of the skin, and/or protect the skin. Emollients are typically water-immiscible, oily or waxy materials. Non-limiting examples of emollients are described herein.

Lotions and creams according to some embodiments of the present invention preferably comprise a solution carrier system and one or more emollients. Lotions typically comprise from about 1% to about 20%, preferably from about 5% to about 10%, of emollient; from about 50% to about 90%, preferably from about 60% to about 80%, water. A cream typically comprises from about 5% to about 50%, preferably from about 10% to about 20%, of emollient; and from about 45% to about 85%, preferably from about 50% to about 75%, water.

Ointments according to some embodiments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent. For example, an ointment may comprise from about 2% to about 10% of an emollient; and from about 0.1% to about 2% of a thickening agent. Non-limiting examples of thickening agents are described herein.

Preferred topical compositions according to some embodiments of the present invention comprise an emulsion. Emulsions of the present invention may contain one or more of the following:

a) Hydrophobic Component

Emulsions according to some embodiments of the present invention contain a hydrophobic phase comprising a lipid, oil, oily or other hydrophobic component. The compositions of the present invention preferably comprise from about 1% to about 50%, preferably from about 1% to about 30%, and more preferably from about 1% to about 10% by weight of the composition of a hydrophobic component. The hydrophobic component may be derived from animals, plants, or petroleum and may be natural or synthetic (i.e., man-made). Preferred hydrophobic components are substantially water-insoluble, more preferably essentially water-insoluble.

Nonlimiting examples of suitable hydrophobic components include those selected from the group consisting of:

(1) Mineral oil, which is also known as petrolatum liquid, is a mixture of liquid hydrocarbons obtained from petroleum.

(2) Petrolatum, which is also known as petroleum jelly, is a colloidal system of nonstraight-chain solid hydrocarbons and high-boiling liquid hydrocarbons, in which most of the liquid hydrocarbons are held inside the micelles.

(3) Straight and branched chain hydrocarbons having from about 7 to about 40 carbon atoms. Nonlimiting examples of these hydrocarbon materials include dodecane, isododecane, squalane, cholesterol, hydrogenated polyisobutylene, docosane, hexadecane, isohexadecane. Also useful are the $C_{7-40}$ isoparaffins, which are $C_{7-40}$ branched hydrocarbons, e.g., $C_{13-14}$ isoparaffin.

(4) $C_1$-$C_{30}$ alcohol esters of $C_1$-$C_{30}$ carboxylic acids and of $C_2$-$C_{30}$ dicarboxylic acids, including straight and branched chain materials as well as aromatic derivatives (as used herein in reference to the hydrophobic component, mono- and poly-carboxylic acids include straight chain, branched chain and aryl carboxylic acids). Nonlimiting examples include diisopropyl sebacate, diisopropyl adipate, isopropyl myristate, isopropyl palmitate, methyl palmitate, myristyl propionate, 2-ethylhexyl palmitate, isodecyl neopentanoate, di-2-ethylhexyl maleate, cetyl palmitate, myristyl myristate, stearyl stearate, isopropyl stearate, methyl stearate, cetyl stearate, behenyl behenrate, dioctyl maleate, dioctyl sebacate, diisopropyl adipate, cetyl octanoate, diisopropyl dilinoleate.

(5) mono-, di- and tri-glycerides of $C_1$-$C_{30}$ carboxylic acids, e.g., caprilic/capric triglyceride, PEG-6 caprylic/capric triglyceride, PEG-8 caprylic/capric triglyceride.

(6) alkylene glycol esters of $C_1$-$C_{30}$ carboxylic acids, e.g., ethylene glycol mono- and di-esters, and propylene glycol mono- and di-esters of $C_1$-$C_{30}$ carboxylic acids e.g., ethylene glycol distearate.

(7) propoxylated and ethoxylated derivatives of the foregoing materials.

(8) $C_1$-$C_{30}$ mono- and poly-esters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose heptaoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7-8, and in which the fatty acid moieties are $C_{18}$ mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose.

(9) Organopolysiloxane oils. The organopolysiloxane oil may be volatile, non-volatile, or a mixture of volatile and non-volatile silicones. The term "nonvolatile" as used in this context refers to those silicones that are liquid under ambient conditions. The term "volatile" as used in this context refers to all other silicone oils. Suitable organopolysiloxanes can be selected from a wide variety of silicones spanning a broad range of volatilities and viscosities. Nonvolatile polysiloxanes are preferred. Examples of suitable organopolysiloxane oils include polyalkylsiloxanes, cyclic polyalkylsiloxanes, and polyalkylarylsiloxanes.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones, as described in U.S. Pat. No. 5,968,528.

(10) Vegetable oils and hydrogenated vegetable oils. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

(11) Animal fats and oils e.g., lanolin and derivatives thereof, cod liver oil.

(12) Also useful are $C_4$-$C_{20}$ alkyl ethers of polypropylene glycols, $C_1$-$C_{20}$ carboxylic acid esters of polypropylene glycols, and di-$C_8$-$C_{30}$ alkyl ethers. Nonlimiting examples of these materials include PPG-14 butyl ether, PPG-15 stearyl ether, dioctyl ether, dodecyl octyl ether, and mixtures thereof.

b) Hydrophilic Component

In some embodiments, emulsions of the present invention also comprise a hydrophilic component, e.g., water or other hydrophilic diluent. The hydrophilic phase can thus comprise water, or a combination of water and one or more water soluble or dispersible ingredients. Hydrophilic components comprising water are preferred.

c) Other Components

In some embodiments, emulsions and other topical compositions of the present invention may comprise a variety of other ingredients such as disclosed herein. As will be understood by the skilled artisan, a given component will distribute primarily into either a hydrophilic phase or hydrophobic phase, depending on the hydrophilicity of the component in the composition.

Emulsions of the present invention preferably include one or more compounds selected from emulsifiers, surfactants, structuring agents, and thickeners.

(1) Emulsifiers/Surfactants

The emulsion may contain an emulsifier and/or surfactant, generally to help disperse and suspend the discontinuous phase within the continuous phase. A wide variety of such agents can be employed. Known or conventional emulsifiers/surfactants can be used in the composition, provided that the selected agent is chemically and physically compatible with essential components of the composition, and provides the desired dispersion characteristics. Suitable agents include non-silicone-containing emulsifiers/surfactants, silicone emulsifiers/surfactants, and mixtures thereof.

In a preferred embodiment, the composition comprises a hydrophilic emulsifier or surfactant. The compositions of the present invention preferably comprise from about 0.05% to about 5%, more preferably from about 0.05% to about 1% of at least one hydrophilic surfactant.

Preferred hydrophilic surfactants are selected from nonionic surfactants. Among the nonionic surfactants that are useful herein are those that can be broadly defined as condensation products of long chain alcohols, e.g. $C_{8-30}$ alcohols, with sugar or starch polymers, i.e., glycosides. Examples of long chain alcohols from which the alkyl group can be derived include decyl alcohol, cetyl alcohol, stearyl alcohol, lauryl alcohol, myristyl alcohol, oleyl alcohol, and the like. Commercially available examples of these surfactants include decyl polyglucoside and lauryl polyglucoside.

Other useful nonionic surfactants include the condensation products of alkylene oxides with fatty acids (i.e. alkylene oxide esters of fatty acids). Other nonionic surfactants are the condensation products of alkylene oxides with fatty alcohols (i.e. alkylene oxide ethers of fatty alcohols). Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, $C_1$-$C_{30}$ fatty acid esters of $C_1$-$C_{30}$ fatty alcohols, alkoxylated derivatives of $C_1$-$C_{30}$ fatty acid esters of $C_1$-$C_{30}$ fatty alcohols, alkoxylated ethers of $C_1$-$C_{30}$ fatty alcohols, polyglyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, and mixtures thereof. Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another emulsifier useful herein are fatty acid ester blends based on a mixture of sorbitan or sorbitol fatty acid ester and sucrose fatty acid ester. The preferred fatty acid ester emulsifier is a blend of sorbitan or sorbitol $C_{16}$-$C_{20}$ fatty acid ester with sucrose $C_{10}$-$C_{16}$ fatty acid ester, especially sorbitan stearate and sucrose cocoate.

The hydrophilic surfactants useful herein can alternatively or additionally include any of a wide variety of cationic, anionic, zwitterionic, and amphoteric surfactants such as are known in the art. See, e.g., Allured, M. 2009 McCutcheon's Emulsifiers and Detergents, McCutcheon's Publications, Apr. 1, 2009.

Exemplary cationic surfactants useful herein include those disclosed in U.S. Pat. No. 5,968,528. The cationic surfactants useful herein include cationic ammonium salts such as quaternary ammonium salts, and amino-amides.

A wide variety of anionic surfactants are also useful herein. See e.g., U.S. Pat. No. 5,968,528. Nonlimiting examples of anionic surfactants include the alkoyl isethionates (e.g., $C_{12}$-$C_{30}$), alkyl and alkyl ether sulfates and salts thereof, alkyl and alkyl ether phosphates and salts thereof, alkyl methyl taurates (e.g., $C_{12}$-$C_{30}$), and soaps (e.g., alkali metal salts, e.g., sodium or potassium salts) of fatty acids.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilizing group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, alkyl sarcosinates (e.g., $C_{12}$-$C_{30}$), and alkanoyl sarcosinates.

In some embodiments, preferred emulsions of the present invention include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain $C_2$-$C_{30}$ pendant side chains. Still other useful dimethicone copolyols include materials having various cationic, anionic, amphoteric, and zwitterionic pendant moieties.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide side chains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant $C_2$-$C_{30}$ straight, branched, or cyclic alkyl moieties. Examples of commercially available dimethicone copolyols useful herein sold by Dow Corning Corporation are Dow Corning™. 190, 193, Q2-5220, 2501 Wax, 2-5324 fluid, and 3225C (this later material being sold as a mixture with cyclomethicone).

Cetyl dimethicone copolyol is commercially available as a mixture with polyglyceryl-4 isostearate (and) hexyl laurate and is sold under the tradename ABIL™ WE-09. Cetyl dimethicone copolyol is also commercially available as a mixture with hexyl laurate (and) polyglyceryl-3 oleate (and) cetyl dimethicone and is sold under the tradename ABIL™ WS-08. Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate.

Dimethicone copolyol emulsifiers useful herein are described, for example, in U.S. Pat. No. 5,968,528.

(2) Structuring Agent

The compositions hereof, and especially the emulsions hereof, may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention comprise from about 1% to about 20%, more preferably from about 1% to about 10%, most preferably from about 2% to about 9%, of one or more structuring agents.

Preferred structuring agents are those having an HLB of from about 1 to about 8 and having a melting point of at least about 45° C. Suitable structuring agents are those selected from the group consisting of saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C.

In some embodiment, the preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, and mixtures thereof.

(3) Thickening Agent (Including Thickeners and Gelling Agents)

In some embodiments, the compositions of the present invention can also comprise a thickening agent, preferably from about 0.1% to about 5%, more preferably from about 0.1% to about 3%, and most preferably from about 0.25% to about 2%, of a thickening agent.

Nonlimiting classes of thickening agents include those selected, from the group consisting of:

(i) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred carboxylic acid polymers are of two general types. The first type of polymer is a crosslinked homopolymer of an acrylic acid monomer or derivative thereof (e.g., wherein the acrylic acid has substituents on the two and three carbon positions independently selected from the group consisting of 4 alkyl, —CN, —COOH, and mixtures thereof). The second type of polymer is a crosslinked copolymer having a first monomer selected from the group consisting of an acrylic acid monomer or derivative thereof (as just described in the previous sentence), a short chain alcohol (i.e., a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof, and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers, the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters, $C_{1-4}$ alcohol ethacrylate esters, and mixtures thereof, with the $C_{1-4}$ alcohol acrylate esters, $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof.

Examples of commercially available homopolymers of the first type useful herein include the carbomers, which are homopolymers of acrylic acid crosslinked with allyl ethers of sucrose or pentaerytritol. The carbomers are available as the Carbopol™ 900 series. Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an ally ether of sucrose or pentaerytritol. These copolymers are known as acrylates/$C_{10-30}$ alkyl acrylate crosspolymers and are commercially available as Carbopol™ 1342, Carbopol™ 1382, Pemulen TR-1, and Pemulen TR-2. In other words, examples of carboxylic acid polymer thickeners useful herein are those selected from the group consisting of carbomers, acrylates/$C_{10-30}$ alkyl acrylate crosspolymers, and mixtures thereof.

(ii) Crosslinked Polyacrylate Polymers

The crosslinked polyacrylate polymers useful as thickeners or gelling agents include both cationic and nonionic polymers, with the cationics being generally preferred. Non-limiting examples of suitable crosslinked polyacrylate polymers are disclosed in U.S. Pat. No. 5,968,528.

(iii) Polyacrylamide Polymers

Also useful herein are polyacrylamide polymers, especially non-ionic polyacrylamide polymers including substituted branched or unbranched polymers. These polymers can be formed from a variety of monomers including acrylamide and methacrylamide which are unsubstituted or substituted with one or two alkyl groups (preferably $C_{1-5}$). Preferred are acrylate amide and methacrylate amide monomers in which the amide nitrogen is unsubstituted, or substituted with one or two $C_{1-5}$ alkyl groups (preferably methyl, ethyl, or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. These polymers have a molecular weight greater than about 1,000,000 preferably greater than about 1,5000,000 and range up to about 30,000,000. Most preferred among these polyacrylamide polymers is the non-ionic polymer given the CTFA designation polyacrylamide and isoparaffin and laureth-7.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H.

(iv) Polysaccharides

A wide variety of polysaccharides are useful herein. By "polysaccharides" are meant gelling agents containing a backbone of repeating sugar (i.e. carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10-30}$ straight chain or branched chain alkyl group through an ether linkage. Typically these polymers are ethers of $C_{10-30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose.

v) Gums

Other additional thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboyxmethyl dextran, sodium carrageenan, tragacanth gum, xanthan gum, and mixtures thereof.

(vi) Crosslinked Vinyl Ether/Maleic Anhydride Copolymers

Other additional thickening and gelling agents useful herein include crosslinked copolymers of alkyl vinyl ethers and maleic anhydride.

(vii) Crosslinked Poly(N-Vinylpyrrolidones)

Crosslinked polyvinyl(N-pyrrolidones) useful herein as additional thickening and gelling agents These gelling agents typically contain from about 0.25% to about 1% by weight of a crosslinking agent selected from the group consisting of divinyl ethers and diallyl ethers of terminal diols containing from about 2 to about 12 carbon atoms, divinyl ethers and diallyl ethers of polyethylene glycols containing from about 2 to about 600 units, dienes having from about 6 to about 20 carbon atoms, divinyl benzene, vinyl and allyl ethers of pentaerythritol, and the like.

Preferred compositions of the present invention include a thickening agent selected from the group consisting of carboxylic acid polymers, crosslinked polyacrylate polymers, polyacrylamide polymers, and mixtures thereof, more preferably selected from the group consisting of crosslinked polyacrylate polymers, polyacrylamide polymers, and mixtures thereof.

Optional Components

The topical compositions of the present invention may comprise a wide variety of optional components, provided that such optional components are physically and chemically compatible with the essential components described herein, and do not unduly impair stability, efficacy or other use benefits associated with the compositions of the present invention. Optional components may be dispersed, dissolved or the like in the carrier of the present compositions.

Optional components include aesthetic agents and active agents. For example, the compositions may include, in addition to the essential components of the invention, absorbents (including oil absorbents such as clays an polymeric absorbents), abrasives, anticaking agents, antifoaming agents, antimicrobial agents (e.g., a compound capable of destroying microbes, preventing the development of microbes or preventing the pathogenic action of microbes and useful, for example, in controlling acne and/or preserving the topical composition), binders, biological additives, buffering agents, bulking agents, chemical additives, cosmetic biocides, denaturants, cosmetic astringents, drug astringents, external analgesics, film formers, humectants, opacifying agents, fragrances, perfumes, pigments, colorings, essential oils, skin sensates, emollients, skin soothing agents, skin healing agents, pH adjusters, plasticizers, preservatives, preservative enhancers, propellants, reducing agents, skin-conditioning agents, skin penetration enhancing agents, skin protectants, solvents, suspending agents, emulsifiers, thickening agents, solubilizing agents, polymers for aiding the film-forming properties and substantivity of the composition (such as a copolymer of eicosene and vinyl pyrrolidone), waxes, sunscreens, sunblocks, ultraviolet light absorbers or scattering agents, sunless tanning agents, antioxidants and/or radical scavengers, chelating agents, sequestrants. Such other materials are known in the art. Nonexclusive examples of such materials are described in Pharmaceutical Dosage Forms-Disperse Systems; Lieberman, Rieger & Banker, Vols. 1 (1988) & 2 (1989); or in U.S. Pat. No. 5,968,528.

The composition of the invention may comprise an emollient. The emollient may be selected from one or more of the following classes: Triglyceride esters which include, but are not limited to, vegetable and animal fats and oils such as castor oil, cocoa butter, safflower oil, cottonseed oil, corn oil, olive oil, cod liver oil, almond oil, avocado oil, palm oil, sesame oil, squalene, kikui oil and soybean oil; Acetoglyceride esters, such as acetylated monoglycerides; Ethoxylated glycerides, such as ethoxylated glyceryl monostearate; Alkyl esters of fatty acids having 10 to 20 carbon atoms which include, but are not limited to, methyl, isopropyl, and butyl esters of fatty acids such as hexyl laurate, isohexyl laurate, isohexyl palmitate, isopropyl palmitate, methyl palmitate, decyloleate, isodecyl oleate, hexadecyl stearate decyl stearate, isopropyl isostearate, methyl isostearate, diisopropyl adipate, diisohexyl adipate, dihexyldecyl adipate, diisopropyl sebacate, lauryl lactate, myristyl lactate, and cetyl lactate; Alkenyl esters of fatty acids having 10 to 20 carbon atoms such as oleyl myristate, oleyl stearate, and oleyl oleate; Fatty acids having 10 to 20 carbon atoms such as pelargonic, lauric, myristic, palmitic, stearic, isostearic, hydroxystearic, oleic, linoleic, ricinoleic, arachidic, behenic, and erucic acids; Fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; Lanolin and lanolin derivatives such as lanolin, lanolin oil, lanolin wax, lanolin alcohols, lanolin fatty acids, isopropyl lanolate, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, and liquid and semisolid lanolin absorption bases; Polyhydric alcohol esters such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, sorbitan fatty acid esters, and polyoxyethylene sorbitan fatty acid esters; Wax esters such as beeswax, spermaceti, myristyl myristate, stearyl stearate; Beeswax derivatives such as polyoxyethylene sorbitol beeswax which are reaction products of beeswax with ethoxylated sorbitol of varying ethylene oxide content, forming a mixture of ether esters; Vegetable waxes including, but not limited to, carnauba and candelilla waxes; Phospholipids such as lecithin and derivatives; Sterols including, but not limited to, cholesterol and cholesterol fatty acid esters; and Amides such as fatty acid amides, ethoxylated fatty acid amides, and solid fatty acid alkanolamides.

The composition may comprise humectants, e.g., of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, hexylene glycol, butylene glycol (e.g., 1,3-butylene glycol), hexane triol (e.g., 1,2,6-hexanetriol), glycerol, ethoxylated glycerol, propoxylated glycerol, sodium 2-pyrrolidone-5-carboxylate, soluble collagen, dibutyl phthalate, gelatin and mixtures thereof.

Further optional components are guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid and derivatives thereof (e.g., salt derivatives such as sodium hyaluraonate); lactamide monoethanolamine; acetamide monoethanolamine; urea; panthenol; sugars; starches; silicone fluids; silicone gums; and mixtures thereof. Also useful are the propoxylated glycerols.

Applications Using Applicators, Sprays, Fine Mist, Foams, Mousse or Aerosols

In some embodiments, particularly preferred pharmaceutical compositions involve solutions, liquids, suspensions and powders. In some embodiments, particularly preferred pharmaceutical compositions comprise delivery of said composition to the affected skin by way of a spray, fine mist, foam, mousse or aerosol. In some embodiments, particularly preferred pharmaceutical compositions comprise delivery of said composition to the affected skin by way of a spray, fine mist, foam, mousse or aerosol, said composition forming a film, barrier, occlusive film or non-occlusive film on the skin upon application or in situ.

Such formulations are may be applied to the skin using a roll-on or other application device, as a foam, mousse, fine spray or mist or in aerosol form. Pharmaceutical compositions and methods for application of such are well known in the prior art.

Some examples of suitable vehicles are given in U.S. Pat. Nos. 3,598,122; 3,598,123; 3,742,951; 3,814,097; 3,921, 636; 3,993,072; 3,993,073; 3,996,934; 4,031,894; 4,060,084; 4,069,307; 4,201,211; 4,230,105; 4,292,299; 4,292,303; 5,323,769; 5,023,085; 5,474,783; 4,941,880; 4,077,407; 6,916,486; 6,818,226; 6,916,487; 6,923,983; 6,929,801; 6,978,945; 6,998,138; and 7,094,422, all hereby incorporated by reference in their entirety.

DETAILED DESCRIPTION OF THE PREFERRED EMBODIMENTS

The following examples illustrate various aspects of the present invention. They are not to be construed to limit the claims in any manner whatsoever. A wide variety of methods known in the art for the preparation of immediate release and controlled release dosage forms may be incorporated into the invention. Other suitable dosage forms may also be prepared by modification of the examples herein and by use of material other than those specifically disclosed herein, including those which may hereafter become known to the art to be capable of performing the necessary functions. Similarly, other suitable methods for the evaluation of dosage forms may also be used by modification of the examples herein and by use of methods other than those specifically disclosed herein, including those which may hereafter become known to the art to be capable of performing the necessary functions. Other suitable modifications and adaptations of the variety of conditions and parameters normally encountered and obvious to those skilled in the art are within the spirit and scope of the invention.

Other drugs for the treatment of pain may be included in the same dosage form. Other drugs for the treatment of side effects of mepivacaine may also be included in the same dosage form. The percent loading of the mepivacaine agent and the other incorporated therapeutic agent may be varied depending on the physiochemical and pharmaceutical properties of said agent and ingredients (excipients), the pharmacologic effects of said agent, and the desired degree of release or non-release from the dosage form and other factors identified herein.

The ingredients or excipients, including functional excipients used for the preparation of the dosage form may be modified depending on the selection, dose and desired duration of effect of the mepivacaine.

The dose and dosing frequency of the mepivacaine formulation will vary depending on of the nature of the patient population, the characteristics of the medical condition under treatment, and other factors described herein. Similarly, the in vitro and in vivo release characteristics of the mepivacaine dosage form, including the in vitro, in vivo and ex vivo release, permeability and skin retention rates, the in vitro dissolution rate and plasma concentration time profile may be modified based on the clinical need of the patient, and other factors described herein.

A wide variety of formulations of mepivacaine for application to the skin have been prepared and evaluated by the applicant.

In Vivo Pharmacologic Evaluation

Example 1

Introduction and Objective

This study evaluated the effects of topical mepivacaine in DMSO painful HIV-associated peripheral neuropathy. HIV peripheral neuropathy in the rat was induced by sciatic nerve exposure to gp120.

Methods

Surgical Procedure:

Under anesthesia, the left sciatic nerve of male rats was isolated by blunt dissection of the biceps, without damaging the perineurium. The HIV-1 viral envelope protein, gp120 was embedded in a carrier matrix and delivered directly to the sciatic nerve. The muscular layer was closed using 3-0 silk and the skin sealed with veterinarian-grade cyanoacrylate.

Mepivacaine Administration:

A gauze pad was saturated with either mepivacaine in DMSO (vehicle) or vehicle alone and secured to the left plantar hind paw for 5 min. Rats were immediately tested after removal of the pad. Rats were then tested again at 5, 10 and 15 minutes after removal of the pad. Mepivacaine was tested at various concentrations. The treatment assignment was masked. A period of 48 hrs was allowed between retesting of the rats. The continued presence of hyperalgesia in the rats was confirmed by pre-drug application baseline testing on each test day.

Behavioral Testing:

Plantar hind paw response to noxious heat and pressure application was evaluated before and one week following sciatic nerve surgery to confirm onset of hyperalgesia following gp120 administration. Following 15-20 min acclimation in the test chamber, a thermal heat stimulus was aimed at the mid-plantar hind paw as rats stand on a glass surface. The latency to a withdrawal response was recoded electronically. The stimulus intensity was adjusted to result in mean pre-surgical baseline latencies of approximately 12 seconds. Each hind paw was tested once to obtain a hind paw withdrawal latency. Mechanical allodynia was assessed by application of increasing pressure (32 g/sec) to the plantar hind paw over time. The withdrawal threshold (measured in grams) was reached when the rat withdrew its paw from the apparatus. The pre-surgical withdrawal threshold of naïve rats was about 175 g. Each hind paw was tested once to obtain a hind paw withdrawal threshold. Antinociception, or analgesia, was defined quantally as an increase in response over baseline.

Statistical Analyses:

Statistical analysis for thermal hyperalgesia and mechanical allodynia were performed and statistical significance was declared if the two-sided p-value was ≤0.05. All computations were performed using SigmaStat™ for Windows™, Version 3.5.

Results

Mechanical Allodynia.

Figure 6:
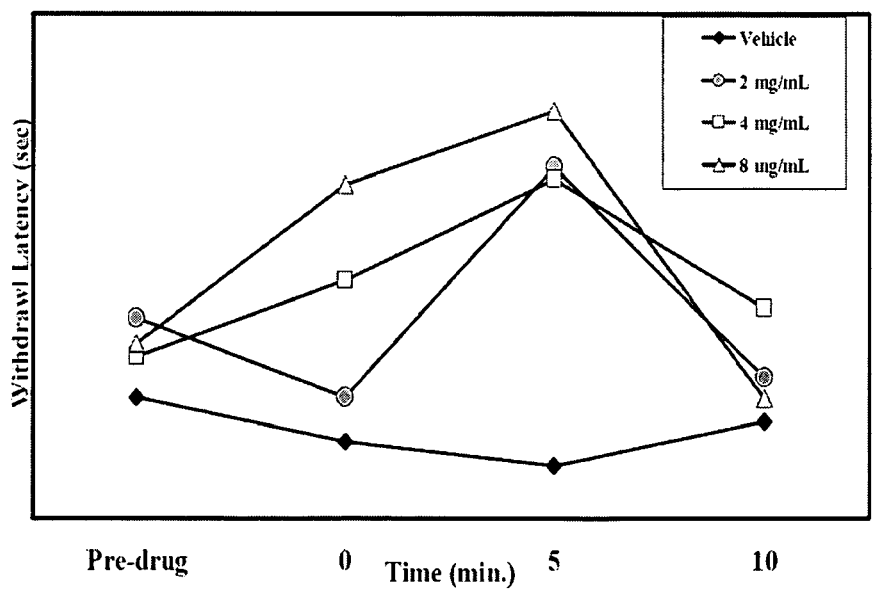

Topical mepivacaine demonstrated short lived and variable antinociceptive effects for mechanical allodynia in the gp120 model of painful HIV-associated peripheral neuropathy. Mepivacaine 2 mg/mL, 4 mg/mL and 8 mg/mL doses were significantly different from control (≤0.05, all treatments). FIG. 6 shows the anti-allodynic effects of mepivacaine base at baseline and following topical application of 2 mg/mL, 4 mg/mL and 8 mg/mL in DMSO.

Thermal Hyperalgesia.

Figure 7:
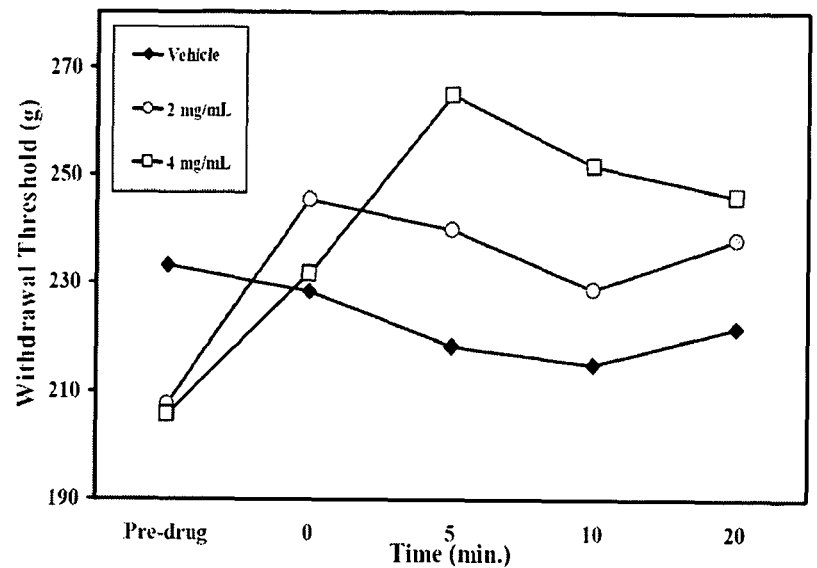

Topical mepivacaine demonstrated short lived and variable antinociceptive effects for thermal hyperalgesia in the gp120 model of painful HIV-associated peripheral neuropathy. Mepivacaine 2 mg/mL, 4 mg/mL and 8 mg/mL doses were significantly different from control (≤0.05, all treatments). FIG. 7 shows the effect on thermal hyperalgesia of mepivacaine base at baseline and following topical application of 2 mg/mL, 4 mg/mL and 8 mg/mL. Vehicle control showed no discernible effects.

Example 2

Introduction and Objective

This study evaluated the effects of topical mepivacaine in DMSO painful HIV-associated peripheral neuropathy. HIV peripheral neuropathy in the rat was induced by sciatic nerve exposure to zalcitabine plus gp120.

Methods

Surgical Procedure:

Under anesthesia, the left sciatic nerve of male rats was isolated by blunt dissection of the biceps, without damaging the perineurium. The HIV-1 viral envelope protein, gp120 was embedded in a carrier matrix and delivered directly to the sciatic nerve. The muscular layer was closed using 3-0 silk and the skin sealed with veterinarian-grade cyanoacrylate. Rats received intravenous tail injection of zalcitabine.

Mepivacaine Administration:

A gauze pad was saturated with either mepivacaine in DMSO (vehicle) or vehicle alone and secured to the left plantar hind paw for 5 min. Rats were immediately tested after removal of the pad. Rats were then tested again at 5, 10 and 15 minutes after removal of the pad. Mepivacaine was tested at various concentrations. The treatment assignment was masked. A period of 48 hrs was allowed between retesting of the rats. The continued presence of hyperalgesia in the rats was confirmed by pre-drug application baseline testing on each test day.

Behavioral Testing:

Plantar hind paw response to noxious heat and pressure application was evaluated before and one week following sciatic nerve surgery to confirm onset of hyperalgesia following gp120 administration. Following 15-20 min acclimation in the test chamber, a thermal heat stimulus was aimed at the mid-plantar hind paw as rats stand on a glass surface. The latency to a withdrawal response was recoded electronically. The stimulus intensity was adjusted to result in mean pre-surgical baseline latencies of approximately 12 seconds. Each hind paw was tested once to obtain a hind paw withdrawal latency. Mechanical allodynia was assessed by application of increasing pressure (32 g/sec) to the plantar hind paw over time. The withdrawal threshold (measured in grams) was reached when the rat withdrew its paw from the apparatus. The pre-surgical withdrawal threshold of naïve rats was about 175 g. Each hind paw was tested once to obtain a hind paw withdrawal threshold. Antinociception, or analgesia, was defined quantally as an increase in response over baseline.

Statistical Analyses: Statistical analysis for thermal hyperalgesia and mechanical allodynia were performed and statistical significance was declared if the two-sided p-value was ≤0.05. All computations were performed using SigmaStat™ for Windows™, Version 3.5.

Results

Mechanical Allodynia.

Figure 8:
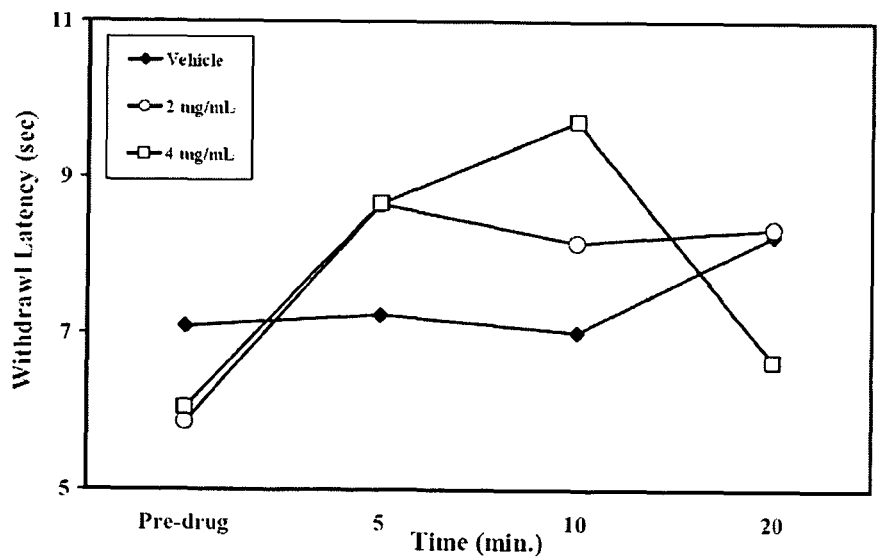

Topical mepivacaine demonstrated short lived and variable antinociceptive effects for mechanical allodynia in the combined HIV viral envelope protein (gp120) and nucleoside analog reverse transcriptase inhibitor (NRTI) model of painful HIV-associated peripheral neuropathy. Mepivacaine 2 mg/mL and 4 mg/mL doses were significantly different from control (≤0.05, both treatments). FIG. 8 shows antiallodynic effects of mepivacaine base at baseline and following topical application of 2 mg/mL and 4 mg/mL. Vehicle control showed no discernible effects.

Thermal Hyperalgesia.

Figure 9:
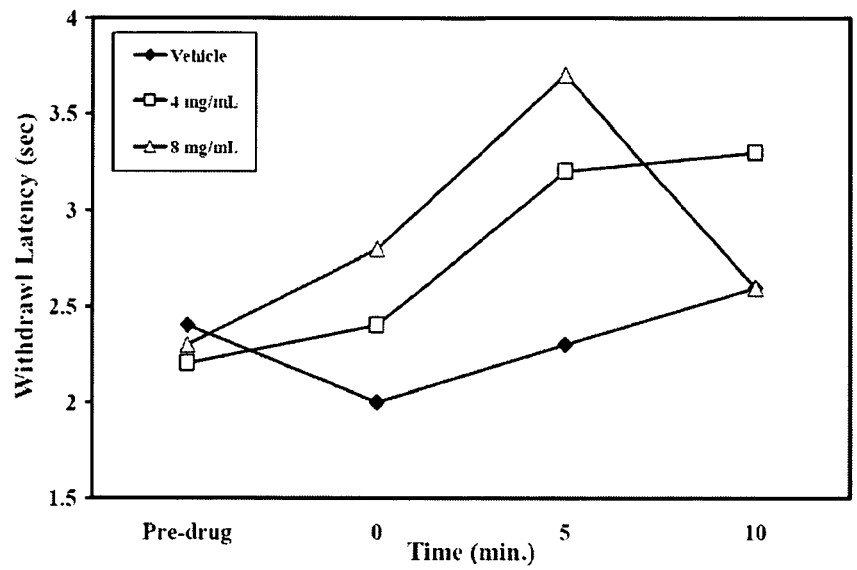

Topical mepivacaine demonstrated short lived and variable antinociceptive effects for mechanical allodynia in the combined HIV viral envelope protein (gp120) and nucleoside analog reverse transcriptase inhibitor (NRTI) model of painful HIV-associated peripheral neuropathy. Mepivacaine 2 mg/mL and 4 mg/mL doses were significantly different from control (≤0.05, both treatments). FIG. 9 shows effect on thermal hyperalgesia of mepivacaine base at baseline and following topical application of 2 mg/mL and 4 mg/mL. Vehicle control showed no discernible effects.

Example 3

Introduction and Objective

This study evaluated the effects of topical in DMSO mepivacaine in the tail-flick model.

Methods

Male mice were maintained on a 12-h light/dark cycle with food and water available ad libitum. Mice were housed in groups of five until testing Treatments:

Drugs were given topically in DMSO (vehicle) on the tail by immersion of the tail in treatment solution for 5 minutes. Tail-flick latencies were then determined on the region of the tail immersed in the drug, unless otherwise stated. Mice were immediately tested after removal of the tail from the treatment solution and retested at 5 and 10 minutes. Mepivacaine was tested at various concentrations. The treatment assignment was masked.

Behavioral Testing:

Analgesia was assessed with the tail-flick assay. Responses were measured by exposing the distal part of the tail to a thermal stimulus, and the latency of exposure was determined. The tail flick latency is the time interval between onset of the heat stimulus and withdrawal of the tail the thermal stimulus. Baseline latencies ranged from 2 to 3 s. Testing was performed immediately after termination of topical administration into the tail and at 5 and 10 minutes thereafter. Antinociception, or analgesia, was defined quantally as an increase in response over baseline.

Statistical Analyses:

Statistical analysis was performed and statistical significance was declared if the two-sided p-value was ≤0.05. All computations were performed using SigmaStat™ for Windows™, Version 3.5.

Results

Figure 10:
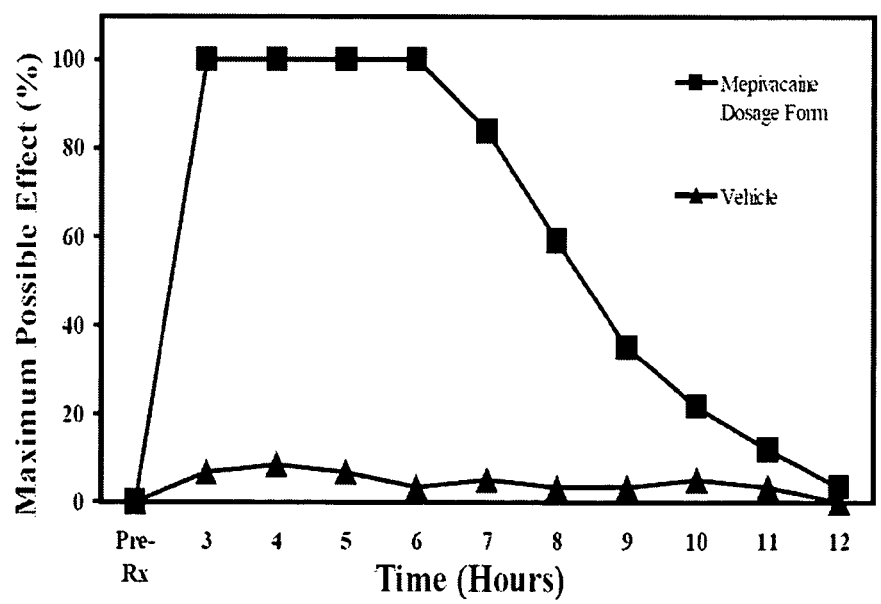

Topical mepivacaine demonstrated short lived and variable analgesia. There was an overall statistically significant treatment effect in the ANOVA by treatment (P≤0.038). Mepivacaine 4 mg/mL and 8 mg/mL doses were significantly different from control (≤0.05, both treatments). FIG. 10 shows the antinociceptive effects of mepivacaine base at baseline and following brief topical application of 4 mg/mL and 8 mg/mL. Vehicle control showed no discernible effects.

Example 3A

Introduction and Objective

This study evaluated the effects of a semisolid pharmaceutical dosage form of the invention on analgesia on cutaneous analgesia.

Methods

Male rats were maintained on a 12-h light/dark cycle with food and water available ad libitum. Testing was preceded by a 10 to 14 day acclimation period. After brief anesthesia, animals were prepared by clipping the fur of the back and the left and right flanks using an electric hair clipper, followed by depilation of a 2.5 cm×2.5 cm area of the lateral thoracolumbar region approximately 24 hours prior to the application of test article or vehicle. The application site of the thoracolumbar region, an area slightly larger than 2 cm×2 cm was outlined using an indelible marker. Test article or vehicle was applied to the outlined skin surface and a gauze pad was affixed over the area of application. Cutaneous analgesia was assessed on six occasions at each scheduled timepoint (0, 3, 4, 5, 6, 7, 8, 9, 10, 11, 12, 14, 24 and 26 hours post-treatment initiation) using the Touch-Test™ Sensory Evaluators (Semmes-Weinstein Monofilaments) with a force of 26 g.

Results

Figure 11:
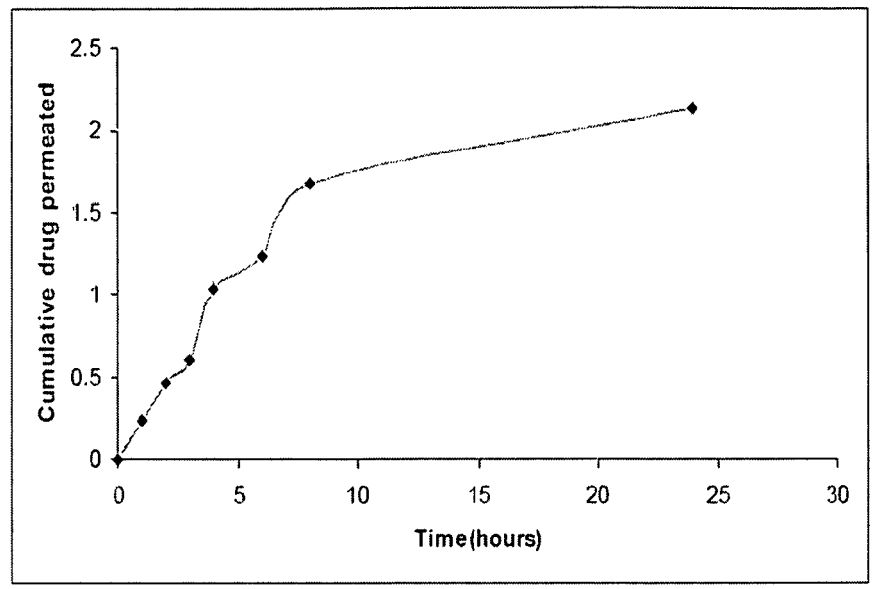

The semisolid topical mepivacaine doisage form of the invention demonstrated robust, long-lasting and consistent analgesia. There was an overall statistically significant treatment effect in the ANOVA by treatment. FIG. 11 shows the antinociceptive effects of the mepivacaine dosage form of the invention versus vehicle control.

Pharmaceutical Development & Skin Permeability Evaluation

Example 4

| Mepivacaine Hydrogel Patch | |
|---|---|
| Ingredient | Purpose |
| Mepivacaine base | Active medicament |
| Gelatin | Viscosity enhancer |
| Kaolin | Diluent |
| D-Sorbitol | Humectant |
| Glycerol | Humectant |
| Propylene glycol | Humectant |
| Polyacrylic acid, Na, 45% sol. in $H_2O$ | Viscosity enhancer |
| Carboxy methyl cellulose Na (250,000) | Viscosity enhancer |
| Polyacrylic acid (4,000,000) | Hydrogel matrix component |
| Polyacrylic acid (450,000) | Hydrogel matrix component |
| Urea | Humectant |
| Tartaric acid | pH adjustment |
| Methyl-4-hydroxybenzoate | Preservative |
| Propyl-4-hydroxybenzoate | Preservative |
| Dihydroxyalumiunum aminoacetate | Cross linking agent |
| Ethanol | Solvent |
| Purified water | Solvent |
| Polyethylene terephthalate film (PET) | Release liner |
| Sigmacote (silicon oil solution) | Release agent |
| Non woven polyester felt | Backing material |

Mepivacaine Base Solution 2.5 g Mepivacaine base was suspended in 2.5 g of propylene glycol. It was not sufficiently soluble to form a solution in propylene glycol at this ratio so 5 g of absolute ethanol was added. (Mepivacaine base solubility is 40 g/100 ml in EtOH) A clear solution was formed after stirring.

Gelatin, Polyacrylic Acid, Kaolin and D-Sorbitol Mixture 20 g of ethanol was added to 1 g of polyacrylic acid (450,000 grade) in a beaker and the mix stirred until a clear mobile solution was obtained. 0.5 g of gelatin was added to 19 g of purified water and the mix heated with stirring until a clear solution was obtained. The polyacrylic acid solution in ethanol was added with stirring to the hot gelatin solution while maintaining heating. After some initial gelatinous precipitation the materials redissolved to form a milky mobile solution/suspension. 0.5 g kaolin and 7.5 g d-sorbitol were added while maintaining heating and stirring.

Excipient Mix 10 g of glycerol and 5.5 g of polyacrylic acid, sodium salt, as a 45% solution in water, was added to a beaker. 2.5 g Carboxymethylcellulose sodium (250,000), 0.5 g urea, 0.75 g tartaric acid, 0.05 g methyl paraoxybenzoate (Methylparaben), 0.03 g propyl paraoxybenzoate (propyl paraben) and 0.15 g dihydroxy aluminum aminoacetate (aluminum glycinate) were progressively added to the beaker with continuous stirring. The mix formed a mobile dispersion which slowly thickened to a viscous paste.

Mepivacaine Base/Adhesive Mix

The mepivacaine base solution containing propylene glycol and ethanol was added slowly with continued heating and stirring to the hot gelatin, polyacrylic acid, kaolin and d-sorbitol mix. The mix took on the viscosity of a paste but remained uniform and lump free. The remaining excipient mix was added to the hot mix with vigorous stirring. This gave a viscous sticky homogeneous mix. The adhesive mix was too thick and sticky for immediate application so 10 g of ethanol was added to reduce its viscosity. Initially a cohesive gel was formed however, after persistent mixing followed by high shear mixing this redispersed to form a mobile, opaque white suspension.

Patch Preparation

Non-woven polyester felt was used as the backing material. 100 mm square pieces were used. A weight corresponding to one fifth of the above total quantities was spread over each patch. The material from the hot mix was spread evenly over each patch using a spatula. The mix spread easily and adhered well to the non woven felt. It did not soak in, as could happen if the viscosity was too low, but remained as an adhesive layer above, and bonded to, the felt backing. There was sufficient time to spread the mix evenly although it cooled quickly, becoming cohesive and gelatinous. The patches were allowed to air dry for several hours then further dried overnight in a hot air oven at 50° C. PET film was cut slightly oversize to apply as a tear off liner. Before application the contact side was wetted using Sigmacote™ solution, a convenient way of adding a thin film of silicon oil to the liner as a release aid.

Mepivacaine Patch

The active/adhesive formulation used produced a hot, visually uniform mix with the consistency of cream which spread evenly and appeared to adhere well to the backing. After drying the mix left a visually even, tacky coating on the felt backing. The tear off liner was removed from test patches freshly after application and up to two weeks later. In all cases the tear off liner separated from the adhesive layer without transfer of material or damage to the adhesive layer. A patch was applied to various materials including wood, metal, glass and skin and, after pressing firmly to maximize adhesion, was pulled off. In all cases the adhesive layer stuck firmly to the test material yet removed cleanly. No material was removed from the adhesive layer and transferred to the test material.

Example 5

| Mepivacaine Gel Formulation | | |
|---|---|---|
| Ingredient | Purpose | % w/w |
| Mepivacaine base or HCl | Active medicament | 1.0-20.0% |
| Propylene glycol | Solvent | 1.0-20.0% |
| Ethanol | Solvent | 1.0-20.0% |
| Carbopol | Viscosity enhancer | 0.5-10.0% |
| Hydroxypropyl methylcellulose | Viscosity enhancer | 0.5-10.0% |
| Ethylcellulose | Viscosity enhancer | 0.5-10.0% |
| Transcutol P | Penetration enhancer | 0.1-20.0% |
| Other Penetration enhancer | Penetration enhancer | 0.1-20.0% |
| Triethanolamine | pH adjustment | q.s |
| Hydrochloric acid | pH adjustment | q.s. |
| Sodium metabisulfite | Antioxidant | 0.01-5.0% |
| Methylparaben | Preservative | 0.01-1.0% |
| Propylparaben | Preservative | 0.01-1.0% |
| Purified water | Solvent | q.s. to 100% |

Drug Solution

Mepivacaine base or hydrochloride salt was dissolved in propylene glycol and ethanol. A clear solution was formed after stirring and sonication.

Gelling Agents Dispersion

Various amount of gelling agents, such as Carbopol 971P, Carbopol 980P, and/or Methocel K4M, was dispersed in small amounts of water. Mixing was continued until a lump-free dispersion was obtained.

Gel Formation

The drug solution was then added slowly into the gel dispersion. The dispersion was continuous stirring until a uniform, homogenous gel was obtained. Sodium metabisulfite and methylparaben was then added to the gel while continuous stirring. Various amounts of penetration enhancer were added to the gel while continuous stirring. pH was adjusted with triethanolamine and/or hydrochloric acid to pre-determined pH.

In Vitro Drug Release

The in-vitro drug release from gel formulations was studies using nylon membrane (0.22 μm) or hairless rat abdominal skin with Franz-diffusion cell. The effective surface area is 3.14 cm² and receptor cell volume of 18 mL. The receptor compartment was filled with phosphate buffer at pH 6.8 or 7.4 and maintained at 37±0.5° C. with constant stirring. 0.4-0.5 gm of gel was placed o the donor compartment. One mL sample was collected from the receptor compartment at predetermined time interval and replaced by equal volume of fresh receptor solution to maintain constant volume. Permeation rate at steady state, Jss (drug flux) was obtained by dividing the slope of the linear portion of the graph to the area of the diffusion cell.

Example 6

Mepivacaine Gel Formulation

| Ingredient | Purpose | % w/w |
|---|---|---|
| Mepivacaine HCl | Active medicament | 10.0% |
| Propylene glycol | Solvent | 10.0% |
| Ethanol | Solvent | 10.0% |
| Methocel K4M | Viscosity enhancer | 3.0% |
| Triethanolamine | pH adjustment | q.s |
| Hydrochloric acid | pH adjustment | q.s. |
| Sodium metabisulfite | Antioxidant | 0.01% |
| Methylparaben | Preservative | 0.1% |
| Purified water | Solvent | q.s. to 100% |

Observations

The obtained gel was clear, transparent and homogenous gel at pH about 7.30. The drug flux (Jss) at steady state was reported at 1.0035 (mg/cm²/hr) at pH 6.8 phosphate buffer using nylon membrane.

Example 7

Mepivacaine Gel Formulation

| Ingredient | Purpose | % w/w |
|---|---|---|
| Mepivacaine HCl | Active medicament | 10.0% |
| Propylene glycol | Solvent | 10.0% |
| Ethanol | Solvent | 10.0% |
| Carbopol 980P | Viscosity enhancer | 2.5% |
| Transcutol P | Penetration enhancer | 5.0% |
| Triethanolamine | pH adjustment | q.s |
| Hydrochloric acid | pH adjustment | q.s. |
| Sodium metabisulfite | Antioxidant | 0.01% |
| Methylparaben | Preservative | 0.1% |
| Purified water | Solvent | q.s. to 100% |

Observations

The obtained gel was clear, transparent and homogenous gel at pH about 7.24. The drug flux (Jss) at steady state was reported at 1.0837 (mg/cm²/hr) at pH 6.8 phosphate buffer using nylon membrane.

Example 8

Mepivacaine Gel Formulation

| Ingredient | Purpose | % w/w |
|---|---|---|
| Mepivacaine HCl | Active medicament | 10.0% |
| Propylene glycol | Solvent | 10.0% |
| Methocel K4M | Viscosity enhancer | 4.0% |
| Methylparaben | Preservative | 0.07% |
| Propylparaben | Preservative | 0.03% |
| Purified water | Solvent | q.s. to 100% |

The obtained gel was clear, transparent and homogenous gel at pH about 6.5. The drug flux (Jss) at steady state was reported at 0.428 (mg/cm²/hr) at pH 7.4 phosphate buffer using hairless rat skin.

Example 9

Mepivacaine Gel Formulation

| Ingredient | Purpose | % w/w |
|---|---|---|
| Mepivacaine base | Active medicament | 10.0% |
| Propylene glycol | Solvent | 10.0% |
| Ethanol | Solvent | 10.0% |
| Methocel K4M | Viscosity enhancer | 2.5% |
| Triethanolamine | pH adjustment | q.s |
| Hydrochloric acid | pH adjustment | q.s. |
| Sodium metabisulfite | Antioxidant | 0.01% |
| Methylparaben | Preservative | 0.1% |
| Purified water | Solvent | q.s. to 100% |

Observations

The obtained gel was clear, transparent and homogenous gel at pH about 7. The drug flux (Jss) at steady state was reported at 0.863 (mg/cm²/hr) at pH 6.8 phosphate buffer using nylon membrane.

Example 10

| Mepivacaine Gel Formulation | | |
|---|---|---|
| Ingredient | Purpose | % w/w |
| Mepivacaine base | Active medicament | 10.0% |
| Propylene glycol | Solvent | 10.0% |
| Ethanol | Solvent | 10.0% |
| Methocel K4M | Viscosity enhancer | 0.5% |
| Carbopol 980P | Viscosity enhancer | 2.5% |
| Triethanolamine | pH adjustment | q.s |
| Hydrochloric acid | pH adjustment | q.s. |
| Sodium metabisulfite | Antioxidant | 0.01% |
| Methylparaben | Preservative | 0.1% |
| Purified water | Solvent | q.s. to 100% |

Observations

The obtained gel was clear, transparent and homogenous gel at pH about 7. The drug flux (Jss) at steady state was reported at 1.0143 (mg/cm$^2$/hr) at pH 6.8 phosphate buffer using nylon membrane.

Mepivacaine Microemulsion System

Example 11

| Composition of Microemulsion | |
|---|---|
| COMPONENT | MEPIVACAINE BASE 5% |
| Oleic acid | 5% w/v |
| Tween-80 | 30 |
| Ethanol | 30 |
| Disodium EDTA | 0.1 |
| Sodium metabisulfite | 0.1 |
| Water up to | 100 |

Preparation of Microemulsion Based Gel:

The microemulsion was incorporated into a Carbopol based gel

Method of Preparation of Carbopol Gel

The required quantity of Carbopol 940 (1% w/w) was weighed and dispersed in small quantity of distilled water to prepare an aqueous dispersion. The dispersion was allowed to hydrate for 4 to 5 hours. Equivalent amount of microemulsion containing drug was incorporated. The dispersion was neutralized with triethanolamine if necessary under gentle stirring to avoid the inclusion of air. The pH was adjusted between 6 and 7. The final weight of gel was adjusted to 100 grams with distilled water. The gel was allowed to stand overnight to remove entrapped air from the gel.

| Formulation of drug loaded Carbopol gel | |
|---|---|
| Components | Mepivacaine Base Gel 5% |
| Carbopol 940 | 1% w/w |
| Triethanolamine | q.s to adjust pH |
| Optimized microemulsion | 80% w/v |
| Distilled water | q.s. to 100% w/w |

Addition of microemulsion into the Carbopol gel was carried out so that the final concentration of mepivacaine base in Carbopol gel was 5% w/w. The assayed content of the mepivacaine microemulsion based gel 5% was 98.8%

Example 12

Preparation of Mepivacaine Hydrochloride Gel in HPMC

The required amount of HPMC K4M was taken and dispersed in adequate quantity of distilled water with continuous stirring and hydrated overnight. Adequate amount of drug was dissolved in water. Methylparaben and propyl paraben was dissolved in propylene glycol. This mixture was added to drug mixture and then added to HPMC gel base. The final weight of gel was adjusted to 100 g with distilled water. The gel was allowed to stand overnight to remove entrapped air from the gel.

| Formulation of Mepivacaine HCl 10% gel | |
|---|---|
| Components | % w/w |
| Mepivacaine HCl | 10 |
| HPMC K4M | 4 |
| Propylene glycol | 10 |
| Methylparaben | 0.07 |
| Propylparaben | 0.03 |
| Distilled water | q.s to 100 |

The assayed content of the mepivacaine HCl HPMC 10% gel was 98.9%

Example 13

Mepivacaine HCl Cream

Method of Preparation of Drug Loaded Cream

The required quantity of cetostearyl alcohol and cetomacrogol 1000 were taken for the preparation of the emulsifying wax. The required quantity of white soft paraffin and liquid paraffin were taken and mixed with the emulsifying wax. The ingredients were melted and mixed.

Mepivacaine HCl was dissolved in distilled water and heated to 45° C. The oil phase was added into the water phase with continuous stirring until it reached room temp. The preservative and fragrance were added. Germaben II E was used as a preservative. [Composition of Germaben II E is diazolidinyl urea (30%), Methylparaben (11%), propyl paraben (3%) & propylene glycol (56%).]

| Formula for Cream Base | | |
|---|---|---|
| Emulsifying wax | Cetostearyl alcohol | 80% |
| | Cetomacrogol 1000 | 20% |
| Emulsifying ointment | Emulsifying wax | 30% |
| | Liquid Paraffin | 35% |
| | White soft paraffin | 35% |
| Cream base | Water | 70% |
| | Emulsifying ointment | 30% |

| Formula for Cream | |
|---|---|
| Components | Mepivacaine HCL Cream |
| Drug | 10% |
| Emulsifying ointment | 30% |

Formula for Cream

| Components | Mepivacaine HCL Cream |
|---|---|
| Rose oil | 0.1% |
| Germaben II E | 0.1% |
| Water | q.s to 100% |

The assayed content of the mepivacaine HCl 10% cream was gel was 99.2%.

Other topical delivery systems, such as cream, microemulsion, nanogel, hydrogel, emulgel, nanoparticles, etc. can also be prepared.

Although Carbopol is a widely used in the preparation of semisolid topical dosage forms, a significant number of mepivacaine containing Carbopol gels failed to prove viable at an early stage. Examples 14 to 20 show Carbopol based gels of topical mepivacaine which proved to be suboptimal.

Example 14

The stability of mepivacaine semisolid dosage forms of examples 11, 12 and 13 was evaluated at 30° C./65% RH and 40° C./75% RH in triplicate at 1, 3 and 6 months using a sensitive and specific analytical HPLC method. All three dosage forms demonstrated robust stability under the testing conditions.

Example 15

| Component | % w/w |
|---|---|
| Mepivacaine | 5% |
| Oleic acid | 10% |
| Tween 80 | 40% |
| n-Butanol | 25% |
| Water | q.s. to 100% |
| Carbopol 940 | 0.90% |
| Triethylamine | q.s. |

The gel was very sticky and became cloudy within 2 to 3 days.

Example 16

| Component | % w/w |
|---|---|
| Mepivacaine | 5% |
| Tween 80 | 13% |
| PG | 30% |
| Carbopol 940 | 1% |
| Glycerin | 0.08% |
| Triethylamine | Q.S. |
| Water | Q.S. (to 100%) |

A clear non sticky, transparent gel was formed at pH 7 but the gel became turbid within few days.

Example 17

| Component | % w/w |
|---|---|
| Mepivacaine | 5% |
| Oleic Acid | 5% |
| Tween 80 | 30% |
| Ethanol | 30% |
| Carbopol 940 | 1% |
| Triethylamine | Q.S. |
| Water | Q.S. (to 100%) |

A clear non sticky, transparent gel was formed at pH 7 but the gel became turbid within a few days.

Example 18

| Component | % w/w |
|---|---|
| Mepivacaine | 5% |
| Oleic Acid | 5% |
| Tween 80 | 30% |
| Ethanol | 30% |
| Disodium EDTA | 0.1% |
| Sodium Metabisulfite | 0.1% |
| Carbopol 940 | 1% |
| Triethylamine | Q.S. |
| Water | Q.S. (to 100%) |

The pH of the gel was adjusted to 5.0 but a suitable gel could not be formed at that pH.

Example 19

| Component | % w/w |
|---|---|
| Mepivacaine | 5% |
| Oleic Acid | 5% |
| Tween 80 | 30% |
| Ethanol | 30% |
| Disodium EDTA | 0.1% |
| Sodium Metabisulfite | 0.1% |
| Carbopol 940 | 1% |
| Triethylamine | Q.S. |
| Water | Q.S. (to 100%) |

The pH was adjusted to 8.0 but a suitable gel could not formed at that pH

Example 20

| Component | % w/w |
|---|---|
| Mepivacaine | 5% |
| Oleic Acid | 5% |
| Tween 80 | 30% |
| Ethanol | 30% |
| Disodium EDTA | 0.1% |
| Sodium Metabisulfite | 0.1% |
| Carbopol 940 | 1% |
| Triethylamine | Q.S. |
| Water | Q.S. (to 100%) |

The pH was adjusted to 6.0-7.0. A clear non-sticky, transparent gel was formed. However, the batch failed in stability.

Example 21

| Component | % w/w |
|---|---|
| Mepivacaine HCl | 10% |
| Cetostearyl alcohol | 7.2% |
| Cetomacrogol 1000 | 1.8% |
| liquid paraffin | 10.50% |
| White soft paraffin | 10.50% |
| Water | Q.S. (to 100%) |

A white cream formulation was produced. However, it discolored after few days. Inclusion of Rose oil and Germaben II E in the above dosage form provided a stable formulation which resisted discoloration (see Example 13)

Example 22

| Component | % w/w |
|---|---|
| Mepivacaine HCL | 10% |
| HPMC K4 M | 3% |
| PG | 30% |
| Water | Q.S. (to 100%) |

A clear non-sticky, transparent gel was formed at pH-6. However, its viscosity was suboptimal.

Example 23

| Component | % w/w |
|---|---|
| Mepivacaine HCL | 10% |
| HPMC K4 M | 4% |
| PG | 10% |
| Water | Q.S. (to 100%) |

A clear non-sticky, transparent gel was formed at pH-6. However, it became turbid and yellow within a few days. Inclusion of parabens provided a satisfactory gel (see Example 12).

Example 24

A number of dosage forms were prepared to understand the behavior of mepivacaine in a semisolid dosage form for application to the skin. The dosage forms were then evaluated for: (i) their physical appearance (e.g., in transparency and clarity) and homogeneity by visual observations; (ii) pH; (iii) flux and permeability; (iv) effects of formulation pH on flux and (v) ex-vivo permeation.

The pH of the gel formulations was determined by using a pH meter. 1 gm of the gel was dissolved in 100 ml of distilled water and measured using a digital pH meter.

For the assay of the drug in gels, 0.3-0.5 g accurately weighed gel was dissolved in PBS pH 6.8 in a 100 ml volumetric flask under sonication for 30 mins and the volume was made up to 100 mL with the same. The resultant mixture was filtered through Whatmann filter paper (0.2μ). The absorbance of the sample was determined spectrophotometrically at 263 nm. The concentration of mepivacaine was estimated from regression equation of the calibration curve.

The in-vitro drug release from gel formulations was studied across the Nylon 6, 6 membrane (0.22 μm) using Franz-diffusion cell with effective surface area of 3.14 $cm^2$ and receptor cell volume of 18 mL. The receptor compartment was filled with PBS pH 6.8 and maintained at 37±0.5° C. with constant magnetic stirring. 0.3-0.5 gm of gel was placed on the donor compartment. The samples (1 mL) were collected from the receptor compartment (dilutions made if required) at predetermined time interval for a period of 6-8 h and replaced by equal volume of fresh receptor solution to maintain constant volume. The amount of drug in the samples was assayed spectrophotometrically at 263 nm against appropriate blank.

Ex vivo skin permeation studies across porcine skin were conducted in Franz diffusion cell. The freshly excised porcine skin was sandwiched between the donor and the receiver compartment of the cell with the stratum corneum facing the donor compartment. The area of diffusion for all ex vivo experiments was 3.14 $cm^2$. The capacity of the receiver compartment was 16 mL. The skin was equilibrated for 6 hr with the receptor medium (phosphate buffer pH 6.8). A blank sample of 1 mL was withdrawn from the receptor compartment and analyzed to ensure that the diffusion cells did not have any residual absorbance. The buffer solution was replaced after every 30 min. The 6-hr sample showed no absorbance indicating complete stabilization of the skin. The receptor solution (PBS pH 6.8) was then introduced into the magnetically stirred receptor compartment maintained at 37° C. by an electric water bath. The donor compartment was maintained at the ambient temperature at 37° C. On the surface of the stratum corneum, 500 mg of the gel was applied and it was covered with foil. At specified intervals of 0.25, 0.5, 1, 2, 3, 4, 5, 6, 7, 8, 24 hr, 1 mL sample were withdrawn from receptor compartment and replaced with an equivalent amount of the receptor medium. The samples were analyzed for drug content by UV spectrophotometric method at 263 nm using PBS pH 6.8 as blank. Sampling port was covered with aluminum foil to prevent the evaporation of receptor medium. The transdermal flux was determined using Franz-diffusion cell. The flux (permeation rate, $\mu g/cm^2/hr$) of the drug was determined directly as the slope of the linear portion of the curve of amount of drug permeated ($\mu g/cm^2$) vs. time (hr). Permeability coefficient was calculated by dividing flux by initial drug concentration.

| Formulations 14 to 20 | | | | | | | |
|---|---|---|---|---|---|---|---|
| | Formulation (% w/w) | | | | | | |
| Component | MH 14 | MH 15 | MH 16 | MH 17 | MH 18 | MH 19 | MH 20 |
| Mepivacaine HCl | 10 | 10 | 10 | 10 | 10 | 10 | 10 |
| Propylene glycol | 10 | 10 | 10 | 10 | 10 | 10 | 10 |
| Ethanol | 10 | 10 | 10 | 10 | 10 | 10 | 10 |
| Isopropyl myristate | 0.5 | 1 | 2 | | | | |
| Transcutol P | | | | 0.5 | 1 | 2 | 5 |
| Carbopol 980P NF | 2.5 | 2.5 | 2.5 | 2.5 | 2.5 | 2.5 | 2.5 |
| Triethanolamine | q.s | q.s | q.s | q.s | q.s | q.s | q.s |

Formulations 14 to 20

| Component | MH 14 | MH 15 | MH 16 | MH 17 | MH 18 | MH 19 | MH 20 |
|---|---|---|---|---|---|---|---|
| Sodium metabisulfite | 0.01 | 0.01 | 0.01 | 0.01 | 0.01 | 0.01 | 0.01 |
| Methylparaben | 0.1 | 0.1 | 0.1 | 0.1 | 0.1 | 0.1 | 0.1 |
| Distilled water q.s | 100 | 100 | 100 | 100 | 100 | 100 | 100 |

Formulations 21 to 27

| Component | MH 21 | MH 22 | MH 23 | MH 24 | MH 25 | MH 26 | MH 27 |
|---|---|---|---|---|---|---|---|
| Mepivacaine HCl | 10 | 10 | 10 | 10 | 10 | 10 | 10 |
| Propylene glycol | 10 | 10 | 10 | 10 | 10 | 10 | 10 |
| Ethanol | 10 | 10 | 10 | 10 | 10 | 10 | 10 |
| Labrasol | 0.5 | 1 | 2 | 5 | | | |
| Oleic acid | | | | | 0.5 | 1 | 2 |
| Carbopol 980P NF | 2.5 | 2.5 | 2.5 | 2.5 | 2.5 | 2.5 | 2.5 |
| Triethanolamine | q.s | q.s | q.s | q.s | q.s | q.s | q.s |
| Sodium metabisulfite | 0.01 | 0.01 | 0.01 | 0.01 | 0.01 | 0.01 | 0.01 |
| Methyl paraben | 0.1 | 0.1 | 0.1 | 0.1 | 0.1 | 0.1 | 0.1 |
| Distilled water q.s | 100 | 100 | 100 | 100 | 100 | 100 | 100 |

Formulations 28 to 36

| Component | MH 28 | MH 29 | MH 30 | MH 31 | MH 32 | MH 33 | MH 34 | MH 35 | MH 36 |
|---|---|---|---|---|---|---|---|---|---|
| Mepivacaine HCl | 10 | 10 | 10 | 10 | 10 | 10 | 10 | 10 | 10 |
| Propylene glycol | 10 | 10 | 10 | 10 | 10 | 10 | 10 | 10 | 10 |
| Ethanol | 10 | 10 | 10 | 10 | 10 | 10 | 10 | 10 | 10 |
| d-Limonene | 0.5 | 1 | 2 | | | | | | |
| Geraniol | | | | 0.5 | 1 | 2 | | | |
| Eucalyptol | | | | | | | 0.5 | 1 | 2 |
| Carbopol 980P NF | 2.5 | 2.5 | 2.5 | 2.5 | 2.5 | 2.5 | 2.5 | 2.5 | 2.5 |
| Triethanolamine | q.s | q.s | q.s | q.s | q.s | q.s | q.s | q.s | q.s |
| Sodium metabisulfite | 0.01 | 0.01 | 0.01 | 0.01 | 0.01 | 0.01 | 0.01 | 0.01 | 0.01 |
| Methyl paraben | 0.1 | 0.1 | 0.1 | 0.1 | 0.1 | 0.1 | 0.1 | 0.1 | 0.1 |
| Distilled water q.s | 100 | 100 | 100 | 100 | 100 | 100 | 100 | 100 | 100 |

Formulations 37 to 41

| Component | MH 37 | MH 38 | MH 39 | MH 40 | MH 41 |
|---|---|---|---|---|---|
| Mepivacaine HCl | 10 | 10 | 10 | 10 | 10 |
| Propylene glycol | 10 | 10 | 10 | 10 | 10 |
| Ethanol | 10 | 10 | 10 | 10 | 10 |
| Menthol | 0.5 | | | | |
| Menthone | | 0.5 | | | |
| Eugenol | | | 0.5 | | |
| (−) Carvone | | | | 0.5 | |
| Brij 35 | | | | | 0.5 |
| Carbopol 980 P NF | 2.5 | 2.5 | 2.5 | 2.5 | 2.5 |
| Triethanolamine | q.s | q.s | q.s | q.s | q.s |
| Sodium metabisulfite | 0.01 | 0.01 | 0.01 | 0.01 | 0.01 |
| Methyl paraben | 0.1 | 0.1 | 0.1 | 0.1 | 0.1 |
| Distilled water q.s | 100 | 100 | 100 | 100 | 100 |

Example 25

The influence of pH on the permeability of mepivacaine HCl from a variety of gel dosage forms was evaluated. The in-vitro drug release from gel formulations was studied across the Nylon 6, 6 membrane (0.22 μm) using Franz-diffusion cell with effective surface area of 3.14 cm$^2$ and receptor cell volume of 18 mL. The receptor compartment was filled with PBS pH 6.8 and maintained at 37±0.5° C. with constant magnetic stirring. 0.3-0.5 gm of gel was placed on the donor compartment. The samples (1 mL) were collected from the receptor compartment (dilutions made if required) at predetermined time interval for a period of 6-8 h and replaced by equal volume of fresh receptor solution to maintain constant volume. The amount of drug in the samples was assayed spectrophotometrically at 263 nm against appropriate blank. Studies were carried using HPMC K4M 3% as gelling agent with or without containing carvone (0.5%) as a penetration enhancer, so as to assess the effects of pH per se and pH in the presence of penetration enhancers. When Carbopol 3% was used as gelling agent, it gets precipitated out at pH below 5. HPMC gel formulations at pH 8.5 result in precipitation of mepivacaine from the gel. An opaque and gritty gel in physical appearance is obtained. Hence, diffusion studies of Formulation No: 50 & 51 was not performed. As the pH of the formulation decreased, the flux obtained also decreased. The maximum flux was obtained at pH 7.5. However it is not significantly higher than the flux obtained at pH 6.8. This the optimal flux for gel formulations of mepivacaine are greater than about 6 and less than about 8, more preferably, greater than about 6.5 and less than about 8. The results of this study are indicated in the Table below.

Effect of pH on Flux

| Mepivacaine % w/w | Carvone % w/w | pH | Total flux (mg/cm²/hr) |
|---|---|---|---|
| 10 | — | 4.5 | 0.4095 |
| 10 | 0.5 | 4.5 | 0.4251 |
| 10 | — | 5.5 | 0.6000 |
| 10 | 0.5 | 5.5 | 0.5847 |
| 10 | — | 6.8 | 0.7531 |
| 10 | 0.5 | 6.8 | 0.7245 |
| 10 | — | 7.5 | 0.7442 |
| 10 | 0.5 | 7.5 | 0.8035 |
| 10 | — | 8.5 | Not Done |
| 10 | 0.5 | 8.5 | Not Done |

Example 26

Results of the physicochemical evaluation of the gel formulations are presented below.

| Dosage | Permeation Enhancer | Physical Appearance | Homogeneity | pH | Drug Content (%) |
|---|---|---|---|---|---|
| MH 14 | IPM 0.5% | Transparent | homogeneous | 7.24 | 99.65 ± 0.12 |
| MH 15 | IPM 1% | Opaque | homogeneous | 7.15 | 99.74 ± 0.32 |
| MH 16 | IPM 2% | Opaque | homogeneous | 6.90 | 99.5 ± 0.52 |
| MH 17 | Transcutol P 0.5% | Clear, Transparent | homogeneous | 7.25 | 99.25 ± 0.45 |
| MH 18 | Transcutol P 1% | Clear, Transparent | homogeneous | 7.10 | 99.45 ± 0.68 |
| MH 19 | Transcutol P 2% | Clear, Transparent | homogeneous | 7.15 | 99.40 ± 0.89 |
| MH 20 | Transcutol P 5% | Clear, Transparent | homogeneous | 7.24 | 99.86 ± 0.78 |
| MH 21 | Labrasol 0.5% | Clear, Transparent | homogeneous | 7.32 | 99.25 ± 0.94 |
| MH 22 | Labrasol 1% | Clear, Transparent | homogeneous | 6.90 | 99.63 ± 0.58 |
| MH 23 | Labrasol 2% | Clear, Transparent | homogeneous | 7.10 | 99.32 ± 0.67 |
| MH 24 | Labrasol 5% | Clear, Transparent | homogeneous | 7.25 | 99.48 ± 0.72 |
| MH 25 | Oleic acid 0.5% | Transparent | homogeneous | 7.10 | 99.63 ± 0.41 |
| MH 26 | Oleic acid 1% | Opaque | homogeneous | 7.15 | 99.45 ± 0.64 |
| MH 27 | Oleic acid 2% | Opaque | homogeneous | 7.05 | 99.75 ± 0.83 |
| MH 28 | d-limonene 0.5% | Clear, Transparent | homogeneous | 7.28 | 99.24 ± 0.76 |
| MH 29 | d-limonene 0.5% | Opaque | homogeneous | 6.85 | 99.84 ± 0.55 |
| MH 30 | d-limonene 0.5% | Opaque | homogeneous | 7.20 | 99.55 ± 0.49 |
| MH 31 | Geraniol 0.5% | Clear, Transparent | homogeneous | 7.15 | 99.76 ± 0.84 |
| MH 32 | Geraniol 1% | Opaque | homogeneous | 7.20 | 99.63 ± 0.63 |
| MH 33 | Geraniol 2% | Opaque | homogeneous | 7.28 | 99.54 ± 0.56 |
| MH 34 | Eucalyptol 0.5% | Clear, Transparent | homogeneous | 7.42 | 99.47 ± 0.84 |
| MH 35 | Eucalyptol 1% | Opaque | homogeneous | 7.15 | 99.74 ± 0.91 |
| MH 36 | Eucalyptol 2% | Opaque | homogeneous | 7.20 | 99.64 ± 0.63 |
| MH 37 | Menthol 0.5% | Translucent | homogeneous | 7.24 | 99.21 ± 0.15 |
| MH 38 | Menthone 0.5% | Translucent | homogeneous | 7.15 | 99.82 ± 0.30 |
| MH 39 | Eugenol 0.5% | Clear, Transparent | homogeneous | 6.90 | 99.05 ± 0.47 |
| MH 40 | (−) Carvone 0.5% | Clear, Transparent | homogeneous | 7.25 | 99.25 ± 0.45 |
| MH 41 | Brij 35 0.5% | Clear, Transparent | homogeneous | 7.10 | 99.65 ± 0.25 |

Example 27

Results of the flux and permeability co-efficient data of the gel formulations are presented below.

| Dosage | Penetration enhancer | Drug flux at steady state Jss (mg/cm²/hr) | Permeability co-efficient Kp (cm²/sec) |
|---|---|---|---|
| MH 14 | IPM 0.5% | 1.0796 | $2.1592 \times 10^{-2}$ |
| MH 15 | IPM 1% | 0.9652 | $1.9304 \times 10^{-2}$ |
| MH 16 | IPM 2% | Diffusion not performed since gel was opaque in appearance. | |
| MH 17 | Transcutol P 0.5% | 0.7799 | $1.5598 \times 10^{-2}$ |
| MH 18 | Transcutol P 1% | 0.8968 | $1.7936 \times 10^{-2}$ |
| MH 19 | Transcutol P 2% | 0.9076 | $1.8152 \times 10^{-2}$ |
| MH 20 | Transcutol P 5% | 1.1092 | $2.2184 \times 10^{-2}$ |
| MH 21 | Labrasol 0.5% | 0.8614 | $1.7228 \times 10^{-2}$ |
| MH 22 | Labrasol 1% | 0.926 | $1.8520 \times 10^{-2}$ |
| MH 23 | Labrasol 2% | 0.950 | $1.900 \times 10^{-2}$ |
| MH 24 | Labrasol 5% | 0.7232 | $1.4464 \times 10^{-2}$ |
| MH 25 | Oleic acid 0.5% | 0.8729 | $1.7458 \times 10^{-2}$ |
| MH 26 | Oleic acid 1% | Not performed - gel opaque | |
| MH 27 | Oleic acid 2% | Not performed - gel opaque | |
| MH 28 | d-limonene 0.5% | 0.8566 | $1.7132 \times 10^{-2}$ |
| MH 29 | d-limonene 1% | Not performed - gel opaque | |
| MH 30 | d-limonene 2% | Not performed - gel opaque | |
| MH 31 | Geraniol 0.5% | 0.9340 | $2.9745 \times 10^{-2}$ |
| MH 32 | Geraniol 1% | Not performed - gel opaque | |
| MH 33 | Geraniol 2% | Diffusion not performed since gel was opaque in appearance. | |
| MH 34 | Eucalyptol 0.5% | 0.8617 | $1.7234 \times 10^{-2}$ |
| MH 35 | Eucalyptol 1% | Not performed - gel opaque | |
| MH 36 | Eucalyptol 2% | Not performed - gel opaque | |
| MH 37 | Menthol 0.5% | Not performed - gel translucent | |
| MH 38 | Menthone 0.5% | Not performed - gel translucent | |
| MH 39 | Eugenol 0.5% | 1.078 | $2.1560 \times 10^{-2}$ |
| MH 40 | (−) Carvone 0.5% | 0.8503 | $1.7006 \times 10^{-2}$ |
| MH 41 | Brij 35 0.5% | 0.7732 | $1.5464 \times 10^{-2}$ |

Example 28

Figure 13:
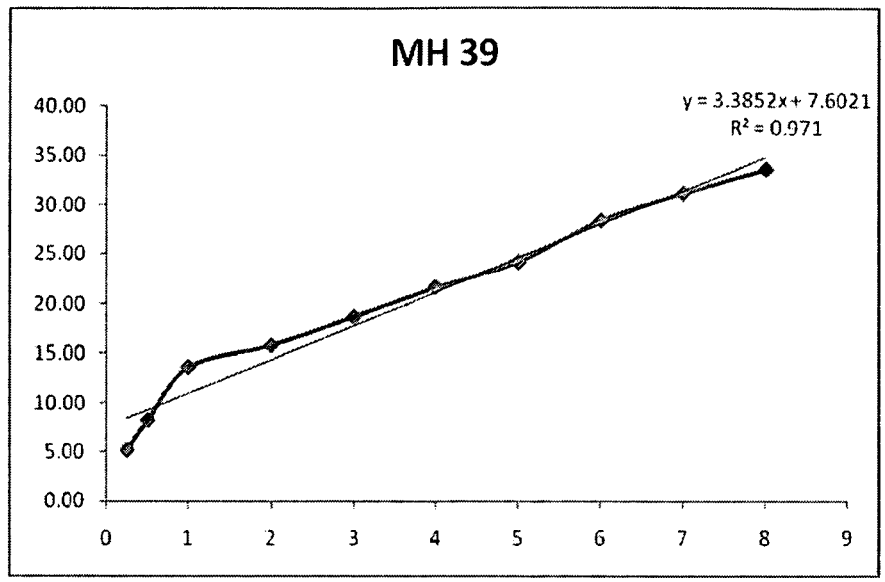
FIGS. 13 and 14 show the permeability of dosage forms MH 39 and MH 40 (see Example 28).
Figure 14:
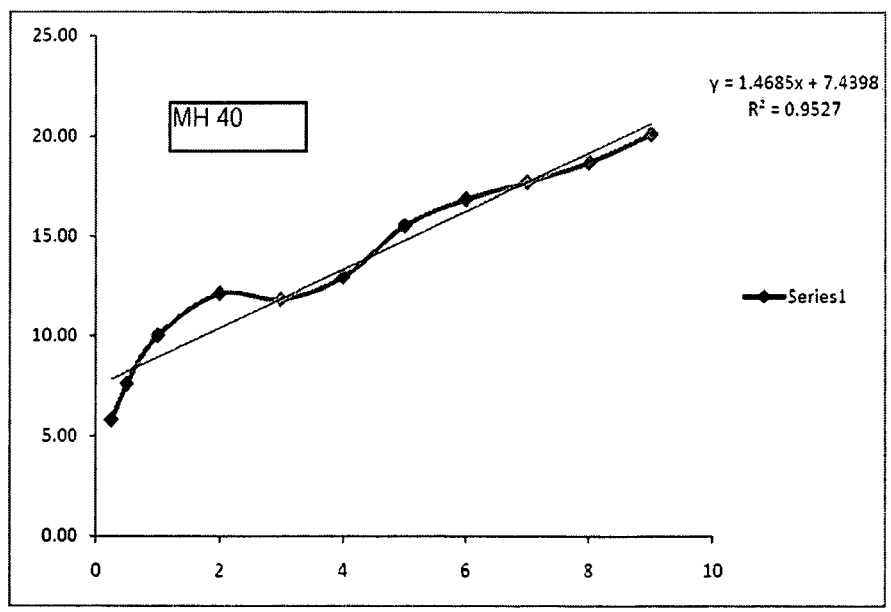

Ex vivo studies were performed with dosage forms comprising 0.5% Eugenol and 0.5% (-) Carvone as penetration enhancer for Mepivacaine HCl gel formulation. FIG. 13 and FIG. 14 show the permeability of dosage forms MH 39 and MH 40.

Ex-vivo permeation study performed using porcine ear skin

| Components | Dosage Form (% w/w) | |
| --- | --- | --- |
| | MH 39 | MH 40 |
| Mepivacaine HCl | 10 | 10 |
| Propylene glycol | 10 | 10 |
| Ethanol | 10 | 10 |
| Eugenol | 0.5 | — |
| Carvone | — | 0.5 |
| Carbopol 980P NF | 2.5 | 2.5 |
| *Triethanolamine (to adjust pH) | q.s | q.s |
| Sodium metabisulfite | 0.01 | 0.01 |
| Methylparaben | 0.1 | 0.1 |
| Distilled water q.s | 100 | 100 |
| Flux (mg/cm$^2$/hr) | 0.4977 | 0.4675 |

Figure 12:
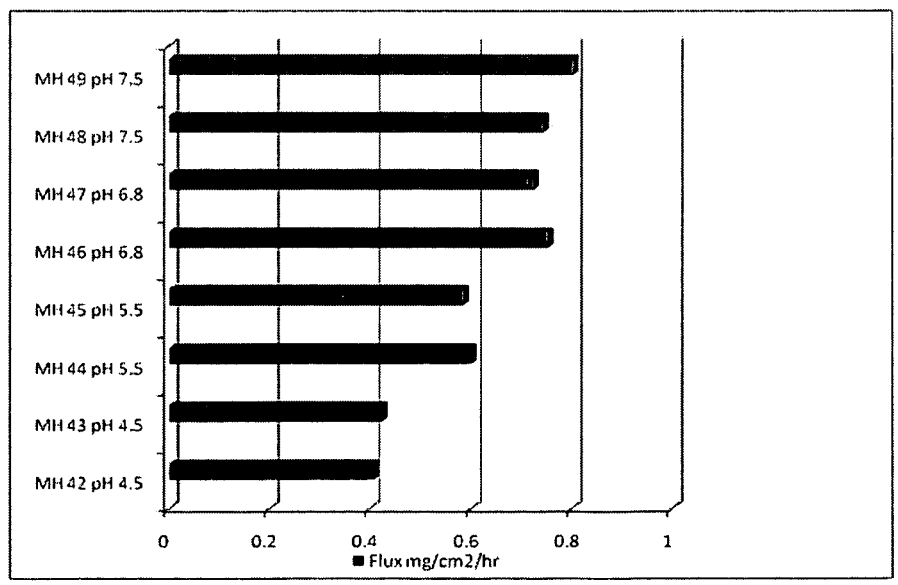
FIG. 12 shows the influence of dosagte form pH on mepivacaine flux.

The influence of pH on the permeability of mepivacaine HCl from a variety of gel dosage forms was evaluated (see FIG. 12)

The included examples are illustrative but not limiting of the methods and composition of the present invention. Other suitable modifications and adaptations of the variety of conditions and parameters normally encountered and obvious to those skilled in the art are within the spirit and scope of the invention.

The dosage form may comprise any pharmaceutically acceptable excipients, in any desired amounts and with any desired physicochemical or mechanical properties (e.g., particle size, melting point, viscosity). Preferably, the pharmaceutical excipient is about 0.000001% to about 99.99%, more preferably, about 0.001% to about 95%, and even more preferably, about 0.01% to about 90%.

Mepivacaine and the any excipients comprising the dosage form may be incorporated in any desired order to prepare the dosage form. Mepivacaine and any incorporated excipients may be processed (e.g., cured, milled, co-mingled, heated, made into a liquid, adjusted for moisture content, purified) prior to incorporation into the dosage form and the dosage form may also be further processed after manufacture (e.g., cured at ambient temperature, cured at a specified temperature) prior to packaging and sale. The proportion of ingredients used for the preparation of the dosage form agent may be modified. In some embodiments, a change in the dose or amount mepivacaine will not require a significant change in amount of other ingredients. In other embodiments, a proportional change in the amount of other ingredients is required to maintain the desired properties. In yet other embodiments, a change in the dose or amount mepivacaine necessitates a change in the nature and/or amount of ingredients to provide the required characteristics of the mepivacaine (e.g., onset of effect, duration of effect, rate and extent of absorption, therapeutic concentrations and effect, etc.).

These and other embodiments of the present invention will readily occur to those of ordinary skill in the art in view of the disclosure herein. The included examples are illustrative but not limiting of the methods and composition of the present invention. Other suitable modifications and adaptations of the variety of conditions and parameters normally encountered and obvious to those skilled in the art are within the spirit and scope of the invention. Additionally, it is understood that each of the various embodiments of the pharmaceutical compositions described herein may be used with each of the various embodiments of the described method of the present invention as described herein.

All patents literature (e.g., patents and patent applications) and non-patent literature (e.g., textbooks, textbook chapters, journal articles, other publications, references, software, data and databases) cited herein are incorporated by reference in their entirety for all purposes.

Having now fully described the invention, it will be understood to those of ordinary skill in the art that the same can be performed within a wide and equivalent range of conditions, formulations, and other parameters without affecting the scope of the invention or any embodiment thereof.

What is claimed is:

1. A pharmaceutical dosage form for application to skin for topical and transdermal delivery of an active agent, the dosage form comprising a liquid carrier that includes a single active agent in a plurality of liposomes and a film-forming polymer, wherein the single active agent is chosen from a therapeutically effective amount of mepivacaine, a pharmaceutically acceptable salt of mepivacaine, or a mixture of these; and wherein the film-forming polymer is in an amount sufficient to form a stable film when the dosage form is applied to human skin.

2. The dosage form of claim 1, wherein the carrier is a reservoir containing mepivacaine, a pharmaceutically acceptable salt of mepivacaine, or a mixture of these.

3. The dosage form of claim 1, wherein the carrier is a matrix comprising a controlled release material and mepivacaine, a pharmaceutically acceptable salt of mepivacaine, or a mixture of these.

4. The dosage form of claim 1, further comprising an adhesive.

5. The dosage form of claim 1, wherein the pH of the carrier is from 6.3 to 8.3.

6. The dosage form of claim 1, the carrier further including a pharmaceutical excipient chosen from the group consisting of essential oils, ethoxydiglycol oleate, ethoxydiglycol, butylene glycol cocoate, glyceryl behenate, polyoxyethylene lauryl ether, cajeput oil, camphor, (-)carvone, carvacrol, cetostearyl isononanoate, cineole, clove oil, cocyl caprylocaprate, d-limonene, decodecylmethyl sulfoxide, decyl oleate, dimethyl sulfoxide, dioctyl sulfosuccinate, eucalyptol, eugenol, geraniol, isopropyl myristate, isopropyl palmitate, isopropyl myristate, menthol, menthone, propylene glycol dicaprylocaprate, caprylocaproyl rnacrogolglycerides, menthol, lemon grass oil, lemon oil, medium chain triglycerides, octyldodecanol, oleic acid, oleyl alcohol, oleyloleat, peppermint oil, polyoxyl 20, cetostearyl ether, propylene glycol, terpineol, poloxamers and diethylene glycol monoethyl ether.

7. The dosage form of claim 6, wherein the excipient is selected from the group consisting of (-)carvone, polyoxyethylene lauryl ether, eucalyptol, eugenol, geraniol, isopropyl myristate, menthol, menthone, oleic acid, diethylene glycol monoethyl ether and dimethylsulfoxide.

8. The dosage form of claim 1, being a patch comprising a border for contacting the skin, the border exhibiting greater skin adhesion than the remainder of the patch.

* * * * *

UNITED STATES PATENT AND TRADEMARK OFFICE
CERTIFICATE OF CORRECTION

PATENT NO. : 11,607,407 B2
APPLICATION NO. : 13/641240
DATED : March 21, 2023
INVENTOR(S) : Najib Babul It is certified that error appears in the above-identified patent and that said Letters Patent is hereby corrected as shown below:

On the Title Page

Column 2, item (57) Abstract, "or it" should be --or its--.

Page 3, Column 2, Other Publications, Line 43, "Exension" should be --Extension--.

In the Specification

Column 1, Line 15, "it" should be --its--.

Column 3, Line 28, "also known" should be --also known as--.

Column 3, Lines 47-48, "evaluated studies" should be --evaluated by studies--.

Column 4, Lines 24-25, "any major market" should be --in any major market--.

Column 4, Lines 38-39, "in efficacy" should be --inefficacy--.

Column 4, Line 55, "have been" should be --has been--.

Column 6, Line 20, "fibromylagia" should be --fibromyalgia--.

Column 6, Line 39, "target" should be --targeting--.

Column 6, Lines 45-48, "(ii) no public data on mepivacaine application to the skin for the management of chronic pain; (ii) no public data on mepivacaine application to the skin for the management of chronic pain" should be --(ii) no public data on mepivacaine application to the skin for the management of chronic pain--.

Column 6, Line 53, "any major market" should be --in any major market--.

Signed and Sealed this
Seventeenth Day of October, 2023

Katherine Kelly Vidal
*Director of the United States Patent and Trademark Office*

Column 6, Line 57, "mechanism" should be --mechanisms--.

Column 6, Line 62, "weeks months" should be --weeks, months--.

Column 8, Line 8, "when the dosage" should be --the dosage--.

Column 8, Line 18, "administration lidocaine" should be --administration of lidocaine--.

Column 8, Line 22, "administration lidocaine" should be --administration of lidocaine--.

Column 11, Line 64, "form a gel" should be --form of a gel--.

Column 11, Line 67, "form a cream" should be --form of a cream--.

Column 12, Line 3, "form an ointment" should be --form of an ointment--.

Column 12, Line 9, "form a solution" should be --form of a solution--.

Column 12, Line 16, "form a suspension" should be --form of a suspension--.

Column 12, Line 19, "form a lotion" should be --form of a lotion--.

Column 12, Line 22, "form a hydrogel matrix" should be --form of a hydrogel matrix--.

Column 12, Lines 30-39, the two paragraphs are duplicates. Please remove Lines 35-39.

Column 12, Line 58, "etc" should be --etc.--.

Column 12, Line 60, "application to the skin drug" should be --application to the skin--.

Column 12, Line 64, "etc" should be --etc.--.

Column 12, Line 66, "application to the skin drug" should be --application to the skin--.

Column 13, Line 2, "etc" should be --etc.--.

Column 13, Line 4, "application to the skin drug" should be --application to the skin--.

Column 13, Line 18, "etc" should be --etc.--.

Column 13, Line 22, "form of layer" should be --form a layer--.

Column 13, Line 35, "that the remained" should be --than the remainder--.

Column 13, Line 37, "of portion" should be --of a portion--.

Column 13, Line 56, "of portion" should be --of a portion--.

Column 14, Line 65, "from" should be --form--.

Column 15, Lines 2-5, "In other preferred embodiments, the dosage from provides. In other preferred embodiments the dosage form provides up to about 504 hours," should be --In other preferred embodiments, the dosage form provides up to about 504 hours,--.

Column 15, Line 13, "from" should be --form--.

Column 15, Line 26, "from" should be --form--.

Column 15, Line 37, "from" should be --form--.

Column 15, Line 45, "from" should be --form--.

Column 15, Line 48, "lag time to which" should be --lag time which--.

Column 15, Line 53, "from" should be --form--.

Column 15, Line 60, "from" should be --form--.

Column 16, Line 1, "from" should be --form--.

Column 16, Line 11, "from" should be --form--.

Column 16, Line 22, "from" should be --form--.

Column 16, Line 39, "from" should be --form--.

Column 16, Line 65, "from" should be --form--.

Column 17, Line 5, "from" should be --form--.

Column 17, Line 8, "less than about 1.4 hr, or less than about 1.4 hr," should be --less than about 1.4 hr, or less than about 1.3 hr,--.

Column 17, Line 15, "from" should be --form--.

Column 17, Line 25, "from" should be --form--.

Column 17, Line 36, "from" should be --form--.

Column 17, Line 55, "from" should be --form--.

Column 18, Line 5, "from" should be --form--.

Column 18, Line 19, "from" should be --form--.

Column 18, Line 30, "from" should be --form--.

Column 18, Line 43, "from" should be --form--.

Column 18, Line 54, "from" should be --form--.

Column 18, Line 66, "from" should be --form--.

Column 19, Line 12, "from" should be --form--.

Column 19, Line 21, "from" should be --form--.

Column 19, Line 24, "is less than" should be --of less than--.

Column 19, Line 33, "from" should be --form--.

Column 19, Line 36, "from" should be --form--.

Column 19, Line 38, "from" should be --form--.

Column 19, Line 58, "from" should be --form--.

Column 19, Line 63, "from" should be --form--.

Column 19, Line 65, "from" should be --form--.

Column 20, Line 19, "from" should be --form--.

Column 20, Line 22, "from" should be --form--.

Column 20, Line 25, "from" should be --form--.

Column 20, Line 34, "from" should be --form--.

Column 20, Line 39, "from" should be --form--.

Column 20, Line 42, "from" should be --form--.

Column 20, Line 56, "from" should be --form--.

Column 20, Line 64, "from" should be --form--.

Column 21, Line 12, "from" should be --form--.

CERTIFICATE OF CORRECTION (continued)
U.S. Pat. No. 11,607,407 B2

Column 21, Line 15, "from" should be --form--.

Column 21, Line 30, "from" should be --form--.

Column 21, Line 34, "from" should be --form--.

Column 21, Line 47, "from providing a of mepivacaine" should be --form providing a $C_{min}$ of mepivacaine--.

Column 21, Line 50, "from" should be --form--.

Column 21, Line 59, "from" should be --form--.

Column 21, Line 63, "from" should be --form--.

Column 21, Line 67, "from" should be --form--.

Column 22, Line 16, "from" should be --form--.

Column 22, Line 46, "from" should be --form--.

Column 23, Line 17, "from" should be --form--.

Column 23, Line 31, "from" should be --form--.

Column 23, Line 43, "from" should be --form--.

Column 23, Line 48, "from" should be --form--.

Column 23, Line 64, "from" should be --form--.

Column 24, Line 4, "from" should be --form--.

Column 24, Line 21, "from" should be --form--.

Column 24, Line 42, "$W_{50}$ on of" should be --$W_{50}$ of--.

Column 24, Line 47, "from" should be --form--.

Column 24, Line 64, "from" should be --form--.

Column 25, Line 7, "HVD on of" should be --HVD of--.

Column 25, Line 12, "from" should be --form--.

CERTIFICATE OF CORRECTION (continued)
U.S. Pat. No. 11,607,407 B2

Column 25, Line 24, "HVD on of" should be --HVD of--.

Column 25, Line 29, "from" should be --form--.

Column 25, Line 47, "from" should be --form--.

Column 25, Line 66, "from" should be --form--.

Column 26, Line 24, "from" should be --form--.

Column 26, Line 39, "from" should be --form--.

Column 26, Line 45, "from" should be --form--.

Column 27, Line 33, "is delivered is in a" should be --is delivered in a--.

Column 29, Line 28, "patients" should be --patient's--.

Column 29, Line 33, "from" should be --form--.

Column 29, Line 47, "from" should be --form--.

Column 29, Line 62, "from" should be --form--.

Column 30, Line 9, "from" should be --form--.

Column 30, Line 24, "from" should be --form--.

Column 30, Line 67, "about 2% to about, 50%" should be --about 2% to about 50%--.

Column 31, Line 25, "from" should be --form--.

Column 31, Line 34, "from" should be --form--.

Column 32, Lines 3-9, "0.17 hours, between about 5% to about 90% at 0.25 hours, between 10% to about 100% at 0.5 hours and greater than about 60% at 1 hour; or greater than about 5% at 0.5 hours, greater than about 10% at 0.75 hours, and greater than about 40% at 1 hour; or greater than about 5% at 0.5 hours, greater than about 10% at 0.75 hours, and greater than about 40% at 1 hour." should be --0.17 hour, between about 5% to about 90% at 0.25 hour, between 10% to about 100% at 0.5 hour and greater than about 60% at 1 hour; or greater than about 5% at 0.5 hour, greater than about 10% at 0.75 hour, and greater than about 40% at 1 hour; or greater than about 5% at 0.5 hour, greater than about 10% at 0.75 hour, and greater than about 40% at 1 hour.--.

Column 35, Line 51, "the significant the significant" should be --the significant--.

Column 37, Lines 51-52, "mechanism based approaches to treatment has been suggested." should be --mechanism-based approaches to treatment have been suggested.--.

Column 37, Line 56, "have been demonstrated efficacy" should be --have demonstrated efficacy--.

Column 38, Line 33, "and only," should be --and only--.

Column 41, Line 11, "also known Varicella-Zoster" should be --also known as Varicella-Zoster--.

Column 41, Line 23, "referred to ad" should be --referred to as--.

Column 41, Line 39, "In a most patients" should be --In most patents--.

Column 44, Line 67, "in the in the" should be --in the--.

Column 45, Line 32, "In clinically studies," should be --In clinical studies,--.

Column 47, Line 56, "is also an important is associated with" should be --is also associated with--.

Column 49, Line 11, "result" should be --results--.

Column 50, Line 61, "T There is a need" should be --There is a need--.

Column 51, Lines 66-67, "on the market any major market." should be --on the market in any major market.--.

Column 52, Line 6, "given as free base of as pharmaceutically acceptable salts," should be --given as free base as pharmaceutically acceptable salts,--.

Column 52, Line 31, "terephlhalates," should be --terephthalates,--.

Column 52, Line 41, "in may be substituted" should be --may be substituted--.

Column 53, Line 13, "are greater than" should be --is greater than--.

Column 53, Line 47, "(p=0.10)" should be --(p=0.10).--.

Column 54, Line 13, "are" should be --is--.

Column 54, Line 13, "Inc," should be --Inc.--.

Column 54, Line 22, "enhancer" should be --enhancers--.

Column 54, Line 33, "contain" should be --contains--.

Column 54, Line 62, "In some particularly embodiments," should be --In some particularly preferred embodiments,--.

Column 54, Line 66 to Column 55, Line 1, "site which not the site where pain or neuropathy are felt, but ... distal to where pain or neuropathy are" should be --site which is not the site where pain or neuropathy is felt, but ... distal to where pain or neuropathy is--.

Column 58, Lines 22-23, "invention provides comprises a mepivacaine dosage forms" should be --invention comprises a mepivacaine dosage form--.

Column 60, Line 37, "weeks" should be --weeks,--.

Column 61, Lines 36-37, "co-administered may be used" should be --co-administered ingredients may be used--.

Column 61, Lines 38-40, "In some embodiment, co-administered may be used to provide a different therapeutic effects" should be --In some embodiments, co-administered pharmaceutically active ingredients may be used to provide different therapeutic effects--.

Column 61, Line 62, "An" should be --A--.

Column 62, Line 11, "In some preferred embodiments of the dosage form" should be --In some preferred embodiments the dosage form--.

Column 62, Line 17, "In some preferred embodiments of the dosage form" should be --In some preferred embodiments the dosage form--.

Column 62, Line 38, "or an individual" should be --or individual--.

Column 62, Line 65, "and adhesive layer" should be --an adhesive layer--.

Column 64, Line 36, "are also" should be --is also--.

Column 65, Line 36, "typically a preferably" should be --typically preferably--.

Column 66, Line 37, "such as," should be --such as--.

Column 66, Line 42, "are also" should be --is also--.

Column 66, Lines 55-57, "In some preferred embodiments, the invention provides for a transdermal dosage form comprises a transdermal dosage forms of about" should be --In some preferred embodiments, the invention comprises a transdermal dosage form of about--.

Column 66, Line 64, "variety circumstances" should be --variety of circumstances--.

Column 68, Line 19, "according some" should be --according to some--.

Column 68, Lines 23-24, "the reservoir is formed, from a hydrophobic, a lipophilic and/or ... , such as," should be --the reservoir is formed from a hydrophobic, a lipophilic and/or ... , such as--.

Column 71, Line 20, "comprise" should be --comprises--.

Column 71, Line 45, "0.0625" should be --0.0625 mm--.

Column 71, Line 48, "as," should be --as--.

Column 72, Line 12, "such polymethyl" should be --such as polymethyl--.

Column 72, Line 40, "include," should be --include--.

Column 73, Line 56, "up to up to" should be --up to--.

Column 74, Line 7, "such hexane" should be --such as hexane--.

Column 79, Line 3, "can be may be" should be --may be--.

Column 81, Line 54, "final, composition" should be --final composition--.

Column 82, Line 40, "interfere" should be --interference--.

Column 83, Line 58, "are" should be --is--.

Column 85, Line 36, "provide" should be --provides--.

Column 86, Line 49, "polymers" should be --polymer--.

Column 87, Line 64, "surfactants," should be --surfactant,--.

Column 88, Line 5, "surfactants," should be --surfactant,--.

Column 90, Line 31, "on" should be --one--.

Column 91, Line 4, "vehicle of prepared" should be --vehicle prepared--.

Column 91, Lines 29-30, "embodiment the invention" should be --embodiment of the invention--.

Column 91, Line 46, "methods" should be --method--.

Column 91, Line 62, "from" should be --form--.

Column 91, Line 63, "permeation enhancers." should be --permeation enhancer.--.

Column 92, Line 47, "may be comprise" should be --may comprise--.

Column 92, Line 50, "may be comprise" should be --may comprise--.

CERTIFICATE OF CORRECTION (continued)

Column 92, Line 55, "limited Ethoxydiglycol oleate" should be --limited to, ethoxydiglycol oleate--.

Column 93, Lines 61-62, "permeation enhancers" should be --permeation enhancer--.

Column 96, Line 30, "includes but is not limited to" should be --include but are not limited to--.

Column 100, Line 11, "Another emulsifier" should be --Other emulsifiers--.

Column 103, Line 63, "1,5000,000" should be --1,500,000--.

Column 104, Line 54, "useful" should be --are useful--.

Column 104, Line 55, "agents" should be --agents.--.

Column 105, Line 16, "an" should be --and--.

Column 106, Line 61, "are may be" should be --may be--.

Column 107, Line 43, "on of the nature of" should be --on the nature of--.

Column 110, Lines 27-28, "tail the thermal stimulus." should be --tail from the thermal stimulus.--.

Column 111, Line 6, "doisage" should be --dosage--.

Column 111, Line 39 (Example 4 chart), "Non woven" should be --Non-woven--.

Column 111, Line 46, "EtOH)" should be --EtOH).--.

Column 112, Line 10, "formed" should be --formed;--.

Column 112, Line 20, "non woven" should be --non-woven--.

Column 113, Line 12, "continuous stirring" should be --continuously stirred--.

Column 113, Lines 14-15, "was then added to the gel while continuous stirring." should be --were then added to the gel while continuously stirring.--.

Column 113, Line 16, "continuous" should be --continuously--.

Column 113, Lines 20-21, "studies" should be --studied--.

Column 113, Line 26, "placed o" should be --placed on--.

Column 116, Line 14, "was dissolved" should be --were dissolved--.

Column 117, Lines 14-15, "cream was gel was" should be --cream gel was--.

Column 117, Line 19, "is a widely used" should be --is widely used--.

Column 117, Lines 66-67, "A clear non sticky, transparent gel was formed at pH 7 but the gel became turbid within few days." should be --A clear, non-sticky, transparent gel was formed at pH 7, but the gel became turbid within a few days.--.

Column 118, Lines 14-15, "A clear non sticky, transparent gel was formed at pH 7 but the gel became turbid within a few days." should be --A clear, non-sticky, transparent gel was formed at pH 7, but the gel became turbid within a few days.--.

Column 118, Lines 48-49, "could not formed" should be --could not be formed--.

Column 119, Line 13, "after few days." should be --after a few days--.

Column 120, Line 43, "sample" should be --samples--.

Column 122, Line 62, "interval" should be --intervals--.

Column 122, Line 67, "were carried" should be --were carried out--.

Column 123, Lines 9-10, "Formulation No. 50 & 51 was not performed." should be --Formulations No. 50 & 51 were not performed.--.

Column 123, Line 13, "This" should be --Thus--.

Column 123, Line 14, "are" should be --is--.

Column 125, Line 41, "Mepivacaine and the any excipients" should be --Mepivacaine and any excipients--.

Column 126, Line 8, "patents" should be --patent--.